United States Patent
Senger et al.

(10) Patent No.: US 9,458,477 B2
(45) Date of Patent: Oct. 4, 2016

(54) FATTY ACID DESATURASES, ELONGASES, ELONGATION COMPONENTS AND USES THEREOF

(75) Inventors: Toralf Senger, Heidelberg (DE); Jörg Bauer, Durham, NC (US); Laurent Marty, Heidelberg (DE)

(73) Assignee: BASF Plant Science Company GmbH, Ludwigshafen (DE)

( * ) Notice: Subject to any disclaimer, the term of this patent is extended or adjusted under 35 U.S.C. 154(b) by 416 days.

(21) Appl. No.: 13/880,275

(22) PCT Filed: Oct. 19, 2011

(86) PCT No.: PCT/EP2011/068237
§ 371 (c)(1),
(2), (4) Date: May 21, 2013

(87) PCT Pub. No.: WO2012/052468
PCT Pub. Date: Apr. 26, 2012

(65) Prior Publication Data
US 2013/0291228 A1    Oct. 31, 2013

Related U.S. Application Data

(60) Provisional application No. 61/405,255, filed on Oct. 21, 2010, provisional application No. 61/431,456, filed on Jan. 11, 2011.

(30) Foreign Application Priority Data

Oct. 21, 2010  (EP) .................................. 10188419
Jan. 11, 2011  (EP) .................................. 11150545

(51) Int. Cl.
| | | |
|---|---|---|
| C12N 9/10 | (2006.01) | |
| C12N 15/82 | (2006.01) | |
| C12P 7/64 | (2006.01) | |
| C12N 9/02 | (2006.01) | |

(52) U.S. Cl.
CPC ........... *C12P 7/6427* (2013.01); *C12N 9/0083* (2013.01); *C12N 9/1029* (2013.01); *C12N 15/8247* (2013.01); *Y02P 20/52* (2015.11)

(58) Field of Classification Search
None
See application file for complete search history.

(56) References Cited

U.S. PATENT DOCUMENTS

| | | |
|---|---|---|
| 7,183,458 B1 | 2/2007 | Heinz et al. |
| 2005/0089879 A1 | 4/2005 | Feussner et al. |
| 2005/0214761 A1 | 9/2005 | Lerchl et al. |
| 2006/0218668 A1 | 9/2006 | Cirpus et al. |
| 2007/0028326 A1 | 2/2007 | Cirpus et al. |
| 2008/0076166 A1 | 3/2008 | Cirpus et al. |
| 2008/0155705 A1 | 6/2008 | Zank et al. |
| 2008/0160054 A1 | 7/2008 | Heinz et al. |
| 2009/0158462 A1 | 6/2009 | Cirpus et al. |
| 2010/0088776 A1 | 4/2010 | Bauer et al. |
| 2010/0192238 A1 | 7/2010 | Bauer et al. |
| 2010/0199365 A1 | 8/2010 | Senger et al. |
| 2012/0210465 A1 | 8/2012 | Lerchl et al. |
| 2013/0116421 A1 | 5/2013 | Cirpus et al. |

FOREIGN PATENT DOCUMENTS

| | | |
|---|---|---|
| CA | 2 378 423 A1 | 1/2001 |
| CA | 2 559 360 A1 | 9/2005 |
| EP | 1 790 731 A2 | 5/2007 |
| WO | WO-00/34439 A1 | 6/2000 |
| WO | WO-00/75341 A1 | 12/2000 |
| WO | WO-01/02591 A1 | 1/2001 |
| WO | WO-01/59128 A2 | 8/2001 |
| WO | WO-01/85968 A2 | 11/2001 |
| WO | WO-02/26946 A2 | 4/2002 |
| WO | WO-02/057465 A2 | 7/2002 |
| WO | WO-02/077213 A2 | 10/2002 |
| WO | WO-03/012092 A1 | 2/2003 |
| WO | WO-03/064638 A2 | 8/2003 |
| WO | WO-03/072784 A1 | 9/2003 |
| WO | WO-03/093482 A2 | 11/2003 |
| WO | WO-2004/057001 A2 | 7/2004 |
| WO | WO-2004/090123 A2 | 10/2004 |
| WO | WO-2005/012316 A2 | 2/2005 |
| WO | WO-2005/083053 A2 | 9/2005 |
| WO | WO-2005/083093 A2 | 9/2005 |
| WO | WO-2006/069710 A1 | 7/2006 |
| WO | WO-2006/100241 A2 | 9/2006 |
| WO | WO-2007/042510 A2 | 4/2007 |
| WO | WO-2007/093776 A2 | 8/2007 |
| WO | WO-2007/136877 A2 | 11/2007 |
| WO | WO-2008/006202 A1 | 1/2008 |
| WO | WO-2008/022963 A2 | 2/2008 |
| WO | WO-2008/040787 A2 | 4/2008 |
| WO | WO-2009/016202 A2 | 2/2009 |
| WO | WO-2009/016208 A2 | 2/2009 |

OTHER PUBLICATIONS

Maali-Amiri et al (Lipid Fatty Acid Composition of Potato Plants Transformed with the D12-Desaturase Gene from Cyanobacterium. ISSN 1021-4437, Russian Journal of Plant Physiology, 2007, vol. 54, No. 5, pp. 600-606).*

(Continued)

*Primary Examiner* — Medina A Ibrahim
*Assistant Examiner* — Wayne Zhong
(74) *Attorney, Agent, or Firm* — Drinker Biddle & Reath LLP

(57) ABSTRACT

The invention provides isolated nucleic acid molecules which encode a fatty acid desaturase, KCS, KCR, DH and ECR from *Nannochloropsis oculata*. The invention also provides recombinant expression vectors containing desaturase, KCS, KCR, DH and ECR nucleic acid molecules, host cells into which the expression vectors have been introduced, and methods for large-scale production of long chain polyunsaturated fatty acids (LCPUFAs), e.g., ARA, EPA and DHA.

20 Claims, 5 Drawing Sheets

(56) References Cited

OTHER PUBLICATIONS

Hill et al (Functional analysis of conserved histidines in ADP-glucose pyrophosphorylase from *Escherichia coli*. Biochem. Biophys. Res. Comm. 244:573-577, 1998).*
Guo et al (Protein tolerance to random amino acid change, Proc. Natl. Acad. Sci. USA 101:9205-9210, 2004).*
Fourgoux-Nicol et al (1999, Plant Molecular Biology 40: 857-872).*
Friedberg (Automated protein function prediction—the genomic challenge. Brief. Bioinformatics. 7:225-242, 2006).*
Sperling, P., et al., "The Evolution of Desaturases", Prostaglandins, Leukotrienes and Essential Fatty Acids, 2003, vol. 68, pp. 73-95.
Crawford, M. A., et al., "Are Deficits of Arachidonic and Docosahexaenoic Acids Responsible for the Neural and Vascular Complications of Preterm Babies?", Am. J. Clin. Nutr., 1997, vol. 66(suppl), pp. 1032S-1041S.
Giusto, N. M., et al., "Lipid Metabolism in Vertebrate Retinal Rod Outer Segments", Progress in Lipid Research, 2000, vol. 39, pp. 315-391.
Martinez, M., "Tissue Levels of Polyunsaturated Fatty Acids During Early Human Development", The Journal of Pediatrics, 1992, vol. 120, pp. S129-S138.
Horrocks, L. A., et al., "Health Benefits of Docosahexaenoic Acid (DHA)", Pharmacological Research, 1999, vol. 40, No, 3, pp. 211-225.
Spector, A. A., "Essentiality of Fatty Acids", Lipids, 1999, vol. 34, pp. S1-S3.
"Biochemistry & Molecular Biology of Plants", Buchanan, B. B., et al., eds., American Society of Plant Physiologists, Rockville, Maryland, 2000 (29 pages).
Hoffman, C. S., "Preparation of Yeast DNA, RNA and Proteins", Section IV, Unit 13.11 (Supplement 39) in "Current Protocols in Molecular Biology", 1997, pp. 13.11.1-13.11.4.
Deblaere, R., et al., "Efficient Octopine Ti Plasmid-Derived Vectors for *Agrobacterium*-Mediated Gene Transfer to Plants", Nucleic Acids Research, 1985, vol. 13, No. 13, pp. 4777-4788.
Qiu, X., et al., "Identification of a Δ4 Fatty Acid Desaturase from *Thraustochytrium* sp. Involved in the Biosynthesis of Docosahexanoic Acid by Heterologous Expression in *Saccharomyces serevisiae* and *Brassica juncea*", The Journal of Biological Chemistry, 2001, vol. 276, No. 34, pp. 31561-31566.
Arondel, V., et al., "Map-Based Cloning of a Gene Controlling Omega-3 Fatty Acid Desaturation in *Arabidopsis*", Science, 1992, vol. 258, pp. 1353-1355.
Broadwater, J. A., et al., "Desaturation and Hydroxylation: Residues 148 and 324 of *Arabidopsis* FAD2, in Addition to Substrate Chain Length, Exert a Major Influence in Partitioning of Catalytic Specificity", The Journal of Biological Chemistry, 2002, vol. 277, No. 18, pp. 15613-15620.
Broun, P., et al., "Catalytic Plasticity of Fatty Acid Modification Enzymes Underlying Chemical Diversity of Plant Lipids", Science, 1998, vol. 282, pp. 1315-1317.
Calvo, A. M., et al., "Genetic Connection between Fatty Acid Metabolism and Sporulation in *Aspergillus nidulans*", The Journal of Biological Chemistry, 2001, vol. 276, No. 28, pp. 25766-25774.
Knutzon, D. S., et al., "Identification of Δ5-Desaturase from *Mortierella alpina* by Heterologous Expression in Bakers' Yeast and Canola", The Journal of Biological Chemistry, 1998, vol. 273, No. 45, pp. 29360-29366.
Mantle, P. G., et al., "Differentiation of *Claviceps purpurea* in Axenic Culture", Journal of General Microbiology, 1976, vol. 93, pp. 321-334.
Mey, G., et al., "The Biotrophic, Non-Appressorium-Forming Grass Pathogen *Claviceps purpurea* Needs a *Fus3/Pmk1* Homologous Mitogen-Activated Protein Kinase for Colonization of Rye Ovarian Tissue", MPMI, 2002, vol. 15, No. 4, pp. 303-312.
Okuley, J., et al., "Arabidopsis *FAD2* Gene Encodes the Enzyme that is Essential for Polyunsaturated Lipid Synthesis", The Plant Cell, 1994, vol. 6, pp. 147-158.
Qi, B., et al., "Production of Very Long Chain Polyunsaturated Omega-3 and Omega-6 Fatty Acids in Plants", Nature Biotechnology, 2004, vol. 22, No. 6, pp. 739-745.
Shanklin, J., et al., "Desaturation and Related Modifications of Fatty Acids", Annu. Rev. Plant Physiol. Plant Mol. Biol., 1998, vol. 49, pp. 611-641.
Tudzynski, P., et al., "Biotechnology and Genetics of Ergot Alkaloids", Appl. Microbiol. Biotechnol., 2001, vol. 57, pp. 593-605.
International Search Report for PCT/EP2011/068237 mailed May 29, 2012.
Schneider, J. C., et al., "A Mutant of *Nannochloropsis* Deficient in Eicosapentaenoic Acid Production", Phytochemistry, 1995, vol. 40, No. 3, pp. 807-814.
International Preliminary Report on Patentability for PCT/EP2011/068237 mailed Apr. 23, 2013.

* cited by examiner

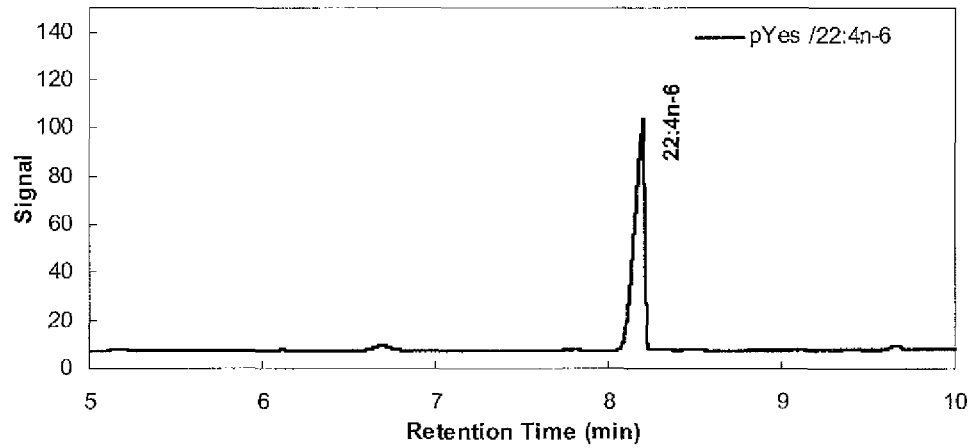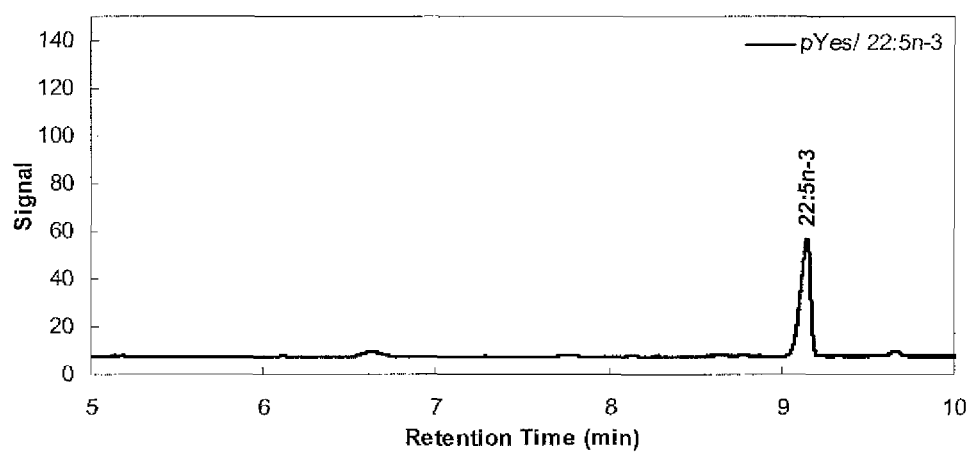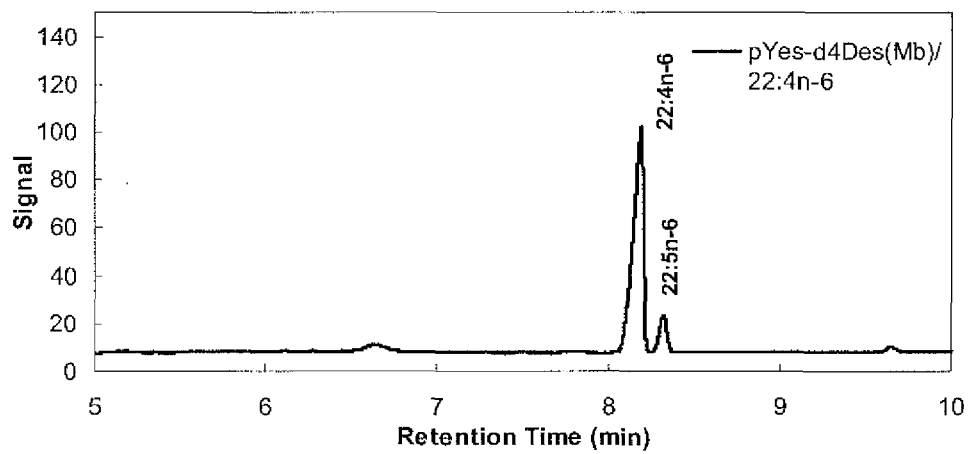

cont.
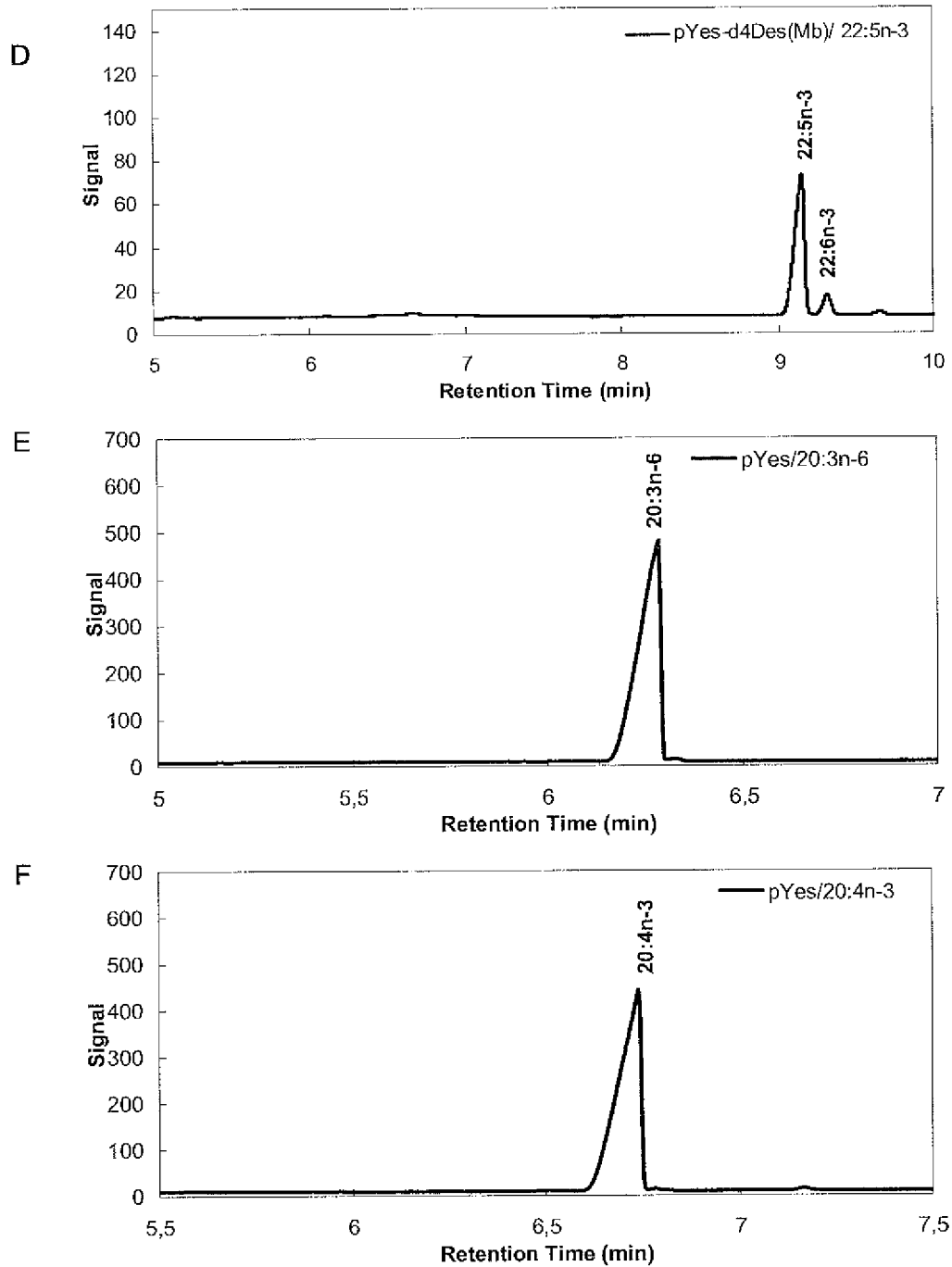

cont.
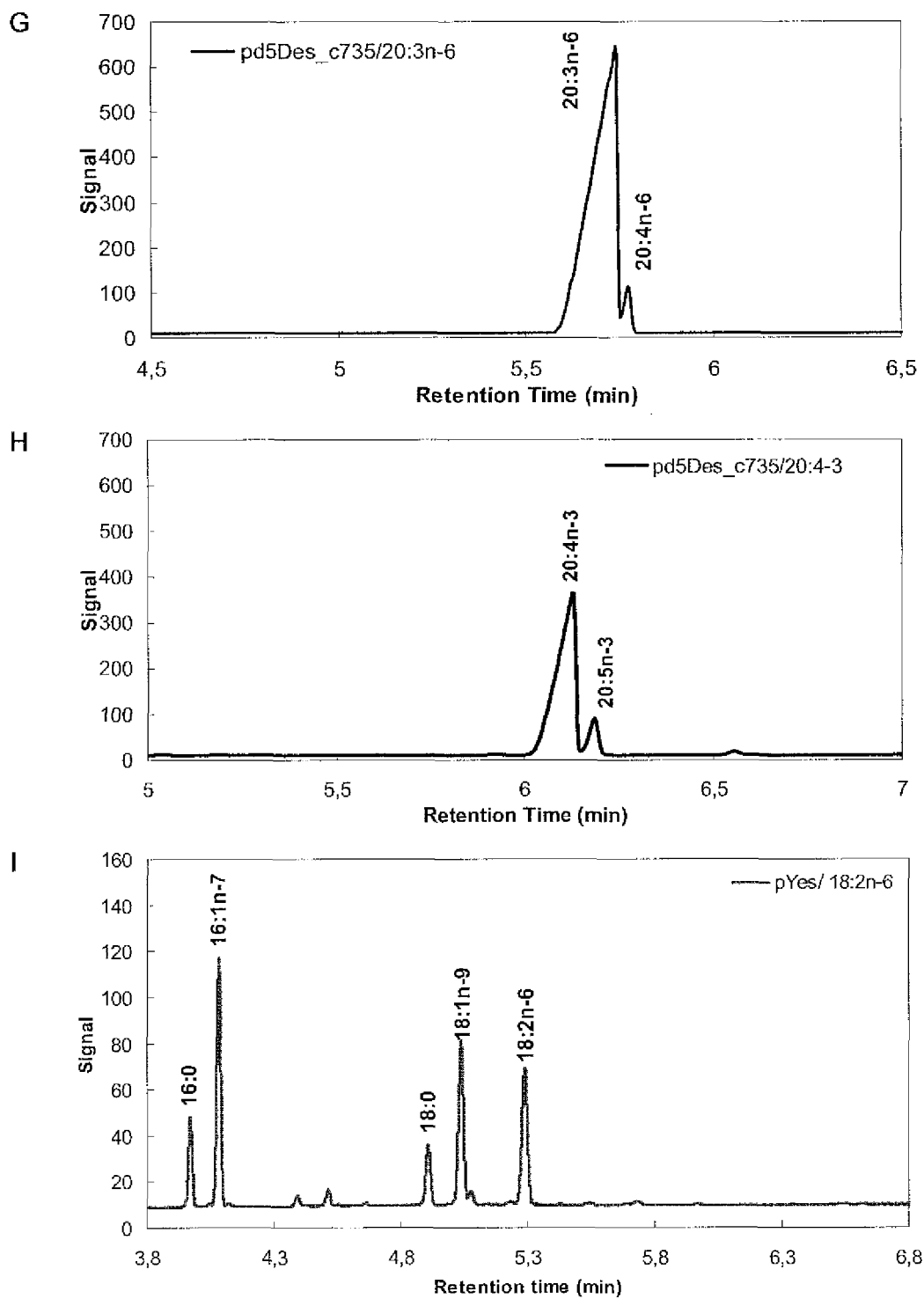

cont.
J
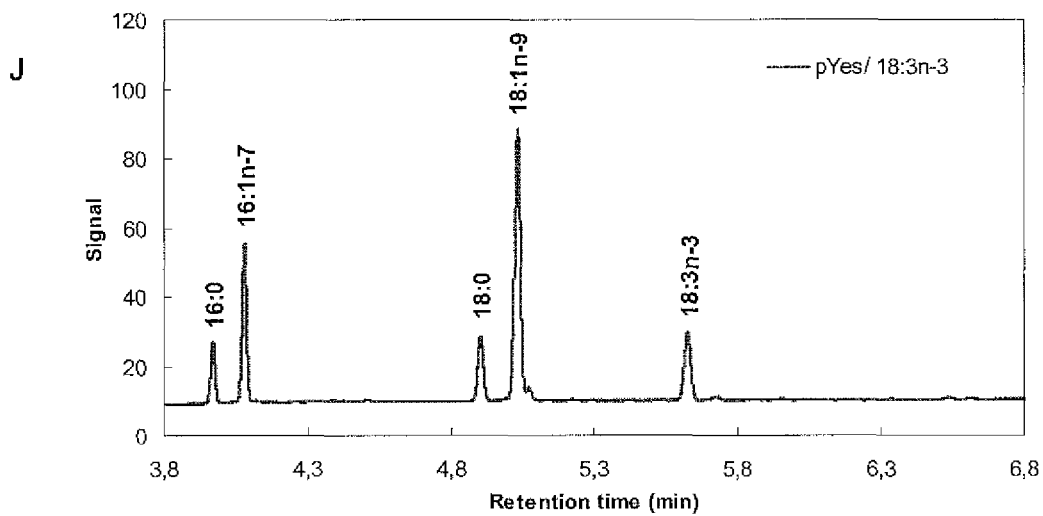
K
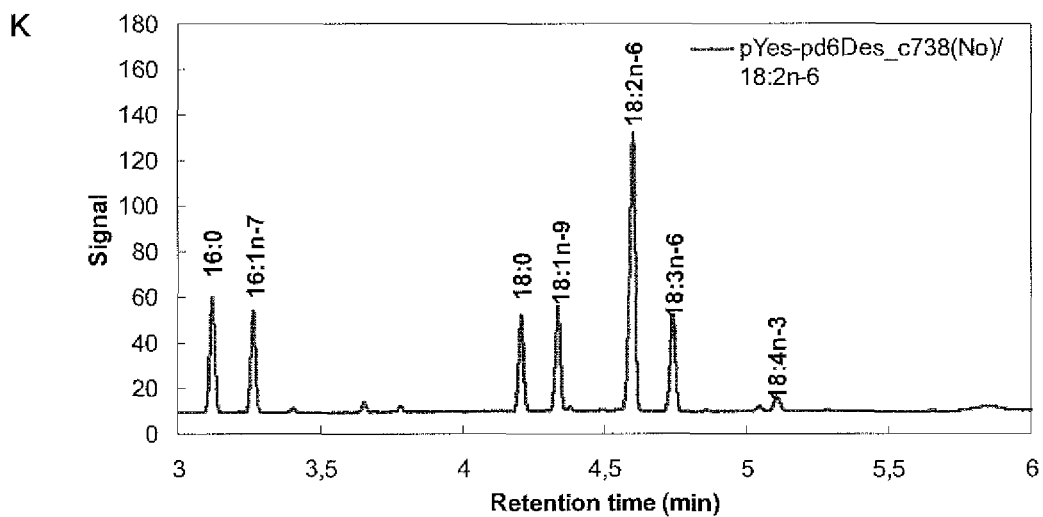

cont.
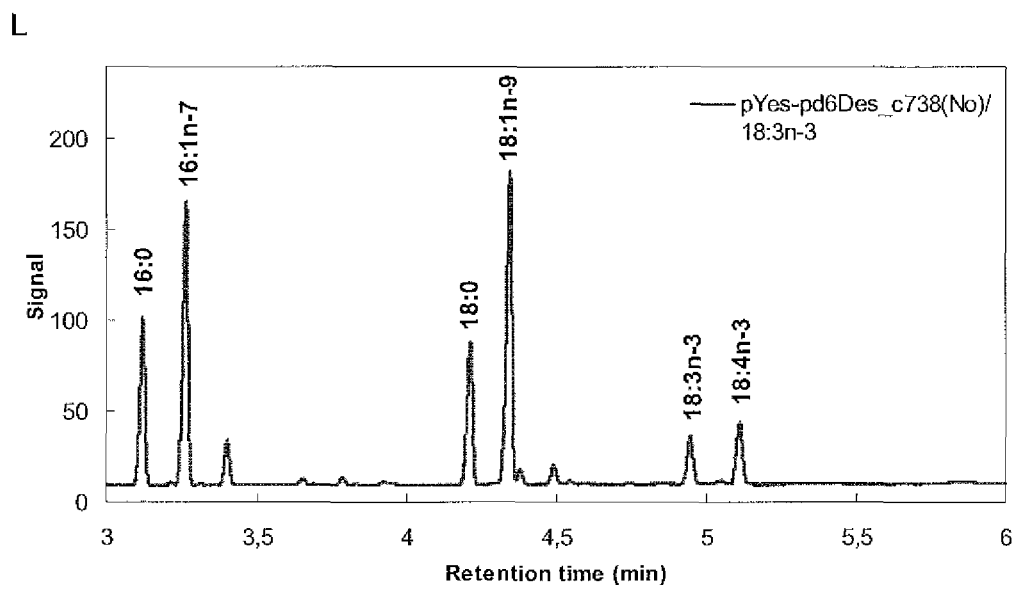

SEQUENCE LISTING

<160> NUMBER OF SEQ ID NOS: 132

<210> SEQ ID NO 1
<211> LENGTH: 1581
<212> TYPE: DNA
<213> ORGANISM: Nannochloropsis oculata

<400> SEQUENCE: 1

```
atgccgcccc agaacgacgc cgcgcttgga ggcggctttt ccgcaaccg cttcaaccgg      60
aaaaactcca cttcctctct catcatcgat gactccccgg ccaccagcac tgagtctgtg    120
gcggcggcag gagcaacagt agcagcgaca gcagccgccg ccgggggcaa gacttacaca    180
tgggaggaag tggcggaaca caacacggag aagagcctgt gggtgactgt gcgaggaaag    240
gtgtacgata tcagcagctg ggtgaataac cacccgggag gaaggagat tctgttgctg     300
gcagcgggca gggatatcac ctatgccttc gactcgtacc accccttcac ggagaagccg    360
acgcaggtcc tggcaagtt tgagatcggc accgtctcct cccacgagtt cccacaatac     420
aaacccgaca caagggggttt ttacaagacg ctgtgcacgc gctaggggga ctactttaag    480
caggaaaaac tgaaccccgaa ggacccgctt ccagggatgt ggcgaatgct cctagtggcg    540
gtggtagcct ttgcctcctt catggtgtgc aacgggtggg tgggactgga gggaggagtg    600
ttggcagggt ggggagcgag gtttgtggcg gcggtggtgt ttggtgtgtg ccaggcgttg    660
cccctactgc acgtgatgca cgactcgtcc catttggcat tcgggaacac ggagaggtgg    720
tggcaagtag gggggaggct ggcgatggac ttctttgcgg gagcgaatat gacgagctgg    780
cacaaccagc acgtgatagg gcatcacatt tacacgaacg tgttcatggc cgacccggat    840
ctgcccgaca aggatgcagg ggatccgagg aggctggtga agaagcaggc gtgggaaggc    900
atgtacaagt ggcagcacct ctacctgccg cccttgtacg gcatcctggg catcaagttc    960
cgggtgcagg acgtgatgga gacgtacggg agcggatcga atgggccagt gagggtcaac   1020
cccctgagca cgtggcaatg gggggagatg gtcttcacca aggccttctg gtttgggtgg   1080
cgggtggcgt tccctctcat gtcggcgagc tttcagacga gcatggccat gttctggccc   1140
ttgttcttcg tgagtgagtt tatgacaggg tatttcctgg cattcaactt ccaggtgtcg   1200
catgtctcga ccgagtgcga ctatcccctg ggggaggcgc cgagggagga agcggtggag   1260
ggagtggtag gggggaagga ggggatcaag gacgagtggg ccgtgagtca ggtgaagagc   1320
agcgtggact atgcgcacaa caacgccttg accacctta tgtgcggggc attgaattat   1380
caggtgaccc accatctgtt tccgactgta agtcagtacc attacccaaa gattgcgccc   1440
atcatccagg atgtatgcaa ggagttcaac gtcgattaca aagtcctccc ggattttgcg   1500
tcggcgttcc atgctcacat tgcgcatttg aaggcctttg ggggagagg ggggaggcg     1560
gcggaggtgc acatgggcta g                                              1581
```

<210> SEQ ID NO 2
<211> LENGTH: 526
<212> TYPE: PRT
<213> ORGANISM: Nannochloropsis oculata

<400> SEQUENCE: 2

```
Met Pro Pro Gln Asn Asp Ala Ala Leu Gly Gly Gly Phe Phe Arg Asn
 1               5                  10                  15

Arg Phe Asn Arg Lys Asn Ser Thr Ser Ser Leu Ile Ile Asp Asp Ser
             20                  25                  30

Pro Ala Thr Ser Thr Glu Ser Val Ala Ala Gly Ala Thr Val Ala
         35                  40                  45

Ala Thr Ala Ala Ala Ala Gly Gly Lys Thr Tyr Thr Trp Glu Glu Val
     50                  55                  60

Ala Glu His Asn Thr Glu Lys Ser Leu Trp Val Thr Val Arg Gly Lys
 65                  70                  75                  80
```

```
Val Tyr Asp Ile Ser Ser Trp Val Asn Asn His Pro Gly Gly Lys Glu
                85                  90                  95

Ile Leu Leu Leu Ala Ala Gly Arg Asp Ile Thr Tyr Ala Phe Asp Ser
            100                 105                 110

Tyr His Pro Phe Thr Glu Lys Pro Thr Gln Val Leu Gly Lys Phe Glu
        115                 120                 125

Ile Gly Thr Val Ser Ser His Glu Phe Pro Gln Tyr Lys Pro Asp Thr
    130                 135                 140

Arg Gly Phe Tyr Lys Thr Leu Cys Thr Arg Val Gly Asp Tyr Phe Lys
145                 150                 155                 160

Gln Glu Lys Leu Asn Pro Lys Asp Pro Leu Pro Gly Met Trp Arg Met
                165                 170                 175

Leu Leu Val Ala Val Ala Phe Ala Ser Phe Met Val Cys Asn Gly
            180                 185                 190

Trp Val Gly Leu Glu Gly Gly Val Leu Ala Gly Trp Gly Ala Arg Phe
            195                 200                 205

Val Ala Ala Val Val Phe Gly Val Cys Gln Ala Leu Pro Leu Leu His
        210                 215                 220

Val Met His Asp Ser Ser His Leu Ala Phe Gly Asn Thr Glu Arg Trp
225                 230                 235                 240

Trp Gln Val Gly Gly Arg Leu Ala Met Asp Phe Phe Ala Gly Ala Asn
                245                 250                 255

Met Thr Ser Trp His Asn Gln His Val Ile Gly His His Ile Tyr Thr
                260                 265                 270

Asn Val Phe Met Ala Asp Pro Asp Leu Pro Asp Lys Asp Ala Gly Asp
            275                 280                 285

Pro Arg Arg Leu Val Lys Lys Gln Ala Trp Glu Gly Met Tyr Lys Trp
        290                 295                 300

Gln His Leu Tyr Leu Pro Pro Leu Tyr Gly Ile Leu Gly Ile Lys Phe
305                 310                 315                 320

Arg Val Gln Asp Val Met Glu Thr Tyr Gly Ser Gly Ser Asn Gly Pro
                325                 330                 335

Val Arg Val Asn Pro Leu Ser Thr Trp Gln Trp Gly Glu Met Val Phe
                340                 345                 350

Thr Lys Ala Phe Trp Phe Gly Trp Arg Val Ala Phe Pro Leu Met Ser
            355                 360                 365

Ala Ser Phe Gln Thr Ser Met Ala Met Phe Trp Pro Leu Phe Phe Val
        370                 375                 380

Ser Glu Phe Met Thr Gly Tyr Phe Leu Ala Phe Asn Phe Gln Val Ser
385                 390                 395                 400

His Val Ser Thr Glu Cys Asp Tyr Pro Leu Gly Glu Ala Pro Arg Glu
                405                 410                 415

Glu Ala Val Glu Gly Val Val Gly Gly Lys Glu Gly Ile Lys Asp Glu
            420                 425                 430

Trp Ala Val Ser Gln Val Lys Ser Ser Val Asp Tyr Ala His Asn Asn
        435                 440                 445

Ala Leu Thr Thr Phe Met Cys Gly Ala Leu Asn Tyr Gln Val Thr His
    450                 455                 460

His Leu Phe Pro Thr Val Ser Gln Tyr His Tyr Pro Lys Ile Ala Pro
465                 470                 475                 480

Ile Ile Gln Asp Val Cys Lys Glu Phe Asn Val Asp Tyr Lys Val Leu
                485                 490                 495

Pro Asp Phe Ala Ser Ala Phe His Ala His Ile Ala His Leu Lys Ala
```

```
                500               505               510
        Phe Gly Gly Arg Gly Gly Glu Ala Ala Glu Val His Met Gly
              515               520               525

<210> SEQ ID NO 3
<211> LENGTH: 1972
<212> TYPE: RNA
<213> ORGANISM: Nannochloropsis oculata

<400> SEQUENCE: 3
caauuuucag caaaguaaua aagauaauaa acaaaaacaa uccuauaaag gaaaaacaac      60
aggaacacuc cgagaaggau gccgccccag aacgacgccg cgcuuggagg cggcuuuuuc     120
cgcaaccgcu ucaaccggaa aaacuccacu uccucucuca ucaucgauga cuccccggcc     180
accagcacug agucugugge ggcggcagga gcaacaguag cagcgacagc agccgccgcc     240
gggggcaaga cuuacacaug ggaggaagug gcggaacaca acacggagaa gagccugugg     300
gugacugugc gaggaaaggu guacgauauc agcagcuggg ugaauaacca cccgggaggg     360
aaggagauuc uguugcuggc agcgggcagg gauaucaccu augccuucga cucguaccac     420
cccuucacgg agaagccgac gcagguccug gcaaguuug  agaucggcac cgucuccucc     480
cacgaguucc cacaauacaa acccgacaca agggguuuuu acaagacgcu gugcacgcgc     540
guagggggacu acuuuaagca ggaaaaacug aacccgaagg acccgcuucc agggaugugg     600
cgaaugcucc uaguggcggu gguagccuuu gccuccuuca ugguguguaa cgggugggug     660
ggacuggagg gaggagguguu ggcagggugg ggagcgaggu uguggcggc ggugguguuu     720
ggugugugcc aggcguugcc ccuacugcac gugaugcacg acucguccca uuuggcauuc     780
gggaacacgg agaggugguug gcaaguaggg gggaggcugg cgauggacuu cuuugcggga     840
gcgaauauga cgagcuggca caaccagcac gugauagggc aucacauuua cacgaacgug     900
uucaugcccg acccggaucu gcccgacaag gaugcagggg auccgaggag cuggugaag     960
aagcaggcgu gggaaggcau guacaagugg cagcaccucu accugccgcc cuuguacggc    1020
auccugggca ucaaguuccg ggugcaggac gugauggaga cguacgggag cggaucgaau    1080
gggccaguga gggucaaccc ccugagcacg uggcaauggg gggagauggu cuucaccaag    1140
gccuucuggu uggggguggcg gguggcguuc ccucucaugu cggcgagcuu cagacgagc    1200
auggccaugu ucuggcccuu guucuucgug agugaguuua ugacagggua uuccuggca    1260
uucaacuucc aggugucgca ugucucgacc gagugcgacu auccccuggg ggaggcgccg    1320
agggaggaag cgguggaggg aguggauaggg ggaaggagg ggaucaagga cgagugggcc    1380
gugagucagg ugaagagcag cguggacuau gcgcacaaca acgccuugac caccuuuaug    1440
ucgggcau ugaauuauca ggugacccac caucuguuuc cgacuguaag ucaguaccau    1500
uaccccaaga uugcgcccau cauccaggau guaugcaagg aguucaacgu cgauuacaaa    1560
guccucccgg auuuugcguc ggcguuccau gcucacauug cgcauugaa ggccuuuggg    1620
gggagagggg gggaggcggc ggaggugcac augggcuagg gaagucucug acgaccauaa    1680
uaaaggaggg gaaagaaguu gacagcggcg uggauccuuu gaaggggguug uggggauguu    1740
gaagaaaug aagaugaaaaa aagaagaug ggggaggaag aaauagaaga agagugcaau    1800
agaagagaga uggcauacga ggagacgacg gcgucgggug ugaugaugucu cgcguccuuu    1860
ugggguguuuu caggaccuga guuuuuaauc gugugcgugu guucaccau uuuauuuuaa    1920
ugcugacaau auuugauaag gaaaagaguu aggccgacca aaagaagcaa cu            1972
```

<210> SEQ ID NO 4
<211> LENGTH: 1425
<212> TYPE: DNA
<213> ORGANISM: Nannochloropsis oculata

<400> SEQUENCE: 4

| | | | | | |
|---|---|---|---|---|---|
| atgggacgcg | gtggcgagcg | gatcgagacg | acggagtctt | gagcttcac | ggccgataag | 60 |
| gcaggcacaa | tcaagcagcg | tggggggaag | atcacctggg | atgaggtgcg | tcagcataag | 120 |
| acgccgcaag | acgcttggct | ggtgtaccgg | aacaaggtct | acgacgtatc | gggctggcaa | 180 |
| gatcaccccg | ggggaaacgt | catcttcacg | cacgccggag | gggactgcac | ggacatcttc | 240 |
| gcggcgttcc | accctctagg | cgccacctcc | tatcttgatc | ctttctacat | cggggagttg | 300 |
| gagccgggct | cggacaagaa | gcccgcagcg | caggcgaact | tgagcgtgc | ctacagggac | 360 |
| ttgagggga | agttgattac | gggcgggttt | ttcaaggcga | ccctttgta | ctatgtctgg | 420 |
| aaggtggtct | cgacagttgc | tcttgctgta | ggcgcttggg | tgctggtggc | ttggtcggag | 480 |
| aacctgggcg | tgcagatgct | gtcggcgttg | ttggtggccc | tgttctggca | gcaatgtggc | 540 |
| tggttggccc | atgacttctt | gcaccaccag | gtcttcaaga | tcgggccctt | cggtgacctg | 600 |
| gccggcatcg | ttatcggcaa | tgtctttcag | ggtttctccg | tggcgtggtg | gaagaacaag | 660 |
| cacaacaccc | accacgcggt | ccccaacctc | gtcgagtcat | ctccggacgc | gcaagacgga | 720 |
| gatcctgaca | ttgacaccat | gcccatcctg | gcctggtcgc | tcaagatggc | ggacagggcg | 780 |
| cagcaattct | cttgggggcc | cttctttgtc | aggcatcagt | cgctgttgta | cttccccatc | 840 |
| ttgcttgtgg | cgcggatttc | ctggttgatg | cagtcgttct | tgtttgtctt | tgactccgtc | 900 |
| cctggcgcga | gcctgtgggc | gaccaagggg | gcgacggctg | agaggcaggc | gatcaagaat | 960 |
| gtggggttgg | aaaaggtggg | gcttgtggtt | cactaccttt | ggtacggtgc | gctcatgctg | 1020 |
| tgccacatgt | ccttgccccg | ggccctgctg | tacttcctgg | ccagtcaaat | gatgtgcggg | 1080 |
| ttcttgctcg | cgcttgtttt | cgggctgggg | cacaacggca | tggctgttta | cgacgcggat | 1140 |
| gcccggcccg | acttctggaa | gctgcaggtg | acgacgacga | ggaacgtgac | tggctcatgg | 1200 |
| ttggtgcagt | ggttctgtgg | cgggctgggg | taccaggtgg | accaccacct | gttccccatg | 1260 |
| gtccccggc | accggctggg | gaagctccac | gggctcgtgg | aagggttctg | cagggagcac | 1320 |
| gaggtgaagt | atcacgagac | gaacatgtgg | gaggggacga | aggaggtgct | ggcgcatttg | 1380 |
| agcagtgtga | caaaggagtt | cgtggccgac | ttccccgcca | tgtaa | | 1425 |

<210> SEQ ID NO 5
<211> LENGTH: 474
<212> TYPE: PRT
<213> ORGANISM: Nannochloropsis oculata

<400> SEQUENCE: 5

Met Gly Arg Gly Gly Glu Arg Ile Glu Thr Thr Glu Ser Leu Ser Phe
1               5                   10                  15

Thr Ala Asp Lys Ala Gly Thr Ile Lys Gln Arg Gly Gly Lys Ile Thr
            20                  25                  30

Trp Asp Glu Val Arg Gln His Lys Thr Pro Gln Asp Ala Trp Leu Val
        35                  40                  45

Tyr Arg Asn Lys Val Tyr Asp Val Ser Gly Trp Gln Asp His Pro Gly
    50                  55                  60

Gly Asn Val Ile Phe Thr His Ala Gly Gly Asp Cys Thr Asp Ile Phe
65                  70                  75                  80

```
Ala Ala Phe His Pro Leu Gly Ala Thr Ser Tyr Leu Asp Pro Phe Tyr
             85                  90                  95

Ile Gly Glu Leu Glu Pro Gly Ser Asp Lys Lys Pro Ala Ala Gln Ala
        100                 105                 110

Asn Phe Glu Arg Ala Tyr Arg Asp Leu Arg Gly Lys Leu Ile Thr Gly
        115                 120                 125

Gly Phe Phe Lys Ala Asn Pro Leu Tyr Tyr Val Trp Lys Val Val Ser
    130                 135                 140

Thr Val Ala Leu Ala Val Gly Ala Trp Val Leu Val Ala Trp Ser Glu
145                 150                 155                 160

Asn Leu Gly Val Gln Met Leu Ser Ala Leu Leu Val Ala Leu Phe Trp
                165                 170                 175

Gln Gln Cys Gly Trp Leu Ala His Asp Phe Leu His His Gln Val Phe
            180                 185                 190

Lys Asn Arg Ala Phe Gly Asp Leu Ala Gly Ile Val Ile Gly Asn Val
        195                 200                 205

Phe Gln Gly Phe Ser Val Ala Trp Trp Lys Asn Lys His Asn Thr His
    210                 215                 220

His Ala Val Pro Asn Leu Val Glu Ser Ser Pro Asp Ala Gln Asp Gly
225                 230                 235                 240

Asp Pro Asp Ile Asp Thr Met Pro Ile Leu Ala Trp Ser Leu Lys Met
                245                 250                 255

Ala Asp Arg Ala Gln Gln Phe Ser Trp Gly Pro Phe Phe Val Arg His
            260                 265                 270

Gln Ser Leu Leu Tyr Phe Pro Ile Leu Leu Val Ala Arg Ile Ser Trp
        275                 280                 285

Leu Met Gln Ser Phe Leu Phe Val Phe Asp Ser Val Pro Gly Ala Ser
    290                 295                 300

Leu Trp Ala Thr Lys Gly Ala Thr Ala Glu Arg Gln Ala Ile Lys Asn
305                 310                 315                 320

Val Gly Leu Glu Lys Val Gly Leu Val Val His Tyr Leu Trp Tyr Gly
                325                 330                 335

Ala Leu Met Leu Cys His Met Ser Leu Pro Arg Ala Leu Leu Tyr Phe
            340                 345                 350

Leu Ala Ser Gln Met Met Cys Gly Phe Leu Leu Ala Leu Val Phe Gly
        355                 360                 365

Leu Gly His Asn Gly Met Ala Val Tyr Asp Ala Asp Ala Arg Pro Asp
    370                 375                 380

Phe Trp Lys Leu Gln Val Thr Thr Thr Arg Asn Val Thr Gly Ser Trp
385                 390                 395                 400

Leu Val Gln Trp Phe Cys Gly Gly Leu Gly Tyr Gln Val Asp His His
                405                 410                 415

Leu Phe Pro Met Val Pro Arg His Arg Leu Gly Lys Leu His Gly Leu
            420                 425                 430

Val Glu Gly Phe Cys Arg Glu His Glu Val Lys Tyr His Glu Thr Asn
        435                 440                 445

Met Trp Glu Gly Thr Lys Glu Val Leu Ala His Leu Ser Ser Val Thr
    450                 455                 460

Lys Glu Phe Val Ala Asp Phe Pro Ala Met
465                 470

<210> SEQ ID NO 6
<211> LENGTH: 1565
<212> TYPE: RNA
```

<213> ORGANISM: Nannochloropsis oculata

<400> SEQUENCE: 6

| | | | | | |
|---|---|---|---|---|---|
| agcaaacaug | ggacgcggug | gcgagcggau | cgagacgacg | gagucuuuga | gcuucacggc | 60 |
| cgauaaggca | ggcacaauca | agcagcgugg | ggggaagauc | accugggaug | aggugcguca | 120 |
| gcauaagacg | ccgcaagacg | cuuggcuggu | guaccggaac | aaggucuacg | acguaucggg | 180 |
| cuggcaagau | caccccgggg | gaaacgucau | cuucacgcac | gccggagggg | acugcacgga | 240 |
| caucuucgcg | gcguuccacc | cucuaggcgc | caccuccuau | cuugauccuu | ucuacaucgg | 300 |
| ggaguuggag | ccgggcucgg | acaagaagcc | cgcagcgcag | gcgaacuuug | agcgugccua | 360 |
| cagggacuug | aggggaagu | ugauuacggg | cggguuuuuc | aaggcgaacc | cuuuguacua | 420 |
| ugucuggaag | guggucucga | caguugcucu | ugcuguaggc | gcuugggugc | ugguggcuug | 480 |
| gucggagaac | cugggcgugc | agaugcuguc | ggcguuguug | guggcccugu | ucuggcagca | 540 |
| auguggcugg | uuggcccaug | acuucuugca | ccaccagguc | uucaagaauc | gggccuucgg | 600 |
| ugaccuggcc | ggcaucguua | ucggcaaugu | cuucagggu | uucuccgugg | cguggugggaa | 660 |
| gaacaagcac | aacacccacc | acgcggucc | caaccucguc | gagucaucuc | cggacgcgca | 720 |
| agacggagau | ccugacauug | acaccaugcc | caucccggcc | uggucgcuca | agauggcgga | 780 |
| cagggcgcag | caauucucuu | gggggcccuu | cuuugucagg | caucagucgc | uguuguacuu | 840 |
| ccccaucuug | cuuguggcgc | ggauuuccug | guugaugcag | ucguucugu | uugucuuuga | 900 |
| cuccgucccu | ggcgcgagcc | ugugggcgac | caaggggcg | acggcugaga | ggcaggcgau | 960 |
| caagaaugug | ggguuggaaa | aggugggcu | ugugguucac | uaccuugguu | acggugcgcu | 1020 |
| caugcugugc | cacauguccu | ugccccgggc | ccugcuguac | uuccuggcca | gucaaaugau | 1080 |
| gugcggguuc | uugcucgcgc | uuguuucgg | gcuggggcac | aacggcaugg | cuguuuacga | 1140 |
| cgcggaugcc | cggcccgacu | ucuggaagcu | gcaggugacg | acgacgagga | acgugacugg | 1200 |
| cucaugguug | gugcaguggu | ucuguggcgg | gcuggggauc | cagguggacc | accaccuguu | 1260 |
| ccccauggguc | cccccggcacc | ggcuggggaa | gcuccacggg | cucguggaag | gguucugcag | 1320 |
| ggagcacgag | gugaaguauc | acgagacgaa | cauguggggga | gggacgaagg | aggugcuggc | 1380 |
| gcauuugagc | agugugacaa | aggaguucgu | ggccgacuuc | cccgccaugu | aaagggaugg | 1440 |
| agggagagag | ggggaggaaau | gagaugaugu | aagagcggca | auuagaaaau | agaaguuauu | 1500 |
| ggagagagca | agcacugcgu | ggacgcgugu | gacggugcga | gucucuuguu | cuggcugaug | 1560 |
| uauug | | | | | | 1565 |

<210> SEQ ID NO 7
<211> LENGTH: 1527
<212> TYPE: DNA
<213> ORGANISM: Nannochloropsis oculata

<400> SEQUENCE: 7

| | | | | | |
|---|---|---|---|---|---|
| atggccgatg | tcgagtccat | caatccccg | ggcagctcgc | cgagcaagcc | caaggggccc | 60 |
| gacccgctcg | tggacgtggc | ggccaagccc | accaagttcc | acgtctctgg | taaggaatat | 120 |
| gaccctgatc | tgctctggta | catccacggc | agggcctacg | atctaacgga | ctgggtacgt | 180 |
| ttccatccgg | gtgggcaaga | tgctctcctg | aatgcccaag | gtcgcgatgg | cacggcgctc | 240 |
| tttgaatcct | accatttttt | tacgaccga | gcgcgcaatt | tgctggcgaa | aatgacgcct | 300 |
| gtggaggtgc | cccccgaggt | gcttaaaaag | tacgtgatgg | acacatcgga | ggccaatttc | 360 |
| ttcatcctcc | ccgacggatc | ctacgatccc | ttctggggagg | ctatccggga | ccgctgcaag | 420 |

```
aaagtctatg aagatgatcc aaccttgacg cgcacgtcag gctggggcat ctacttgttt    480
cacatggcac tgctgctggt ggtgcagccg ctgatttact actatggata cttgcaggag    540
tgggcgctct ggtctcactt gtcggcgttc gccatgggca tcgtcgtctg gattggggga    600
cgcctcggcc acgacgcggg ccattacgca gtctgcccca agaaatatta cagcggctgg    660
ttcactgcga tctgttcggg attcgcgctg accaacatcg gctactggca gttgctgcac    720
acggtcatgc accacaccta cacgaacatg gacaacgacc ccgacctata tcattacgtc    780 ttcttttttgc gcgaccacgc caactacccg tacaggatcc tccaccgtct gcagattcac    840
cgtatctggt gttacatcgt ctggagcgcc accaccgccg gcctcctgat cctggagccc    900
gttgccatgc tcgtcaccgg ttccgccact cgggggacca agacgcgcct gcacaaaaag    960
cgatacatct tctggtcctt catgattatc cacttgctcc tcttcccggc cgtctacctg   1020
gctttgccca tctacttgac atgggacacg gatgagagca agtataccat catctccacg   1080
cgcgttggta gctggattta cttcatgatg ggctccggct tgtgtttcgg tatcttttcc   1140
cagtcgaacc attttttcggc gcggtgtgtg gaggcggcca ccaagccgac ctcgtggggt   1200
gtgcgtcaaa tcgagacggc cgccaacttc tgtatcaact cctggttctg gtccatcatc   1260
acggcaggga tcaacgtcca aatcgagcac accttttcc cgtccgtcgc gtctgacaag    1320
ctcgataagc tcatccccat cgtccaagag acgtgcaaag agtacaacgt cgactacaag   1380
aactacagct ccttccgcga gatattggcc agtgtacacg cgtacctcga tcacctggcg   1440
aagcccttgc cttccgacgg cgatgtgaat attctcggct ccacaagcg caagcgcacg    1500 agcgccaaca taacctcctc ttcgtaa                                       1527
```

<210> SEQ ID NO 8
<211> LENGTH: 508
<212> TYPE: PRT
<213> ORGANISM: Nannochloropsis oculata

<400> SEQUENCE: 8

```
Met Ala Asp Val Glu Ser Ile Lys Ser Pro Gly Ser Pro Ser Lys
1               5                   10                  15

Pro Lys Gly Pro Asp Pro Leu Val Asp Val Ala Ala Lys Pro Thr Lys
                20                  25                  30

Phe His Val Ser Gly Lys Glu Tyr Asp Pro Asp Leu Leu Trp Tyr Ile
            35                  40                  45

His Gly Arg Ala Tyr Asp Leu Thr Asp Trp Val Arg Phe His Pro Gly
        50                  55                  60

Gly Gln Asp Ala Leu Leu Asn Ala Gln Gly Arg Asp Gly Thr Ala Leu
65                  70                  75                  80

Phe Glu Ser Tyr His Phe Phe Thr Asp Arg Ala Arg Asn Leu Leu Ala
                85                  90                  95

Lys Met Thr Pro Val Glu Val Pro Pro Glu Val Leu Lys Lys Tyr Val
            100                 105                 110

Met Asp Thr Ser Glu Ala Asn Phe Phe Ile Leu Pro Asp Gly Ser Tyr
        115                 120                 125

Asp Pro Phe Trp Glu Ala Ile Arg Asp Arg Cys Lys Lys Val Tyr Glu
    130                 135                 140

Asp Asp Pro Thr Leu Thr Arg Thr Ser Gly Trp Gly Ile Tyr Leu Phe
145                 150                 155                 160

His Met Ala Leu Leu Leu Val Val Gln Pro Leu Ile Tyr Tyr Tyr Gly
                165                 170                 175
```

Tyr Leu Gln Glu Trp Ala Leu Trp Ser His Leu Ser Ala Phe Ala Met
            180                 185                 190

Gly Ile Val Val Trp Ile Gly Gly Arg Leu Gly His Asp Ala Gly His
        195                 200                 205

Tyr Ala Val Cys Pro Lys Lys Tyr Tyr Ser Gly Trp Phe Thr Ala Ile
    210                 215                 220

Cys Ser Gly Phe Ala Leu Thr Asn Ile Gly Tyr Trp Gln Leu Leu His
225                 230                 235                 240

Thr Val Met His His Thr Tyr Thr Asn Met Asp Asn Asp Pro Asp Leu
                245                 250                 255

Tyr His Tyr Val Phe Phe Leu Arg Asp His Ala Asn Tyr Pro Tyr Arg
            260                 265                 270

Ile Leu His Arg Leu Gln Ile His Arg Ile Trp Cys Tyr Ile Val Trp
        275                 280                 285

Ser Ala Thr Thr Ala Gly Leu Leu Ile Leu Glu Pro Val Ala Met Leu
    290                 295                 300

Val Thr Gly Ser Ala Thr Arg Gly Thr Lys Thr Arg Leu His Lys Lys
305                 310                 315                 320

Arg Tyr Ile Phe Trp Ser Phe Met Ile Ile His Leu Leu Leu Phe Pro
                325                 330                 335

Ala Val Tyr Leu Ala Leu Pro Ile Tyr Leu Thr Trp Asp Thr Asp Glu
            340                 345                 350

Ser Lys Tyr Thr Ile Ile Ser Thr Arg Val Gly Ser Trp Ile Tyr Phe
        355                 360                 365

Met Met Gly Ser Gly Leu Cys Phe Gly Ile Phe Ser Gln Ser Asn His
    370                 375                 380

Phe Ser Ala Arg Cys Val Glu Ala Ala Thr Lys Pro Thr Ser Trp Gly
385                 390                 395                 400

Val Arg Gln Ile Glu Thr Ala Ala Asn Phe Cys Ile Asn Ser Trp Phe
                405                 410                 415

Trp Ser Ile Ile Thr Ala Gly Ile Asn Val Gln Ile Glu His His Leu
            420                 425                 430

Phe Pro Ser Val Ala Ser Asp Lys Leu Asp Lys Leu Ile Pro Ile Val
        435                 440                 445

Gln Glu Thr Cys Lys Glu Tyr Asn Val Asp Tyr Lys Asn Tyr Ser Ser
    450                 455                 460

Phe Arg Glu Ile Leu Ala Ser Val His Ala Tyr Leu Asp His Leu Ala
465                 470                 475                 480

Lys Pro Leu Pro Ser Asp Gly Asp Val Asn Ile Leu Gly Phe His Lys
                485                 490                 495

Arg Lys Arg Thr Ser Ala Asn Ile Thr Ser Ser Ser
            500                 505

<210> SEQ ID NO 9
<211> LENGTH: 1963
<212> TYPE: RNA
<213> ORGANISM: Nannochloropsis oculata

<400> SEQUENCE: 9
agauaauaaa caaaaacaau ccuauaaagg aaaaacaaca ggaucgagcu ucccuacugu    60
ucacucaacc ccgaauucac cgcagcccac uacgauggcc gaugucgagu ccaucaaauc   120
cccgggcagc ucgccgagca agcccaaggg gcccgacccg cucgugggacg uggcggccaa   180 gcccaccaag uuccacgucu cugguaagga auaugacccu gaucugcucu gguacaucca   240

```
cggcagggcc uacgaucuaa cggacugggu acguuccau ccggugggc aagaugcucu    300 ccugaaugcc caaggucgcg auggcacggc gcucuuugaa uccuaccauu uuuuuacgga    360
ccgagcgcgc aauuugcugg cgaaaaugac gccuguggag gugcccccg aggugcuuaa    420 aaaguacgug auggacacau cggaggccaa uucuucauc ucccccgacg gauccuacga    480
ucccuucugg gaggcuaucc gggaccgcug caagaaaguc uaugaagaug auccaaccuu    540
gacgcgcacg ucaggcuggg gcaucuacuu guuucacaug gcacugcugc uggugguggca    600 gccgcugauu uacuacuaug gauacuugca ggagugggcg cucuggucuc acugucggc    660 guucgccaug ggcaucgucg ucuggauugg gggacgccuc ggccacgacg cgggccauua    720
cgcagucugc cccaagaaau auuacagcgg cugguucacu gcgaucuguu cgggauucgc    780
gcugaccaac aucggcuacu ggcaguugcu gcacacgguc augcaccaca ccuacacgaa    840
cauggacaac gaccccgacc uauaucauua cgucuucuuu uugcgcgacc acgccaacua    900
cccguacagg auccuccacc gucugcagau ucaccguauc uggguuuaca ucgucuggag    960
cgccaccacc gccggccucc ugauccugga gcccguugcc augcucguca ccgguuccgc    1020
cacucggggg accaagacgc gccugcacaa aaagcgauac aucuucuggu ccuucaugau    1080
uauccacuug cuccucuucc cggccgucua ccuggcuuug cccaucuacu ugacaugga    1140 cacggaugag agcaaguaua ccaucaucuc cacgcgcguu ggagcugga uuuacuucau    1200 gaugggcucc ggcuuguguu ucgguaucuu uucccagucg aaccauuuuu cggcgcggug    1260
uguggaggcg gccaccaagc cgaccucgug gggugugcgu caaaucgaga cggccgccaa    1320
cuucuguauc aacuccuggu ucuggccau caucacggca gggaucaacg uccaaaucga    1380
gcaccaccuu uucccgguccg ucgcgucuga caagcucgau aagcucaucc ccaucgucca    1440
agagacgugc aaagaguaca acgucgacua caagaacuac agcuccuucc gcgagauauu    1500
ggccagugua cacgcguacc ucgaucaccu ggcgaagccc uugccuuccg acggcgaugu    1560
gaauauucuc ggcuuccaca gcgcaagcg cacgagcgcc aacauaaccu ccucuucgua    1620
augcgagggg gaaaggagg aagagagggg guggaagaga uaggaguugg uacgagggu    1680 gaaaggagug acgugggag acaaggagag gagcucuauc cuuuuuuccc cucgcugccg    1740
ccuccuccuc ccauuuugug uauuuaauaa gucagaauga auguaaagau auguuuuuu    1800 uuaaaaacgc gucacacaca cacaugcgca ccguugagga aaggggcga ugcacguucg    1860 aagcaaggag auuaagaaga aaagaagggg aaaagaacaa gcgagagcag aagagggaga    1920
aggagaagca gaagaagaaa agaagaagag acaauaacga cgu                     1963

<210> SEQ ID NO 10
<211> LENGTH: 1449
<212> TYPE: DNA
<213> ORGANISM: Nannochloropsis oculata

<400> SEQUENCE: 10
atggcgccgc gcgatgtgga gaccatttct agtcccgcaa tcaaggacac cctggcggag     60
gctgtgagtc agatggcccc gtctaaggag gtgaataaga ataggctctg gtacatccac    120
ggcaaggcct acgacctcac agacttcatc tacaagcacc tggtggccc taccgtcctc    180 ctcaacaccc aggggcggga ttgcacggca ctgtttgagg cttccatcc cttcacggac    240 cggccagcca ctattttgag caagatgaag gaggtgactg tgtcccccga aattcttgct    300
gagaagtgca cggacatcag caagggcaac tggttttatc tgcccgatgg taccccggac    360
```

| | |
|---|---|
| ccgttctggg ccgcgttgaa ggagcggtgc gggaaatata tgcgggaaaa taaggtggac | 420 |
| aggacgatga aatggtcgac tttcttgttg catgtcttcc tgctgttaat ccagccgccg | 480 |
| atgtggtggt tcggctacgt gaacgcatac ccgtggtact cgcacgcggc ggccttggcg | 540 |
| atggggtga cgacgtggat cgccggagg ctgggccatg acggagggca tttcgcgatc | 600 |
| tcccgcaagt actggataaa ccgcgtgttt gggaactggg caggcctggg gttgagtaac | 660 |
| atgagctact gggagatttt gcataatgtc gaccaccaca cggacaccaa cacgagaag | 720 |
| gatccagatt tgtaccacta cgtgatcttc ctgcgcgacc accccaatta cccgtggtca | 780 |
| atattccacc ggttgcaggt ggcgaggatt tattgctact tggtctggag tttcaccacg | 840 |
| gcgggtttgt taatgatcga gcccatgaac atgctcttga cagggtcggg cacaaggccc | 900 |
| ccaacggtga ggttggcaaa tttccgatta ttcttttggg tgaagctggt gttccacatg | 960 |
| ctcttgttcc cgaccgtgat gttggcgatc cccatgtggc tgacgtggga cagctcggag | 1020 |
| aacaaagggg tggtgttcgc catccggttt gcgagttttg tgatatattg tggggtgacc | 1080 |
| gggctcttgt ttgggatctt ttcgcaggtg aaccacttct cggaggattg cattgcggcc | 1140 |
| gccagtcgcg atacgtcctg ggccgtgcgc caggtggaga cggcggcgaa tttctgcgtg | 1200 |
| gactcgtggt tttggtcctt tattaccgcg gaattcaca tccagattga gcatcatttg | 1260 |
| ttccctccct tgtcctcgga ccgtgtcctt cctctcgtgc cgatcgtgga ggcgacgtgc | 1320 |
| aaagagtttg gggtgaacta caaaaacttc aagacgtttc cgtccatcct cgattctgtg | 1380 |
| cacgcttata tcgacaccct ggcctttccg aacaaggcgg tagatgcaac aacggcggcg | 1440 |
| gcggggtaa | 1449 |

<210> SEQ ID NO 11
<211> LENGTH: 482
<212> TYPE: PRT
<213> ORGANISM: Nannochloropsis oculata

<400> SEQUENCE: 11

```
Met Ala Pro Arg Asp Val Glu Thr Ile Ser Ser Pro Ala Ile Lys Asp
1               5                   10                  15

Thr Leu Ala Glu Ala Val Ser Gln Met Ala Pro Ser Lys Glu Val Asn
            20                  25                  30

Lys Asn Arg Leu Trp Tyr Ile His Gly Lys Ala Tyr Asp Leu Thr Asp
        35                  40                  45

Phe Ile Tyr Lys His Pro Gly Gly Pro Thr Val Leu Leu Asn Thr Gln
    50                  55                  60

Gly Arg Asp Cys Thr Ala Leu Phe Glu Ala Phe His Pro Phe Thr Asp
65                  70                  75                  80

Arg Pro Ala Thr Ile Leu Ser Lys Met Lys Glu Val Thr Val Ser Pro
                85                  90                  95

Glu Ile Leu Ala Glu Lys Cys Thr Asp Ile Ser Lys Gly Asn Trp Phe
            100                 105                 110

Tyr Leu Pro Asp Gly Thr Pro Asp Pro Phe Trp Ala Ala Leu Lys Glu
        115                 120                 125

Arg Cys Gly Lys Tyr Met Arg Glu Asn Lys Val Asp Arg Thr Met Lys
    130                 135                 140

Trp Ser Thr Phe Leu Leu His Val Phe Leu Leu Ile Gln Pro Pro
145                 150                 155                 160

Met Trp Trp Phe Gly Tyr Val Asn Ala Tyr Pro Trp Tyr Ser His Ala
                165                 170                 175
```

```
Ala Ala Leu Ala Met Gly Val Thr Thr Trp Ile Ala Gly Arg Leu Gly
            180                 185                 190

His Asp Gly Gly His Phe Ala Ile Ser Arg Lys Tyr Trp Ile Asn Arg
        195                 200                 205

Val Phe Gly Asn Trp Ala Gly Leu Gly Leu Ser Asn Met Ser Tyr Trp
210                 215                 220

Glu Ile Leu His Asn Val Asp His His Thr Asp Thr Asn Thr Glu Lys
225                 230                 235                 240

Asp Pro Asp Leu Tyr His Tyr Val Ile Phe Leu Arg Asp His Pro Asn
                245                 250                 255

Tyr Pro Trp Ser Ile Phe His Arg Leu Gln Val Ala Arg Ile Tyr Cys
            260                 265                 270

Tyr Leu Val Trp Ser Phe Thr Thr Ala Gly Leu Leu Met Ile Glu Pro
        275                 280                 285

Met Asn Met Leu Leu Thr Gly Ser Gly Thr Arg Pro Pro Thr Val Arg
290                 295                 300

Leu Ala Asn Phe Arg Leu Phe Phe Trp Val Lys Leu Val Phe His Met
305                 310                 315                 320

Leu Leu Phe Pro Thr Val Met Leu Ala Ile Pro Met Trp Leu Thr Trp
                325                 330                 335

Asp Ser Ser Glu Asn Lys Gly Val Val Phe Ala Ile Arg Phe Ala Ser
            340                 345                 350

Phe Val Ile Tyr Cys Gly Val Thr Gly Leu Leu Phe Gly Ile Phe Ser
        355                 360                 365

Gln Val Asn His Phe Ser Glu Asp Cys Ile Ala Ala Ser Arg Asp
370                 375                 380

Thr Ser Trp Ala Val Arg Gln Val Glu Thr Ala Ala Asn Phe Cys Val
385                 390                 395                 400

Asp Ser Trp Phe Trp Ser Phe Ile Thr Ala Gly Ile His Ile Gln Ile
                405                 410                 415

Glu His His Leu Phe Pro Ser Leu Ser Ser Asp Arg Val Leu Pro Leu
            420                 425                 430

Val Pro Ile Val Glu Ala Thr Cys Lys Glu Phe Gly Val Asn Tyr Lys
        435                 440                 445

Asn Phe Lys Thr Phe Pro Ser Ile Leu Asp Ser Val His Ala Tyr Ile
450                 455                 460

Asp Thr Leu Ala Phe Pro Asn Lys Ala Val Asp Ala Thr Thr Ala Ala
465                 470                 475                 480

Ala Gly

<210> SEQ ID NO 12
<211> LENGTH: 1954
<212> TYPE: RNA
<213> ORGANISM: Nannochloropsis oculata

<400> SEQUENCE: 12
uuauuucuga ucuuacuccc acgcauccau auccauuuac cccgccucaa cggucgauug    60
aaacgagcug cugcuguucc uauuucuuuu gcccaauucu agcaagccuu ccugaggga   120 cuguccgac ccucggcccu cgcuaagcaa uccaccaaau ucucuuccuu caguccugc    180 aaaggcucca ugugaugguug ucacgcuauu uuuuugugcu gucguucgac acaaaguauc   240
uccucaagca aggaagcgug ccgacccucu cucgcacugc cgguagaagu guaagguuga    300
gugaaucaau auuccuggag ggcaaagcaa guccauggu uggagaugc cucugcaccc    360
```

| ucaacaacac accggaaaag cagcucccuu uuugcuccau gccuuccaag cccaccuug | 420 |
| ucaaagcccg ccucucacac gcacccuuca acuaucccuc ccgcucacau acaggcaagg | 480 |
| caagcuacgg uugcucgcuc guucgauggc gccgcgcgau guggagacca uuucuaguccc | 540 |
| cgcaaucaag gacacccugg cggaggcugu gagucagaug gccccgucua aggaggugaa | 600 |
| uaagaauagg cucugguaca uccacggcaa ggccuacgac cucacagacu ucaucuacaa | 660 |
| gcacccuggu ggcccuaccg uccuccucaa cacccagggg cgggauugca cggcacuguu | 720 |
| ugaggcuuuc caucccuuca cggaccggcc agccacuauu uugagcaaga ugaaggaggu | 780 |
| gacugugucc cccgaaauuc uugcugagaa gugcacggac aucagcaagg caacugguu | 840 |
| uuaucugccc gaugguaccc cggacccguu cugggccgcg uugaaggagc ggugcgggaa | 900 |
| auauaugcgg gaaaauaagg uggacaggac gaugaaaugg ucgacuuucu guuugcaugu | 960 |
| cuuccugcug uuaauccagc cgccgaugug ugguucggc uacgugaacg cauacccgug | 1020 |
| guacucgcac gcggcggccu uggcgauggg ggugacgacg uggaucgccg ggaggcuggg | 1080 |
| ccaugacgga gggcauuucg cgaucucccg caaguacugg auaaaccgcg uguuggaa | 1140 |
| cugggcaggc cugggguuga guaacaugag cuacugggag auuuugcaua augucgacca | 1200 |
| ccacacggac accaacacgg agaaggaucc agauuuguac cacucguga ucuuccugcg | 1260 |
| cgaccacccc aauuacccgu ggucaauauu ccaccgguug caggugcga ggauuuauug | 1320 |
| cuacuugguc uggaguuuca ccacggcggg uuuguuaaug aucgagccca ugaacaugcu | 1380 |
| cuugacaggg ucgggcacaa ggccccaac ggugagguug gcaaauuccc gauuauucuu | 1440 |
| uugggugaag cugguguucc acaugcucuu guucccgacc gugauguugg cgaucccau | 1500 |
| guggcugacg ugggacagcu cggagaacaa aggggugug uucgccaucc gguuugcgag | 1560 |
| uuuugugaua uauugggggg ugaccgggcu cuuguuggg aucuuuucgc aggugaacca | 1620 |
| cuucucggag gauugcauug cggccgccag ucgcgauacg uccugggccg ugcgccaggu | 1680 |
| ggagacggcg gcgaauuucu gcguggacuc guggguuugg uccuuuauua ccgcgggaau | 1740 |
| ucacauccag auugagcauc auuuguuccc uuccuugucc ucggaccgug uccuuccucu | 1800 |
| cgugccgauc guggaggcga cgugcaaaga guuuggggug aacuacaaaa acuucaagac | 1860 |
| guuuccguccc auccucgauu cugugcacgc uuauaucgac accuuggccu uuccgaacaa | 1920 |
| ggcgguagau gcaacaacgg cggcggcggg guaa | 1954 |

<210> SEQ ID NO 13
<211> LENGTH: 1080
<212> TYPE: DNA
<213> ORGANISM: Nannochloropsis oculata

<400> SEQUENCE: 13

| atggtcttcc agctcgcccg agactctgtc tcggccctgg tctatcattt caaagaaggg | 60 |
| aaccttaact ggcctatgat tatctacctt gtcctcgtcc acttggcggg ctacatcggt | 120 |
| ctgaccacca tcctggcttg caatggcaa accccttctcg aagcgttcat cctatggccg | 180 |
| atcactgggc tggggattac ggccggcgta catcgacttt gggcgcaccg ttcctacaac | 240 |
| gccacgttgc cttaccgtat cctgttgatg ttgttcaact ctattgcgaa tcagggcagc | 300 |
| atctaccact ggtcccgtga ccaccgcgtg caccacaagt actccgagac ggatgccgac | 360 |
| ccacacaacg ctaccgcgg cttcttcttc gcgcacatgg gctggctcat cgtcaagaag | 420 |
| cacccccaagg ttgtcgaagg ggggaagcaa cttgatttct ccgacttggc tgctgatccc | 480 |
| gtagtgcgat tccagcgtga ctgggacccg tggttcgctc aattcatgtg ctttgtcatg | 540 |

```
ccagcgcttg tcgcatcgag gttctggggt gaggcgttct ggaacgcctt ctgggtggct    600
ggggctctga ggtatatgtt ggtgttgcac ttcacctgga tggtcaacag tgcggcccac    660
ttgtacgggg accacccctta cgacccgacc atgtggccgg cagagaaccc gctggtgtcg   720
gtggtggcga tcggagaggg ctggcacaac tggcaccatc gttacccgta cgactacgct    780
gcttccgagt ttgggatatc gcagcagttc aacccgacca aggcgttcat tgatttttt     840 gcggccattg ggatggtgac gaaccgaaag cgtgcgaccg gggcttgggc gaagctcaag    900
gagtcgaggg caagggatga ggcgaatggg aagagcatga aggatttcaa ggggagggc     960 tcgggttctg actacggcac gacaaacacc aattacgcgg tgtcgaacaa aactgtcgta   1020
gccgataagg gggcgcaaca accaggatgg gaggagagta atcaccccaa gtacaattaa   1080
```

<210> SEQ ID NO 14
<211> LENGTH: 359
<212> TYPE: PRT
<213> ORGANISM: Nannochloropsis oculata

<400> SEQUENCE: 14

```
Met Val Phe Gln Leu Ala Arg Asp Ser Val Ser Ala Leu Val Tyr His
1               5                   10                  15

Phe Lys Glu Gly Asn Leu Asn Trp Pro Met Ile Ile Tyr Leu Val Leu
            20                  25                  30

Val His Leu Ala Gly Tyr Ile Gly Leu Thr Thr Ile Leu Ala Cys Lys
        35                  40                  45

Trp Gln Thr Leu Leu Glu Ala Phe Ile Leu Trp Pro Ile Thr Gly Leu
    50                  55                  60

Gly Ile Thr Ala Gly Val His Arg Leu Trp Ala His Arg Ser Tyr Asn
65                  70                  75                  80

Ala Thr Leu Pro Tyr Arg Ile Leu Leu Met Leu Phe Asn Ser Ile Ala
                85                  90                  95

Asn Gln Gly Ser Ile Tyr His Trp Ser Arg Asp His Arg Val His His
            100                 105                 110

Lys Tyr Ser Glu Thr Asp Ala Asp Pro His Asn Ala Thr Arg Gly Phe
        115                 120                 125

Phe Phe Ala His Met Gly Trp Leu Ile Val Lys Lys His Pro Lys Val
    130                 135                 140

Val Glu Gly Gly Lys Gln Leu Asp Phe Ser Asp Leu Ala Ala Asp Pro
145                 150                 155                 160

Val Val Arg Phe Gln Arg Asp Trp Asp Pro Trp Phe Ala Gln Phe Met
                165                 170                 175

Cys Phe Val Met Pro Ala Leu Val Ala Ser Arg Phe Trp Gly Glu Ala
            180                 185                 190

Phe Trp Asn Ala Phe Trp Val Ala Gly Ala Leu Arg Tyr Met Leu Val
        195                 200                 205

Leu His Phe Thr Trp Met Val Asn Ser Ala Ala His Leu Tyr Gly Asp
    210                 215                 220

His Pro Tyr Asp Pro Thr Met Trp Pro Ala Glu Asn Pro Leu Val Ser
225                 230                 235                 240

Val Val Ala Ile Gly Glu Gly Trp His Asn Trp His His Arg Tyr Pro
                245                 250                 255

Tyr Asp Tyr Ala Ala Ser Glu Phe Gly Ile Ser Gln Gln Phe Asn Pro
            260                 265                 270

Thr Lys Ala Phe Ile Asp Phe Phe Ala Ala Ile Gly Met Val Thr Asn
```

```
            275                 280                 285
Arg Lys Arg Ala Thr Gly Ala Trp Ala Lys Leu Lys Glu Ser Arg Ala
    290                 295                 300

Arg Asp Glu Ala Asn Gly Lys Ser Met Lys Asp Phe Lys Gly Arg Gly
305                 310                 315                 320

Ser Gly Ser Asp Tyr Gly Thr Thr Asn Thr Asn Tyr Ala Val Ser Asn
                325                 330                 335

Lys Thr Val Val Ala Asp Lys Gly Ala Gln Gln Pro Gly Trp Glu Glu
            340                 345                 350

Ser Asn His Pro Lys Tyr Asn
        355

<210> SEQ ID NO 15
<211> LENGTH: 1534
<212> TYPE: RNA
<213> ORGANISM: Nannochloropsis oculata

<400> SEQUENCE: 15
aaaaguaaua aagauaauaa acaaaaacaa uccuauaaag gaaaaacaac agacaaaccc      60
gcaaucaugg ucuuccagcu cgcccgagac ucugucucgg cccuggucua ucauuucaaa    120
gaagggaacc uuaacuggcc uaugauuauc uaccuugucc ucguccacuu ggcgggcuac    180
aucggucuga ccaccauccu ggcuugcaaa uggcaaaccc uucucgaagc guucauccua    240
uggccgauca cugggcuggg gauuacggcc ggcguacauc gacuuugggc gcaccguucc    300
uacaacgcca cguugccuua ccguauccug uugauguugu caacucuau ugcgaaucag     360 ggcagcaucu accacugguc ccgugaccac cgcgugcacc acaaguacuc cgagacggau    420
gccgacccac acaacgcuac ccgcggcuuc uucuucgcgc acaugggcug gcucaucguc    480
aagaagcacc ccaagguugu cgagggggg aagcaacuug auuucuccga cuuggcugcu     540
gaucccguag ucgauucca gcugacugg gacccguggu cgcucaauu caugugcuuu       600 gucaugccag cgcuugucgc aucgagguuc uggggugagg cguucuggaa cgccuucugg    660
guggcugggg cucugaggua uauguggug uugcacuuca ccuggauggu caacagugcg     720
gcccacuugu acggggacca cccuuacgac ccgaccaugu ggccggcaga gaacccgcug    780
gugucggugg uggcgaucgg agagggcugg cacaacuggc accaucguua cccguacgac    840
uacgcugcuu ccgaguuugg gauaucgcag caguucaacc cgaccaaggc guucauugau    900
uuuuuugcgg ccauugggau ggugacgaac cgaaagcgug cgaccggggc uugggcgaag    960
cucaaggagu cgagggcaag ggaugaggcg aauggaaga gcaugaagga uucaagggg     1020 aggggcucgg guucugacua cggcacgaca acaccaauu acgcgguguc gaacaaaacu    1080
gucguagccg auaaggggc gcaacaacca ggauggagg agaguaauca ccccaaguac     1140
aauuaauuug gugguauuu uguuauuugu aagaggaagg gaaaagggga aaacuauuug    1200
ucaagacaga gaagagauau ggauacagag agcgacgac ggguguuuu cgagacuugu     1260 uucuuguuug uucauuaaca gcaacagcaa uaagaaaggg auagaggaau gaguaaagcg    1320
acagcgauug aagcggaagu guaagaggag acggguagaaa acaucagaac aguagucacg    1380
gagauggcag gaagggaguu ucagcggcgc aagggauaag ggagagagug cguucugaaa    1440
uggaggcagg aauguccugg ugucgguccg uuucuuacuu gucucucucu gucucuuccu    1500
acuuccguac gcuacccacc accuucuucg uccu                                1534

<210> SEQ ID NO 16
```

<211> LENGTH: 1317
<212> TYPE: DNA
<213> ORGANISM: Nannochloropsis oculata

<400> SEQUENCE: 16

```
atgggacgcg gcggtgagaa gacggtgacc cctcttccca aaaagcccct cctggatgcc      60
gcctccacga tcagcagcac ggtcagacca agcaaggcag tagaggccat gcccacggag     120
gagctccgca agaaggccgt acagtacggt attgacactt cggccgaccg cgaaacactg     180
ctgagggagc tggctcccta cggcgatatc ctcctccgca atgacgcccc caagtcccta     240
ccccttgccc ctcctccttt caccctctcc gatatcaaga atgccgtccc ccgtcactgc     300
ttcgagcgtt ccctctctac ctccctcttc cacctgacta ttgacttgat ccaagtcgcc     360
atccttgggt accttgcctc actactgggc cactcggacg tcccgcccat gtctcgctat     420
atcctatggc cattgtactg gtatgcgcaa ggctctgtac tgacgggtgt gtgggtcatt     480
gcccacgaat gcggacacca atcgttttcg ccctatgaga gcgtgaacaa cttctttggg     540
tggctcttgc actcggcctt gcttgtgccc taccactcgt ggaggatctc ccatggaaag     600
caccacaaca cacggggag ctgcgagaac gacgaggtgt tgcgccgcc tatcaaggag     660
gagttgatgg acgagatttt gcttcactcc cctttggcga acctagtgca gattgtcatc     720
atgttgacca tcgggtggat gccgggttac ctgctgctga acgcgacggg gcccaggaag     780
tacaagggat tgatcaatag ccatttcaat ccgaattcgg cgttgttttc tcccaaggat     840
cgcctggaca tcatttggtc agacatcggt ttttttgttg ccttggcctg cgtggtgtat     900
gcctgtgtgc agtttggatt tcagacggtg ggaaagtact acctgttgcc gtacatggtg     960
gtcaactacc atctcgttct aatcacgtac ctgcagcata cggatgtctt catccccac    1020
ttccgaggga gtgagtggac gtggtttagg ggcgccctct gcacagtcga caggtccttt    1080
ggctggcttt tggatcacac gtttcaccat atcagtgata ctcatgtgtg tcaccatata    1140
tttagcaaaa tgccttttta tcacgcgcag gaggcgagcg agcatatccg gaaagcgctg    1200
ggcgactatt atttgaagga tgacaccccg atttggaagg cattgtggcg gagttacacg    1260
ctgtgcaagt acgtggattc ggaggagacg acggtgttct acaagcagcg agcatag      1317
```

<210> SEQ ID NO 17
<211> LENGTH: 438
<212> TYPE: PRT
<213> ORGANISM: Nannochloropsis oculata

<400> SEQUENCE: 17

```
Met Gly Arg Gly Gly Glu Lys Thr Val Thr Pro Leu Pro Lys Lys Pro
1               5                   10                  15

Leu Leu Asp Ala Ala Ser Thr Ile Ser Ser Thr Val Arg Pro Ser Lys
            20                  25                  30

Ala Val Glu Ala Met Pro Thr Glu Glu Leu Arg Lys Lys Ala Val Gln
        35                  40                  45

Tyr Gly Ile Asp Thr Ser Ala Asp Arg Glu Thr Leu Leu Arg Glu Leu
    50                  55                  60

Ala Pro Tyr Gly Asp Ile Leu Leu Arg Asn Asp Ala Pro Lys Ser Leu
65                  70                  75                  80

Pro Leu Ala Pro Pro Pro Phe Thr Leu Ser Asp Ile Lys Asn Ala Val
                85                  90                  95

Pro Arg His Cys Phe Glu Arg Ser Leu Ser Thr Ser Leu Phe His Leu
            100                 105                 110
```

Thr Ile Asp Leu Ile Gln Val Ala Ile Leu Gly Tyr Leu Ala Ser Leu
115                 120                 125

Leu Gly His Ser Asp Val Pro Pro Met Ser Arg Tyr Ile Leu Trp Pro
130                 135                 140

Leu Tyr Trp Tyr Ala Gln Gly Ser Val Leu Thr Gly Val Trp Val Ile
145                 150                 155                 160

Ala His Glu Cys Gly His Gln Ser Phe Ser Pro Tyr Glu Ser Val Asn
                165                 170                 175

Asn Phe Phe Gly Trp Leu Leu His Ser Ala Leu Leu Val Pro Tyr His
            180                 185                 190

Ser Trp Arg Ile Ser His Gly Lys His Asn Asn Thr Gly Ser Cys
        195                 200                 205

Glu Asn Asp Glu Val Phe Ala Pro Pro Ile Lys Glu Glu Leu Met Asp
210                 215                 220

Glu Ile Leu Leu His Ser Pro Leu Ala Asn Leu Val Gln Ile Val Ile
225                 230                 235                 240

Met Leu Thr Ile Gly Trp Met Pro Gly Tyr Leu Leu Leu Asn Ala Thr
                245                 250                 255

Gly Pro Arg Lys Tyr Lys Gly Leu Ile Asn Ser His Phe Asn Pro Asn
                260                 265                 270

Ser Ala Leu Phe Ser Pro Lys Asp Arg Leu Asp Ile Ile Trp Ser Asp
275                 280                 285

Ile Gly Phe Phe Val Ala Leu Ala Cys Val Val Tyr Ala Cys Val Gln
            290                 295                 300

Phe Gly Phe Gln Thr Val Gly Lys Tyr Tyr Leu Leu Pro Tyr Met Val
305                 310                 315                 320

Val Asn Tyr His Leu Val Leu Ile Thr Tyr Leu Gln His Thr Asp Val
                325                 330                 335

Phe Ile Pro His Phe Arg Gly Ser Glu Trp Thr Trp Phe Arg Gly Ala
            340                 345                 350

Leu Cys Thr Val Asp Arg Ser Gly Trp Leu Asp His Thr Phe
        355                 360                 365

His His Ile Ser Asp Thr His Val Cys His His Ile Phe Ser Lys Met
370                 375                 380

Pro Phe Tyr His Ala Gln Glu Ala Ser Glu His Ile Arg Lys Ala Leu
385                 390                 395                 400

Gly Asp Tyr Tyr Leu Lys Asp Asp Thr Pro Ile Trp Lys Ala Leu Trp
                405                 410                 415

Arg Ser Tyr Thr Leu Cys Lys Tyr Val Asp Ser Glu Glu Thr Thr Val
                420                 425                 430

Phe Tyr Lys Gln Arg Ala
        435

<210> SEQ ID NO 18
<211> LENGTH: 2049
<212> TYPE: RNA
<213> ORGANISM: Nannochloropsis oculata

<400> SEQUENCE: 18 aaaacaaca gacgcacuuu ccacccaucc gaaccaaauc augggacgcg gcggugagaa      60
gacggugacc ccucucccca aaagccccu ccuggaugcc gccuccacga ucagcagcac     120
ggucagacca agcaaggcag uagaggccau gcccacggag gagcuccgca agaaggccgu     180
acaguacggu auugacacuu cggccgaccg cgaaacacug cugagggagc uggcucccua     240

```
cggcgauauc cuccuccgca augacgcccc caagucccua ccccuugccc cuccuccuuu   300
cacccucucc gauaucaaga augccguccc ccgucacugc uucgagcguu cccucucuac   360
cucccucuuc caccugacua uugacuugau ccaagucgcc auccuugggu accuugccuc   420
acuacugggc cacucggacg ucccgcccau gucucgcuau auccuauggc cauuguacug   480
guaugcgcaa ggcucuguac ugacggugu gugggucauu gcccacgaau gcggacacca   540
aucguuuucg cccuaugaga gcgugaacaa cuucuuuggg uggcucuugc acucggccuu   600
gcuugugccc uaccacucgu ggaggaucuc ccauggaaag caccacaaca acacggggag   660
cugcgagaac gacgaggugu uugcgccgcc uaucaaggag gaguugaugg acgagauuuu   720
gcuucacucc ccuuuggcga accuagugca gauugucauc auguugacca ucgguggau    780 gccggguuac cugcugcuga acgcgacggg gcccaggaag uacaagggau ugaucaauag   840
ccauuucaau ccgaauucgg cguuguuuuc ucccaaggau cgccuggaca ucauuugguc   900
agacaucggu uuuuuguug ccuuggccug cguggugua gccugugugc aguuuggauu     960 ucagacgguag gaaaguacu accguugcc guacaugguag ucaacuacc aucucguucu   1020 aaucacguac cugcagcaua cggaugucu cauccccac uuccgaggga gugaguggac    1080 guggguuuagg ggcgcccucu gcacagucga cagguccuuu ggcuggcuuu uggaucacac 1140
guuucaccau aucagugaua ucaugugug ucaccauaua uuuagcaaaa ugccuuuua   1200 ucacgcgcag gaggcgagcg agcauauccg gaaagcgcug ggcgacuauu auuugaagga   1260
ugacaccccg auuuggaagg cauuguggcg gaguuacacg cugugcaagu acguggauuc   1320
ggaggagacg acguguucu acaagcagcg agcauagaua gcgagaaagg ugguuugggag  1380 cgaggaauga cauggggggu uuuauugagg aaguacuag ugacgugauu guugugugga    1440
ugugcggcug agcgugugga cgcgacagag ggcgggggug agugugagu uuauuuuca     1500 uguuugcaga accagagaaa ugagugaaga gauggaggag agauagacgu gagaaaagga   1560
cagaugagau gccguauuac auacgcgucu guuugagca ugugugugc uuugucggca    1620 ucggcauagg ugugaauuuu ggugucgucg acuuccuuaa ucucugacua uuucucgugc   1680
acaacuggac gaagagagcu gaagagguga gaguugaugg agggagggag gagagcaaca   1740
gcacaaauaa aauacguagc uacugauaug acgagggaag gagagaagag aaaaaagaga   1800
uuauucacag agagggaggg aauccuucuu uaauagugag aguaaucgua guagaauuag   1860
guuuuggaag aagaaucgag aagagaaaaa gcggaagagc gcgucccac uugugccuuu    1920 uuuuagggga ggaaggggg ggagaggggg agguuaguag uuuaaggcau ccaucaacaa    1980
caaaucaaac cacagggaaa ggaaaaacaa cauuaauuuu acauaaaaaa aaaaaaaaaa   2040
aaaaaaaaa                                                          2049
```

<210> SEQ ID NO 19
<211> LENGTH: 1242
<212> TYPE: DNA
<213> ORGANISM: Nannochloropsis oculata

<400> SEQUENCE: 19

```
atggttgagc aaacattgcc gaccttatcc cagattaaaa aaaacatccc cgagaagtgc    60
ttccagaaat cccttctccg ctccttctac tacatgctga gggacttcgc tgccttggcg   120
gcgctctact acatttaccc gactgtgcag tccaaatacg gcttgcctgg tttgtttgtg   180
tggtggaacc tcgcaggttt ctttatgtgg tgcttgttcg tgattggaca cgactgcggc   240
cacggatcct tttccgatca taaatggctt aatgatattt gcggtcatat atgccacgcc   300
```

-continued

```
cccttgatgg tgccctattg gccttggcag aagtcccacc gcctccacca catgtatcac    360
aaccacctga cgaaggacat gtcgcacccg tggatgacca aggaggtgtt cgaggacttg    420
actcccttcg agcaggcgtt gctcgagaat ccactctccc tcttcatcaa gtatacattc    480
ctctaccttt tcgcgggcaa gatggatggc agccacgtgg ttccgttctc ccccctcttc    540
accgacacca aggagcgggt gcaatgcgcg gtctcgaccc tctgcatggt tcttgcaggc    600
gctctggtgt atattggtct cgagggtggg aaggagggag ggctggcaag gatagggtca    660
gtgtatgtgg cgccgttgct ggtgttcaac gcctggatta ccatggtgac gtatttgcaa    720
caccacgacg aggacacgaa ggtgtatgcg gaggggagt ggaattacat caagggagct     780
ctcgagacga ttgaccgcga atatggcatg gcattgacg acctgtctca acatcacg      840
gatggtcacg tagcgcacca cctcttcttc acccagatcc cgcactacca tctcacggct    900
gccacggccg ccgtcaggca gtgtttgcag cccacgggta cctacaagaa gagaaggagc    960
tggaatttcc tcgcccgctt caccgagctc aactacaggt tgaaatacgt ggcgggccag   1020
ggcgtgctct cctacgtgga ttgggaggcc gcccgcaaga ccccgctcc cgccgttgcc   1080
gccccttcct cctcccccttc ctcctcgtct ccctcccca atgtggctgc tgtgaaggcg   1140
gcggctcctg ttcccgtcgt agctgctgct gttgccgctc ccgtccgagt tggaagacca   1200
acacgcaagc gctctcccac ccgttcttcc tccctccgt aa                       1242
```

<210> SEQ ID NO 20
<211> LENGTH: 413
<212> TYPE: PRT
<213> ORGANISM: Nannochloropsis oculata

<400> SEQUENCE: 20

```
Met Val Glu Gln Thr Leu Pro Thr Leu Ser Gln Ile Lys Lys Asn Ile
1               5                   10                  15

Pro Glu Lys Cys Phe Gln Lys Ser Leu Leu Arg Ser Phe Tyr Tyr Met
                20                  25                  30

Leu Arg Asp Phe Ala Ala Leu Ala Ala Leu Tyr Tyr Ile Tyr Pro Thr
            35                  40                  45

Val Gln Ser Lys Tyr Gly Leu Pro Gly Leu Phe Val Trp Trp Asn Leu
        50                  55                  60

Ala Gly Phe Phe Met Trp Cys Leu Phe Val Ile Gly His Asp Cys Gly
65                  70                  75                  80

His Gly Ser Phe Ser Asp His Lys Trp Leu Asn Asp Ile Cys Gly His
                85                  90                  95

Ile Cys His Ala Pro Leu Met Val Pro Tyr Trp Pro Trp Gln Lys Ser
                100                 105                 110

His Arg Leu His His Met Tyr His Asn His Leu Thr Lys Asp Met Ser
            115                 120                 125

His Pro Trp Met Thr Lys Glu Val Phe Glu Asp Leu Thr Pro Phe Glu
        130                 135                 140

Gln Ala Leu Leu Glu Asn Pro Leu Ser Leu Phe Ile Lys Tyr Thr Phe
145                 150                 155                 160

Leu Tyr Leu Phe Ala Gly Lys Met Asp Gly Ser His Val Val Pro Phe
                165                 170                 175

Ser Pro Leu Phe Thr Asp Thr Lys Glu Arg Val Gln Cys Ala Val Ser
            180                 185                 190

Thr Leu Cys Met Val Leu Ala Gly Ala Leu Val Tyr Ile Gly Leu Glu
        195                 200                 205
```

-continued

```
Gly Gly Lys Glu Gly Gly Leu Ala Arg Ile Gly Ser Val Tyr Val Ala
        210                 215                 220
Pro Leu Leu Val Phe Asn Ala Trp Ile Thr Met Val Thr Tyr Leu Gln
225                 230                 235                 240
His His Asp Glu Asp Thr Lys Val Tyr Ala Glu Gly Glu Trp Asn Tyr
                245                 250                 255
Ile Lys Gly Ala Leu Glu Thr Ile Asp Arg Glu Tyr Gly Met Gly Ile
            260                 265                 270
Asp Asp Leu Ser His Asn Ile Thr Asp Gly His Val Ala His His Leu
        275                 280                 285
Phe Phe Thr Gln Ile Pro His Tyr His Leu Thr Ala Ala Thr Ala Ala
290                 295                 300
Val Arg Gln Cys Leu Gln Pro Thr Gly Thr Tyr Lys Lys Arg Arg Ser
305                 310                 315                 320
Trp Asn Phe Leu Ala Arg Phe Thr Glu Leu Asn Tyr Arg Leu Lys Tyr
                325                 330                 335
Val Ala Gly Gln Gly Val Leu Ser Tyr Val Asp Trp Glu Ala Ala Arg
            340                 345                 350
Lys Thr Pro Ala Pro Ala Val Ala Ala Pro Ser Ser Pro Ser Ser Ser
        355                 360                 365
Ser Ser Ser Leu Pro Asn Val Ala Ala Val Lys Ala Ala Pro Val
370                 375                 380
Pro Val Val Ala Ala Val Ala Ala Pro Val Arg Val Gly Arg Pro
385                 390                 395                 400
Thr Arg Lys Arg Ser Pro Thr Arg Ser Ser Ser Pro Pro
                405                 410
```

<210> SEQ ID NO 21
<211> LENGTH: 2079
<212> TYPE: RNA
<213> ORGANISM: Nannochloropsis oculata

<400> SEQUENCE: 21

| | | | | | |
|---|---|---|---|---|---|
| aaaauuuuca | gcaaaguaau | caagauaaua | aacaaaaaca | auccuauaaa | ggaaaaacaa | 60 |
| cagaggacaa | caccccguug | ccgcccaccu | guuguugagu | ugcugccucu | ugccuucccu | 120 |
| ccauacgagu | cagcacuucc | acgccgacac | caaaucgacu | uccucagagu | accuauauac | 180 |
| uagccaccag | caccccuacc | uacaaacaug | guugagcaaa | cauugccgac | cuuaucccag | 240 |
| auuaaaaaaa | acaucccega | gaagugcuuc | cagaaaucce | uucuccgcuc | cuucuacuac | 300 |
| augcugaggg | acuucgcugc | cuuggcggcg | cucuacuaca | uuuacccgac | ugugcaguce | 360 |
| aaauacggcu | ugccugguuu | guuugugugg | uggaaccucg | cagguuucuu | uaugggugc | 420 |
| uuguucguga | uuggacacga | cugcggccac | ggauccuuuu | ccgaucauaa | auggcuuaau | 480 |
| gauauuugcg | gucauauaug | ccacgccccc | uugaugguge | ccuauuggcc | uuggcagaag | 540 |
| ucccaccgcc | uccaccacau | guaucacaac | caccugacga | aggacauguc | gcaccccgugg | 600 |
| augaccaagg | aggugcuccga | ggacuugacu | cccuucgagc | aggcguugcu | cgagaaucca | 660 |
| cucucccucu | ucaucaagua | uacauuccuc | uaccuuuucg | cgggcaagau | ggauggcagc | 720 |
| cacgugguuc | cguucucccc | ccucuucacc | gacaccaagg | agcggugca | augcgcgguc | 780 |
| ucgacccucu | gcauggauucu | ugcaggcgcu | cugguguaua | uuggucucga | ggugggaag | 840 |
| gagggagggc | uggcaaggau | aggucagug | uauguggcgc | guugcugguu | guucaacgcc | 900 |
| uggauuacca | ugugugacgua | uuugcaacac | cacgacgagg | acacgaaggu | guaugcggag | 960 |

```
ggggagugga auuacaucaa gggagcucuc gagacgauug accgcgaauu uggcaugggc    1020
auugacgacc ugucucacaa caucacggau ggucacguag cgcaccaccu cuucuucacc    1080
cagaucccgc acuaccaucu cacggcugcc acggccgccg ucaggcagug uuugcagccc    1140 acgguaccu acaagaagag aaggagcugg aauuuccucg cccgcuucac cgagcucaac     1200
uacagguuga aauacguggc gggccagggc gugcucuccu acguggauug ggaggccgcc    1260
cgcaagaccc ccgcucccgc cguugccgcc ccuuccuccu ccccuuccuc cucgucuucc    1320
cuccccaaug uggcugcugu gaaggcggcg gcuccuguuc ccgucguagc ugcugcuguu    1380
gccgcucccg uccgaguugg aagaccaaca cgcaagcgcu cucccacccg uucuuccucc    1440
ccuccguaaa uaauuguuau agagggaggg gggaugaagu agauaguauu gcuuuacaug    1500 ugucugguu aaaaccagc aacccguaag gagugguggg gagugaggga gggagggaua     1560
gaaggaggag acgucuguug acugagagug ucuaauuuaa guguuggaau gcaaggaccg    1620
agaggagcag gaggaagaac aggaggaaga agaggaggag gaagauagag acaagaagu    1680 gggcagaugg ugguugcugu ucauccucuu ucccuuucuu ccuccuuuca ucucgagaaa    1740
agauagcaga cggugugauc gucugucgau guguaugugu guguaugugc ccucucgcga    1800
cuagaagaga gagagguuuu gaucugaucc ucacauuggu uucuucuaua uuuuauaucag   1860 aaagagugaa gaauugauua aggcuaaaauu uaacugauuu uuaaaguccg uuaccacacu    1920
gacauccuag ucguuuccag uagcaauuac ggguagcagc aguaguagca gcagcagcag    1980
cagcagcaac aacccacaaga agaagaacca auaauagaga cgaguagggu aggaagggga   2040
ggaagggaaa auagguuagg augccuugag aaggccgga                            2079

<210> SEQ ID NO 22
<211> LENGTH: 906
<212> TYPE: DNA
<213> ORGANISM: Nannochloropsis oculata

<400> SEQUENCE: 22
atgaagtggg tcctgcaaga aggggtggac ttccagcccc atggccccaa cagccgcgga      60
acgatgtaca cgcaaatttt ccaagtcctc ccggccctgg agcccttta tatgaactgg      120 gagaagacct atgactctgc cattgtcttt gacttgatga agagcatgcc ttgggtcccg      180
atcgtagcgg tggtagttta tgtcgtagga atcttcggtg ggcaagccat catgaagaac      240
aagaagccct ttgatttgaa gtggccgctt gcgtactgga acttggcttt gtccctgttt      300
tcgatcatgg gcatgattcg cgtggttcct caccttgcct acctgacggc gaccaagggg      360
ttgagtgttg tggcgtgcgg agccccgag cctctgtatg caacgctgc ggtgggttt         420 tgggtgcaag cttttattct gtccaaattg gcggagctga tcgacacggc cttcatcgtc      480
ttgcggaaga agccccctaca gttcttgcac tggtaccacc acgtgacggt cctcctgttc      540
acctggtttt gctacacaaa ggagaatccg ggtattattt tcgtggctat gaatttctcg      600
gtgcatgcca tcatgtatgg ctactacttc ctgatggcca ttcaggtccg accgtcttgg      660
ctgaagccca tctacatcac catgatgcaa atctctcaaa tggtggtggg cgtcaccaca      720
gctgtctttt acatcatgaa gatccgatcg ggcgagacgt gcgccgtgga tcaggaactg      780
ctgattgcct gtggggtgat gtattcgacc tacctgtatt tgttctgtga gtttgcggtg      840
aagaggttta ttttgggtgg gaaggggcca gcaggggcgc cgaagggtaa gacaaaagca      900
cagtag                                                                906
```

<210> SEQ ID NO 23
<211> LENGTH: 301
<212> TYPE: PRT
<213> ORGANISM: Nannochloropsis oculata

<400> SEQUENCE: 23

```
Met Lys Trp Val Leu Gln Glu Gly Val Asp Phe Gln Pro His Gly Pro
1               5                   10                  15

Asn Ser Arg Gly Thr Met Tyr Thr Gln Ile Phe Gln Val Leu Pro Ala
            20                  25                  30

Leu Glu Pro Phe Tyr Met Asn Trp Glu Lys Thr Tyr Asp Ser Ala Ile
        35                  40                  45

Val Phe Asp Leu Met Lys Ser Met Pro Trp Val Pro Ile Val Ala Val
50                  55                  60

Val Val Tyr Val Val Gly Ile Phe Gly Gly Gln Ala Ile Met Lys Asn
65                  70                  75                  80

Lys Lys Pro Phe Asp Leu Lys Trp Pro Leu Ala Tyr Trp Asn Leu Ala
                85                  90                  95

Leu Ser Leu Phe Ser Ile Met Gly Met Ile Arg Val Val Pro His Leu
            100                 105                 110

Ala Tyr Leu Thr Ala Thr Lys Gly Leu Ser Val Val Ala Cys Gly Ala
        115                 120                 125

Pro Glu Pro Leu Tyr Gly Asn Ala Ala Val Gly Phe Trp Val Gln Ala
130                 135                 140

Phe Ile Leu Ser Lys Leu Ala Glu Leu Ile Asp Thr Ala Phe Ile Val
145                 150                 155                 160

Leu Arg Lys Lys Pro Leu Gln Phe Leu His Trp Tyr His His Val Thr
                165                 170                 175

Val Leu Leu Phe Thr Trp Phe Cys Tyr Thr Lys Glu Asn Pro Gly Ile
            180                 185                 190

Ile Phe Val Ala Met Asn Phe Ser Val His Ala Ile Met Tyr Gly Tyr
        195                 200                 205

Tyr Phe Leu Met Ala Ile Gln Val Arg Pro Ser Trp Leu Lys Pro Ile
210                 215                 220

Tyr Ile Thr Met Met Gln Ile Ser Gln Met Val Val Gly Val Thr Thr
225                 230                 235                 240

Ala Val Phe Tyr Ile Met Lys Ile Arg Ser Gly Glu Thr Cys Ala Val
                245                 250                 255

Asp Gln Glu Leu Leu Ile Ala Cys Gly Val Met Tyr Ser Thr Tyr Leu
            260                 265                 270

Tyr Leu Phe Cys Glu Phe Ala Val Lys Arg Phe Ile Leu Gly Gly Lys
        275                 280                 285

Gly Ala Ala Gly Ala Pro Lys Gly Lys Thr Lys Ala Gln
290                 295                 300
```

<210> SEQ ID NO 24
<211> LENGTH: 1086
<212> TYPE: RNA
<213> ORGANISM: Nannochloropsis oculata

<400> SEQUENCE: 24

```
aaacgagcug aaauuuucag caaaguaauc aagauaauaa acaaaaacaa uccuauaaaa    60
ggaaaaacaa caggcggcac cagagccagc acaggaucua cgcuccuuuc ccgucaauua   120 ugaaguggu ccugcaagaa ggguggacu uccagcccca uggccccaac agccgcggaa    180
```

| | |
|---|---|
| cgauguacac gcaaauuuuc caaguccucc cggcccugga gcccuuuuau augaacuggg | 240 |
| agaagaccua ugacucugcc auugucuuug acuugaugaa gagcaugccu ugggucccga | 300 |
| ucguagcggu gguaguuuau gucguaggaa ucuucggugg gcaagccauc augaagaaca | 360 |
| agaagcccuu ugauuugaag uggccgcuug cguacuggaa cuuggcuuug ucccuguuuu | 420 |
| cgaucauggg cauguuucgc guggyuccuc accuugccua ccugacggcg accaaggggu | 480 |
| ugaguguugu ggcgugcgga gcccccgagc ucucguaugg caacgcugcg gugggguuuu | 540 |
| gggugcaagc uuuuauucug uccaaauugg cggagcugau cgacacggcc uucaucgucu | 600 |
| ugcggaagaa gccccuacag uucuugcacu gguaccacca cgugacgguc cuccuguuca | 660 |
| ccugguuuug cuacacaaag gagaauccgg guauuauuuu cguggcuaug aauuucucgg | 720 |
| ugcaugccau caugauggc uacuacuucc ugauggccau ucagguccga ccgucuuggc | 780 |
| ugaagcccau cuacaucacc augaugcaaa ucucucaaau ggugguggc gucaccacag | 840 |
| cugucuuuua caucaugaag auccgaucgg gcgagacgug cgccguggau caggaacugc | 900 |
| ugauugccug uggggugaug uauucgaccu accuguauuu guucugugag uugcgguga | 960 |
| agagguuuau uuugggugg aagggggcag caggggcgcc gaagggguaag acaaaagcac | 1020 |
| aguagggagg aaggggggaaa gaggggaggggg acguuagcag aggaggagga ggaggaggag | 1080 |
| gaggag | 1086 |

<210> SEQ ID NO 25
<211> LENGTH: 1023
<212> TYPE: DNA
<213> ORGANISM: Nannochloropsis oculata

<400> SEQUENCE: 25

| | |
|---|---|
| atgtcttggt ttttggaccc cgctcccctc tacaagacca gcgagtatgt cacccgtgat | 60 |
| cctgtcaatc ccgtccgctt tgtacaagtg tttcaatcca tcccagcact cgaacccttg | 120 |
| tacactgagt gggaaaagaa ttttaatgtc aaggagtctt accgcatcat ccagacaac | 180 |
| tgctgggtcc ccgtcatcgc cgtcatcctc tatctatcct tcctagtcga aggcaggaac | 240 |
| tatgtggaac gacgaaaaaa agcaggcaaa ggccccgtta atctcggtcg gtttcctgca | 300 |
| atctggaatg ggttcttggc cattttttcg attcttgggg ccttgcgcgt ggtccctcat | 360 |
| ttccttttt tgttcactca caaggatttt aaggaaacag tttgcgaggc tcctgatacg | 420 |
| gcggggtacg gtgatggggc ggcagggatg tgggtgatgt tgtttacggt ctcaaaggtg | 480 |
| tttgaattga tggatacggt gattttggtg ttgaagggca agaaccctat gttcttgcac | 540 |
| tggtaccacc acgtgacggt gcttctctac acatggttct cgtactcggc ccgcaacccc | 600 |
| ggcctgtact tgtcgccat gaactacacc gtacacgcgg tcatgtattc gtactactt | 660 |
| ctgatggaga tcaagctctg gccgaagtcg ctcagcccca tttttatcac cctcatgcaa | 720 |
| atctcccaaa tgcttgtcgg ggtcgctatc acggccgccg cctacatcta tcaacgcgac | 780 |
| ccttcctgtg gtgtcgtccg cgacttgatt ccctggtgtg ccgctatgta tgccacatac | 840 |
| ctctatttct ttgtcgagtt ttttgtcgag cgcttcttgg cagcgtcgag taagaaggca | 900 |
| gggagggagg aaggggaggg agggaagagt aaattggcca aaaaggatat cgggaccgcg | 960 |
| gccttctctc tagtgactgc gaatggagca tcggtgatgg ggaatggaaa gaagatggcg | 1020 |
| taa | 1023 |

<210> SEQ ID NO 26
<211> LENGTH: 340

<212> TYPE: PRT
<213> ORGANISM: Nannochloropsis oculata

<400> SEQUENCE: 26

Met Ser Trp Phe Leu Asp Pro Ala Pro Leu Tyr Lys Thr Ser Glu Tyr
1               5                   10                  15

Val Thr Arg Asp Pro Val Asn Pro Val Arg Phe Val Gln Val Phe Gln
            20                  25                  30

Ser Ile Pro Ala Leu Glu Pro Leu Tyr Thr Glu Trp Glu Lys Asn Phe
        35                  40                  45

Asn Val Lys Glu Ser Tyr Arg Ile Ile Arg Asp Asn Cys Trp Val Pro
    50                  55                  60

Val Ile Ala Val Ile Leu Tyr Leu Ser Phe Leu Val Glu Gly Arg Asn
65                  70                  75                  80

Tyr Val Glu Arg Arg Lys Lys Ala Gly Lys Gly Pro Val Asn Leu Gly
                85                  90                  95

Arg Phe Pro Ala Ile Trp Asn Gly Phe Leu Ala Ile Phe Ser Ile Leu
            100                 105                 110

Gly Ala Leu Arg Val Val Pro His Phe Leu Phe Leu Phe Thr His Lys
        115                 120                 125

Asp Phe Lys Glu Thr Val Cys Glu Ala Pro Asp Thr Ala Gly Tyr Gly
    130                 135                 140

Asp Gly Ala Ala Gly Met Trp Val Met Leu Phe Thr Val Ser Lys Val
145                 150                 155                 160

Phe Glu Leu Met Asp Thr Val Ile Leu Val Leu Lys Gly Lys Asn Pro
                165                 170                 175

Met Phe Leu His Trp Tyr His His Val Thr Val Leu Leu Tyr Thr Trp
            180                 185                 190

Phe Ser Tyr Ser Ala Arg Asn Pro Gly Leu Tyr Phe Val Ala Met Asn
        195                 200                 205

Tyr Thr Val His Ala Val Met Tyr Ser Tyr Tyr Phe Leu Met Glu Ile
    210                 215                 220

Lys Leu Trp Pro Lys Ser Leu Ser Pro Ile Phe Ile Thr Leu Met Gln
225                 230                 235                 240

Ile Ser Gln Met Leu Val Gly Val Ala Ile Thr Ala Ala Tyr Ile
                245                 250                 255

Tyr Gln Arg Asp Pro Ser Cys Gly Val Val Arg Asp Leu Ile Pro Trp
            260                 265                 270

Cys Ala Ala Met Tyr Ala Thr Tyr Leu Tyr Phe Phe Val Glu Phe Phe
        275                 280                 285

Val Glu Arg Phe Leu Ala Ala Ser Ser Lys Leu Ala Gly Arg Glu Glu
    290                 295                 300

Gly Glu Gly Gly Lys Ser Lys Leu Ala Lys Lys Asp Ile Gly Thr Ala
305                 310                 315                 320

Ala Phe Ser Leu Val Thr Ala Asn Gly Ala Ser Val Met Gly Asn Gly
                325                 330                 335

Lys Lys Met Ala
            340

<210> SEQ ID NO 27
<211> LENGTH: 1894
<212> TYPE: RNA
<213> ORGANISM: Nannochloropsis oculata

<400> SEQUENCE: 27

| | |
|---|---:|
| auuuucagca aaguaaucaa gauaauaaac aaaaacaauc cuauaaagga aaacaacagg | 60 |
| ccuagcgcgg acgcacacaa gacauuagcu agucagagcg agaaucaagc cucacgcaca | 120 |
| uuugcaccac ucaaaggcaa acgaacuacc acugaacgc cgcagcgcca uccuccucca | 180 |
| acaaccccaa gcaagcaacc auaccauguc uugguuuuug accccgcuc cccucuacaa | 240 |
| gaccagcgag uaugucaccc gugauccugu caaucccguc cgcuuuguac aaguguuuca | 300 |
| auccauccca gcacucgaac ccuuguacac ugaguggga agaauuuua augucaagga | 360 |
| gucuuaccgc aucauccgag acaacugcug gguccccguc aucgccguca uccucuaucu | 420 |
| auccuuccua gucgaaggca ggaacuaugu ggaacgacga aaaaaagcag gcaaaggccc | 480 |
| cguuaaucuc ggucgguuuc cugcaaucug gaaugggguc uuggccauuu uuucgauucu | 540 |
| uggggccuug cgcguggucc cucauuuccu uuuuuuguuc acucacaagg auuuuaagga | 600 |
| aacaguuugc gaggcuccug auacggcggg guacggugau ggggcggcag ggaugugggu | 660 |
| gauguuguuu acgucucaa agguguuga auugauggau acggugauuu ugguguugaa | 720 |
| gggcaagaac ccuauguucu ugcacuggua ccaccacgug acggugcuuc ucuacacaug | 780 |
| guucucguac ucggcccgca accccggccu guacuuuguc gccaugaacu acaccguaca | 840 |
| cgcggucaug uauucguacu acuuucugau ggagaucaag cucuggccga agucgcucag | 900 |
| ccccauuuuu aucaccccuca ugcaaaucuc ccaaaugcuu ucggggucg cuaucacggc | 960 |
| cgccgccuac aucaucaac gcgacccuuc cuguggguc guccgcgacu ugauucccug | 1020 |
| gugugccgcu auguaugcca cauaccucua uucuuugucc gaguuuuuug ucgagcgcuu | 1080 |
| cuuggcagcg ucgaguaaga aggcagggag ggaggaaggg gaggagggga agaguaaauu | 1140 |
| ggccaaaaag gauaucggga ccgcggccuu cucucuagug acugcgaaug gagcaucggu | 1200 |
| gauggggaau ggaaagaaga uggcguaaau gauugcaucc ugaacgaagg agagggaaga | 1260 |
| agggagaucu aggagggaug cgguggagag agggaggagu ggacaguuga ugacccaaga | 1320 |
| ggauagcgag guggaaaaag gaaggugga gaagacggag gaggggggg aagaggagga | 1380 |
| ggacuuugag uaggcggua uaaaauaug ggaauaaaaa uugaccauga cccaucagcc | 1440 |
| gagacacaca cauacacgcg cucggacucg guucgguccg gacaccgccg cuuauccugu | 1500 |
| ccaccgcaca cgggcgagga ggaggagaga ggagcagaag aaucgauaga gagggacccu | 1560 |
| cuugaaugaa acaggauguc caaggaagac accuuuuguu guauauggag gggaggaggg | 1620 |
| agggaggacc agggauagug gauguauuuc uaaaagaugc uuuuuauuu aauugaaaag | 1680 |
| guuggaugaa guggaacgag agagaggcag agauaacaaa auaccacaaa ugagcgaaau | 1740 |
| cagaagacgg aagggaagga aggaaaacaa aaaggaaggg augcuuuauu uucuguaugu | 1800 |
| gugaguggua aaguagcaug uguagcacag aguuacacac gcgcgcgcag cagagcagca | 1860 |
| gaagagaaag gagcgaagga uaaaaaaaaa aaaa | 1894 |

<210> SEQ ID NO 28
<211> LENGTH: 1095
<212> TYPE: DNA
<213> ORGANISM: Nannochloropsis oculata

<400> SEQUENCE: 28

| | |
|---|---:|
| atgctgagca aaagcttcaa taccaccacc tgcacatcct ccttctactg ccccccctct | 60 |
| accctcattc cggtcacgcg ggagctggct ggcaacacct acacctttt gcagttctgg | 120 |
| cagctcttcc cctggaccaa gcatttctac acccaatttg aaaagaattt tgacgtccgt | 180 |
| ccatggttta tgttcgtgca tgggaactgg tgggtgcccg tggtggcgat tgcgatgtat | 240 |

```
ggggtgatga tcgtcacgtt gccgaagtac accgcaaaga agccggtcaa gtgtgacgtg      300
gccctcgcat actggaattg tttccttgcc ctgttttcca cactcggagc cattcgcatc      360
gtcccccacc tgatgtggtt ctcggccact cacacattca gagacacggt gtgcactcca      420
ccgcagatga tgaacggcga tggggcctca gggctgtggt gtttattatt tacactctca      480
aaggtgcttg aattgcttga cacgatgttt gtctgtctca agggacggac gcccatattc      540
ttgcattggt accaccacgt gaccgtccta agctttacat gggccgccta cgccgcccgg      600
cacccaggca tgtattttat cggcatgaac tacaccgtgc acgccattat gtattcctac      660
ttcttcctca tggccattaa ggccaagccc aggtggctca atcccatgta tatcacccttt     720 ttgcagattt ttcaaatgat ggccgggatc gtcatcaccc tctgcggctt ccattacatc      780
gctcgcgacc cgtccacctg cggcgttgtc ccccacgtcc tatacttcca aggcctcata      840
tacggttcct acctttatct cttcctcgag tttctcatta aacgtttttt ttcctcgggt      900
aaggtcaaga cctcgtcctc ctccgcatcc tccccccctc cctcctgccc ggccgtggcg      960
tcgaacggtg cgacggccac agaaatcgag aagacggggt ggcagaagct gtctgctgga     1020
ggagcaggag gagcaggaac agcagcgaac ggagacggtt atggaagtga cgtggacttg     1080
aagaaagcac agtag                                                     1095

<210> SEQ ID NO 29
<211> LENGTH: 364
<212> TYPE: PRT
<213> ORGANISM: Nannochloropsis oculata

<400> SEQUENCE: 29

Met Leu Ser Lys Ser Phe Asn Thr Thr Thr Cys Thr Ser Ser Phe Tyr
1               5                   10                  15

Cys Pro Pro Ser Thr Leu Ile Pro Val Thr Arg Glu Leu Ala Gly Asn
            20                  25                  30

Thr Tyr Thr Phe Leu Gln Phe Trp Gln Leu Phe Pro Trp Thr Lys His
        35                  40                  45

Phe Tyr Thr Gln Phe Glu Lys Asn Phe Asp Val Arg Pro Trp Phe Met
    50                  55                  60

Phe Val His Gly Asn Trp Trp Val Pro Val Ala Ile Ala Met Tyr
65                  70                  75                  80

Gly Val Met Ile Val Thr Leu Pro Lys Tyr Thr Ala Lys Lys Pro Val
                85                  90                  95

Lys Cys Asp Val Ala Leu Ala Tyr Trp Asn Cys Phe Leu Ala Leu Phe
            100                 105                 110

Ser Thr Leu Gly Ala Ile Arg Ile Val Pro His Leu Met Trp Phe Ser
        115                 120                 125

Ala Thr His Thr Phe Arg Asp Thr Val Cys Thr Pro Pro Gln Met Met
    130                 135                 140

Asn Gly Asp Gly Ala Ser Gly Leu Trp Cys Leu Leu Phe Thr Leu Ser
145                 150                 155                 160

Lys Val Leu Glu Leu Leu Asp Thr Met Phe Val Cys Leu Lys Gly Arg
                165                 170                 175

Thr Pro Ile Phe Leu His Trp Tyr His Val Thr Val Leu Ser Phe
            180                 185                 190

Thr Trp Ala Ala Tyr Ala Ala Arg His Pro Gly Met Tyr Phe Ile Gly
        195                 200                 205

Met Asn Tyr Thr Val His Ala Ile Met Tyr Ser Tyr Phe Phe Leu Met
```

```
                210               215               220
Ala Ile Lys Ala Lys Pro Arg Trp Leu Asn Pro Met Tyr Ile Thr Phe
225             230                  235                 240

Leu Gln Ile Phe Gln Met Met Ala Gly Ile Val Ile Thr Leu Cys Gly
            245                 250                 255

Phe His Tyr Ile Ala Arg Asp Pro Ser Thr Cys Gly Val Val Pro His
            260                 265                 270

Val Leu Tyr Phe Gln Gly Leu Ile Tyr Gly Ser Tyr Leu Tyr Leu Phe
            275                 280                 285

Leu Glu Phe Leu Ile Lys Arg Phe Phe Ser Ser Gly Lys Val Lys Thr
290                 295                 300

Ser Ser Ser Ser Ala Ser Ser Pro Pro Pro Ser Cys Pro Ala Val Ala
305                 310                 315                 320

Ser Asn Gly Ala Thr Ala Thr Glu Ile Glu Lys Thr Gly Trp Gln Lys
            325                 330                 335

Leu Ser Ala Gly Gly Ala Gly Gly Ala Gly Thr Ala Ala Asn Gly Asp
            340                 345                 350

Gly Tyr Gly Ser Asp Val Asp Leu Lys Lys Ala Gln
            355                 360
```

<210> SEQ ID NO 30
<211> LENGTH: 1685
<212> TYPE: RNA
<213> ORGANISM: Nannochloropsis oculata

<400> SEQUENCE: 30

```
aauuucagc  aaaguaauca  agauaauaaa  caaaaacaau  ccuauaaagg  aaaaacaaca    60
gauauacaac  aggcagcagg  uagagagcaa  aaagaggucg  uggucacgcg  aaaguagauu   120
cuguagccac  ucgcuauccc  aucccuccca  cacucgcguc  gcagccgucu  ugaccaucac   180
cuccacacca  ccacccaucc  ccuccgugaa  ccaugcugag  caaaagcuuc  aauaccacca   240
ccugcacauc  uccuucuac   ugcccccccu  cuacccucau  uccggucacg  cgggagcugg   300
cuggcaacac  cuacaccuuu  uugcaguucu  ggcagcucuu  ccccggacc   aagcauuucu   360
acacccaauu  ugaaaagaau  uuugacgucc  guccaugguu  uauguucgug  cauggaacu    420
gguggugcc   cguggugggcg  auugcgaugu  auggggugau  gaucgucacg  uugccgaagu   480
acaccgcaaa  gaagccgguc  aagugugacg  uggcccucgc  auacuggaau  uguuccuug    540
cccuguuuuc  cacacucgga  gccauucgca  ucguccccca  ccugaugugg  uucucggcca   600
cucacacauu  cagagacacg  gugugcacuc  caccgcagau  gaugaacggc  gauggggccu   660
cagggcugug  guguuuauua  uuuacacucu  caaaggugcu  ugaauugcuu  gacacgaugu   720
uugucugucu  caaggacgg   acgcccauau  ucuugcauug  guaccaccac  gugaccgucc   780
uaagcuuuac  augggccgcc  uacgccgccc  ggcacccagg  cauguauuuu  aucggcauga   840
acuacaccgu  gcacgccauu  auguauuccu  acuucuuccu  cauggccauu  aaggccaagc   900
ccagguggcu  caaucccaug  uauaucaccu  uuugcagau   uuucaaaug   auggccggga   960
ucgucaucac  ccucugcggc  uuccauuaca  ucgcucgcga  cccguccacc  ugcggcguug  1020
ucccccacgu  ccuauacuuc  caaggccuca  uauacgguuc  cuaccuuuau  cucuuccucg  1080
aguuucucau  uaaacguuuu  uuuccucgg   guaaggucaa  gaccucgucc  uccucegcau  1140
ccucccccc   uccuccgc    ccggccgugg  cgucgaacgg  ugcgacggcc  acagaaaucg  1200
agaagacggg  guggcagaag  cugucugcug  gaggagcagg  aggagcagga  acagcagcga  1260
```

```
acggagacgg uuauggaagu gacguggacu ugaagaaagc acaguaguaa guaguaugga    1320
ucgagaagaa gggaagcagg aaggaaggaa gggagacgag cacugaacuu ggccagcaac    1380
gaaaggaaca aucagcauca auggcugcgu gguaagagag agacagagag agagagagag    1440
agagacagag agaugagagg ugugagagag cgagagacag agagagagag agagagagaa    1500
agagagagag agauugagac acgcacacac acacagacga aagcaagaua guguagugac    1560
aaauaauaga aaaaccgaau aacacugacg aaagggaaaa uacgguacua gaaagaaugc    1620
uagcaaggac aaaaccacag acaacaaucg gacagcugua uuaauaaguc agacacacac    1680
gcaag                                                               1685
```

<210> SEQ ID NO 31
<211> LENGTH: 951
<212> TYPE: DNA
<213> ORGANISM: Nannochloropsis oculata

<400> SEQUENCE: 31

```
atggaggccc ccctcccgca cctctgcacc agctcgtggt actgcccgcc cgagaccctg     60
gtagccacgc aacgtgacta ctcatcgcgc aacatccatt actcattcct ccagctctgg    120
cagctcttcc ccttcctcga gaagttttat gcgccttttg agaagaactt caatcccatt    180
ccgatctttg aattcatttc ggccaactgg tggatcccct acacgtccct gatcttgtat    240
atttccatga ttgttttcct gcctcggatc atgaaaaatc gcccggtgaa agatctaagc    300
aagcccttag cttgttggaa tttcttcctt gcagtgtata gcaccattgg tgcaattcgt    360
gtcgtccctc atttgttatg gttcgtgtcc acacatacct ttaaggagac tgtctgcacc    420
gctccatata ggatcaatgg cgatggtgcc actggtctat gggtgacgtt gttcacgctc    480
tctaaggtcg tggagttggt ggacacgctc ttcatttgct tgaaagggaa gaaacccatt    540
ttcttgcact ggtatcatca cgtttccgtc ctctacttca cttgggcggc ccatgaggcg    600
gcgcatgctg gcatgtattt tatcggcatg aactacaccg tgcactcggt tatgtattcc    660
tactacttcc tcatggccat caaggccaag cccaggtggc tcaaccctat ctacatcacc    720
tttatgcaaa tcgcgcaaat gatcgtgggt gtcatcatta ccgcctttgg attctactac    780
tcctccaagg ataacacttg tgcggttgac cctttcgtgt tgaagatctc gggggtgatt    840
tacgcgtcct atctctattt gttcatggaa ttcatgatca aacggttttt ccttggtgcc    900
ggagcagggg ccggtgggag gaagaaggcg ggtgcctccc cagaaaggtg a             951
```

<210> SEQ ID NO 32
<211> LENGTH: 316
<212> TYPE: PRT
<213> ORGANISM: Nannochloropsis oculata

<400> SEQUENCE: 32

```
Met Glu Ala Pro Leu Pro His Leu Cys Thr Ser Ser Trp Tyr Cys Pro
1               5                   10                  15

Pro Glu Thr Leu Val Ala Thr Gln Arg Asp Tyr Ser Ser Arg Asn Ile
            20                  25                  30

His Tyr Ser Phe Leu Gln Leu Trp Gln Leu Phe Pro Phe Leu Glu Lys
        35                  40                  45

Phe Tyr Ala Pro Phe Glu Lys Asn Phe Asn Pro Ile Pro Ile Phe Glu
    50                  55                  60

Phe Ile Ser Ala Asn Trp Trp Ile Pro Tyr Thr Ser Leu Ile Leu Tyr
65                  70                  75                  80
```

```
Ile Ser Met Ile Val Phe Leu Pro Arg Ile Met Lys Asn Arg Pro Val
                85                  90                  95

Lys Asp Leu Ser Lys Pro Leu Ala Cys Trp Asn Phe Phe Leu Ala Val
            100                 105                 110

Tyr Ser Thr Ile Gly Ala Ile Arg Val Val Pro His Leu Leu Trp Phe
        115                 120                 125

Val Ser Thr His Thr Phe Lys Glu Thr Val Cys Thr Ala Pro Tyr Arg
    130                 135                 140

Ile Asn Gly Asp Gly Ala Thr Gly Leu Trp Val Thr Leu Phe Thr Leu
145                 150                 155                 160

Ser Lys Val Val Glu Leu Val Asp Thr Leu Phe Ile Cys Leu Lys Gly
                165                 170                 175

Lys Lys Pro Ile Phe Leu His Trp Tyr His His Val Ser Val Leu Tyr
            180                 185                 190

Phe Thr Trp Ala Ala His Glu Ala Ala His Ala Gly Met Tyr Phe Ile
        195                 200                 205

Gly Met Asn Tyr Thr Val His Ser Val Met Tyr Ser Tyr Tyr Phe Leu
    210                 215                 220

Met Ala Ile Lys Ala Lys Pro Arg Trp Leu Asn Pro Ile Tyr Ile Thr
225                 230                 235                 240

Phe Met Gln Ile Ala Gln Met Ile Val Gly Val Ile Ile Thr Ala Phe
                245                 250                 255

Gly Phe Tyr Tyr Ser Ser Lys Asp Asn Thr Cys Ala Val Asp Pro Phe
            260                 265                 270

Val Leu Lys Ile Ser Gly Val Ile Tyr Ala Ser Tyr Leu Tyr Leu Phe
        275                 280                 285

Met Glu Phe Met Ile Lys Arg Phe Phe Leu Gly Ala Gly Ala Gly Ala
    290                 295                 300

Gly Gly Arg Lys Lys Ala Gly Ala Ser Pro Glu Arg
305                 310                 315

<210> SEQ ID NO 33
<211> LENGTH: 1060
<212> TYPE: RNA
<213> ORGANISM: Nannochloropsis oculata

<400> SEQUENCE: 33
aaauuuucag caaaguaauc aagauaauaa acaaaaacaa uccuauaaag gaaaaacaac      60
agcucguauc aaacauggag gcccccuccc cgcaccucug caccagcucg ugguacugcc     120
cgcccgagac ccugguagcc acgcaacgug acuacucauc gcgcaacauc cauuacucau     180
uccuccagcu cuggcagcuc uucccuuccu cgagaaguuu uaugcgccuu uugagaaga     240 acuucaauccc cauuccgauc uuugaauuca uuucggccaa cuggugauc cccuacacgu    300 cccugaucuu guauauuucc augauuguuu uccugccucg gaucaugaaa aaucgcccgg    360
ugaaagaucu aagcaagccc uuagcuuguu ggaauuucuu ccuugcagug uauagccaca    420
uuggugcaau ucgugucguc ccucauuugu uaugguucgu guccacacau accuuuaagg    480
agacugucug caccgcucca uauaggauca auggcgaugg ugccacuggu cuaugggug    540 cguuguucac gcucucuaag gucguggagu ugguggacac gcucuucauu gcuugaaag    600 ggaagaaaacc cauuuucuug cacugguauc aucacguuuc cguccucuac uucacuuggg    660
cggcccauga ggcggcgcau gcuggcaugu auuuuaucgg caugaacuac accgugcacu    720
cgguuaugua uuccuacuac uuccucaugg ccaucaaggc caagcccagg uggcucaacc    780
```

```
cuaucuacau caccuuuaug caaaucgcgc aaaugaucgu gggugucauc auuaccgccu    840
uuggauucua cuacuccucc aaggauaaca cuugugcggu ugacccuuuc guguugaaga    900
ucucgggggu gauuuacgcg uccuaucucu auuuguucau ggaauucaug aucaaacggu    960
uuuuccuugg ugccggagca ggggccggug ggaggaagaa ggcgggugcc uccccagaaa   1020
ggugagacga agaaggcgcu cuaagcuuac guacgwucgc                         1060
```

<210> SEQ ID NO 34
<211> LENGTH: 831
<212> TYPE: DNA
<213> ORGANISM: Nannochloropsis oculata

<400> SEQUENCE: 34

```
atggccgccg cccttctttc agactaccaa aaagcctgcg cggatttgtc ggccgccatc     60
tttaagtggg ctgaccctgc gggcgccatg gtcaaagcac cgactcgtac ctggccattg    120
gcgggtttgg acgtggccct ggccatcgcg gctttctacc tcgtcatcgt ctttgtgggc    180
tcggccatga tgaggaatgc gaagcccgta aaattatacg gcctgcaatt cttctacaac    240
atctcccagg tcgccttatg ctcctacatg tgcatcgagg ccgccatcca ggcctaccgt    300
aacaactaca cctttcttcc ttgcgagccg ttcaaccccc ccagcccgcc catcgccccc    360
ctcctctggc tcttctacgt ctccaaggtc ttcgacttcg ccgacaccat cttcatcatc    420
ctgggcaaga agtggaacca gctttctttt ctgcatgtgt accaccacgt gaccatcttt    480
ttggtctact ggttgaatct gaatgcgggg tatgatggcg atattttcct gactgtcatt    540
ctgaacgggg ccattcacac ggtgatgtac acttactact cctctctat gcacaccaag    600 gacatttggt ggaagaagta tttgacgctc ttccagatta ttcagttcct gaccatgaat    660
gctcaggcgg tctacttgtt gtgtgtggat tgcaagggct tttcgcctca gatcacgaag    720
ctgtatctgg ggtacatcct gtcgcttttg gtgctgttcc tcaacttta tttcaagtcc    780 tattctggtg taaaatccaa tggaaagaag ccggctctca agaagattta a             831
```

<210> SEQ ID NO 35
<211> LENGTH: 276
<212> TYPE: PRT
<213> ORGANISM: Nannochloropsis oculata

<400> SEQUENCE: 35

```
Met Ala Ala Ala Leu Leu Ser Asp Tyr Gln Lys Ala Cys Ala Asp Leu
 1               5                  10                  15

Ser Ala Ala Ile Phe Lys Trp Ala Asp Pro Ala Gly Ala Met Val Lys
                20                  25                  30

Ala Pro Thr Arg Thr Trp Pro Leu Ala Gly Leu Asp Val Ala Leu Ala
            35                  40                  45

Ile Ala Ala Phe Tyr Leu Val Ile Val Phe Val Gly Ser Ala Met Met
        50                  55                  60

Arg Asn Ala Lys Pro Val Lys Leu Tyr Gly Leu Gln Phe Phe Tyr Asn
 65                  70                  75                  80

Ile Ser Gln Val Ala Leu Cys Ser Tyr Met Cys Ile Glu Ala Ala Ile
                85                  90                  95

Gln Ala Tyr Arg Asn Asn Tyr Thr Phe Leu Pro Cys Glu Pro Phe Asn
            100                 105                 110

Pro Thr Ser Pro Pro Ile Ala Pro Leu Leu Trp Leu Phe Tyr Val Ser
        115                 120                 125

Lys Val Phe Asp Phe Ala Asp Thr Ile Phe Ile Ile Leu Gly Lys Lys
```

```
            130                 135                 140
Trp Asn Gln Leu Ser Phe Leu His Val Tyr His Val Thr Ile Phe
145                 150                 155                 160

Leu Val Tyr Trp Leu Asn Leu Asn Ala Gly Tyr Asp Gly Asp Ile Phe
                165                 170                 175

Leu Thr Val Ile Leu Asn Gly Ala Ile His Thr Val Met Tyr Thr Tyr
            180                 185                 190

Tyr Phe Leu Ser Met His Thr Lys Asp Ile Trp Trp Lys Lys Tyr Leu
        195                 200                 205

Thr Leu Phe Gln Ile Ile Gln Phe Leu Thr Met Asn Ala Gln Ala Val
    210                 215                 220

Tyr Leu Leu Cys Val Asp Cys Lys Gly Phe Ser Pro Gln Ile Thr Lys
225                 230                 235                 240

Leu Tyr Leu Gly Tyr Ile Leu Ser Leu Leu Val Leu Phe Leu Asn Phe
                245                 250                 255

Tyr Phe Lys Ser Tyr Ser Gly Val Lys Ser Asn Gly Lys Lys Pro Ala
            260                 265                 270

Leu Lys Lys Ile
        275

<210> SEQ ID NO 36
<211> LENGTH: 1302
<212> TYPE: RNA
<213> ORGANISM: Nannochloropsis oculata

<400> SEQUENCE: 36
aaauuuucag caaaguaauc aagauaauaa acaaaaacaa uccuauaaaa ggaaaaacaa      60
cagaucggaa aucagcccuc gcuugcccca ucaccacuac aagcaacaug gccgccgccc     120
uucuuucaga cuaccaaaaa gccugcgcgg auuugucggc cgccaucuuu aaguggcug     180 acccugcggg cgccaugguc aaagcaccga cucguaccug gccauggcg gguuuggacg     240 uggcccuggc caucgcggcu uucuaccucg ucaucgucuu uguggcucg gccaugauga     300 ggaaugcgaa gcccguaaaa uuauacggcc ugcaauucuu cuacaacauc ucccaggucg     360
ccuuaugcuc cuacaugugc aucgaggccg ccauccaggc cuaccguaac aacuacaccu     420
uucuuccuug cgagccguuc aaccccacca gcccgcccau cgccccccuc cucuggcucu     480
ucuacgucuc caaggucuuc gacuucgccg acaccaucuu caucauccug ggcaagaagu     540
ggaaccagcu uucuuuucug caugugacc accacgugac caucuuuuug gucuacuggu     600
ugaaucugaa ugcggggau gauggcgaua uuuccugac ugucauucug aacggggcca     660
uucacacggu gauguacacu uacuacuucc ucucuaugca caccaaggac auuggugga     720 agaaguauuu gacgcucuuc cagauuauuc aguccugac caugaaugcu caggcggucu     780
acuuguugug uggauugc aaggcuuuu cgccucagau cacgaagcug uaucgggu     840 acauccuguc gcuuuggug cuguccuca acuuuauuu caagccuau ucgguguaa     900 aauccaaugg aaagaagccg gcucucaaga agauuuaaac ggaaaaugau ugauugguu     960 uggcgggaau ggaagggaga gauuggugc gaggagagcg aggccaugcg cacaugcgac    1020
gacgccggaa cgacaacaac aacaacaacg aacugcaaga uggugcacgu gucugagaag    1080
agacguagug gcuucgauau gcauacauau uuacagauga cauccaucuc auaaaaaag    1140 aaagggaaaa augaguagag uuucggcug ggggauagg ggggagcacg aguaaaaauu    1200
acacauuauu gaaagcuugc caacugcagg auguuucgc acagaggucc ugaacaugaa    1260
```
agagaacaag aaggacuuuc caaaaaaaaa aaaaaaaaau aa    1302

<210> SEQ ID NO 37
<211> LENGTH: 897
<212> TYPE: DNA
<213> ORGANISM: Nannochloropsis oculata

<400> SEQUENCE: 37

```
atgtcgttcc tcattcgcac tcccgttgac caaatcaagc cctacttctc agaggcggcg    60
caaacccact acactcagct gtttcagcac tttcccatgt tggagcgggt ctattttccc   120
tttgagaaaa atttccatgc agaacccttt gtgaattttg ccaaggcaac atggcctttg   180
ctgcccttgg cgctctgcac ggcgtacgcg ctgatgatcg tcattggcac ccgtgttatg   240
aagaccagag agaaattcga ctggcgaggc cccctcgctt actggaacct gacgcttttcc   300
ctcttctcct tctgcggcat gctccgcacc gtaccccatc tgctcaacaa catcaccacc   360
ttgtcgttcc gcgacaccgt gtgcacgtcc gcggccagga gctacgggga aggggcttcg   420
ggcctatggg tgatgctctt catcttcagc aaaaattccgg aattggttga cacggtctttt   480
attgtcttcc gcaaaagcaa gctgcagttc ctgcattggt accaccacat cactgtcctc   540
ctcttctgct ggcactcgta cgcgacggaa tcctccacgg gcctctactt cgtggcgatg    600
aattactccg tgcatgccat tatgtacggc tactactatt tgatggccat taaagcctgg   660
cctaaatgga ttccggccca ccttattacc gtcgcgcaaa tctcgcaaat ggtcgttgga   720
acttccctct gcattgcctc ctactactac aagaaggacg ttaccctg tgcggtggag     780
tgggagaacg tcacctcggg cgcgcttatg tacggctcgt acctctattt attcagcgaa   840
ttctttgtcc gccgattctt gctctcgtcg ggcaagccca agacgaagac gatttaa     897
```

<210> SEQ ID NO 38
<211> LENGTH: 298
<212> TYPE: PRT
<213> ORGANISM: Nannochloropsis oculata

<400> SEQUENCE: 38

```
Met Ser Phe Leu Ile Arg Thr Pro Val Asp Gln Ile Lys Pro Tyr Phe
1               5                   10                  15

Ser Glu Ala Ala Gln Thr His Tyr Thr Gln Leu Phe Gln His Phe Pro
            20                  25                  30

Met Leu Glu Arg Val Tyr Phe Pro Phe Glu Lys Asn Phe His Ala Glu
        35                  40                  45

Pro Phe Val Asn Phe Ala Lys Ala Thr Trp Pro Leu Leu Pro Leu Ala
    50                  55                  60

Leu Cys Thr Ala Tyr Ala Leu Met Ile Val Ile Gly Thr Arg Val Met
65                  70                  75                  80

Lys Thr Arg Glu Lys Phe Asp Trp Arg Gly Pro Leu Ala Tyr Trp Asn
                85                  90                  95

Leu Thr Leu Ser Leu Phe Ser Phe Cys Gly Met Leu Arg Thr Val Pro
            100                 105                 110

His Leu Leu Asn Asn Ile Thr Thr Leu Ser Phe Arg Asp Thr Val Cys
        115                 120                 125

Thr Ser Ala Ala Arg Ser Tyr Gly Glu Gly Ala Ser Gly Leu Trp Val
    130                 135                 140

Met Leu Phe Ile Phe Ser Lys Ile Pro Glu Leu Val Asp Thr Val Phe
145                 150                 155                 160

Ile Val Phe Arg Lys Ser Lys Leu Gln Phe Leu His Trp Tyr His His
```

```
                   165                 170                 175
Ile Thr Val Leu Leu Phe Cys Trp His Ser Tyr Ala Thr Glu Ser Ser
            180                 185                 190

Thr Gly Leu Tyr Phe Val Ala Met Asn Tyr Ser Val His Ala Ile Met
        195                 200                 205

Tyr Gly Tyr Tyr Tyr Leu Met Ala Ile Lys Ala Trp Pro Lys Trp Ile
    210                 215                 220

Pro Ala His Leu Ile Thr Val Ala Gln Ile Ser Gln Met Val Val Gly
225                 230                 235                 240

Thr Ser Leu Cys Ile Ala Ser Tyr Tyr Lys Lys Asp Gly Tyr Pro
                245                 250                 255

Cys Ala Val Glu Trp Glu Asn Val Thr Ser Gly Ala Leu Met Tyr Gly
            260                 265                 270

Ser Tyr Leu Tyr Leu Phe Ser Glu Phe Phe Val Arg Arg Phe Leu Leu
        275                 280                 285

Ser Ser Gly Lys Pro Lys Thr Lys Thr Ile
    290                 295

<210> SEQ ID NO 39
<211> LENGTH: 2441
<212> TYPE: RNA
<213> ORGANISM: Nannochloropsis oculata

<400> SEQUENCE: 39
aaauuucagc aaaguaauca agauaauaaa caaaaacaau ccuauaaaag gaaaaacaac      60
aggcucucuu ucuuucgucg ucagcagcag cagcaguagc aguagcagca guaacuaagg     120
caagaagcau gucguccuc auucgcacuc ccguugacca aaucaagccc uacuucucag     180
aggcggcgca aacccacuac acucagcugu uucagcacuu ucccauguug gagcgggucu     240
auuuucccuu ugagaaaaau uuccaugcag aacccuuugu gaauuuugcc aaggcaacau     300
ggccuuugcu gcccuuggcg cucugcacgg cguacgcgcu gaugaucguc auuggcaccc     360
guguuaugaa gaccagagag aaauucgacu ggcgaggccc ccucgcuuac uggaaccuga     420
cgcuuucccu cuuucccuuc ugcggcaugc uccgcaccgu accccaucug cucaacaaca     480
ucaccaccuu gucguuccgc gacaccgugu gcacguccgc ggccaggagc uacggggaag     540
gggcuucggg ccuaugggug augcucuuca ucuucagcaa aauuccggaa uugguugaca     600
cggucuuuau ugucuuccgc aaaagcaagc ugcaguuccu gcauggguac caccacauca     660
cuguccuccu cuucugcugg cacucguacg cgacggaauc cuccacgggc cucuacuucg     720
uggcgaugaa uuacuccgug caugccauua guacggcua cuacuauuug auggccauua     780
aagccuggcc uaaauggauu ccggcccacc uuauuaccgu cgcgcaaauc ucgcaaauug     840
ucguuggaac uucccucugc auugccuccu acuacuacaa gaaggacggu uaccccugug     900
cgguggagug ggagaacguc accucggccg cgcuuaugua cggcucguac cucuauuuau     960
ucagcgaauu cuuugucgc cgauucuugc ucucgucggg caagcccaag acgaagacga    1020
uuuaaaggaa gagaagagaa ggaggacagg gcgggaaggg uggaggggu ucucgcgacu    1080
cguuuacggu guugucgug cgcaagcauu ugucuugccu ucgacaagc cguaagcgaa    1140
gacgauuuaa ggagggaagg aggggaggag ggguugauga cauggcgga aaauauaugg    1200
aaagcgggag agcauggug uauauacguc uaaccucuuc ccuuccuuua uuuuuaacu    1260
uaauuuauu cauuuaaaua uuucauuuua auuuauuuau caagugugug ugugacagac    1320
cgcuucaugg gaaucggaca gaaaagaaua aucauaaucu ucuuguuauu uuuauuuuua    1380
```

```
gaguuuguuu caauguagca gaggaaaggg aagagagaaa cggggagcua acggaagag      1440 agaaagucag cagacacaga ggcagcaggg augagagaga gagggagggg auauauuucg      1500
guguauguuc uccaggcuuu guuuucuccg auggacuugu guuuagacgu gcgaguaugg      1560
gcgugagcaa gagacagaga gagagagaaa gagaacgagu gagguuagag auagagaaga      1620
aagaaagaca ggcguuacag ggagaggaaa gaaagaggaa ggagggagga agaagaacac      1680
caacacaagg cagcaggacc cccgacgaga caaaagcaag aagauuaugu guauccucac      1740
aaacaucgga ucgagacggg aagaucuaaa aaagcagaac gaagaaggcg acaagcaagc      1800
acgaaaguag agacagagac gucauccacc augucaucac caaaaacauu ccuccacaca      1860
cguucacugg acagaaaaga aagccuuacg acaaaaucg aggagagaga ggauaagaag      1920
gaagagaggu aaagaagga gggagggag gaggaaggga aggaguaagg gaaggaugag        1980
ccugucaauc cuuuguuuuu ucccaaagaa aagagaagac ggggaaugg acugcuggua      2040 cccguccugu cgaagggcgg aaacugagag gagucuuauu uccucuucuu gugggguagu      2100
agcagcagcu gcaguagcaa ugagaagaau agcgacaucg auucaaauua aagggagagg      2160
caggaacaag aaacgaaagu guuucgcgcu uuccgcaugc acacauacau aaaggcgucg      2220
caugugugug cugcucccuu ugugucauug uuucugccg gcuguggag ggaaagggag        2280 gguggagcga ugguuuggcg uugcgucgag ccgagacuca gcagggguga ggaaggcgaa      2340
cagaccaagg agaagcggac cacacggaca aauuuaaggg accucaauua aagaaaguac      2400
acauccuggu uuacaaaaaa aaaaaaaaaa aaaaaaaaa a                          2441
```

<210> SEQ ID NO 40
<211> LENGTH: 903
<212> TYPE: DNA
<213> ORGANISM: Nannochloropsis oculata

<400> SEQUENCE: 40

```
atggcagtgg ccttgctcga ggtgctgggc aagtacgtgc cttccgagaa ctacacggag       60 cgttttaca cggtgcgcgg gaatgagttc caccaagtct tccaaggctt cccagccctt      120
tctccttttt acatggactg ggagaaaaag tacaatgcgg agaaggtctt ttggttcatc      180
atcgacaact cgtggattcc ctggttctcg ctgtgcgtgt atttgctctt catcttcggc      240
taccccgccc tagccaaacg ttataatata ggctacatct ccgcgcggac acagatggcc      300
agctggaatt tcttgctggc atcgtttagt tggattggag ccatgcgggt ggtacctcac      360
tttttcttcc tgctcaagga cgtgggcttt gaagaggtgc tatgcggggc gccggagccg      420
ctgtatggcg atggcgccgt cgggttctgg atccaggcgt tcgtcttgag caaggtggcc      480
gagctgctcg acacggtctt cgtagtgcta aggcaaaaag atccgatctt cttgcattgg      540
taccaccacg tgaccgtgct tctcttcacc tggttcacgt actctaagga gaatccgggt      600
atcattttca tcgccatgaa ctactcggtc acgccgtca tgtacacgta ctactggctg       660
gccatcgtca agcgcgtccc cgactggttc cccacctggc tcataacgct tgcacaaatc      720
gcccagatga tcgtgggagt gtttgtcgcg tacaactact accgcatcat gtcctcgggg      780
ggctcctgtg ccgtctcggt cgacttgttg tgggcatgcg ggttgatgta ctcgacgtac      840
ctttatttgt tttgtgaatt tgccgtccgg agatacatcc taggcgggag cagcagggg      900 tga                                                                    903
```

<210> SEQ ID NO 41

-continued

```
<211> LENGTH: 300
<212> TYPE: PRT
<213> ORGANISM: Nannochloropsis oculata

<400> SEQUENCE: 41

Met Ala Val Ala Leu Leu Glu Val Leu Gly Lys Tyr Val Pro Ser Glu
1               5                   10                  15

Asn Tyr Thr Glu Arg Phe Tyr Thr Val Arg Gly Asn Glu Phe His Gln
            20                  25                  30

Val Phe Gln Gly Phe Pro Ala Leu Ser Pro Phe Tyr Met Asp Trp Glu
        35                  40                  45

Lys Lys Tyr Asn Ala Glu Lys Val Phe Trp Phe Ile Ile Asp Asn Ser
 50                  55                  60

Trp Ile Pro Trp Phe Ser Leu Cys Val Tyr Leu Leu Phe Ile Phe Gly
65                  70                  75                  80

Tyr Pro Ala Leu Ala Lys Arg Tyr Asn Ile Gly Tyr Ile Ser Ala Arg
                85                  90                  95

Thr Gln Met Ala Ser Trp Asn Phe Leu Leu Ala Ser Phe Ser Trp Ile
            100                 105                 110

Gly Ala Met Arg Val Val Pro His Phe Phe Phe Leu Leu Lys Asp Val
        115                 120                 125

Gly Phe Glu Glu Val Leu Cys Gly Ala Pro Glu Pro Leu Tyr Gly Asp
    130                 135                 140

Gly Ala Val Gly Phe Trp Ile Gln Ala Phe Val Leu Ser Lys Val Ala
145                 150                 155                 160

Glu Leu Leu Asp Thr Val Phe Val Val Leu Arg Gln Lys Asp Pro Ile
                165                 170                 175

Phe Leu His Trp Tyr His His Val Thr Val Leu Leu Phe Thr Trp Phe
            180                 185                 190

Thr Tyr Ser Lys Glu Asn Pro Gly Ile Ile Phe Ile Ala Met Asn Tyr
        195                 200                 205

Ser Val His Ala Val Met Tyr Thr Tyr Tyr Trp Leu Ala Ile Val Lys
    210                 215                 220

Arg Val Pro Asp Trp Phe Pro Thr Trp Leu Ile Thr Leu Ala Gln Ile
225                 230                 235                 240

Ala Gln Met Ile Val Gly Val Phe Val Ala Tyr Asn Tyr Tyr Arg Ile
                245                 250                 255

Met Ser Ser Gly Gly Ser Cys Ala Val Ser Val Asp Leu Leu Trp Ala
            260                 265                 270

Cys Gly Leu Met Tyr Ser Thr Tyr Leu Tyr Leu Phe Cys Glu Phe Ala
        275                 280                 285

Val Arg Arg Tyr Ile Leu Gly Gly Ser Ser Arg Gly
    290                 295                 300

<210> SEQ ID NO 42
<211> LENGTH: 1053
<212> TYPE: RNA
<213> ORGANISM: Nannochloropsis oculata

<400> SEQUENCE: 42
cucaauuuuc agcaaaguaa ucaagauaau aacaaaaaca auccauaaaa aggaaaaaca      60
acaggagcac ucccagcaga cgcagcagca gcaacagccg uagcaggagc aggaggaucg     120
gcgguggagc agcaguagua ucagucaugg caguggccuu gcucgaggug cugggcaagu     180
acgugccuuc cgagaacuac acggagcguu uuuacacggu gcgcgggaau gaguccacc      240
```

| | |
|---|---|
| aagucuucca aggcuucccca gcccuuucuc cuuuuuacau ggacugggag aaaaaguaca | 300 |
| augcggagaa ggucuuuugg uucaucaucg acaacucgug gauucccugg uucucgcugu | 360 |
| gcguguauuu gcucuucauc uucggcuacc ccgcccuagc caaacguuau aauauaggcu | 420 |
| acaucuccgc gcggacacag auggccagcu ggaauuucuu gcuggcaucg uuuaguugga | 480 |
| uuggagccau gcgggguggua ccucacuuuu ucuuccugcu caaggacgug ggcuuugaag | 540 |
| aggugcuaug cggggcgccg gagccgcugu auggcgaugg cgccgucggg uucuggaucc | 600 |
| aggcguucgu cuugagcaag guggccgagc ugcucgacac ggucuucgua gugcuaaggc | 660 |
| aaaaagaucc gaucuucuug cauugguacc accacgugac cgugcuucuc uuccaccggu | 720 |
| ucacguacuc uaaggagaau ccggguauca uuuucaucgc caugaacuac ucgguccacg | 780 |
| ccgucaugua cacguacuac uggcuggcca ucgucaagcg cguccccgac ugguucccca | 840 |
| ccuggcucau aacgcuugca caaucgcccc agaugaucgu gggagugjuuu gucgcguaca | 900 |
| acuacuaccg caucaugucc ucgggggggcu ccugugccgu cucggucgac uuguuguggg | 960 |
| caugcggguu gauguacucg acguaccuuu auuuguuuug ugaauuugcc guccggagau | 1020 |
| acauccuagg cgggagcagc aggggguugag uga | 1053 |

<210> SEQ ID NO 43
<211> LENGTH: 1485
<212> TYPE: DNA
<213> ORGANISM: Nannochloropsis oculata

<400> SEQUENCE: 43

| | |
|---|---|
| atgcuuucag tttatttccc cgctatcttg tacgcgctca tcgccgtgct tgttgcccag | 60 |
| ctattcgtag acgtttcgga ccacggacgg gaaatcaagg aattcgtaca catggtcgag | 120 |
| tccgttaaga ccgtcggcct ctcccttctc atgaaagtca cccccctctt cattctcggc | 180 |
| ctctggtggg tcaccaataa acaccgaccc atctacctgg tcaacttcgc cacctacaag | 240 |
| ccccccccagt cctggaaagt gagccaagcc gacgtgatgg agatcatgaa acgcaaaggc | 300 |
| tgcttcaccg agaaatccct tggagttcatg gagaggattc tgaccaacag tggcacgggt | 360 |
| cctagtacag cctggccgcc cgggatcctc aagttgttga ggaggaaggt ggagacggag | 420 |
| gaggggggaag aggtggaggg attggatgtg gatgaggagg acgaggtgga tgtgacggcg | 480 |
| gaccagacgg aggaggggggc gagggaggag gcagaggcag tgatttatgg ggcagtgcag | 540 |
| gatgtattgg acaagaccgg agtcaaggcg aaagagattg atattttgat catcaattgc | 600 |
| tctctcttct cgccgacccc gagcctgtgt gccatggtag cccatcattt ccagatgcgg | 660 |
| caggacgttt tgtcgtttaa tcttgcgggc atggggtgct ccgccggtct ggtgagcatt | 720 |
| gacctggcca acgactgtt ggaatcccga ccacgaagcc gggccctggt ggtgagcacg | 780 |
| gaaaatttga cgcaggcgtt ttaccacggc aacgaccgag ccttcctctt gcagaacacc | 840 |
| ttgtttcgat gtgaggggc cgcggtcttg ctctcgaatc gagtccagga cggcttgagg | 900 |
| gccaagttca agctgttgca tgtcgtccgg tcccagggca cggacaagca ttcgtacgac | 960 |
| gctgtctact ccacgcaaga cgacgaaggc gagaagggtg tgcgtctctc gaaggatatt | 1020 |
| gtgaaggtcg ctggtcgact gatggaaaag aacctcactg ccattggtcc caaagtcctc | 1080 |
| tcggtgggag agatgggcaa ggcgattgtg acactggtgg ccaggaaggt cagtcatgcc | 1140 |
| atgcgccgtt tcctcaaggc caggggtggg tcgacattgc agcacgccgt gcctgaggtg | 1200 |
| caggtctaca ccccgaattt tagccgatgc gtggattttt actgcctccc tccctcccctc | 1260 |
| gcctcggacg aacgggatcg aaaagatttg cagttgttgc ccgagcactt ggagccgtcg | 1320 | aggatgacgt tgtatgatta cggtaatacc agtagctcgt ccatatggta cgagatggag    1380 tatatctgcg aaaagatgga tttgaggcgg gggcagcggg tgttgcaggt ggcgtttggg    1440 agtgggttta agtgcaatag tgccgtatgg gtaagcttgc acgtg                    1485

<210> SEQ ID NO 44
<211> LENGTH: 495
<212> TYPE: PRT
<213> ORGANISM: Nannochloropsis oculata

<400> SEQUENCE: 44

```
Met Leu Ser Val Tyr Phe Pro Ala Ile Leu Tyr Ala Leu Ile Ala Val
1               5                   10                  15

Leu Val Ala Gln Leu Phe Val Asp Val Ser Asp His Gly Arg Glu Ile
            20                  25                  30

Lys Glu Phe Val His Met Val Glu Ser Val Lys Thr Val Gly Leu Ser
        35                  40                  45

Leu Leu Met Lys Val Thr Pro Leu Phe Ile Leu Gly Leu Trp Trp Val
    50                  55                  60

Thr Asn Lys His Arg Pro Ile Tyr Leu Val Asn Phe Ala Thr Tyr Lys
65                  70                  75                  80

Pro Pro Gln Ser Trp Lys Val Ser Gln Ala Asp Val Met Glu Ile Met
                85                  90                  95

Lys Arg Lys Gly Cys Phe Thr Glu Lys Ser Leu Glu Phe Met Glu Arg
            100                 105                 110

Ile Leu Thr Asn Ser Gly Thr Gly Pro Ser Thr Ala Trp Pro Pro Gly
        115                 120                 125

Ile Leu Lys Leu Leu Arg Arg Lys Val Glu Thr Glu Glu Gly Glu Glu
    130                 135                 140

Val Glu Gly Leu Asp Val Asp Glu Asp Glu Val Asp Val Thr Ala
145                 150                 155                 160

Asp Gln Thr Glu Glu Gly Ala Arg Glu Glu Ala Glu Ala Val Ile Tyr
                165                 170                 175

Gly Ala Val Gln Asp Val Leu Asp Lys Thr Gly Val Lys Ala Lys Glu
            180                 185                 190

Ile Asp Ile Leu Ile Ile Asn Cys Ser Leu Phe Ser Pro Thr Pro Ser
        195                 200                 205

Leu Cys Ala Met Val Ala His His Phe Gln Met Arg Gln Asp Val Leu
    210                 215                 220

Ser Phe Asn Leu Ala Gly Met Gly Cys Ser Ala Gly Leu Val Ser Ile
225                 230                 235                 240

Asp Leu Ala Lys Arg Leu Leu Glu Ser Arg Pro Arg Ser Arg Ala Leu
                245                 250                 255

Val Val Ser Thr Glu Asn Leu Thr Gln Ala Phe Tyr His Gly Asn Asp
            260                 265                 270

Arg Ala Phe Leu Leu Gln Asn Thr Leu Phe Arg Cys Gly Gly Ala Ala
        275                 280                 285

Val Leu Leu Ser Asn Arg Val Gln Asp Gly Leu Arg Ala Lys Phe Lys
    290                 295                 300

Leu Leu His Val Arg Ser Gln Gly Thr Asp Lys His Ser Tyr Asp
305                 310                 315                 320

Ala Val Tyr Ser Thr Gln Asp Asp Glu Gly Glu Lys Gly Val Arg Leu
                325                 330                 335

Ser Lys Asp Ile Val Lys Val Ala Gly Arg Leu Met Glu Lys Asn Leu
```

|   |   |   | 340 |   |   | 345 |   |   | 350 |   |   |
|---|---|---|---|---|---|---|---|---|---|---|---|
| Thr | Ala | Ile | Gly | Pro | Lys | Val | Leu | Ser | Val | Gly | Glu | Met | Gly | Lys | Ala |

Thr Ala Ile Gly Pro Lys Val Leu Ser Val Gly Glu Met Gly Lys Ala
    355                 360                 365

Ile Val Thr Leu Val Ala Arg Lys Val Ser His Ala Met Arg Arg Phe
370                 375                 380

Leu Lys Ala Arg Gly Trp Ser Thr Leu Gln His Ala Val Pro Glu Val
385                 390                 395                 400

Gln Val Tyr Thr Pro Asn Phe Ser Arg Cys Val Asp Phe Tyr Cys Leu
            405                 410                 415

Pro Pro Ser Leu Ala Ser Asp Glu Arg Asp Arg Lys Asp Leu Gln Leu
                420                 425                 430

Leu Pro Glu His Leu Glu Pro Ser Arg Met Thr Leu Tyr Asp Tyr Gly
            435                 440                 445

Asn Thr Ser Ser Ser Ile Trp Tyr Glu Met Glu Tyr Ile Cys Glu
    450                 455                 460

Lys Met Asp Leu Arg Arg Gly Gln Arg Val Leu Gln Val Ala Phe Gly
465                 470                 475                 480

Ser Gly Phe Lys Cys Asn Ser Ala Val Trp Val Ser Leu His Val
                485                 490                 495

<210> SEQ ID NO 45
<211> LENGTH: 1755
<212> TYPE: RNA
<213> ORGANISM: Nannochloropsis oculata

<400> SEQUENCE: 45
auuucuccuc cucccucccu uccuccugcc cuccucccuc gccuccucca ccuccuccuc     60
cccucccucc acgccgaccg cccacggguu acgacacaau acccucuccu ccucccuggc    120
ggguucugcg ggcgggcugu ccuaugaaga ccaccucucc gccucuuccu accgcgcacg    180
acccucccga uuccuaaagc uaguaaauug guggcacaug cuuucaguuu auuucccgc    240 uaucuuguac gcgcucaucg ccgugcugu ugcccagcua uucguagacg uucggaccaa    300
cggacgggaa ucaaggaau cguacacau ggucgagucc guuaagaccg ucggccucuc    360
ccuucucaug aaagucaccc cccucuucau ucucggccuc uggugggguca ccaauaaaca    420 ccgacccauc uaccuggnca acuucgccac cuacaagccc ccccaguccu ggaaagugag    480
ccaagccgac gugauggaga ucaugaaacg caaaggcugc uucaccgaga auccuugga    540 guucauggag aggauucuga ccaacagugg cacgggnccu aguacagccu ggccgcccgg    600
gauccucaag uuguuagga ggaaggugga acggagagag ggggaagagg uggagggauu    660
ggaugnggau gaggaggacg agguggaugu gacggcggac cagacggagg agggggcgag    720 ggaggagca gagcagaguga uuuauggggc agugcaggau guauuggaca agaccggagu    780
caaggcgaaa gagauugaua uuuugaucau caauugcucu cucuucucgc cgaccccgag    840
ccugugugcc auguagcccc aucauuucca gaugcggcag gacguuuugu cguuaaucu    900 ugcgggcaug gggugcuccg ccggucuggu gagcauugac cuggcaaac gacuguugga    960 aucccgacca cgaagccggg cccuggguggu gagcacggaa aauuugacgc aggcguuua   1020 ccacggcaac gaccgagccu uccucuugca gaacaccuug uuucgaugug aggggccgc   1080 ggucuugcuc ucgaaucgag uccaggacgg cuugagggcc aaguucaagc uguugcaugu   1140 cguccgguccc cagggcacgg acaagcauuc uacgcgcu gucuaccca cgcaagacga   1200 cgaaggcgag aaggguuugc gucucucgaa ggauauugug aaggucgcug gucgacugau   1260

| | |
|---|---:|
| ggaaaagaac ucacugcca uuggucccaa aguccucucg gugggagaga ugggcaaggc | 1320 |
| gauugugaca cugguggcca ggaaggucag ucaugccaug cgccguuucc ucaaggccag | 1380 |
| gggguggucg acauugcagc acgccgugcc ugaggugcag gucuacaccc cgaauuuuag | 1440 |
| ccgaugcgug gauuuuuacu gccucccucc cucccucgcc ucggacgaac gggaucgaaa | 1500 |
| agauuugcag uuguugcccg agcacuugga gccgucgagg augacguugu augauuacgg | 1560 |
| uaauaccagu agcucgucca uauggυacga gauggaguau aucugcgaaa agauggauuu | 1620 |
| gaggcggggg cagcgggugu ugcaggugge guuugggagu ggguuaagu gcaauagugc | 1680 |
| cguaugggua agcuugcacg uguagguacg aggaggagaa gggauagaaa aaaaaaaaa | 1740 |
| aaaaaaaaaa aaaaa | 1755 |

<210> SEQ ID NO 46
<211> LENGTH: 966
<212> TYPE: DNA
<213> ORGANISM: Nannochloropsis oculata

<400> SEQUENCE: 46

| | |
|---|---:|
| atgcccaagc ttccagagat ctctaccatc tccaaactct tatgggcgga cccttctaag | 60 |
| attgtccctt acaaaagcat cccggacaat gtgcccttca cacagctctt ccagcattac | 120 |
| ccggtcttag atcccttgta cacccagtat gagaagaact tctatgccag tacgtacgtc | 180 |
| aaatttgcgc aagacacctg gccggtcctt ccccttgcct tgtgtggagt gtacgcgctg | 240 |
| atgatcatcc ttggcaccaa agtcatggcc tctcggccca agcacgagtg gaagacggcc | 300 |
| ttggcgtgct ggaacctgat gttgagcatt ttttccttct gtgggatggt taggacggta | 360 |
| ccgcatttgg tgcacaacgt ggtgacgttg cccttcaagg cacgatctg ccggcaccca | 420 |
| gcggaaacgt acgggaagg agcctgcggc atgtgggtga tgcttttat ctttagcaaa | 480 |
| gtccccgagt tagtggacac ggtctttatc gtcttccgca aaagcaagct gcagttcctc | 540 |
| cactggtacc accacatcac tgtcctcctc ttctgctggc actcctacgc cgtcacctcc | 600 |
| tccacaggcc tctacttcgt ggcgatgaac tactccgtgc atgccatcat gtacgcctac | 660 |
| tactacctga ccgctgttgg cgcctggccc atatggatcc cccctccat catcaccgtc | 720 |
| gcgcagatct cgcaaatgat cgtcggtgtt gggatctgtg cttcttcctt ttacttcctg | 780 |
| tacacggacc ctaagcattg tcaggtgaag catcagaatg tgtatgcggg ggcgttgatg | 840 |
| tatggcagct acctatactt gttctgtgat tttttgtgc gacgtttctt gagaggaggc | 900 |
| aaaccaaggg tgggagagga gaagagcgcg gtgttgacca tggccaagaa aatcaaggcg | 960 |
| atgtaa | 966 |

<210> SEQ ID NO 47
<211> LENGTH: 321
<212> TYPE: PRT
<213> ORGANISM: Nannochloropsis oculata

<400> SEQUENCE: 47

Met Pro Lys Leu Pro Glu Ile Ser Thr Ile Ser Lys Leu Leu Trp Ala
1               5                   10                  15

Asp Pro Ser Lys Ile Val Pro Tyr Lys Ser Ile Pro Asp Asn Val Pro
            20                  25                  30

Phe Thr Gln Leu Phe Gln His Tyr Pro Val Leu Asp Pro Leu Tyr Thr
        35                  40                  45

Gln Tyr Glu Lys Asn Phe Tyr Ala Ser Thr Tyr Val Lys Phe Ala Gln
    50                  55                  60

Asp Thr Trp Pro Val Leu Pro Leu Ala Leu Cys Gly Val Tyr Ala Leu
 65                  70                  75                  80

Met Ile Ile Leu Gly Thr Lys Val Met Ala Ser Arg Pro Lys His Glu
                 85                  90                  95

Trp Lys Thr Ala Leu Ala Cys Trp Asn Leu Met Leu Ser Ile Phe Ser
            100                 105                 110

Phe Cys Gly Met Val Arg Thr Val Pro His Leu Val His Asn Val Val
        115                 120                 125

Thr Leu Pro Phe Lys Asp Thr Ile Cys Arg His Pro Ala Glu Thr Tyr
130                 135                 140

Gly Glu Gly Ala Cys Gly Met Trp Val Met Leu Phe Ile Phe Ser Lys
145                 150                 155                 160

Val Pro Glu Leu Val Asp Thr Val Phe Ile Val Phe Arg Lys Ser Lys
                165                 170                 175

Leu Gln Phe Leu His Trp Tyr His Ile Thr Val Leu Leu Phe Cys
            180                 185                 190

Trp His Ser Tyr Ala Val Thr Ser Ser Thr Gly Leu Tyr Phe Val Ala
        195                 200                 205

Met Asn Tyr Ser Val His Ala Ile Met Tyr Ala Tyr Tyr Tyr Leu Thr
210                 215                 220

Ala Val Gly Ala Trp Pro Ile Trp Ile Pro Pro Ser Ile Ile Thr Val
225                 230                 235                 240

Ala Gln Ile Ser Gln Met Ile Val Gly Val Gly Ile Cys Ala Ser Ser
                245                 250                 255

Phe Tyr Phe Leu Tyr Thr Asp Pro Lys His Cys Gln Val Lys His Gln
            260                 265                 270

Asn Val Tyr Ala Gly Ala Leu Met Tyr Gly Ser Tyr Leu Tyr Leu Phe
        275                 280                 285

Cys Asp Phe Phe Val Arg Arg Phe Leu Arg Gly Gly Lys Pro Arg Val
290                 295                 300

Gly Glu Glu Lys Ser Ala Val Leu Thr Met Ala Lys Lys Ile Lys Ala
305                 310                 315                 320

Met

<210> SEQ ID NO 48
<211> LENGTH: 1689
<212> TYPE: RNA
<213> ORGANISM: Nannochloropsis oculata

<400> SEQUENCE: 48
aauuuucagc aaaguaauca agauaauaac aaaacaauc cucuaaaagg aaaacaacag      60
gcucuccuuc aucgucgaga gaggauaacc gagcccgcgc cgcgcaggaa gaggaggagc    120
agcagcacuu cucacuuacg cagcauugga agaagaugcc caagcuucca gagaucucua    180
ccaucuccaa acucuuaugg gcggacccuu cuaagauugu cccuuacaaa agcaucccgg    240
acaaugugcc cuucacacag cucuuccagc auuacccggu cuuagauccc uuguacaccc    300
aguaugagaa gaacuucuau gccaguacgu acgucaaauu ugcgcaagac accuggccgg    360
uccuuccccu ugccuugugu ggaguguacg cgcugaugau cauccuuggc accaaaguca    420
uggcucucg gcccaagcac gagugaaga cggccuuggc gugcuggaac cugauguuga    480
gcauuuuuc cuucuguggg augguuagga cgguaccgca uuuggugcac aacguggua    540
cguugcccuu caaggacacg aucugccggc acccagcgga aacguacggg gaaggagccu    600

| | |
|---|---:|
| gcggcaugug ggugaugcuu uuuaucuuua gcaaaguccc cgaguuagug gacacggucu | 660 |
| uuaucgucuu ccgcaaaagc aagcugcagu uccuccacug guaccaccac aucacugucc | 720 |
| uccucuucug cuggcacucc uacgccguca ccuccuccac aggccucuac uucguggcga | 780 |
| ugaacuacuc cgugcaugcc aucauguacg ccuacuacua ccugaccgcu guuggcgccu | 840 |
| ggcccauaug gauccccccc uccaucauca ccgucgcgca gaucucgcaa augaucgucg | 900 |
| guguugggau cugugcuucu uccuuuuacu uccuguacac ggacccuaag cauugucagg | 960 |
| ugaagcauca gaauguguau gcgggggcgu ugauguaugg cagcuaccua uacuuguucu | 1020 |
| gugauuuuuu ugugcgacgu uucuugagag gaggcaaacc aaggguggga gaggagaaga | 1080 |
| gcgcggυguu gaccauggcc aagaaaauca aggcgaugua aggaaggugu aaugugaggg | 1140 |
| uggaagggaa ggaagaaagg agggagggag ggaaggaggg acggucgca gggccaggcu | 1200 |
| uuguuuugga gacaggauuc gugugugugu gaagcguauc uucacaagaa uggaccgaca | 1260 |
| gaacgaaggg agggagggaa ggagauaugg agggagagau agaacgagaa cugcaguagc | 1320 |
| aggcagacca agguaaauag gaaggaagcu aaaaaaucgc ggcacgauga accacgagag | 1380 |
| cacagcgccc accguggaau ggaaaggaga agaaugaga gagcgacgag acgagcgggg | 1440 |
| aguggagaag gaaaagaag gaggaacagc ucaaggagag uccgccguga uugugugagc | 1500 |
| guaaauacgu uguugaccug ucggcgcaug cucccccccc ccccucaccu cucuugugug | 1560 |
| uauagggaac agcgauaaug caggacagug ggagacggag gacgaacuua agaaauugau | 1620 |
| gagacacaga ucacaacgaa ugaucgcaaa gaaagaaaca aaaccaaaa aaaaaaaaaa | 1680 |
| aaaaaaaaa | 1689 |

<210> SEQ ID NO 49
<211> LENGTH: 1071
<212> TYPE: DNA
<213> ORGANISM: Nannochloropsis oculata

<400> SEQUENCE: 49

| | |
|---|---:|
| atgggtctcg acgtgaagga gaaagcgctc ctgagctttg tagccaaggt gacgctgccg | 60 |
| ctcgtggccg tgctggggcc gctcgtggct tacactggca tttgggaaca acctttgtgg | 120 |
| ttcttggggc tgatgacggc gggcgtgtac actgtcaagc tcttgtccta cgtggccgag | 180 |
| cgccttacgc gtcgacccaa ggacatggtg ggaagttacg ggaagtgggc catcgtgacg | 240 |
| ggcgccacct cgggcattgg ggaagcattt gcgcatgagc tggccgggcg ggggatgaac | 300 |
| gtgctgatca ttagtcgcac gccggctaag ctcgaaaaga ccagggcaga gattctccgg | 360 |
| cgtgccccgg aaggcgtgga ggtggaagtg ttggcatacg atttacccg catgggggag | 420 |
| gctgatgcat tttatgcccg cttgagtcaa gtggcggtgg cgctgcacaa gaagggcggg | 480 |
| attggcatgc tcgtcaacaa cgtggggacc aatgtggaaa tcccggagtt ctgcacgag | 540 |
| ctaccggaaa gcgagattct aaacatagtg cgcgtaaatg tggaggggac agtgcgcatg | 600 |
| acacggggca ttttgccctt aatggctgaa cgacgcatgg gtgccattgt caatgtctcg | 660 |
| tcaggctcgg ggaatcatcc cacccccctc ctctccacct acgcagccac caaggctttc | 720 |
| atcaacgaat tctctcgctc cctgcaccac gaggccaaac acgtgggcgt cgacgtcctg | 780 |
| ctcatcaccc cctactacgt ttccaccccc ggcatgtaca ataagccgcc cggcctcctc | 840 |
| aattgctcgg cgcaacgcct ggttcaagac acgctggccg tgctgggacg gtacgacatg | 900 |
| gcgtacccctt acatcgcaca cgctgtcctg ggcaccctga tggacaaata ctgggccacg | 960 |
| cccgcagcgc tattcaagtc catgaacaaa acccggatgc gttccttggc caagaagcaa | 1020 |

```
gcgcaaaaac aggagacctc atcggcgcag gagatcaagg ccgctgcgta g          1071
```

<210> SEQ ID NO 50
<211> LENGTH: 356
<212> TYPE: PRT
<213> ORGANISM: Nannochloropsis oculata

<400> SEQUENCE: 50

| Met | Gly | Leu | Asp | Val | Lys | Glu | Lys | Ala | Leu | Leu | Ser | Phe | Val | Ala | Lys |
|---|---|---|---|---|---|---|---|---|---|---|---|---|---|---|---|
| 1 | | | | 5 | | | | | 10 | | | | | 15 | |

| Val | Thr | Leu | Pro | Leu | Val | Ala | Val | Leu | Gly | Pro | Leu | Val | Ala | Tyr | Thr |
|---|---|---|---|---|---|---|---|---|---|---|---|---|---|---|---|
| | | | 20 | | | | | 25 | | | | | 30 | | |

| Gly | Ile | Trp | Glu | Gln | Pro | Leu | Trp | Phe | Leu | Gly | Leu | Met | Thr | Ala | Gly |
|---|---|---|---|---|---|---|---|---|---|---|---|---|---|---|---|
| | | | 35 | | | | | 40 | | | | | 45 | | |

| Val | Tyr | Thr | Val | Lys | Leu | Leu | Ser | Tyr | Val | Ala | Glu | Arg | Leu | Thr | Arg |
|---|---|---|---|---|---|---|---|---|---|---|---|---|---|---|---|
| | 50 | | | | | 55 | | | | | 60 | | | | |

| Arg | Pro | Lys | Asp | Met | Val | Gly | Ser | Tyr | Gly | Lys | Trp | Ala | Ile | Val | Thr |
|---|---|---|---|---|---|---|---|---|---|---|---|---|---|---|---|
| 65 | | | | | 70 | | | | | 75 | | | | | 80 |

| Gly | Ala | Thr | Ser | Gly | Ile | Gly | Glu | Ala | Phe | Ala | His | Glu | Leu | Ala | Gly |
|---|---|---|---|---|---|---|---|---|---|---|---|---|---|---|---|
| | | | | 85 | | | | | 90 | | | | | 95 | |

| Arg | Gly | Met | Asn | Val | Leu | Ile | Ile | Ser | Arg | Thr | Pro | Ala | Lys | Leu | Glu |
|---|---|---|---|---|---|---|---|---|---|---|---|---|---|---|---|
| | | | 100 | | | | | 105 | | | | | 110 | | |

| Lys | Thr | Arg | Ala | Glu | Ile | Leu | Arg | Arg | Ala | Pro | Glu | Gly | Val | Glu | Val |
|---|---|---|---|---|---|---|---|---|---|---|---|---|---|---|---|
| | | 115 | | | | | 120 | | | | | 125 | | | |

| Glu | Val | Leu | Ala | Tyr | Asp | Phe | Thr | Arg | Met | Gly | Glu | Ala | Asp | Ala | Phe |
|---|---|---|---|---|---|---|---|---|---|---|---|---|---|---|---|
| | 130 | | | | | 135 | | | | | 140 | | | | |

| Tyr | Ala | Arg | Leu | Ser | Gln | Val | Ala | Val | Ala | Leu | His | Lys | Lys | Gly | Gly |
|---|---|---|---|---|---|---|---|---|---|---|---|---|---|---|---|
| 145 | | | | | 150 | | | | | 155 | | | | | 160 |

| Ile | Gly | Met | Leu | Val | Asn | Asn | Val | Gly | Thr | Asn | Val | Glu | Ile | Pro | Glu |
|---|---|---|---|---|---|---|---|---|---|---|---|---|---|---|---|
| | | | | 165 | | | | | 170 | | | | | 175 | |

| Phe | Leu | His | Glu | Leu | Pro | Glu | Ser | Glu | Ile | Leu | Asn | Ile | Val | Arg | Val |
|---|---|---|---|---|---|---|---|---|---|---|---|---|---|---|---|
| | | | 180 | | | | | 185 | | | | | 190 | | |

| Asn | Val | Glu | Gly | Thr | Val | Arg | Met | Thr | Arg | Gly | Ile | Leu | Pro | Leu | Met |
|---|---|---|---|---|---|---|---|---|---|---|---|---|---|---|---|
| | | 195 | | | | | 200 | | | | | 205 | | | |

| Ala | Glu | Arg | Arg | Met | Gly | Ala | Ile | Val | Asn | Val | Ser | Ser | Gly | Ser | Gly |
|---|---|---|---|---|---|---|---|---|---|---|---|---|---|---|---|
| | 210 | | | | | 215 | | | | | 220 | | | | |

| Asn | His | Pro | Thr | Pro | Leu | Leu | Ser | Thr | Tyr | Ala | Ala | Thr | Lys | Ala | Phe |
|---|---|---|---|---|---|---|---|---|---|---|---|---|---|---|---|
| 225 | | | | | 230 | | | | | 235 | | | | | 240 |

| Ile | Asn | Glu | Phe | Ser | Arg | Ser | Leu | His | His | Glu | Ala | Lys | His | Val | Gly |
|---|---|---|---|---|---|---|---|---|---|---|---|---|---|---|---|
| | | | | 245 | | | | | 250 | | | | | 255 | |

| Val | Asp | Val | Leu | Leu | Ile | Thr | Pro | Tyr | Tyr | Val | Ser | Thr | Pro | Gly | Met |
|---|---|---|---|---|---|---|---|---|---|---|---|---|---|---|---|
| | | | 260 | | | | | 265 | | | | | 270 | | |

| Tyr | Asn | Lys | Pro | Pro | Gly | Leu | Leu | Asn | Cys | Ser | Ala | Gln | Arg | Leu | Val |
|---|---|---|---|---|---|---|---|---|---|---|---|---|---|---|---|
| | | 275 | | | | | 280 | | | | | 285 | | | |

| Gln | Asp | Thr | Leu | Ala | Val | Leu | Gly | Arg | Tyr | Asp | Met | Ala | Tyr | Pro | Tyr |
|---|---|---|---|---|---|---|---|---|---|---|---|---|---|---|---|
| | 290 | | | | | 295 | | | | | 300 | | | | |

| Ile | Ala | His | Ala | Val | Leu | Gly | Thr | Leu | Met | Asp | Lys | Tyr | Trp | Ala | Thr |
|---|---|---|---|---|---|---|---|---|---|---|---|---|---|---|---|
| 305 | | | | | 310 | | | | | 315 | | | | | 320 |

| Pro | Ala | Ala | Leu | Phe | Lys | Ser | Met | Asn | Lys | Thr | Arg | Met | Arg | Ser | Leu |
|---|---|---|---|---|---|---|---|---|---|---|---|---|---|---|---|
| | | | | 325 | | | | | 330 | | | | | 335 | |

| Ala | Lys | Lys | Gln | Ala | Gln | Lys | Gln | Glu | Thr | Ser | Ser | Ala | Gln | Glu | Ile |
|---|---|---|---|---|---|---|---|---|---|---|---|---|---|---|---|
| | | | 340 | | | | | 345 | | | | | 350 | | |

| Lys | Ala | Ala | Ala |
|---|---|---|---|
| | | 355 | |

<210> SEQ ID NO 51
<211> LENGTH: 1304
<212> TYPE: RNA
<213> ORGANISM: Nannochloropsis oculata

<400> SEQUENCE: 51

| | | | | | |
|---|---|---|---|---|---|
| aauuuucagc | aaaguaauca | agauaauaaa | caaaaacaau | ccuaaaaagg | aaaaacaaca | 60 |
| gacaggcaga | cacucaacga | ccaaaggaaa | augggucucg | acgugaagga | gaaagcgcuc | 120 |
| cugagcuuug | uagccaaggu | gacgcugccg | cucguggccg | ugcuggggcc | gcucguggcu | 180 |
| uacacuggca | uuugggaaca | accuuugugg | ucuuggggc | ugaugacggc | gggcguguac | 240 |
| acugucaagc | ucuuguccua | cguggccgag | cgccuuacgc | gucgacccaa | ggacaugguq | 300 |
| ggaaguuacg | ggaagugggc | caucgugacg | ggcgccaccu | cgggcauugg | ggaagcauuu | 360 |
| gcgcaugagc | uggccgggcg | ggggaugaac | gugcugauca | uuagucgcac | gccggcuaag | 420 |
| cucgaaaaga | ccagggcaga | gauucuccgg | cgugccccgg | aaggcgugga | ggugaagug | 480 |
| uuggcauacg | auuuuacccg | cauggggagg | gcugaugcau | uuuaugcccg | cuugagucaa | 540 |
| guggcggugc | cgcugcacaa | gaagggcggg | auuggcaugc | ucgucaacaa | cguggggacc | 600 |
| aaugguggaaa | ucccggaguu | ucugcacgag | cuaccggaaa | gcgagauucu | aaacauagug | 660 |
| cgcguaaaug | uggaggggac | agugcgcaug | acacggggca | uuuugcccuu | aauggcugaa | 720 |
| cgacgcaugg | gugccauugu | caaugucucg | ucaggcucgg | ggaaucaucc | caccccccuc | 780 |
| cucuccaccu | acgcagccac | caaggcuuuc | aucaacgaau | ucucucgcuc | ccugcaccac | 840 |
| gaggccaaac | acgugggcgu | cgacguccug | cucaucaccc | ccuacuacgu | uuccaccccc | 900 |
| ggcauguaca | auaagccgcc | cggccuccuc | aauugcucgg | cgcaacgccu | gguucaagac | 960 |
| acgcuggccg | ugcuggacg | guacgacaug | gcguacccuu | acaucgcaca | cgcuguccug | 1020 |
| ggcacccuga | uggacaaaua | cugggccacg | cccgcagcgc | uauucaaguc | caugaacaaa | 1080 |
| acccggaugc | guuccuuggc | caagaagcaa | gcgcaaaaac | aggagaccuc | aucggcgcag | 1140 |
| gagaucaagg | ccgcgcgcua | gggaggucgu | gugugggcga | ggguugguu | cugguguuua | 1200 |
| gaaaugagca | uuacauguac | cagaaggaaa | augccucggc | aaauuucuca | aagaggauua | 1260 |
| agcaaaauua | uaugacuacg | cacauaagaa | aaaaaaaaaa | aaaa | | 1304 |

<210> SEQ ID NO 52
<211> LENGTH: 978
<212> TYPE: DNA
<213> ORGANISM: Nannochloropsis oculata

<400> SEQUENCE: 52

| | | | | | |
|---|---|---|---|---|---|
| atggcatcta | aaggtggcaa | tttggcggtg | gagctggtgg | aggcgctcaa | ggggcagcct | 60 |
| ttggcgctcc | aggtcttggc | cggggtgggg | gctttgctgg | tgctcaagtt | tgtgctcggg | 120 |
| gcggtccagg | ccttctaccg | tttcttcctt | cgccgggca | agaatctgaa | gaagtttggt | 180 |
| gactgggccg | tggtgacagg | cgcgacagac | ggcattggca | aggcgtatgc | attcgagttg | 240 |
| gccaggcaag | ggctgagctt | gttgttgatt | tcccgtacgg | agtccaagct | caaggacacg | 300 |
| gccgcggaaa | tctcggccaa | gtaccccaag | gtccaggtgc | aagtcctcag | catcgacttc | 360 |
| agcaacttca | atgaggccgc | tcaagccagg | gtgggtaaag | tcatcaaggg | cctagatatt | 420 |
| ggtgtcctta | ttaacaacgt | cgggcaaagc | tacgagttcc | ccatgtactt | tgatgagcta | 480 |
| tccgaagacc | aagttcactc | cctcgtcgag | ctcaacgtca | cctccaccct | gcacatgacc | 540 |

-continued

```
cgccttgtcc tccccaccat ggtggcaaag aagaagggtg ccatcgtcaa tctcgcttca    600
gccgcgtccc gtaacccgtc cccttgctc gctctctact cgggcgccaa gtctttcatt    660
gagctcttct ctcaatcgct cgacgccgaa tacaagggca aaggcatccg tgttcaagtc    720
caaactcctc ttttcgtcgc caccaagctg gccaaaatcc gcaaggcgag cctgacggtt    780
ccttctccag ccgggtacgc gaaggcggcg gtacgattca tcgcctatga ggattcggta    840
tcacctttct ggagtcatgc gtttcagttg tatttgatgt cttgcatgcc caagccggtc    900
ttatcggcga tcgtgtttaa catgcatgcg gggctcagga agcggggatt gaagaagaag    960
aatgagaaga gcgcttga                                                  978
```

```
<210> SEQ ID NO 53
<211> LENGTH: 325
<212> TYPE: PRT
<213> ORGANISM: Nannochloropsis oculata

<400> SEQUENCE: 53
```

Met Ala Ser Lys Gly Gly Asn Leu Ala Val Glu Leu Val Glu Ala Leu
1               5                   10                  15

Lys Gly Gln Pro Leu Ala Leu Gln Val Leu Ala Gly Val Gly Ala Leu
            20                  25                  30

Leu Val Leu Lys Phe Val Leu Gly Ala Val Gln Ala Phe Tyr Arg Phe
        35                  40                  45

Phe Leu Arg Pro Gly Lys Asn Leu Lys Lys Phe Gly Asp Trp Ala Val
    50                  55                  60

Val Thr Gly Ala Thr Asp Gly Ile Gly Lys Ala Tyr Ala Phe Glu Leu
65                  70                  75                  80

Ala Arg Gln Gly Leu Ser Leu Leu Ile Ser Arg Thr Glu Ser Lys
            85                  90                  95

Leu Lys Asp Thr Ala Ala Glu Ile Ser Ala Lys Tyr Pro Lys Val Gln
            100                 105                 110

Val Gln Val Leu Ser Ile Asp Phe Ser Asn Phe Asn Glu Ala Ala Gln
        115                 120                 125

Ala Arg Val Gly Lys Val Ile Lys Gly Leu Asp Ile Gly Val Leu Ile
    130                 135                 140

Asn Asn Val Gly Gln Ser Tyr Glu Phe Pro Met Tyr Phe Asp Glu Leu
145                 150                 155                 160

Ser Glu Asp Gln Val His Ser Leu Val Glu Leu Asn Val Thr Ser Thr
                165                 170                 175

Leu His Met Thr Arg Leu Val Leu Pro Thr Met Val Ala Lys Lys Lys
            180                 185                 190

Gly Ala Ile Val Asn Leu Ala Ser Ala Ala Ser Arg Asn Pro Ser Pro
        195                 200                 205

Leu Leu Ala Leu Tyr Ser Gly Ala Lys Ser Phe Ile Glu Leu Phe Ser
    210                 215                 220

Gln Ser Leu Asp Ala Glu Tyr Lys Gly Lys Gly Ile Arg Val Gln Val
225                 230                 235                 240

Gln Thr Pro Leu Phe Val Ala Thr Lys Leu Ala Lys Ile Arg Lys Ala
                245                 250                 255

Ser Leu Thr Val Pro Ser Pro Ala Gly Tyr Ala Lys Ala Ala Val Arg
            260                 265                 270

Phe Ile Ala Tyr Glu Asp Ser Val Ser Pro Phe Trp Ser His Ala Phe
        275                 280                 285

Gln Leu Tyr Leu Met Ser Cys Met Pro Lys Pro Val Leu Ser Ala Ile

```
                  290              295              300
Val Phe Asn Met His Ala Gly Leu Arg Lys Arg Gly Leu Lys Lys Lys
305              310              315              320

Asn Glu Lys Ser Ala
          325
```

<210> SEQ ID NO 54
<211> LENGTH: 1115
<212> TYPE: RNA
<213> ORGANISM: Nannochloropsis oculata

<400> SEQUENCE: 54

| | | | | | |
|---|---|---|---|---|---|
| aaauuuucag | caaaguaauc | aagauaauaa | acaaaaacaa | uccuauaaag | gaaaacaac    60 |
| aggaaccaag | agccaauggc | aucuaaaggu | ggcaauuugg | cgguggagcu | gguggaggcg  120 |
| cucaaggggc | agccuuuggc | gcuccagguc | uuggccgggg | uggggcuuu | gcuggugcuc  180 |
| aaguuugugc | ucggggcggu | ccaggccuuc | uaccguuucu | uccuucgccc | gggcaagaau  240 |
| cugaagaagu | uggugacug  | ggccguggug | acaggcgcga | cagacggcau | ggcaaggcg   300 |
| uaugcauucg | aguuggccag | gcaagggcug | agcuuguugu | ugauuucccg | uacggaguc   360 |
| aagcucaagg | acacggccgc | ggaaaucucg | gccaaguacc | ccaaggucca | ggugcaaguc  420 |
| cucagcaucg | acuucagcaa | cuucaaugag | gccgcucaag | ccaggguggg | uaaagucauc  480 |
| aagggccuag | auauuggugu | ccuuauuaac | aacgucgggc | aaagcuacga | guuccccaug  540 |
| uacuuugaug | agcuauccga | agaccaaguu | cacucccucg | ucgagcucaa | cgucaccucc  600 |
| acccugcaca | ugacccgccu | uguccucccc | accauggugg | caaagaagaa | gggugccauc  660 |
| gucaaucucg | cuucagccgc | gucccguaac | ccgucccccu | ugcucgcucu | cuacucgggc  720 |
| gccaagucuu | ucauugagcu | cuucucucaa | ucgcucgacg | ccgaauacaa | gggcaaaggc  780 |
| auccguguuc | aaguccaaac | uccucuuuuc | gucgccacca | agcuggccaa | aauccgcaag  840 |
| gcgagccuga | cgguuccuuc | uccagccggg | uacgcgaagg | cggcgguacg | auucaucgcc  900 |
| uaugaggauu | cgguaucacc | uuucuggagu | caugcguuuc | aguuguauuu | gaugucuugc  960 |
| augcccaagc | cggucuuauc | ggcgaucgug | uuuaacaugc | augcggggcu | caggaagcgg  1020 |
| ggauugaaga | agaagaauga | gaagagcgcu | ugauagggga | gagggugcgu | ggucuagagg  1080 |
| augagggagg | aagggaauga | aagggaugug | ugugc      |            |             1115 |

<210> SEQ ID NO 55
<211> LENGTH: 1044
<212> TYPE: DNA
<213> ORGANISM: Nannochloropsis oculata

<400> SEQUENCE: 55

| | | | | | |
|---|---|---|---|---|---|
| atggcgttgg | acgtgaagga | gaagaacttg | atcaagttca | ttttaaagcg | cctcgtgccg   60 |
| attctgatag | tcttttttctc | cttcgcctcc | tacatggagc | tgtggaacca | acccgttcga  120 |
| ctgctaggct | tctctctctt | ggctgtctgg | ctggtgaaat | tcctgaacct | ggccctgtat  180 |
| tttgcgcgtg | tcaagctttt | ccctcgcgac | cctctgtcgt | acgggaagtg | ggccattgtc  240 |
| acaggtgcca | ccgcaggaat | cggtgaagcc | ttcgcctacg | agctggccgc | gcgtggcttg  300 |
| aatgtcatca | ttatttcacg | ttccatggaa | agctggaag  | aggtgaagaa | gggcattttg  360 |
| aaagaaactc | ctggagtgga | gattcggtgc | atggcctttg | actcacggga | tcgagagggc  420 |
| gcggatgtct | tctttgcaac | gttgaccgat | acgtgcaaga | gttggtcgg  | tgggttgggc  480 |
| attttggtga | ataacgtcgg | aatggtcaat | gcgctcccgg | aatacatgca | ccaattggac  540 |

```
gcgcgcacca cctatggcat cctccaagtc aacgtcgaag ggaccgtgcg tacgacccga    600
gccgtcgccc cgttcctgat cgaacagcgc aagggtgcta taatcaatgt ctcatccggc    660
tcggggaatc atcccacccc gatgatcagc tgttatgcgt ccaccaaggc ttttatcaca    720
cagttctccc aatgcctgtc acatgaactg agagagtttg gggtggacgt gttagtcgtc    780
accccttact atgtgatttc caatcagttc cgacggaaga aggcgaccta tatcgcaccc    840
acggcccagc ggatggtcca agacacgctg cctactttgg ggtactgcga tgtggcgtac    900
ccttactggt tcacgccctt gtgtgggttc tttgtagggt tgtattggga tgtgggaggg    960
tcagtgatgg cggccatgcg aaggaatcgc gctcggatta tggaggcggc ggcggccaaa   1020
aaagggaaag ggggagtaaa gtag                                          1044
```

<210> SEQ ID NO 56
<211> LENGTH: 347
<212> TYPE: PRT
<213> ORGANISM: Nannochloropsis oculata

<400> SEQUENCE: 56

```
Met Ala Leu Asp Val Lys Glu Lys Asn Leu Ile Lys Phe Ile Leu Lys
1               5                   10                  15

Arg Leu Val Pro Ile Leu Ile Val Phe Phe Ser Phe Ala Ser Tyr Met
            20                  25                  30

Glu Leu Trp Asn Gln Pro Val Arg Leu Leu Gly Phe Ser Leu Leu Ala
        35                  40                  45

Val Trp Leu Val Lys Phe Leu Asn Leu Ala Leu Tyr Phe Ala Arg Val
    50                  55                  60

Lys Leu Phe Pro Arg Asp Pro Leu Ser Tyr Gly Lys Trp Ala Ile Val
65                  70                  75                  80

Thr Gly Ala Thr Ala Gly Ile Gly Glu Ala Phe Ala Tyr Glu Leu Ala
                85                  90                  95

Ala Arg Gly Leu Asn Val Ile Ile Ile Ser Arg Ser Met Glu Lys Leu
            100                 105                 110

Glu Glu Val Lys Lys Gly Ile Leu Lys Glu Thr Pro Gly Val Glu Ile
        115                 120                 125

Arg Cys Met Ala Phe Asp Tyr Thr Asp Arg Glu Gly Ala Asp Val Phe
    130                 135                 140

Phe Ala Thr Leu Thr Asp Thr Cys Lys Ser Leu Val Gly Gly Leu Gly
145                 150                 155                 160

Ile Leu Val Asn Asn Val Gly Met Val Asn Ala Leu Pro Glu Tyr Met
                165                 170                 175

His Gln Leu Asp Ala Arg Thr Thr Tyr Gly Ile Leu Gln Val Asn Val
            180                 185                 190

Glu Gly Thr Val Arg Thr Thr Arg Ala Val Ala Pro Phe Leu Ile Glu
        195                 200                 205

Gln Arg Lys Gly Ala Ile Ile Asn Val Ser Ser Gly Ser Gly Asn His
    210                 215                 220

Pro Thr Pro Met Ile Ser Cys Tyr Ala Ser Thr Lys Ala Phe Ile Thr
225                 230                 235                 240

Gln Phe Ser Gln Cys Leu Ser His Glu Leu Arg Glu Phe Gly Val Asp
                245                 250                 255

Val Leu Val Val Thr Pro Tyr Tyr Val Ile Ser Asn Gln Phe Arg Arg
            260                 265                 270

Lys Lys Ala Thr Tyr Ile Ala Pro Thr Ala Gln Arg Met Val Gln Asp
```

|  | 275 |  |  |  | 280 |  |  |  | 285 |  |  |
|---|---|---|---|---|---|---|---|---|---|---|---|

Thr Leu Pro Thr Leu Gly Tyr Cys Asp Val Ala Tyr Pro Tyr Trp Phe
    290                      295                    300

His Ala Leu Cys Gly Phe Phe Val Gly Leu Tyr Trp Asp Val Gly Gly
305                    310                    315                320

Ser Val Met Ala Ala Met Arg Arg Asn Arg Ala Arg Ile Met Glu Ala
                  325                    330                335

Ala Ala Ala Lys Lys Gly Lys Gly Gly Val Lys
            340                  345

<210> SEQ ID NO 57
<211> LENGTH: 1751
<212> TYPE: RNA
<213> ORGANISM: Nannochloropsis oculata

<400> SEQUENCE: 57

```
aauuuucagc aaaguaauca agauaauaaa caaaaacaau ccuauaaaag gaaaaacaac      60
agaagcccuu ccuuuuucug ugcccuccgc cuuugcauca gccacgaaca ggaacgcggc     120
cacuuuuccc gagcaccgac ugcgcacccu cgucucccgg cuccaccguc cccuucuaca     180
aucauggcgu uggacgugaa ggagaagaac uugaucaagu cauuuuaaa gcgccucgug      240
ccgauucuga uagucuuuuu cuccuucgcc uccuacaugg agcuguggaa ccaacccguu     300
cgacugcuag gcuucucucu cuuggcuguc uggcugguga aauuccugaa ccuggcccug     360
uauuuugcgc gugucaagcu uuucccucgc gacccucugu cguacgggaa gugggccauu     420
gucacaggug ccaccgcagg aaucggugaa gccuucgccu acgagcuggc cgcgcguggc     480
uugaauguca ucauuauuuc acguuccaug gaaaagcugg agaggugaa gaagggcauu       540
uugaaagaaa cuccuggagu ggagauucgg ugcauggccu ugacuacac ggaucgagag       600
ggcgcggaug ucuucuuugc aacguugacc gauacgugca agaguuuggu cgguggguug      660
ggcauuuugg ugaauaacgu cggaaugguc aaugcgcucc cggaauacau gcaccaauug      720
gacgcgcgca ccaccuaugg cauccuccaa gucaacgucg aagggaccgu gcguacgacc      780
cgagccgucg ccccguuccu gaucaacag cgcaagggug cuauaaucaa ugucucaucc       840
ggcucgggga aucaucccac cccgaugauc agcuguuaug cguccaccaa ggcuuuuauc      900
acacaguucu cccaaugccu gucacaugaa cugagagagu uggggugga cguguuaguc       960
gucaccccuu acuaugugau uccaaucag uuccgacgga agaaggcgac cuauaucgca      1020
cccacggccc agcggauggu ccaagacacg cugccuacuu uggggacug cgaugguggcg     1080
uacccuuacu gguuucacgc cuugugugug uucuuuguag gguuguauug ggaugugga    1140
gggucaguga uggcggccau gcgaaggaau cgcgcucgga uuauggaggc ggcggcggcc    1200
aaaaagggaa aaggggagu aaaguaggga aagcagaaau auaggaaagg agggaggugu     1260
caccggcagu agcgacgggu guauaaaagg caacggggaa cgggaaggaa agaagauagg    1320
auggcuaugg ugagaacagg uagacauaaa gaaugagauc aauagagaga gagagagcaa    1380
acagagaguc acaagcgaua gcuaggacga ugacgauuac ggcggacagc uaaacgaaca    1440
agcaggacug ccucagcaga gucgccgcg cucucuuuug uguauggaug ucagaaagau    1500
gagagagggc guggauugga ggggggaug gguuggggg caugguguc uaguuguccg     1560
ccucuucuag cccucucccg ccuccuuuga ccuaucauag auuuguacca ucaaagcagc    1620
accaucagga gcagcaaaac gaaagaaagg aaggaacgaa agaacgaagg uagaaaggaa    1680
aaaauaacaa uaaacagaug uaaaaaaaaa aaaaaaaaaa aaaaaaaaaa aaaaaaaaaa    1740
```
aaaaaaaaaa a                                                                          1751

<210> SEQ ID NO 58
<211> LENGTH: 768
<212> TYPE: DNA
<213> ORGANISM: Nannochloropsis oculata

<400> SEQUENCE: 58

```
atgggaggtg gcagtaaaag cggcacaggc cgcggcagcg gcccagtgag ggcgtacctg     60
aacgcttaca atcttgccca agtgggttg tgggtgatgg tcttggttat taccatcaag    120
gccttgctgg cagacgtaca ccactatgtg ggcgtctgga ccgaggtcgg accggcgacc    180
aagcttgctg ttggcggtgc atggctggag ctggtgcacg ttaccctggg cctggcgggc    240
ggcagtgtct cttcggcgtt ttggcagaac tttgggcggt ccttcgtcct cttcgccatt    300
gtcgacgcct ttaacacacc caaaggcttg gcatggctac cgacgctgct gctggcctgg    360
tctgggggcg agctgattcg gtacccttc tacctgctgg gcagcaacgc cccgcccctc    420
ttggtctggc tccggtattc agccttcctt gtgctctacc cgctgggcat ggcctctgag    480
gtggcgctgc ttctgcacac actgcccgag gccaaggcgg ccgtagagaa tagggacaga    540
ttctgcgtgc gcttacccgg ggctgaggag tggcgggcct tcaacttcta ctactttctg    600
gtgtttgggc tgctagtgct gtacccgttc gccattccct atatgttctt ctacatggtc    660
aagcagcgca caaagcgtct tgggggaat aaggatggga atgagggaga ggcagcacgt    720
gtggcagtcc ccgcgggaag cagcaggaag agccggaagg ccgaatag                768
```

<210> SEQ ID NO 59
<211> LENGTH: 255
<212> TYPE: PRT
<213> ORGANISM: Nannochloropsis oculata

<400> SEQUENCE: 59

Met Gly Gly Gly Ser Lys Ser Gly Thr Gly Arg Gly Ser Gly Pro Val
1               5                   10                  15

Arg Ala Tyr Leu Asn Ala Tyr Asn Leu Ala Gln Ser Gly Leu Trp Val
            20                  25                  30

Met Val Leu Val Ile Thr Ile Lys Ala Leu Leu Ala Asp Val His His
        35                  40                  45

Tyr Val Gly Val Trp Thr Glu Val Gly Pro Ala Thr Lys Leu Ala Val
    50                  55                  60

Gly Gly Ala Trp Leu Glu Leu Val His Val Thr Leu Gly Leu Ala Gly
65                  70                  75                  80

Gly Ser Val Ser Ser Ala Phe Trp Gln Asn Phe Gly Arg Ser Phe Val
                85                  90                  95

Leu Phe Ala Ile Val Asp Ala Phe Asn Thr Pro Lys Gly Leu Ala Trp
            100                 105                 110

Leu Pro Thr Leu Leu Leu Ala Trp Ser Gly Gly Glu Leu Ile Arg Tyr
        115                 120                 125

Pro Phe Tyr Leu Leu Gly Ser Asn Ala Pro Leu Leu Val Trp Leu
    130                 135                 140

Arg Tyr Ser Ala Phe Leu Val Leu Tyr Pro Leu Gly Met Ala Ser Glu
145                 150                 155                 160

Val Ala Leu Leu Leu His Thr Leu Pro Glu Ala Lys Ala Ala Val Glu
                165                 170                 175

Asn Arg Asp Arg Phe Cys Val Arg Leu Pro Gly Ala Glu Glu Trp Arg

|  | | 180 | | | 185 | | | | 190 | | |
|---|---|---|---|---|---|---|---|---|---|---|---|
| Ala | Phe | Asn | Phe | Tyr | Tyr | Phe | Leu | Val | Phe | Gly | Leu | Leu | Val | Leu | Tyr |
| | | | | 195 | | | | | 200 | | | | | 205 | |

| Pro | Phe | Ala | Ile | Pro | Tyr | Met | Phe | Phe | Tyr | Met | Val | Lys | Gln | Arg | Thr |
|---|---|---|---|---|---|---|---|---|---|---|---|---|---|---|---|
| | | 210 | | | | | 215 | | | | | 220 | | | |

| Lys | Arg | Leu | Gly | Gly | Asn | Lys | Asp | Gly | Asn | Glu | Gly | Glu | Ala | Ala | Arg |
|---|---|---|---|---|---|---|---|---|---|---|---|---|---|---|---|
| 225 | | | | | 230 | | | | | 235 | | | | | 240 |

| Val | Ala | Val | Pro | Ala | Gly | Ser | Ser | Arg | Lys | Ser | Arg | Lys | Ala | Glu |
|---|---|---|---|---|---|---|---|---|---|---|---|---|---|---|
| | | | | 245 | | | | | 250 | | | | | 255 |

<210> SEQ ID NO 60
<211> LENGTH: 1293
<212> TYPE: RNA
<213> ORGANISM: Nannochloropsis oculata

<400> SEQUENCE: 60

| aaauaaacaa | aaacaauccu | auaaaggaaa | acaacagca | cacaggcgcu | cccucuucag | 60 |
|---|---|---|---|---|---|---|
| gccccgucgu | caauccuaug | ggaggugca | guaaaagcgg | cacaggccgc | ggcagcggcc | 120 |
| cagugagggc | guaccugaac | gcuuacaauc | uugcccaaag | ugguugugg | gugauggucu | 180 |
| ugguuauuac | caucaaggcc | uugcuggcag | acguacacca | cuaugugggc | gucuggaccg | 240 |
| aggucggacc | ggcgaccaag | cuugcuguug | gcggugcaug | gcuggagcug | gugcacguua | 300 |
| cccugggccu | ggcgggcggc | agugucucu | cggcguuuug | gcagaacuuu | gggcgguccu | 360 |
| ucguccucuu | cgccauuguc | gacgccuuua | acacacccaa | aggcuuggca | uggcuaccga | 420 |
| cgcugcugcu | ggccuggucu | gggggcgagc | ugauucggua | ccccuucuac | cugcugggca | 480 |
| gcaacgcccc | gccccucuug | gucuggcucc | gguauucagc | cuuccuugug | cucuacccgc | 540 |
| ugggcauggc | cucugaggug | gcgcugccuc | ugcacacacu | gcccgaggcc | aaggcggccg | 600 |
| uagagaauag | ggacagauuc | ugcgugcgcu | uacccggggc | ugaggagugg | cgggccuuca | 660 |
| acuucuacua | cuuucgggug | uugggcugc | uagugcugua | cccguucgcc | auucccuaua | 720 |
| uguucuucua | caugugcaag | cagcgcacaa | agcgucuugg | ggggauaag | gaugggaaug | 780 |
| agggagaggc | agcacgugug | gcagucccg | cggaagcag | caggaagagc | cggaaggccg | 840 |
| aauaggaggc | gcaccuugaa | ggcaagaaag | cggguuugca | ggaaagcgaa | ggagaaaagu | 900 |
| agggauggcg | agaugaacag | ugaggcagag | agaauggaca | aggaagcggg | cgguuuggug | 960 |
| ggaucgggga | ccgaggugg | guccgggagc | auagacggga | gaauugagag | uagacacggg | 1020 |
| ggaaaaggcg | augguggagg | gaagaagauu | agaaagacga | aagggaggaa | ggcugaggcg | 1080 |
| gaaagagcau | ggacuugagg | ggaauacaac | cguguccacg | aucacacaag | uagggauggu | 1140 |
| uuugcggucg | cuugcuuaag | acgggcugca | uggguucaau | cgacaaggga | gaggaaaaaa | 1200 |
| aagaggucac | aaaggggaga | agaguaaggc | augcgaaaau | caacaaagca | aaaugugua | 1260 |
| caaaaacaaa | aaaaaaaaa | aaaaaaaaaa | aaa | | | 1293 |

<210> SEQ ID NO 61
<211> LENGTH: 1620
<212> TYPE: DNA
<213> ORGANISM: Nannochloropsis oculata

<400> SEQUENCE: 61

| atgggcaagc | ctcagcgagc | caagggaccg | gaggtgggcc | tcgtcttccc | cacggacaag | 60 |
|---|---|---|---|---|---|---|
| aagggtggcc | gtggctccac | gttcggcaac | aaaggcgctt | gggccgcggc | cgtcgcggct | 120 |
| gtcgaccccg | cggagggcac | aaaggtggag | aaggagaaga | gctggcgcca | gaagtacacc | 180 |

```
aagtacatcg tccgtcaagt gcaactcggc cttaattccc ccaagaatgc cgtcagcatc    240
gctcaaggcg gcctggacta ctgctacaag aactttgaat tcatccgtga cggacagaca    300
tacaagcttg gggaggcttt ggagaaattt ggggttcgc atgccttcga acgggggtg     360 ataaaagggg atgggaagtt gcccaagttc ggcccggagt gccaggttcc gtaccggaag    420
aaggtcctga aggggaggc gttgaaggcg cagttggaca atgggcgag ctacgggacc     480 atcgaaccgt cagcccggga tgcgattacg tacttggtgg acaaccccaa ggtgctggac    540
ctgtcggata aatactttgt cttgcttggg gcagggtcgg ccatggggcc cctcctcacc    600
ctcctctctc ttggcgcgaa catcattgcg attgatctgg ataggcaggg tatttgggaa    660
aggctgatcc gggagactcg aaactcgccg gggacgttga ttttcccct gaagaagaag    720 cagtcggcct tgaagagcga tgcggagatt gcggcccagg cgggagggaa cttgttcacg    780
gacaccccgg agattagggc gtggttgatg ggggtggagc ggggaaagga tctggtggtg    840
ggggcatatg cctacttgga tggggagttg cacgtgaaag tgtctttggc catggacgcg    900
attatccggg acttaaccaa gattaggaag gccacgcccg cttacctctg cacaccgact    960
gacgtccacg tgattaccaa ggaggcgcac gacgcgcgg cgaaggagta taagaagatt    1020
aactttacca acgttgtctc cagactgagc ccattcgccc tgccggggac tgggtacctg    1080
gtcaagaacg cccttgcccc tgtcaaggcg gaggatggtg aggagcttta ccttgtcgac    1140
gggatcgtgg gaagacaagg accaaactac gccttggcga agcggattca gcactggcgg    1200
gcggtggtgg ctcgggaggt ggataaggtg aacgtgtcct ctaacatcgc tccgtccacg    1260
gccaccgtgt cggtgacgag caacaagctc ttcgccttgg cctataaggg tttccatttc    1320
tttgccccgt tggaagtgtt tcaacaagag acgtccaacg ccgtcatggc cgccatgctc    1380
attcacgaca tccgcaaccc caaggtgcct tctaacccta aaaacaagct tcgcaatccg    1440
ctcgagctgt tcacgtatgg atccctccat ggcgggtct ggcgcatggc ttacaagatt    1500
gactcgattg gcgagcccgc agcgttcttg tatctgttca ccacaccctt ggggatgatg    1560
atcgtggtgg ccttctgggc gatagtcttg ggtctgatca agggatacgc tgggttttag    1620
```

<210> SEQ ID NO 62
<211> LENGTH: 539
<212> TYPE: PRT
<213> ORGANISM: Nannochloropsis oculata

<400> SEQUENCE: 62

Met Gly Lys Pro Gln Arg Ala Lys Gly Pro Glu Val Gly Leu Val Phe
1               5                   10                  15

Pro Thr Asp Lys Lys Gly Gly Arg Gly Ser Thr Phe Gly Asn Lys Gly
            20                  25                  30

Ala Trp Ala Ala Ala Val Ala Ala Val Asp Pro Ala Glu Gly Thr Lys
        35                  40                  45

Val Glu Lys Glu Lys Ser Trp Arg Gln Lys Tyr Thr Lys Tyr Ile Val
    50                  55                  60

Arg Gln Val Gln Leu Gly Leu Asn Ser Pro Lys Asn Ala Val Ser Ile
65                  70                  75                  80

Ala Gln Gly Gly Leu Asp Tyr Cys Tyr Lys Asn Phe Glu Phe Ile Arg
                85                  90                  95

Asp Gly Gln Thr Tyr Lys Leu Gly Glu Ala Leu Glu Lys Phe Gly Gly
            100                 105                 110

Ser His Ala Phe Glu Thr Gly Val Ile Lys Gly Asp Gly Lys Leu Pro

-continued

```
            115                 120                 125
Lys Phe Gly Pro Glu Cys Gln Val Pro Tyr Arg Lys Val Leu Lys
            130                 135                 140
Gly Glu Ala Leu Lys Ala Gln Leu Asp Lys Trp Ala Ser Tyr Gly Thr
145                 150                 155                 160
Ile Glu Pro Ser Ala Arg Asp Ala Ile Thr Tyr Leu Val Asp Asn Pro
                    165                 170                 175
Lys Val Leu Asp Leu Ser Asp Lys Tyr Phe Val Leu Gly Ala Gly
                180                 185                 190
Ser Ala Met Gly Pro Leu Leu Thr Leu Leu Ser Leu Gly Ala Asn Ile
                195                 200                 205
Ile Ala Ile Asp Leu Asp Arg Gln Gly Ile Trp Glu Arg Leu Ile Arg
            210                 215                 220
Glu Thr Arg Asn Ser Pro Gly Thr Leu Ile Phe Pro Leu Lys Lys Lys
225                 230                 235                 240
Gln Ser Ala Leu Lys Ser Asp Ala Glu Ile Ala Ala Gln Ala Gly Gly
                245                 250                 255
Asn Leu Phe Thr Asp Thr Pro Glu Ile Arg Ala Trp Leu Met Gly Val
                260                 265                 270
Glu Arg Gly Lys Asp Leu Val Val Gly Ala Tyr Ala Tyr Leu Asp Gly
            275                 280                 285
Glu Leu His Val Lys Val Ser Leu Ala Met Asp Ala Ile Ile Arg Asp
290                 295                 300
Leu Thr Lys Ile Arg Lys Ala Thr Pro Ala Tyr Leu Cys Thr Pro Thr
305                 310                 315                 320
Asp Val His Val Ile Thr Lys Glu Ala His Asp Ala Ala Lys Glu
                    325                 330                 335
Tyr Lys Lys Ile Asn Phe Thr Asn Val Val Ser Arg Leu Ser Pro Phe
                340                 345                 350
Ala Leu Pro Gly Thr Gly Tyr Leu Val Lys Asn Ala Leu Ala Pro Val
                355                 360                 365
Lys Ala Glu Asp Gly Glu Glu Leu Tyr Leu Val Asp Gly Ile Val Gly
            370                 375                 380
Arg Gln Gly Pro Asn Tyr Ala Leu Ala Lys Arg Ile Gln His Trp Arg
385                 390                 395                 400
Ala Val Val Ala Arg Glu Val Asp Lys Val Asn Val Ser Ser Asn Ile
                    405                 410                 415
Ala Pro Ser Thr Ala Thr Val Ser Val Thr Ser Asn Lys Leu Phe Ala
                420                 425                 430
Leu Ala Tyr Lys Gly Phe His Phe Phe Ala Pro Leu Glu Val Phe Gln
            435                 440                 445
Gln Glu Thr Ser Asn Ala Val Met Ala Ala Met Leu Ile His Asp Ile
450                 455                 460
Arg Asn Pro Lys Val Pro Ser Asn Pro Lys Asn Lys Leu Arg Asn Pro
465                 470                 475                 480
Leu Glu Leu Phe Thr Tyr Gly Ser Leu His Gly Gly Val Trp Arg Met
                485                 490                 495
Ala Tyr Lys Ile Asp Ser Ile Gly Glu Pro Ala Ala Phe Leu Tyr Leu
                500                 505                 510
Phe Thr Thr Pro Leu Gly Met Met Ile Val Val Ala Phe Trp Ala Ile
                515                 520                 525
Val Leu Gly Leu Ile Lys Gly Tyr Ala Gly Phe
            530                 535
```

<210> SEQ ID NO 63
<211> LENGTH: 2229
<212> TYPE: RNA
<213> ORGANISM: Nannochloropsis oculata

<400> SEQUENCE: 63

```
cucaauuuuc agcaaaguaa ucaagauaau aacaaaaaca auccuauaaa aggaaaaaca     60
acagacagga agcagcggga cacagcucuu ccuacaccua aaccucucca cacuucucau    120
cucaagaaug ggcaagccuc agcgagccaa gggaccggag gugggccucg ucuuccccac    180
ggacaagaag gguggccgug gcuccacguu cggcaacaaa ggcgcuuggg ccgcggccgu    240
cgcggcuguc gaccccgcgg agggcacaaa gguggagaag gagaagagcu ggcgccagaa    300
guacaccaag uacaucgucc gucaagugca acucggccuu aauuccccca agaaugccgu    360
cagcaucgcu caaggcggcc uggacuacug cuacaagaac uuugaauuca uccgugacgg    420
acagacauac aagcuugggg aggcuuugga gaaauuuggg gguucgcaug ccuucgaaac    480
gggggugaua aaggggaugg gaaguugccc caaguucggc ccggagugcc agguuccgua    540
ccggaagaag guccugaagg gggaggcguu gaaggcgcag uuggacaaau gggcgagcua    600
cgggaccauc gaaccgucag cccgggaugc gauuacguac uggguggaca ccccaaggu     660
gcuggaccug ucggauaaau acuuugucuu gcuggggca gggucggcca uggggccccu     720
ccucacccuc ucucucuug gcgcgaacau cauugcgauu gaucuggaua ggcagggua u    780
uugggaaagg cugauccggg agacucgaaa cucgccgggg acguugauuu ucccccugaa    840
gaagaagcag ucggccuuga agagcgaugc ggagauugcg gcccaggcgg gagggaacuu    900
guucacggac accccggaga uuagggcgug guugauggg g uggagcggg gaaaggaucu    960
ggugguggg gcauaugccu acuuggaugg ggaguugcac gugaaagugu cuuuggccau   1020
ggacgcgauu auccgggacu uaaccaagau uaggaaggcc acgccgcu a ccucugcac   1080
accgacugac guccacguga uuaccaagga ggcgcacgac gcggcggcga aggaguauaa   1140
gaagauuaac uuuaccaacg uugucuccag acugagccca uucgcccugc cggggacugg   1200
guaccuggucc aagaacgccc uugccccugu caaggcggag gauggugagg agcuuuaccu   1260
ugucgacggg aucguggga acaaggacc aaacuacgcc uugcgaagc ggauucagca   1320
cuggcgggcg guggggcuc gggaggugga uaaggugaac guguccucua acaucgcucc   1380
guccacggcc accgugucgg ugacgagcaa caagcucuuc gccuuggccu auaaggguuu   1440
ccauuucuu gccccguugg aaguguuuca acaagagacg uccaacgccg ucauggccgc   1500
caugcucauu cacgacaucc gcaaccccaa ggugccuucu aacccuaaaa acaagcuucg   1560
caauccgcuc gagcuguuca cguauggauc cuccauggc ggggucuggc gcauggcuua   1620
caagauugac ucgauuggcg agccgcagc guucuuguau cuguucacca caccuugggg   1680
gaugaugauc gugguggccu ucuggggcgau aguuuggu cugaucaagg gauacgcugg   1740
guuuuagggg caggaaggga ggcagggagu ggaggaguua gggagagaga ggucuuucu   1800
uuguaugaug uuucaguag uauuccuugu uuaucagucu cgagugugug agucaaggua   1860
ccacuuucgu uuucccuuc uuuccuuuau ggugcuuuuu uuuggcaga agagagagag   1920
aaagagagug gaggggaagc auguaaaccc caaccaacga aaaaaaguga gauggagaga   1980
gaugcgaugg uugucuagca uugagucugg auuccguuua ccacuuucgu ucagcacgc   2040
gcacauugcu guugcuaucg cauacagacg gcaccgugcc ucugaaaaaaa ggggccaagg   2100
```

```
ggacacacga cacagacuuc cuuuauauau cauggaaagg uaaaguaacc caggaaaaac    2160
ugaggaaaag aagaaguaug uucguagaaa auaauagcag aagggaaaaa ggagcaguag    2220
aggcagccc                                                            2229
```

<210> SEQ ID NO 64
<211> LENGTH: 104
<212> TYPE: DNA
<213> ORGANISM: Artificial sequence
<220> FEATURE:
<223> OTHER INFORMATION: Primer

<400> SEQUENCE: 64

```
ataaaagtat caacaaaaaa ttgttaatat acctctatac tttaacgtca aggagaaaaa    60
accccggatc ggcgcgccac catgccgccc cagaacgacg ccgc                    104
```

<210> SEQ ID NO 65
<211> LENGTH: 101
<212> TYPE: DNA
<213> ORGANISM: Artificial sequence
<220> FEATURE:
<223> OTHER INFORMATION: Primer

<400> SEQUENCE: 65

```
aactataaaa aaataaatag ggacctagac ttcaggttgt ctaactcctt cctttcggt    60 tagagcggat ttaattaact agcccatgtg cacctccgcc g                       101
```

<210> SEQ ID NO 66
<211> LENGTH: 104
<212> TYPE: DNA
<213> ORGANISM: Artificial sequence
<220> FEATURE:
<223> OTHER INFORMATION: Primer

<400> SEQUENCE: 66

```
ataaaagtat caacaaaaaa ttgttaatat acctctatac tttaacgtca aggagaaaaa    60
accccggatc ggcgcgccac catgggacgc ggtggcgagc ggat                    104
```

<210> SEQ ID NO 67
<211> LENGTH: 101
<212> TYPE: DNA
<213> ORGANISM: Artificial sequence
<220> FEATURE:
<223> OTHER INFORMATION: Primer

<400> SEQUENCE: 67

```
aactataaaa aaataaatag ggacctagac ttcaggttgt ctaactcctt cctttcggt    60 tagagcggat ttaattaatt acatggcggg gaagtcggcc a                       101
```

<210> SEQ ID NO 68
<211> LENGTH: 104
<212> TYPE: DNA
<213> ORGANISM: Artificial sequence
<220> FEATURE:
<223> OTHER INFORMATION: Primer

<400> SEQUENCE: 68

```
ataaaagtat caacaaaaaa ttgttaatat acctctatac tttaacgtca aggagaaaaa    60
accccggatc ggcgcgccac catggccgat gtcgagtcca tcaa                    104
```

<210> SEQ ID NO 69
<211> LENGTH: 101

```
<212> TYPE: DNA
<213> ORGANISM: Artificial sequence
<220> FEATURE:
<223> OTHER INFORMATION: Primer

<400> SEQUENCE: 69
aactataaaa aaataaatag ggacctagac ttcaggttgt ctaactcctt cctttcggt      60 tagagcggat ttaattaatt acgaagagga ggttatgttg g                        101

<210> SEQ ID NO 70
<211> LENGTH: 104
<212> TYPE: DNA
<213> ORGANISM: Artificial sequence
<220> FEATURE:
<223> OTHER INFORMATION: Primer

<400> SEQUENCE: 70
ataaaagtat caacaaaaaa ttgttaatat acctctatac tttaacgtca aggagaaaaa    60
accccggatc ggcgcgccac catggcgccg cgcgatgtgg agac                     104

<210> SEQ ID NO 71
<211> LENGTH: 101
<212> TYPE: DNA
<213> ORGANISM: Artificial sequence
<220> FEATURE:
<223> OTHER INFORMATION: Primer

<400> SEQUENCE: 71
aactataaaa aaataaatag ggacctagac ttcaggttgt ctaactcctt cctttcggt      60 tagagcggat ttaattaatt accccgccgc gccgttgtt g                         101

<210> SEQ ID NO 72
<211> LENGTH: 104
<212> TYPE: DNA
<213> ORGANISM: Artificial sequence
<220> FEATURE:
<223> OTHER INFORMATION: Primer

<400> SEQUENCE: 72
ataaaagtat caacaaaaaa ttgttaatat acctctatac tttaacgtca aggagaaaaa    60
accccggatc ggcgcgccac catggtcttc cagctcgccc gaga                     104

<210> SEQ ID NO 73
<211> LENGTH: 101
<212> TYPE: DNA
<213> ORGANISM: Artificial sequence
<220> FEATURE:
<223> OTHER INFORMATION: Primer

<400> SEQUENCE: 73
aactataaaa aaataaatag ggacctagac ttcaggttgt ctaactcctt cctttcggt      60 tagagcggat ttaattaatt aattgtactt ggggtgatta c                        101

<210> SEQ ID NO 74
<211> LENGTH: 104
<212> TYPE: DNA
<213> ORGANISM: Artificial sequence
<220> FEATURE:
<223> OTHER INFORMATION: Primer

<400> SEQUENCE: 74
ataaaagtat caacaaaaaa ttgttaatat acctctatac tttaacgtca aggagaaaaa    60
```

```
acccggatc ggcgcgccac catgggacgc ggcggtgaga agac        104
```

<210> SEQ ID NO 75
<211> LENGTH: 101
<212> TYPE: DNA
<213> ORGANISM: Artificial sequence
<220> FEATURE:
<223> OTHER INFORMATION: Primer

<400> SEQUENCE: 75

```
aactataaaa aaataaatag ggacctagac ttcaggttgt ctaactcctt cctttcggt    60 tagagcggat ttaattaact atgctcgctg cttgtagaac a                      101
```

<210> SEQ ID NO 76
<211> LENGTH: 104
<212> TYPE: DNA
<213> ORGANISM: Artificial sequence
<220> FEATURE:
<223> OTHER INFORMATION: Primer

<400> SEQUENCE: 76

```
ataaaagtat caacaaaaaa ttgttaatat acctctatac tttaacgtca aggagaaaaa    60 acccggatc ggcgcgccac catggttgag caaacattgc cgac                    104
```

<210> SEQ ID NO 77
<211> LENGTH: 101
<212> TYPE: DNA
<213> ORGANISM: Artificial sequence
<220> FEATURE:
<223> OTHER INFORMATION: Primer

<400> SEQUENCE: 77

```
aactataaaa aaataaatag ggacctagac ttcaggttgt ctaactcctt cctttcggt    60 tagagcggat ttaattaatt acggaggga ggaagaacgg g                       101
```

<210> SEQ ID NO 78
<211> LENGTH: 104
<212> TYPE: DNA
<213> ORGANISM: Artificial sequence
<220> FEATURE:
<223> OTHER INFORMATION: Primer

<400> SEQUENCE: 78

```
ataaaagtat caacaaaaaa ttgttaatat acctctatac tttaacgtca aggagaaaaa    60 acccggatc ggcgcgccac catgaagtgg gtcctgcaag aagg                    104
```

<210> SEQ ID NO 79
<211> LENGTH: 101
<212> TYPE: DNA
<213> ORGANISM: Artificial sequence
<220> FEATURE:
<223> OTHER INFORMATION: Primer

<400> SEQUENCE: 79

```
aactataaaa aaataaatag ggacctagac ttcaggttgt ctaactcctt cctttcggt    60 tagagcggat ttaattaact actgtgcttt tgtcttaccc t                      101
```

<210> SEQ ID NO 80
<211> LENGTH: 104
<212> TYPE: DNA
<213> ORGANISM: Artificial sequence
<220> FEATURE:
<223> OTHER INFORMATION: Primer

<400> SEQUENCE: 80
ataaaagtat caacaaaaaa ttgttaatat acctctatac tttaacgtca aggagaaaaa     60
accccggatc ggcgcgccac catgtcttgg tttttggacc ccgc                      104

<210> SEQ ID NO 81
<211> LENGTH: 101
<212> TYPE: DNA
<213> ORGANISM: Artificial sequence
<220> FEATURE:
<223> OTHER INFORMATION: Primer

<400> SEQUENCE: 81
aactataaaa aaataaatag ggacctagac ttcaggttgt ctaactcctt cctttccggt      60
tagagcggat ttaattaatt acgccatctt ctttccattc c                         101

<210> SEQ ID NO 82
<211> LENGTH: 104
<212> TYPE: DNA
<213> ORGANISM: Artificial sequence
<220> FEATURE:
<223> OTHER INFORMATION: Primer

<400> SEQUENCE: 82
ataaaagtat caacaaaaaa ttgttaatat acctctatac tttaacgtca aggagaaaaa     60
accccggatc ggcgcgccac catgctgagc aaaagcttca atac                      104

<210> SEQ ID NO 83
<211> LENGTH: 101
<212> TYPE: DNA
<213> ORGANISM: Artificial sequence
<220> FEATURE:
<223> OTHER INFORMATION: Primer

<400> SEQUENCE: 83
aactataaaa aaataaatag ggacctagac ttcaggttgt ctaactcctt cctttccggt      60
tagagcggat ttaattaact actgtgcttt cttcaagtcc a                         101

<210> SEQ ID NO 84
<211> LENGTH: 104
<212> TYPE: DNA
<213> ORGANISM: Artificial sequence
<220> FEATURE:
<223> OTHER INFORMATION: Primer

<400> SEQUENCE: 84
ataaaagtat caacaaaaaa ttgttaatat acctctatac tttaacgtca aggagaaaaa     60
accccggatc ggcgcgccac catggaggcc ccctcccgc acct                       104

<210> SEQ ID NO 85
<211> LENGTH: 101
<212> TYPE: DNA
<213> ORGANISM: Artificial sequence
<220> FEATURE:
<223> OTHER INFORMATION: Primer

<400> SEQUENCE: 85
aactataaaa aaataaatag ggacctagac ttcaggttgt ctaactcctt cctttccggt      60
tagagcggat ttaattaatc acctttctgg ggaggcaccc g                         101

<210> SEQ ID NO 86

```
<211> LENGTH: 104
<212> TYPE: DNA
<213> ORGANISM: Artificial sequence
<220> FEATURE:
<223> OTHER INFORMATION: Primer

<400> SEQUENCE: 86
ataaaagtat caacaaaaaa ttgttaatat acctctatac tttaacgtca aggagaaaaa      60
accccggatc ggcgcgccac catggccgcc gcccttcttt caga                     104

<210> SEQ ID NO 87
<211> LENGTH: 101
<212> TYPE: DNA
<213> ORGANISM: Artificial sequence
<220> FEATURE:
<223> OTHER INFORMATION: Primer

<400> SEQUENCE: 87
aactataaaa aaataaatag ggacctagac ttcaggttgt ctaactcctt cctttcggt      60 tagagcggat ttaattaatt aaatcttctt gagagccggc t                         101

<210> SEQ ID NO 88
<211> LENGTH: 104
<212> TYPE: DNA
<213> ORGANISM: Artificial sequence
<220> FEATURE:
<223> OTHER INFORMATION: Primer

<400> SEQUENCE: 88
ataaaagtat caacaaaaaa ttgttaatat acctctatac tttaacgtca aggagaaaaa      60
accccggatc ggcgcgccac catgtcgttc ctcattcgca ctcc                     104

<210> SEQ ID NO 89
<211> LENGTH: 101
<212> TYPE: DNA
<213> ORGANISM: Artificial sequence
<220> FEATURE:
<223> OTHER INFORMATION: Primer

<400> SEQUENCE: 89
aactataaaa aaataaatag ggacctagac ttcaggttgt ctaactcctt cctttcggt      60 tagagcggat ttaattaatt aaatcgtctt cgtcttgggc t                         101

<210> SEQ ID NO 90
<211> LENGTH: 104
<212> TYPE: DNA
<213> ORGANISM: Artificial sequence
<220> FEATURE:
<223> OTHER INFORMATION: Primer

<400> SEQUENCE: 90
ataaaagtat caacaaaaaa ttgttaatat acctctatac tttaacgtca aggagaaaaa      60
accccggatc ggcgcgccac catggcagtg gccttgctcg aggt                     104

<210> SEQ ID NO 91
<211> LENGTH: 101
<212> TYPE: DNA
<213> ORGANISM: Artificial sequence
<220> FEATURE:
<223> OTHER INFORMATION: Primer

<400> SEQUENCE: 91
aactataaaa aaataaatag ggacctagac ttcaggttgt ctaactcctt cctttcggt      60
```
tagagcggat ttaattaatc aacccctgct gctcccgcct a                              101

<210> SEQ ID NO 92
<211> LENGTH: 104
<212> TYPE: DNA
<213> ORGANISM: Artificial sequence
<220> FEATURE:
<223> OTHER INFORMATION: Primer

<400> SEQUENCE: 92
ataaaagtat caacaaaaaa ttgttaatat acctctatac tttaacgtca aggagaaaaa        60
accccggatc ggcgcgccac catgctttca gtttatttcc ccgc                         104

<210> SEQ ID NO 93
<211> LENGTH: 101
<212> TYPE: DNA
<213> ORGANISM: Artificial sequence
<220> FEATURE:
<223> OTHER INFORMATION: Primer

<400> SEQUENCE: 93
aactataaaa aaataaatag ggacctagac ttcaggttgt ctaactcctt cctttcggt          60 tagagcggat ttaattaaca cgtgcaagct tacccatacg g                            101

<210> SEQ ID NO 94
<211> LENGTH: 104
<212> TYPE: DNA
<213> ORGANISM: Artificial sequence
<220> FEATURE:
<223> OTHER INFORMATION: Primer

<400> SEQUENCE: 94
ataaaagtat caacaaaaaa ttgttaatat acctctatac tttaacgtca aggagaaaaa        60
accccggatc ggcgcgccac catgcccaag cttccagaga tctc                         104

<210> SEQ ID NO 95
<211> LENGTH: 101
<212> TYPE: DNA
<213> ORGANISM: Artificial sequence
<220> FEATURE:
<223> OTHER INFORMATION: Primer

<400> SEQUENCE: 95
aactataaaa aaataaatag ggacctagac ttcaggttgt ctaactcctt cctttcggt          60 tagagcggat ttaattaatt acatcgcctt gattttcttg g                            101

<210> SEQ ID NO 96
<211> LENGTH: 104
<212> TYPE: DNA
<213> ORGANISM: Artificial sequence
<220> FEATURE:
<223> OTHER INFORMATION: Primer

<400> SEQUENCE: 96
ataaaagtat caacaaaaaa ttgttaatat acctctatac tttaacgtca aggagaaaaa        60
accccggatc ggcgcgccac catgggtctc gacgtgaagg agaa                         104

<210> SEQ ID NO 97
<211> LENGTH: 101
<212> TYPE: DNA
<213> ORGANISM: Artificial sequence
<220> FEATURE:

<223> OTHER INFORMATION: Primer

<400> SEQUENCE: 97
aactataaaa aaataaatag ggacctagac ttcaggttgt ctaactcctt cctttttcggt    60 tagagcggat ttaattaact acgcagcggc cttgatctcc t                         101

<210> SEQ ID NO 98
<211> LENGTH: 104
<212> TYPE: DNA
<213> ORGANISM: Artificial sequence
<220> FEATURE:
<223> OTHER INFORMATION: Primer

<400> SEQUENCE: 98
ataaaagtat caacaaaaaa ttgttaatat acctctatac tttaacgtca aggagaaaaa    60
accccggatc ggcgcgccac catggcatct aaaggtggca attt                      104

<210> SEQ ID NO 99
<211> LENGTH: 101
<212> TYPE: DNA
<213> ORGANISM: Artificial sequence
<220> FEATURE:
<223> OTHER INFORMATION: Primer

<400> SEQUENCE: 99
aactataaaa aaataaatag ggacctagac ttcaggttgt ctaactcctt cctttttcggt    60 tagagcggat ttaattaatc aagcgctctt ctcattcttc t                         101

<210> SEQ ID NO 100
<211> LENGTH: 104
<212> TYPE: DNA
<213> ORGANISM: Artificial sequence
<220> FEATURE:
<223> OTHER INFORMATION: Primer

<400> SEQUENCE: 100
ataaaagtat caacaaaaaa ttgttaatat acctctatac tttaacgtca aggagaaaaa    60
accccggatc ggcgcgccac catggcgttg gacgtgaagg agaa                      104

<210> SEQ ID NO 101
<211> LENGTH: 101
<212> TYPE: DNA
<213> ORGANISM: Artificial sequence
<220> FEATURE:
<223> OTHER INFORMATION: Primer

<400> SEQUENCE: 101
aactataaaa aaataaatag ggacctagac ttcaggttgt ctaactcctt cctttttcggt    60 tagagcggat ttaattaact actttactcc cctttccct t                          101

<210> SEQ ID NO 102
<211> LENGTH: 104
<212> TYPE: DNA
<213> ORGANISM: Artificial sequence
<220> FEATURE:
<223> OTHER INFORMATION: Primer

<400> SEQUENCE: 102
ataaaagtat caacaaaaaa ttgttaatat acctctatac tttaacgtca aggagaaaaa    60
accccggatc ggcgcgccac catgggaggt ggcagtaaaa gcgg                      104

```
<210> SEQ ID NO 103
<211> LENGTH: 101
<212> TYPE: DNA
<213> ORGANISM: Artificial sequence
<220> FEATURE:
<223> OTHER INFORMATION: Primer

<400> SEQUENCE: 103
aactataaaa aaataaatag ggacctagac ttcaggttgt ctaactcctt cctttcggt      60 tagagcggat ttaattaact attcggcctt ccggctcttc c                        101

<210> SEQ ID NO 104
<211> LENGTH: 104
<212> TYPE: DNA
<213> ORGANISM: Artificial sequence
<220> FEATURE:
<223> OTHER INFORMATION: Primer

<400> SEQUENCE: 104
ataaaagtat caacaaaaaa ttgttaatat acctctatac tttaacgtca aggagaaaaa     60
accccggatc ggcgcgccac catgggcaag cctcagcgag ccaa                     104

<210> SEQ ID NO 105
<211> LENGTH: 101
<212> TYPE: DNA
<213> ORGANISM: Artificial sequence
<220> FEATURE:
<223> OTHER INFORMATION: Primer

<400> SEQUENCE: 105
aactataaaa aaataaatag ggacctagac ttcaggttgt ctaactcctt cctttcggt      60 tagagcggat ttaattaact aaaacccagc gtatcccttg a                        101

<210> SEQ ID NO 106
<211> LENGTH: 1197
<212> TYPE: DNA
<213> ORGANISM: Phytophthora soja

<400> SEQUENCE: 106
atggcaattc tgaatccgga agcagatagc gcagcaaatc tggcaaccga ttcagaagca     60
aaacagcgtc agctggccga agcaggttat acccatgttg aaggtgcacc ggcaccgctg    120
ccgctggaac tgccgcattt ttcactgcgt gatctgcgtg cagcaattcc gaaacattgt    180
tttgaacgta gctttgttac cagcacctat tatatgatta aaaacgtgct gacctgcgca    240
gcactgtttt atgcagcaac ctttattgat cgtgctggtg cagcagccta tgttctgtgg    300
cctgtttatt ggttttttca gggttcatat ctgaccggtg tttgggttat tgcacatgaa    360
tgtggtcatc aggcctattg tagctcagaa gttgtgaata tctgattgg tctggttctg    420 cattcagcac tgctggttcc gtatcattct ggcgtatta gccatcgtaa acatcattca    480
aataccggta gctgcgaaaa tgatgaagtt tttgttccgg ttacccgtag cgttctggca    540
agcagctgga atgaaaccct ggaagatagt ccgctgtatc agctgtatcg tattgtttat    600
atgctggttg ttggttggat gccgggttac ctgtttttta atgcaaccgg tccgaccaaa    660 tattgggta aatcacgtag ccatttaat ccgtatagcg caatttatgc cgatcgtgaa     720
cgttggatga ttgttctgtc agatattttt ctggttgcaa tgctggcagt tctggcagca    780
ctggttcata ccttagctt taatacgatg tgaagtttt atgtggtgcc gtatttatt      840 gtgaatgcct atctggtgct gattacctat ctgcagcaca ccgataccta tattccgcac    900
```

```
tttcgtgaag gtgaatggaa ttggctgcgt ggtgcactgt gtaccgttga tcgtagcttt    960
ggtccgtttc tggattcagt tgttcatcgt attgttgata cccatgtgtg ccatcatatt   1020
tttagcaaaa tgccgtttta tcattgcgaa gaagccacca acgcaattaa accgctgctg   1080
ggtaaatttt atctgaaaga taccacaccg gttccggttg cactgtggcg ttcatatacc   1140
cattgtaaat ttgtggaaga tgatggcaaa gtggtgtttt acaaaaacaa actgtaa      1197
```

<210> SEQ ID NO 107
<211> LENGTH: 398
<212> TYPE: PRT
<213> ORGANISM: Phytophthora soja

<400> SEQUENCE: 107

```
Met Ala Ile Leu Asn Pro Glu Ala Asp Ser Ala Ala Asn Leu Ala Thr
1               5                   10                  15

Asp Ser Glu Ala Lys Gln Arg Gln Leu Ala Glu Ala Gly Tyr Thr His
            20                  25                  30

Val Glu Gly Ala Pro Ala Pro Leu Pro Leu Glu Leu Pro His Phe Ser
        35                  40                  45

Leu Arg Asp Leu Arg Ala Ala Ile Pro Lys His Cys Phe Glu Arg Ser
    50                  55                  60

Phe Val Thr Ser Thr Tyr Tyr Met Ile Lys Asn Val Leu Thr Cys Ala
65                  70                  75                  80

Ala Leu Phe Tyr Ala Ala Thr Phe Ile Asp Arg Ala Gly Ala Ala Ala
                85                  90                  95

Tyr Val Leu Trp Pro Val Tyr Trp Phe Phe Gln Gly Ser Tyr Leu Thr
            100                 105                 110

Gly Val Trp Val Ile Ala His Glu Cys Gly His Gln Ala Tyr Cys Ser
        115                 120                 125

Ser Glu Val Val Asn Asn Leu Ile Gly Leu Val Leu His Ser Ala Leu
    130                 135                 140

Leu Val Pro Tyr His Ser Trp Arg Ile Ser His Arg Lys His His Ser
145                 150                 155                 160

Asn Thr Gly Ser Cys Glu Asn Asp Glu Val Phe Val Pro Val Thr Arg
                165                 170                 175

Ser Val Leu Ala Ser Ser Trp Asn Glu Thr Leu Glu Asp Ser Pro Leu
            180                 185                 190

Tyr Gln Leu Tyr Arg Ile Val Tyr Met Leu Val Val Gly Trp Met Pro
        195                 200                 205

Gly Tyr Leu Phe Phe Asn Ala Thr Gly Pro Thr Lys Tyr Trp Gly Lys
    210                 215                 220

Ser Arg Ser His Phe Asn Pro Tyr Ser Ala Ile Tyr Ala Asp Arg Glu
225                 230                 235                 240

Arg Trp Met Ile Val Leu Ser Asp Ile Phe Leu Val Ala Met Leu Ala
                245                 250                 255

Val Leu Ala Ala Leu Val His Thr Phe Ser Phe Asn Thr Met Val Lys
            260                 265                 270

Phe Tyr Val Val Pro Tyr Phe Ile Val Asn Ala Tyr Leu Val Leu Ile
        275                 280                 285

Thr Tyr Leu Gln His Thr Asp Thr Tyr Ile Pro His Phe Arg Glu Gly
    290                 295                 300

Glu Trp Asn Trp Leu Arg Gly Ala Leu Cys Thr Val Asp Arg Ser Phe
305                 310                 315                 320

Gly Pro Phe Leu Asp Ser Val Val His Arg Ile Val Asp Thr His Val
```

```
                    325                 330                 335
Cys His His Ile Phe Ser Lys Met Pro Phe Tyr His Cys Glu Glu Ala
            340                 345                 350

Thr Asn Ala Ile Lys Pro Leu Leu Gly Lys Phe Tyr Leu Lys Asp Thr
        355                 360                 365

Thr Pro Val Pro Val Ala Leu Trp Arg Ser Tyr Thr His Cys Lys Phe
    370                 375                 380

Val Glu Asp Asp Gly Lys Val Val Phe Tyr Lys Asn Lys Leu
385                 390                 395

<210> SEQ ID NO 108
<211> LENGTH: 1371
<212> TYPE: DNA
<213> ORGANISM: Ostreococcus tauri

<400> SEQUENCE: 108
atgtgtgttg agaccgagaa caacgatgga atccctactg tggagatcgc tttcgatgga      60
gagagagaaa gagctgaggc taacgtgaag ttgtctgctg agaagatgga acctgctgct     120
ttggctaaga ccttcgctag aagatacgtg gttatcgagg agttgagta cgatgtgacc     180 gatttcaaac accctggagg aaccgtgatt ttctacgctc tctctaacac tggagctgat     240
gctactgagg ctttcaagga gttccaccac agatctagaa aggctaggaa ggctttggct     300
gctttgcctt ctagacctgc taagaccgct aaagtggatg atgctgagat gctccaggat     360
ttcgctaagt ggagaaagga gttggagagg acggattct tcaagccttc tcctgctcac     420
gttgcttaca gattcgctga gttggctgct atgtacgctt gggaaccta cttgatgtac     480 gctagatacg ttgtgtcctc tgtgttggtt tacgcttgct tcttcggagc tagatgtgga     540
tgggttcaac acgagggagg acactcttct ttgaccggaa acatctggtg ggataagaga     600
atccaagctt tcactgctgg attcggattg ctggatctg agatatgtg aactccatg     660 cacaacaagc accacgctac tcctcaaaaa gtgaggcacg atatggattt ggataccact     720
cctgctgttg ctttcttcaa caccgctgtg aggataata gacctagggg attctctaag     780
tactggctca gattgcaagc ttggaccttc attcctgtga cttctggatt ggtgttgctc     840
ttctggatgt tcttcctcca ccctttctaag gctttgaagg gaggaaagta cgaggagctt     900
gtgtggatgt tggctgctca cgtgattaga acctggacca ttaaggctgt tactggattc     960
accgctatgc aatcctacgg actcttcttg gctacttctt gggtttccgg atgctacttg    1020
ttcgctcact ctctactttc tcacacccac ttggatgttg ttcctgctga tgagcacttg    1080
tcttgggtta ggtacgctgt ggatcacacc attgatatcg atccttctca gggatgggtt    1140
aactggttga tgggatactt gaactgccaa gtgattcacc acctcttccc ttctatgcct    1200
caattcagac aacctgaggt gtccagaaga ttcgttgctt tcgctaagaa gtggaacctc    1260
aactacaagg tgatgactta tgctggagct tggaaggcta ctttgggaaa cctcgataat    1320
gtgggaaagc actactacgt gcacggacaa cactctggaa agaccgcttg a              1371

<210> SEQ ID NO 109
<211> LENGTH: 456
<212> TYPE: PRT
<213> ORGANISM: Ostreococcus tauri

<400> SEQUENCE: 109

Met Cys Val Glu Thr Glu Asn Asn Asp Gly Ile Pro Thr Val Glu Ile
1               5                   10                  15
```

Ala Phe Asp Gly Glu Arg Glu Arg Ala Glu Asn Val Lys Leu Ser
            20                  25                  30

Ala Glu Lys Met Glu Pro Ala Ala Leu Ala Lys Thr Phe Ala Arg Arg
        35                  40                  45

Tyr Val Val Ile Glu Gly Val Glu Tyr Asp Val Thr Asp Phe Lys His
    50                  55                  60

Pro Gly Gly Thr Val Ile Phe Tyr Ala Leu Ser Asn Thr Gly Ala Asp
65                  70                  75                  80

Ala Thr Glu Ala Phe Lys Glu Phe His His Arg Ser Arg Lys Ala Arg
                85                  90                  95

Lys Ala Leu Ala Ala Leu Pro Ser Arg Pro Ala Lys Thr Ala Lys Val
            100                 105                 110

Asp Asp Ala Glu Met Leu Gln Asp Phe Ala Lys Trp Arg Lys Glu Leu
        115                 120                 125

Glu Arg Asp Gly Phe Phe Lys Pro Ser Pro Ala His Val Ala Tyr Arg
    130                 135                 140

Phe Ala Glu Leu Ala Ala Met Tyr Ala Leu Gly Thr Tyr Leu Met Tyr
145                 150                 155                 160

Ala Arg Tyr Val Val Ser Ser Val Leu Val Tyr Ala Cys Phe Phe Gly
                165                 170                 175

Ala Arg Cys Gly Trp Val Gln His Glu Gly Gly His Ser Ser Leu Thr
            180                 185                 190

Gly Asn Ile Trp Trp Asp Lys Arg Ile Gln Ala Phe Thr Ala Gly Phe
        195                 200                 205

Gly Leu Ala Gly Ser Gly Asp Met Trp Asn Ser Met His Asn Lys His
    210                 215                 220

His Ala Thr Pro Gln Lys Val Arg His Asp Met Asp Leu Asp Thr Thr
225                 230                 235                 240

Pro Ala Val Ala Phe Phe Asn Thr Ala Val Glu Asp Asn Arg Pro Arg
                245                 250                 255

Gly Phe Ser Lys Tyr Trp Leu Arg Leu Gln Ala Trp Thr Phe Ile Pro
            260                 265                 270

Val Thr Ser Gly Leu Val Leu Leu Phe Trp Met Phe Phe Leu His Pro
        275                 280                 285

Ser Lys Ala Leu Lys Gly Gly Lys Tyr Glu Glu Leu Val Trp Met Leu
    290                 295                 300

Ala Ala His Val Ile Arg Thr Trp Thr Ile Lys Ala Val Thr Gly Phe
305                 310                 315                 320

Thr Ala Met Gln Ser Tyr Gly Leu Phe Leu Ala Thr Ser Trp Val Ser
                325                 330                 335

Gly Cys Tyr Leu Phe Ala His Phe Ser Thr Ser His Thr His Leu Asp
            340                 345                 350

Val Val Pro Ala Asp Glu His Leu Ser Trp Val Arg Tyr Ala Val Asp
        355                 360                 365

His Thr Ile Asp Ile Asp Pro Ser Gln Gly Trp Val Asn Trp Leu Met
    370                 375                 380

Gly Tyr Leu Asn Cys Gln Val Ile His His Leu Phe Pro Ser Met Pro
385                 390                 395                 400

Gln Phe Arg Gln Pro Glu Val Ser Arg Arg Phe Val Ala Phe Ala Lys
                405                 410                 415

Lys Trp Asn Leu Asn Tyr Lys Val Met Thr Tyr Ala Gly Ala Trp Lys
            420                 425                 430

Ala Thr Leu Gly Asn Leu Asp Asn Val Gly Lys His Tyr Tyr Val His

Gly Gln His Ser Gly Lys Thr Ala
    450               455

<210> SEQ ID NO 110
<211> LENGTH: 819
<212> TYPE: DNA
<213> ORGANISM: Thalassiosira pseudonana

<400> SEQUENCE: 110

```
atggatgctt ataacgctgc tatggataag attggagctg ctatcatcga ttggagtgat      60
ccagatggaa agttcagagc tgatagggag gattggtggt tgtgcgattt cagatccgct     120
atcaccattg ctctcatcta catcgctttc gtgatcttgg atctgctgt gatgcaatct     180
ctcccagcta tggacccata ccctatcaag ttcctctaca acgtgtctca aatcttcctc     240
tgcgcttaca tgactgttga ggctggattc ctcgcttata ggaacggata caccgttatg     300
ccatgcaacc acttcaacgt gaacgatcca ccagttgcta acttgctctg gctcttctac     360
atctccaaag tgtgggattt ctgggatacc atcttcattg tgctcggaaa gaagtggaga     420
caactctctt tcttgcacgt gtaccaccac accaccatct tcctcttcta ctggttgaac     480
gctaacgtgc tctacgatgg agatatcttc ttgaccatcc tcctcaacgg attcattcac     540
accgtgatgt acacctacta cttcatctgc atgcacacca aggattctaa gaccggaaag     600
tctttgccaa tctggtggaa gtcatctttg accgctttcc aactcttgca attcaccatc     660
atgatgtccc aagctaccta cttggttttc cacggatgcg ataaggtttc cctcagaatc     720
accatcgtgt acttcgtgta cattctctcc cttttcttcc tcttcgctca gttcttcgtg     780
caatcctaca tggctccaaa gaagaagaag tccgcttga                            819
```

<210> SEQ ID NO 111
<211> LENGTH: 272
<212> TYPE: PRT
<213> ORGANISM: Thalassiosira pseudonana

<400> SEQUENCE: 111

Met Asp Ala Tyr Asn Ala Ala Met Asp Lys Ile Gly Ala Ala Ile Ile
1               5                  10                15

Asp Trp Ser Asp Pro Asp Gly Lys Phe Arg Ala Asp Arg Glu Asp Trp
          20                  25               30

Trp Leu Cys Asp Phe Arg Ser Ala Ile Thr Ile Ala Leu Ile Tyr Ile
        35                  40               45

Ala Phe Val Ile Leu Gly Ser Ala Val Met Gln Ser Leu Pro Ala Met
    50                 55                60

Asp Pro Tyr Pro Ile Lys Phe Leu Tyr Asn Val Ser Gln Ile Phe Leu
65              70                 75              80

Cys Ala Tyr Met Thr Val Glu Ala Gly Phe Leu Ala Tyr Arg Asn Gly
          85                  90               95

Tyr Thr Val Met Pro Cys Asn His Phe Asn Val Asn Asp Pro Pro Val
          100                105             110

Ala Asn Leu Leu Trp Leu Phe Tyr Ile Ser Lys Val Trp Asp Phe Trp
       115               120             125

Asp Thr Ile Phe Ile Val Leu Gly Lys Lys Trp Arg Gln Leu Ser Phe
    130               135             140

Leu His Val Tyr His His Thr Thr Ile Phe Leu Phe Tyr Trp Leu Asn
145            150               155            160

```
Ala Asn Val Leu Tyr Asp Gly Asp Ile Phe Leu Thr Ile Leu Leu Asn
                165                 170                 175

Gly Phe Ile His Thr Val Met Tyr Thr Tyr Tyr Phe Ile Cys Met His
            180                 185                 190

Thr Lys Asp Ser Lys Thr Gly Lys Ser Leu Pro Ile Trp Trp Lys Ser
        195                 200                 205

Ser Leu Thr Ala Phe Gln Leu Leu Gln Phe Thr Ile Met Met Ser Gln
    210                 215                 220

Ala Thr Tyr Leu Val Phe His Gly Cys Asp Lys Val Ser Leu Arg Ile
225                 230                 235                 240

Thr Ile Val Tyr Phe Val Tyr Ile Leu Ser Leu Phe Phe Leu Phe Ala
                245                 250                 255

Gln Phe Phe Val Gln Ser Tyr Met Ala Pro Lys Lys Lys Lys Ser Ala
            260                 265                 270

<210> SEQ ID NO 112
<211> LENGTH: 873
<212> TYPE: DNA
<213> ORGANISM: Physcomitrella patens

<400> SEQUENCE: 112
atggaagttg ttgagaggtt ctacggagag ttggatggaa aggtttccca aggagtgaac      60
gctttgttgg gatctttcgg agttgagttg actgataccc caactactaa gggattgcca     120
ctcgttgatt ctccaactcc aattgtgttg ggagtgtctg tttacttgac catcgtgatc     180
ggaggattgc tttggatcaa ggctagagat ctcaagccaa gagcttctga gccattcttg     240
ttgcaagctt tggtgttggt gcacaacttg ttctgcttcg ctttgtctct ttacatgtgt     300
gtgggaatcg cttaccaagc tatcacctgg agatattcct tgtggggaaa cgcttataac     360
ccaaagcaca aggagatggc tatcctcgtt tacctcttct acatgtccaa gtacgtggag     420
ttcatggata ccgtgatcat gatcctcaag agatctacca gacagatttc tttcctccac     480
gtgtaccacc actcttctat ctcccttatc tggtgggcta ttgctcacca cgctccagga     540
ggagaggctt attggagcgc tgctctcaac tctggagtgc acgtgttgat gtacgcttac     600
tacttcttgg ctgcttgctt gagatcttcc ccaaagctca agaacaagta cctcttctgg     660
ggaagatacc tcacccaatt ccagatgttc cagtttatgc tcaacttggt gcaagcttac     720
tacgatatga agaccaacgc tccatatcca cagtggctca tcaagatcct cttctactac     780
atgatctccc tcttgttcct cttcggaaac ttctacgtgc aaaagtacat caagccatca     840
gatggaaagc aaaagggagc taagaccgag tga                                  873

<210> SEQ ID NO 113
<211> LENGTH: 290
<212> TYPE: PRT
<213> ORGANISM: Physcomitrella patens

<400> SEQUENCE: 113

Met Glu Val Val Glu Arg Phe Tyr Gly Glu Leu Asp Gly Lys Val Ser
1               5                   10                  15

Gln Gly Val Asn Ala Leu Leu Gly Ser Phe Gly Val Glu Leu Thr Asp
            20                  25                  30

Thr Pro Thr Thr Lys Gly Leu Pro Leu Val Asp Ser Pro Thr Pro Ile
        35                  40                  45

Val Leu Gly Val Ser Val Tyr Leu Thr Ile Val Ile Gly Gly Leu Leu
    50                  55                  60
```

```
Trp Ile Lys Ala Arg Asp Leu Lys Pro Arg Ala Ser Glu Pro Phe Leu
 65                  70                  75                  80
Leu Gln Ala Leu Val Leu Val His Asn Leu Phe Cys Phe Ala Leu Ser
                 85                  90                  95
Leu Tyr Met Cys Val Gly Ile Ala Tyr Gln Ala Ile Thr Trp Arg Tyr
            100                 105                 110
Ser Leu Trp Gly Asn Ala Tyr Asn Pro Lys His Lys Glu Met Ala Ile
        115                 120                 125
Leu Val Tyr Leu Phe Tyr Met Ser Lys Tyr Val Glu Phe Met Asp Thr
    130                 135                 140
Val Ile Met Ile Leu Lys Arg Ser Thr Arg Gln Ile Ser Phe Leu His
145                 150                 155                 160
Val Tyr His His Ser Ser Ile Ser Leu Ile Trp Trp Ala Ile Ala His
                165                 170                 175
His Ala Pro Gly Gly Glu Ala Tyr Trp Ser Ala Ala Leu Asn Ser Gly
            180                 185                 190
Val His Val Leu Met Tyr Ala Tyr Tyr Phe Leu Ala Ala Cys Leu Arg
        195                 200                 205
Ser Ser Pro Lys Leu Lys Asn Lys Tyr Leu Phe Trp Gly Arg Tyr Leu
    210                 215                 220
Thr Gln Phe Gln Met Phe Gln Phe Met Leu Asn Leu Val Gln Ala Tyr
225                 230                 235                 240
Tyr Asp Met Lys Thr Asn Ala Pro Tyr Pro Gln Trp Leu Ile Lys Ile
                245                 250                 255
Leu Phe Tyr Tyr Met Ile Ser Leu Leu Phe Leu Phe Gly Asn Phe Tyr
            260                 265                 270
Val Gln Lys Tyr Ile Lys Pro Ser Asp Gly Lys Gln Lys Gly Ala Lys
        275                 280                 285
Thr Glu
    290

<210> SEQ ID NO 114
<211> LENGTH: 1320
<212> TYPE: DNA
<213> ORGANISM: Thraustochytrium sp.

<400> SEQUENCE: 114
atgggaaaag atctgaggg aagatctgct gctagagaga tgactgctga ggctaacgga      60
gataagagaa agaccatcct cattgaggga gtgttgtacg atgctaccaa cttcaaacac    120
ccaggaggtt ccattattaa cttcctcacc gagggagaag ctggagttga tgctacccaa    180
gcttacagag agttccatca gagatccgga aaggctgata agtacctcaa gtccctccca    240
aagttggatg cttctaaggt ggagtctagg ttctctgcta aggagcaggc tagaagggac    300
gctatgacca gggattacgc tgctttcaga gaggagttgg ttgctgaggg atacttcgat    360
ccatctatcc cacacatgat ctacagagtg gtggagattg gctttgtt cgctttgtct     420 ttctggttga tgtctaaggc ttctccaacc tctttggttt tgggagtggt gatgaacgga    480
atcgctcaag aagatgcgg atgggttatg cacgagatgg acacggatc tttcactgga     540 gttatctggc tcgatgatag gatgtgcgag ttcttctacg agttggatg tggaatgtct    600 ggacactact ggaagaacca gcactctaag caccacgctg ctccaaacag attggagcac    660
gatgtggatt tgaacacctt gccactcgtt gctttcaacg agagagttgt gaggaaggtt    720
aagccaggat ctttgttggc tttgtggctc agagttcagg cttatttgtt cgctccagtg    780
```

```
tcttgcttgt tgatcggatt gggatggacc ttgtacttgc acccaagata tatgctcagg      840
accaagagac acatggagtt tgtgtggatc ttcgctagat atatcggatg gttctccttg      900
atgggagctt tgggatattc tcctggaact tctgtgggaa tgtacctctg ctctttcgga      960
cttggatgca tctacatctt cctccaattc gctgtgtctc acacccactt gccagttacc     1020
aacccagagg atcaattgca ctggcttgag tacgctgctg atcacaccgt gaacatctct     1080
accaagtctt ggttggttac ctggtggatg tctaacctca acttccaaat cgagcaccac     1140
ttgttcccaa ccgctccaca attcaggttc aaggagatct ctccaagagt tgaggctctc     1200
ttcaagagac acaacctccc ttactacgat ttgccataca cctctgctgt ttctactacc     1260
ttcgctaacc tctactctgt tggacactct gttggagctg ataccaagaa gcaggattga     1320
```

<210> SEQ ID NO 115
<211> LENGTH: 439
<212> TYPE: PRT
<213> ORGANISM: Thraustochytrium sp.

<400> SEQUENCE: 115

```
Met Gly Lys Gly Ser Glu Gly Arg Ser Ala Ala Arg Glu Met Thr Ala
1               5                   10                  15

Glu Ala Asn Gly Asp Lys Arg Lys Thr Ile Leu Ile Glu Gly Val Leu
            20                  25                  30

Tyr Asp Ala Thr Asn Phe Lys His Pro Gly Gly Ser Ile Ile Asn Phe
        35                  40                  45

Leu Thr Glu Gly Glu Ala Gly Val Asp Ala Thr Gln Ala Tyr Arg Glu
    50                  55                  60

Phe His Gln Arg Ser Gly Lys Ala Asp Lys Tyr Leu Lys Ser Leu Pro
65                  70                  75                  80

Lys Leu Asp Ala Ser Lys Val Glu Ser Arg Phe Ser Ala Lys Glu Gln
                85                  90                  95

Ala Arg Arg Asp Ala Met Thr Arg Asp Tyr Ala Ala Phe Arg Glu Glu
            100                 105                 110

Leu Val Ala Glu Gly Tyr Phe Asp Pro Ser Ile Pro His Met Ile Tyr
        115                 120                 125

Arg Val Val Glu Ile Val Ala Leu Phe Ala Leu Ser Phe Trp Leu Met
    130                 135                 140

Ser Lys Ala Ser Pro Thr Ser Leu Val Leu Gly Val Val Met Asn Gly
145                 150                 155                 160

Ile Ala Gln Gly Arg Cys Gly Trp Val Met His Glu Met Gly His Gly
                165                 170                 175

Ser Phe Thr Gly Val Ile Trp Leu Asp Asp Arg Met Cys Glu Phe Phe
            180                 185                 190

Tyr Gly Val Gly Cys Gly Met Ser Gly His Tyr Trp Lys Asn Gln His
        195                 200                 205

Ser Lys His His Ala Ala Pro Asn Arg Leu Glu His Asp Val Asp Leu
    210                 215                 220

Asn Thr Leu Pro Leu Val Ala Phe Asn Glu Arg Val Val Arg Lys Val
225                 230                 235                 240

Lys Pro Gly Ser Leu Leu Ala Leu Trp Leu Arg Val Gln Ala Tyr Leu
                245                 250                 255

Phe Ala Pro Val Ser Cys Leu Leu Ile Gly Leu Gly Trp Thr Leu Tyr
            260                 265                 270

Leu His Pro Arg Tyr Met Leu Arg Thr Lys Arg His Met Glu Phe Val
        275                 280                 285
```

Trp Ile Phe Ala Arg Tyr Ile Gly Trp Phe Ser Leu Met Gly Ala Leu
            290                 295                 300

Gly Tyr Ser Pro Gly Thr Ser Val Gly Met Tyr Leu Cys Ser Phe Gly
305                 310                 315                 320

Leu Gly Cys Ile Tyr Ile Phe Leu Gln Phe Ala Val Ser His Thr His
                325                 330                 335

Leu Pro Val Thr Asn Pro Glu Asp Gln Leu His Trp Leu Glu Tyr Ala
            340                 345                 350

Ala Asp His Thr Val Asn Ile Ser Thr Lys Ser Trp Leu Val Thr Trp
        355                 360                 365

Trp Met Ser Asn Leu Asn Phe Gln Ile Glu His Leu Phe Pro Thr
    370                 375                 380

Ala Pro Gln Phe Arg Phe Lys Glu Ile Ser Pro Arg Val Glu Ala Leu
385                 390                 395                 400

Phe Lys Arg His Asn Leu Pro Tyr Tyr Asp Leu Pro Tyr Thr Ser Ala
                405                 410                 415

Val Ser Thr Thr Phe Ala Asn Leu Tyr Ser Val Gly His Ser Val Gly
            420                 425                 430

Ala Asp Thr Lys Lys Gln Asp
        435

<210> SEQ ID NO 116
<211> LENGTH: 792
<212> TYPE: DNA
<213> ORGANISM: Isochrysis galbana

<400> SEQUENCE: 116
atggccctcg caaacgacgc gggagagcgc atctgggcgg ctgtgaccga cccggaaatc      60
ctcattggca ccttctcgta cttgctactc aaaccgctgc tccgcaattc cgggctggtg     120
gatgagaaga agggcgcata caggacgtcc atgatctggt acaacgttct gctggcgctc     180
ttctctgcgc tgagcttcta cgtgacggcg accgccctcg gctgggacta tggtacgggc     240
gcgtggctgc gcaggcaaac cggcgacaca ccgcagccgc tcttccagtg cccgtcccg      300 gtttgggact cgaagctctt cacatggacc gccaaggcat ctattactc caagtacgtg      360 gagtacctcg acacggcctg gctggtgctc aagggcaaga gggtctcctt tctccaggcc     420
ttccaccact ttggcgcgcc gtgggatgtg tacctcggca ttcggctgca aacgagggc      480 gtatggatct tcatgttttt caactcgttc attcacacca tcatgtacac ctactacggc     540
ctcaccgccg ccgggtataa gttcaaggcc aagccgctca tcaccgcgat gcagatctgc     600
cagttcgtgg gcggcttcct gttggtctgg gactacatca acgtcccctg cttcaactcg     660
gacaaaggga agttgttcag ctgggctttc aactatgcat acgtcggctc ggtcttcttg     720
ctcttctgcc actttttcta ccaggacaac ttggcaacga gaaatcggc caaggcgggc      780 aagcagctct ag                                                         792

<210> SEQ ID NO 117
<211> LENGTH: 263
<212> TYPE: PRT
<213> ORGANISM: Isochrysis galbana

<400> SEQUENCE: 117

Met Ala Leu Ala Asn Asp Ala Gly Glu Arg Ile Trp Ala Ala Val Thr
1               5                   10                  15

Asp Pro Glu Ile Leu Ile Gly Thr Phe Ser Tyr Leu Leu Leu Lys Pro

```
            20                  25                  30

Leu Leu Arg Asn Ser Gly Leu Val Asp Glu Lys Lys Gly Ala Tyr Arg
        35                  40                  45

Thr Ser Met Ile Trp Tyr Asn Val Leu Leu Ala Leu Phe Ser Ala Leu
    50                  55                  60

Ser Phe Tyr Val Thr Ala Thr Ala Leu Gly Trp Asp Tyr Gly Thr Gly
65                  70                  75                  80

Ala Trp Leu Arg Arg Gln Thr Gly Asp Thr Pro Gln Pro Leu Phe Gln
                85                  90                  95

Cys Pro Ser Pro Val Trp Asp Ser Lys Leu Phe Thr Trp Thr Ala Lys
            100                 105                 110

Ala Phe Tyr Tyr Ser Lys Tyr Val Glu Tyr Leu Asp Thr Ala Trp Leu
        115                 120                 125

Val Leu Lys Gly Lys Arg Val Ser Phe Leu Gln Ala Phe His His Phe
    130                 135                 140

Gly Ala Pro Trp Asp Val Tyr Leu Gly Ile Arg Leu His Asn Glu Gly
145                 150                 155                 160

Val Trp Ile Phe Met Phe Phe Asn Ser Phe Ile His Thr Ile Met Tyr
                165                 170                 175

Thr Tyr Tyr Gly Leu Thr Ala Ala Gly Tyr Lys Phe Lys Ala Lys Pro
            180                 185                 190

Leu Ile Thr Ala Met Gln Ile Cys Gln Phe Val Gly Gly Phe Leu Leu
        195                 200                 205

Val Trp Asp Tyr Ile Asn Val Pro Cys Phe Asn Ser Asp Lys Gly Lys
    210                 215                 220

Leu Phe Ser Trp Ala Phe Asn Tyr Ala Tyr Val Gly Ser Val Phe Leu
225                 230                 235                 240

Leu Phe Cys His Phe Phe Tyr Gln Asp Asn Leu Ala Thr Lys Lys Ser
                245                 250                 255

Ala Lys Ala Gly Lys Gln Leu
            260

<210> SEQ ID NO 118
<211> LENGTH: 1236
<212> TYPE: DNA
<213> ORGANISM: Perkinsus marinus

<400> SEQUENCE: 118
atgtcttctc ttaccctcta cagaggcccc ttttcccgaa tggtgctccc tcgtcaggaa      60
atctgcatcg atggtcgcat atacgatgtc actgagttca tcaatcgtca tccaggtggt     120
aagattatcc tcttccaagt tggtgctgat gccactgatg cttttcgtga gtttcatgct     180
ggcagtgaga aggcagagaa gatcctcaaa accctaccat cccgtgatga tgacggtact     240
ttccttcctt caacccaacg ctccatcatg gatgatttca aacgcctaag agatgacctc     300
gtcagcagag gtgtcttcaa gccaagcgtc atgcatgttg tataccgctg cttggaagtc     360
gttgctctct atctcattgg cttctatttg gctctgtgca ccagtaatgt gtacgttggg     420
tgtgctgtac ttggtgtagc tcaaggtcgt gctggttggt tgatgcatga aggaggtcat     480
cactctctga ctggtaactg gaaagttgac cagttcctcc aagaactatt tttcggcatt     540
ggttgtggta tgtcagctgc gtggtggcgc aatgcacaca acaagcatca cgctgctcct     600
cagcatttag ggaaagatgt tgatctcgag acattgcctc tggtcgcctt caataaggcc     660
gtacttcgag gccgtctacc gtctgtctgg atcagatcac aagctgtgtg ctttgcaccg     720
```

-continued

```
atatcaacac tactggtatc gttcttttgg caattctacc tacacccgag gcatattatt    780
aggacaggtc gacgaatgga gtctttctgg ctactcgtac gctacttagt tattgtgtac    840
ctcgggttca gctatggatt ggtatcggtc ttgttatgtt acatcgcaag tgtgcatgtt    900
ggtggtatgt acatctttgt acacttcgct ctatcacata cacatttacc tgtcattaac    960
cagcatggta gagctaactg gttggaatac gcatctaagc acacagttaa tgtgtcaact   1020
aacaattatt tcgtcacatg gctcatgagt tatttgaatt atcaaataga gcatcatctc   1080
ttcccgtcat gtccccagtt tagattccct ggttacgtca gtatgagggt tcgagaattt   1140
tttcataagc atggattgaa gtaaacgag tcggctatc tacatgcact caatctcaca   1200
ttttcaaatc tggctgctgt tgccatagtg gaatag                              1236
```

<210> SEQ ID NO 119
<211> LENGTH: 411
<212> TYPE: PRT
<213> ORGANISM: Perkinsus marinus

<400> SEQUENCE: 119

```
Met Ser Ser Leu Thr Leu Tyr Arg Gly Pro Phe Ser Arg Met Val Leu
1               5                   10                  15

Pro Arg Gln Glu Ile Cys Ile Asp Gly Arg Ile Tyr Asp Val Thr Glu
            20                  25                  30

Phe Ile Asn Arg His Pro Gly Gly Lys Ile Ile Leu Phe Gln Val Gly
        35                  40                  45

Ala Asp Ala Thr Asp Ala Phe Arg Glu Phe His Ala Gly Ser Glu Lys
    50                  55                  60

Ala Glu Lys Ile Leu Lys Thr Leu Pro Ser Arg Asp Asp Asp Gly Thr
65                  70                  75                  80

Phe Leu Pro Ser Thr Gln Arg Ser Ile Met Asp Asp Phe Lys Arg Leu
                85                  90                  95

Arg Asp Asp Leu Val Ser Arg Gly Val Phe Lys Pro Ser Val Met His
            100                 105                 110

Val Val Tyr Arg Cys Leu Glu Val Ala Leu Tyr Leu Ile Gly Phe
        115                 120                 125

Tyr Leu Ala Leu Cys Thr Ser Asn Val Tyr Val Gly Cys Ala Val Leu
    130                 135                 140

Gly Val Ala Gln Gly Arg Ala Gly Trp Leu Met His Glu Gly Gly His
145                 150                 155                 160

His Ser Leu Thr Gly Asn Trp Lys Val Asp Gln Phe Leu Gln Glu Leu
                165                 170                 175

Phe Phe Gly Ile Gly Cys Gly Met Ser Ala Ala Trp Arg Asn Ala
            180                 185                 190

His Asn Lys His His Ala Ala Pro Gln His Leu Gly Lys Asp Val Asp
        195                 200                 205

Leu Glu Thr Leu Pro Leu Val Ala Phe Asn Lys Ala Val Leu Arg Gly
    210                 215                 220

Arg Leu Pro Ser Val Trp Ile Arg Ser Gln Ala Val Cys Phe Ala Pro
225                 230                 235                 240

Ile Ser Thr Leu Leu Val Ser Phe Phe Trp Gln Phe Tyr Leu His Pro
                245                 250                 255

Arg His Ile Ile Arg Thr Gly Arg Arg Met Glu Ser Phe Trp Leu Leu
            260                 265                 270

Val Arg Tyr Leu Val Ile Val Tyr Leu Gly Phe Ser Tyr Gly Leu Val
        275                 280                 285
```

-continued

```
Ser Val Leu Leu Cys Tyr Ile Ala Ser Val His Val Gly Gly Met Tyr
    290                 295                 300

Ile Phe Val His Phe Ala Leu Ser His Thr His Leu Pro Val Ile Asn
305                 310                 315                 320

Gln His Gly Arg Ala Asn Trp Leu Glu Tyr Ala Ser Lys His Thr Val
                325                 330                 335

Asn Val Ser Thr Asn Asn Tyr Phe Val Thr Trp Leu Met Ser Tyr Leu
            340                 345                 350

Asn Tyr Gln Ile Glu His His Leu Phe Pro Ser Cys Pro Gln Phe Arg
        355                 360                 365

Phe Pro Gly Tyr Val Ser Met Arg Val Arg Glu Phe Phe His Lys His
    370                 375                 380

Gly Leu Lys Tyr Asn Glu Val Gly Tyr Leu His Ala Leu Asn Leu Thr
385                 390                 395                 400

Phe Ser Asn Leu Ala Ala Val Ala Ile Val Glu
                405                 410
```

<210> SEQ ID NO 120
<211> LENGTH: 1128
<212> TYPE: DNA
<213> ORGANISM: Helobdella robusta

<400> SEQUENCE: 120

```
atgaattgtg ttaccgaggt gaacagcatc attgctagcc ttatcaaggc tgctttcctc      60
tactctaacc ctcagaccaa gatcagaggt atcaaccttg atacccagct tcctaagaac     120
ctcccttctg tgatcgagat caagagggtt atcccttctc attgcttcgt tccttctacc     180
tgccgttctc ttctttacgc tctcaaggac gttgttcaga tccttttcgc ttgggttctc     240
ctttggtact tgcttcctct cactaactgg atcgctctca aggttctcat gatcttcgtg     300
tactggggaa tccagggaac tttcttcatg ggactcttcg ttatgggaca tgattgtgga     360
cacggaagct tctctaagta ccgtcttttg aacgatgttg tgggaactat ctctcacgct     420
ttcctcttcg tgccttacta ccagtggaag cttactcatc agaaccacca caagttcacc     480
ggaaacatgg ataaggacga ggttttctac cctgctagag cttctcaaaa gcctagcatc     540
aactctgttc tccctggatt cggatacgga atcggatggt tcacttacct cttcatcgga     600
tacttcccta gaagagtgtc tcacttcaac ctcttcgacg agatgttcag aggacatgaa     660
gttgcttgca ccctttctct tctcacctac ggaatgaacg gaactctttg ctactggttc     720
tacctcagct acggattcaa gatcctcttc gtgttctacc ttgctcctct cttcatctac     780
ggaagctaca tggttatcgt gactttcctt caccactctg aggttaacat cccttggtac     840
gctgatcaaa actggaacta cgtgaaggga cagctttcta ccatcgacag aaactacgga     900
cttgttcacc atgctatcca ctgtatcgga actcatcaga tgcatcacat gttcaccaag     960
atccctcatt accaccttga ggaagctact agacacttcc gttctgcttt ccctgagctt    1020
gttaagtctt gcgacgagcc tatcctctct tctttcgtcc gtatgttcaa gaagtacaac    1080
cagcaacagg ttgtggctga taacgctctc gaggtgtact acaagtga                1128
```

<210> SEQ ID NO 121
<211> LENGTH: 375
<212> TYPE: PRT
<213> ORGANISM: Helobdella robusta

<400> SEQUENCE: 121

```
Met Asn Cys Val Thr Glu Val Asn Ser Ile Ala Ser Leu Ile Lys
1               5                  10                 15

Ala Ala Phe Leu Tyr Ser Asn Pro Gln Thr Lys Ile Arg Gly Ile Asn
            20                  25                  30

Leu Asp Thr Gln Leu Pro Lys Asn Leu Pro Ser Val Ile Glu Ile Lys
        35                  40                  45

Arg Val Ile Pro Ser His Cys Phe Val Pro Ser Thr Cys Arg Ser Leu
    50                  55                  60

Leu Tyr Ala Leu Lys Asp Val Val Gln Ile Leu Phe Ala Trp Val Leu
65                  70                  75                  80

Leu Trp Tyr Leu Pro Leu Thr Asn Trp Ile Ala Leu Lys Val Leu
            85                  90                  95

Met Ile Phe Val Tyr Trp Gly Ile Gln Gly Thr Phe Phe Met Gly Leu
            100                 105                 110

Phe Val Met Gly His Asp Cys Gly His Gly Ser Phe Ser Lys Tyr Arg
            115                 120                 125

Leu Leu Asn Asp Val Val Gly Thr Ile Ser His Ala Phe Leu Phe Val
    130                 135                 140

Pro Tyr Tyr Gln Trp Lys Leu Thr His Gln Asn His His Lys Phe Thr
145                 150                 155                 160

Gly Asn Met Asp Lys Asp Glu Val Phe Tyr Pro Ala Arg Ala Ser Gln
                165                 170                 175

Lys Pro Ser Ile Asn Ser Val Leu Pro Gly Phe Gly Tyr Gly Ile Gly
            180                 185                 190

Trp Phe Thr Tyr Leu Phe Ile Gly Tyr Phe Pro Arg Arg Val Ser His
            195                 200                 205

Phe Asn Leu Phe Asp Glu Met Phe Arg Gly His Glu Val Ala Cys Thr
    210                 215                 220

Leu Ser Leu Leu Thr Tyr Gly Met Asn Gly Thr Leu Cys Tyr Trp Phe
225                 230                 235                 240

Tyr Leu Ser Tyr Gly Phe Lys Ile Leu Phe Val Phe Tyr Leu Ala Pro
                245                 250                 255

Leu Phe Ile Tyr Gly Ser Tyr Met Val Ile Val Thr Phe Leu His His
            260                 265                 270

Ser Glu Val Asn Ile Pro Trp Tyr Ala Asp Gln Asn Trp Asn Tyr Val
    275                 280                 285

Lys Gly Gln Leu Ser Thr Ile Asp Arg Asn Tyr Gly Leu Val His His
290                 295                 300

Ala Ile His Cys Ile Gly Thr His Gln Met His His Met Phe Thr Lys
305                 310                 315                 320

Ile Pro His Tyr His Leu Glu Glu Ala Thr Arg His Phe Arg Ser Ala
                325                 330                 335

Phe Pro Glu Leu Val Lys Ser Cys Asp Glu Pro Ile Leu Ser Ser Phe
            340                 345                 350

Val Arg Met Phe Lys Lys Tyr Asn Gln Gln Val Val Ala Asp Asn
            355                 360                 365

Ala Leu Glu Val Tyr Tyr Lys
    370                 375

<210> SEQ ID NO 122
<211> LENGTH: 1086
<212> TYPE: DNA
<213> ORGANISM: Phytophthora infestans

<400> SEQUENCE: 122
```

```
atggcgacga aggaggcgta tgtgttcccc actctgacgg agatcaagcg gtcgctacct      60
aaagactgtt tcgaggcttc ggtgcctctg tcgctctact acaccgtgcg ttgtctggtg     120
atcgcggtgg ctctaacctt cggtctcaac tacgctcgcg ctctgcccga ggtcgagagc     180
ttctgggctc tggacgccgc actctgcacg ggctacatct tgctgcaggg catcgtgttc     240
tggggcttct tcacggtggg ccacgatgcc ggccacggcg ccttctcgcg ctaccacctg     300
cttaacttcg tggtgggcac tttcatgcac tcgctcatcc tcacgccctt cgagtcgtgg     360
aagctcacgc accgtcacca ccacaagaac acgggcaaca ttgaccgtga cgaggtcttc     420
tacccgcaac gcaaggccga cgaccacccg ctgtctcgca acctgattct ggcgctcggg     480
gcagcgtggc tcgcctattt ggtcgagggc ttccctcctc gtaaggtcaa ccacttcaac     540
ccgttcgagc ctctgttcgt gcgtcaggtg tcagctgtgg taatctctct tctcgcccac     600
ttcttcgtgg ccggactctc catctatctg agcctccagc tgggccttaa gacgatggca     660
atctactact atggacctgt ttttgtgttc ggcagcatgc tggtcattac caccttccta     720
caccacaatg atgaggagac cccatggtac gccgactcgg agtggacgta cgtcaagggc     780
aacctctcgt ccgtggaccg atcgtacggc gcgctcattg acaacctgag ccacaacatc     840
ggcacgcacc agatccacca ccttttccct atcattccgc actacaaact caagaaagcc     900
actgcggcct tccaccaggc tttccctgag ctcgtgcgca agagcgacga gccaattatc     960
aaggctttct tccgggttgg acgtctctac gcaaactacg gcgttgtgga ccaggaggcg    1020
aagctcttca cgctaaagga agccaaggcg gcgaccgagg cggcggccaa gaccaagtcc    1080
acgtaa                                                                1086
```

<210> SEQ ID NO 123
<211> LENGTH: 361
<212> TYPE: PRT
<213> ORGANISM: Phytophthora infestans

<400> SEQUENCE: 123

```
Met Ala Thr Lys Glu Ala Tyr Val Phe Pro Thr Leu Thr Glu Ile Lys
1               5                   10                  15

Arg Ser Leu Pro Lys Asp Cys Phe Glu Ala Ser Val Pro Leu Ser Leu
            20                  25                  30

Tyr Tyr Thr Val Arg Cys Leu Val Ile Ala Val Ala Leu Thr Phe Gly
        35                  40                  45

Leu Asn Tyr Ala Arg Ala Leu Pro Glu Val Glu Ser Phe Trp Ala Leu
    50                  55                  60

Asp Ala Ala Leu Cys Thr Gly Tyr Ile Leu Leu Gln Gly Ile Val Phe
65                  70                  75                  80

Trp Gly Phe Phe Thr Val Gly His Asp Ala Gly His Gly Ala Phe Ser
                85                  90                  95

Arg Tyr His Leu Leu Asn Phe Val Val Gly Thr Phe Met His Ser Leu
            100                 105                 110

Ile Leu Thr Pro Phe Glu Ser Trp Lys Leu Thr His Arg His His His
        115                 120                 125

Lys Asn Thr Gly Asn Ile Asp Arg Asp Glu Val Phe Tyr Pro Gln Arg
    130                 135                 140

Lys Ala Asp Asp His Pro Leu Ser Arg Asn Leu Ile Leu Ala Leu Gly
145                 150                 155                 160

Ala Ala Trp Leu Ala Tyr Leu Val Glu Gly Phe Pro Pro Arg Lys Val
                165                 170                 175
```

```
Asn His Phe Asn Pro Phe Glu Pro Leu Phe Val Arg Gln Val Ser Ala
                180                 185                 190
Val Val Ile Ser Leu Leu Ala His Phe Val Ala Gly Leu Ser Ile
            195                 200                 205
Tyr Leu Ser Leu Gln Leu Gly Leu Lys Thr Met Ala Ile Tyr Tyr Tyr
        210                 215                 220
Gly Pro Val Phe Val Phe Gly Ser Met Leu Val Ile Thr Thr Phe Leu
225                 230                 235                 240
His His Asn Asp Glu Glu Thr Pro Trp Tyr Ala Asp Ser Glu Trp Thr
                245                 250                 255
Tyr Val Lys Gly Asn Leu Ser Ser Val Asp Arg Ser Tyr Gly Ala Leu
                260                 265                 270
Ile Asp Asn Leu Ser His Asn Ile Gly Thr His Gln Ile His His Leu
            275                 280                 285
Phe Pro Ile Ile Pro His Tyr Lys Leu Lys Lys Ala Thr Ala Ala Phe
        290                 295                 300
His Gln Ala Phe Pro Glu Leu Val Arg Lys Ser Asp Glu Pro Ile Ile
305                 310                 315                 320
Lys Ala Phe Phe Arg Val Gly Arg Leu Tyr Ala Asn Tyr Gly Val Val
                325                 330                 335
Asp Gln Glu Ala Lys Leu Phe Thr Leu Lys Glu Ala Lys Ala Ala Thr
                340                 345                 350
Glu Ala Ala Ala Lys Thr Lys Ser Thr
            355                 360
```

<210> SEQ ID NO 124
<211> LENGTH: 903
<212> TYPE: DNA
<213> ORGANISM: Ostreococcus tauri

<400> SEQUENCE: 124

```
atgagcgcct ccggtgcgct gctgcccgcg atcgcgttcg ccgcgtacgc gtacgcgacg     60
tacgcctacg cctttgagtg gtcgcacgcg aatggcatcg acaacgtcga cgcgcgcgag    120
tggatcggtg cgctgtcgtt gaggctcccg gcgatcgcga cgacgatgta cctgttgttc    180
tgcctggtcg gaccgaggtt gatggcgaag cgcgaggcgt cgacccgaa ggggttcatg     240
ctggcgtaca atgcgtatca gacggcgttc aacgtcgtcg tgctcgggat gttcgcgcga    300
gagatctcgg ggctggggca gcccgtgtgg gggtcaacca tgccgtggag cgatagaaaa    360
tcgtttaaga tcctcctcgg ggtgtggttg cactacaaca accaatattt ggagctattg    420
gacactgtgt tcatggttgc gcgcaagaag acgaagcagt tgagcttctt gcacgtttat    480
catcacgccc tgttgatctg ggcgtggtgg ttggtgtgtc acttgatggc cacgaacgat    540
tgtatcgatg cctacttcgg cgcggcgtgc aactcgttca ttcacatcgt gatgtactcg    600
tattatctca tgtcggcgct cggcattcga tgcccgtgga agcgatacat cacccaggct    660
caaatgctcc aattcgtcat tgtcttcgcg cacgccgtgt tcgtgctgcg tcagaagcac    720
tgcccggtca cccttccttg ggcgcaaatg ttcgtcatga cgaacatgct cgtgctcttc    780
gggaacttct acctcaaggc gtactcgaac aagtcgcgcg cgacggcgc gagttccgtg     840
aaaccagccg agaccacgcg cgcgcccagc gtgcgacgca cgcgatctcg aaaaattgac    900
taa                                                                   903
```

<210> SEQ ID NO 125

<211> LENGTH: 300
<212> TYPE: PRT
<213> ORGANISM: Ostreococcus tauri

<400> SEQUENCE: 125

Met Ser Ala Ser Gly Ala Leu Leu Pro Ala Ile Ala Phe Ala Ala Tyr
1               5                   10                  15

Ala Tyr Ala Thr Tyr Ala Tyr Ala Phe Glu Trp Ser His Ala Asn Gly
            20                  25                  30

Ile Asp Asn Val Asp Ala Arg Glu Trp Ile Gly Ala Leu Ser Leu Arg
        35                  40                  45

Leu Pro Ala Ile Ala Thr Thr Met Tyr Leu Leu Phe Cys Leu Val Gly
    50                  55                  60

Pro Arg Leu Met Ala Lys Arg Glu Ala Phe Asp Pro Lys Gly Phe Met
65                  70                  75                  80

Leu Ala Tyr Asn Ala Tyr Gln Thr Ala Phe Asn Val Val Leu Gly
                85                  90                  95

Met Phe Ala Arg Glu Ile Ser Gly Leu Gly Gln Pro Val Trp Gly Ser
                100                 105                 110

Thr Met Pro Trp Ser Asp Arg Lys Ser Phe Lys Ile Leu Leu Gly Val
            115                 120                 125

Trp Leu His Tyr Asn Asn Gln Tyr Leu Glu Leu Leu Asp Thr Val Phe
        130                 135                 140

Met Val Ala Arg Lys Lys Thr Lys Gln Leu Ser Phe Leu His Val Tyr
145                 150                 155                 160

His His Ala Leu Leu Ile Trp Ala Trp Trp Leu Val Cys His Leu Met
                165                 170                 175

Ala Thr Asn Asp Cys Ile Asp Ala Tyr Phe Gly Ala Ala Cys Asn Ser
            180                 185                 190

Phe Ile His Ile Val Met Tyr Ser Tyr Tyr Leu Met Ser Ala Leu Gly
        195                 200                 205

Ile Arg Cys Pro Trp Lys Arg Tyr Ile Thr Gln Ala Gln Met Leu Gln
    210                 215                 220

Phe Val Ile Val Phe Ala His Ala Val Phe Val Leu Arg Gln Lys His
225                 230                 235                 240

Cys Pro Val Thr Leu Pro Trp Ala Gln Met Phe Val Met Thr Asn Met
                245                 250                 255

Leu Val Leu Phe Gly Asn Phe Tyr Leu Lys Ala Tyr Ser Asn Lys Ser
            260                 265                 270

Arg Gly Asp Gly Ala Ser Ser Val Lys Pro Ala Glu Thr Thr Arg Ala
        275                 280                 285

Pro Ser Val Arg Arg Thr Arg Ser Arg Lys Ile Asp
    290                 295                 300

<210> SEQ ID NO 126
<211> LENGTH: 1560
<212> TYPE: DNA
<213> ORGANISM: Thraustochytrium sp.

<400> SEQUENCE: 126
atgactgttg atacgacga ggagatccca ttcgagcaag ttagggctca taacaagcca      60
gacgacgctt ggtgtgctat tcacggacac gtgtacgacg ttaccaagtt cgcttcagtt     120
cacccaggag agatattat cttgctcgct gctggaaagg aagctactgt cctctacgag     180
acctaccatg ttagaggagt gtctgacgct gtgctcagaa agtacagaat aggaaagttg     240

-continued

```
ccagacggac aaggaggagc taacgagaag gagaagagaa ccttgtctgg attgtcctct    300
gcttcttact acacctggaa ctccgatttc tacagagtga tgagggagag agttgtggct    360
agattgaagg agagaggaaa ggctagaaga ggaggatacg aactctggat caaggctttc    420
ttgctccttg ttggattctg gtcctctctt tactggatgt gcaccctcga tccatcttc     480
ggagctatct tggctgctat gtctttggga gtgttcgctg cttttgttgg aacctgcatc    540
caacacgatg aaaccacgg agctttcgct caatctagat gggttaacaa ggtggcagga     600
tggactttgg atatgatcgg agcttctgga atgacttggg agttccaaca cgtgttggga    660
caccacccat acactaactt gatcgaggag gagaacggat gcaaaaggt gtccggaaag     720
aagatggata ccaagttggc tgatcaagag tctgatccag atgtgttctc cacctaccca    780
atgatgagat gcaccccttg gcaccagaag aggtggtatc acaggttcca gcacatctac    840
ggacctttca tcttcggatt catgaccatc aacaaggtgg tgactcaaga tgttggagtg    900
gtgttgagaa agagactctt ccaaatcgat gctgagtgca gatatgcttc cccaatgtac    960
gttgctaggt tctggattat gaaggctttg accgtgttgt atatggttgc tttgccttgt   1020
tatatgcaag gaccttggca cggattgaaa ctcttcgcta tcgctcactt cacttgcgga   1080
gaggttttgg ctaccatgtt catcgtgaac acacattatc gagggagtgtc ttacgcttct   1140
aaggatgctg ttaagggaac tatggctcca ccaaagacta tgcacggagt gaccccaatg   1200
aacaacacta gaaggaggt tgaggctgag gcttctaagt ctggagctgt ggttaagtct    1260
gtgccattgg atgattgggc tgctgttcag tgccaaacct ctgtgaactg gtctgttgga   1320
tcttggtttt ggaaccactt ctctggagga ctcaaccacc aaatcgagca ccacctcttc   1380
ccaggattgt ctcacgagac ctactaccac atccaagacg tggttcaatc tacctgtgct   1440
gagtacggag ttccatacca acacgagcca tctttgtgga ctgcttactg gaagatgctc   1500
gaacacctta gacaattggg aaacgaggag actcacgagt catggcagag agctgcttga   1560
```

<210> SEQ ID NO 127
<211> LENGTH: 309
<212> TYPE: PRT
<213> ORGANISM: Thraustochytrium sp.

<400> SEQUENCE: 127

```
Met Thr Trp Glu Phe Gln His Val Leu Gly His His Pro Tyr Thr Asn
1               5                   10                  15

Leu Ile Glu Glu Glu Asn Gly Leu Gln Lys Val Ser Gly Lys Lys Met
            20                  25                  30

Asp Thr Lys Leu Ala Asp Gln Glu Ser Asp Pro Asp Val Phe Ser Thr
        35                  40                  45

Tyr Pro Met Met Arg Leu His Pro Trp His Gln Lys Arg Trp Tyr His
    50                  55                  60

Arg Phe Gln His Ile Tyr Gly Pro Phe Ile Phe Gly Phe Met Thr Ile
65                  70                  75                  80

Asn Lys Val Val Thr Gln Asp Val Gly Val Val Leu Arg Lys Arg Leu
                85                  90                  95

Phe Gln Ile Asp Ala Glu Cys Arg Tyr Ala Ser Pro Met Tyr Val Ala
            100                 105                 110

Arg Phe Trp Ile Met Lys Ala Leu Thr Val Leu Tyr Met Val Ala Leu
        115                 120                 125

Pro Cys Tyr Met Gln Gly Pro Trp His Gly Leu Lys Leu Phe Ala Ile
    130                 135                 140
```

```
Ala His Phe Thr Cys Gly Glu Val Leu Ala Thr Met Phe Ile Val Asn
145                 150                 155                 160

His Ile Ile Glu Gly Val Ser Tyr Ala Ser Lys Asp Ala Val Lys Gly
                165                 170                 175

Thr Met Ala Pro Pro Lys Thr Met His Gly Val Thr Pro Met Asn Asn
            180                 185                 190

Thr Arg Lys Glu Val Glu Ala Glu Ala Ser Lys Ser Gly Ala Val Val
        195                 200                 205

Lys Ser Val Pro Leu Asp Asp Trp Ala Ala Val Gln Cys Gln Thr Ser
    210                 215                 220

Val Asn Trp Ser Val Gly Ser Trp Phe Trp Asn His Phe Ser Gly Gly
225                 230                 235                 240

Leu Asn His Gln Ile Glu His His Leu Phe Pro Gly Leu Ser His Glu
                245                 250                 255

Thr Tyr Tyr His Ile Gln Asp Val Val Gln Ser Thr Cys Ala Glu Tyr
            260                 265                 270

Gly Val Pro Tyr Gln His Glu Pro Ser Leu Trp Thr Ala Tyr Trp Lys
        275                 280                 285

Met Leu Glu His Leu Arg Gln Leu Gly Asn Glu Glu Thr His Glu Ser
    290                 295                 300

Trp Gln Arg Ala Ala
305

<210> SEQ ID NO 128
<211> LENGTH: 1320
<212> TYPE: DNA
<213> ORGANISM: Monosiga brevicollis

<400> SEQUENCE: 128
atggctagtt cagttgagag ggacgatctt gtttgggtta caacgtgcc atacaacgtg      60 aaagagttcg ctagtagaca ccctggtggt aagactttcg ttagccttta cggtggtagg     120
gacgctactg acgctttcgc tacttatcac cgtagaactt ccctcacaa atctatgcag     180 ggttacgctg ttcctaaaga agttgctgct caacacgagc tgttgctag ctctagcctt     240 agcgaggacg atcctgattt ccttaatctc tgcagagagg ttaacgagtt ccttcacaag     300
actggtagag gtaagggatt cgctcctcct gtttactacc ttaaagtggc tcttatcctc     360
gttgctgctg ttgttctcga agttagtgtt gttagggaac taacgttttt ccttgctgct     420
ctccttggat tcgtgttcgc tcttatagga cttaatattc agcacgacgc taatcacggt     480
gctgttagtc aaagaccttg gatcaatatc gtgctcggaa tgactcagga ttggataggt     540
ggtaactcac ttctttggct tcaccagcac actactattc accacataga gtgtaacgac     600
ctcgatcacg ataggatat gatggataac cctgtgctta ggtttagccc tcttagatca     660
cgttggttct tcaaagcct tcagggattc tacttccttg ctcttgaggc tggttacgct     720
gctaaagtta ttatcggaga ctggtataac ctcttgctta atatgtacga gggtgtgcct     780
attagtagaa ctgttcctgg ttggaggtgg tggtctagtg ttcttgctag aatctgctgg     840
ctcgttagac ttgttgctat ccctgtttac cttcacggtt ggcaagcttg gcttcctagc     900
cttcttgttc ttgctactgt tggaggattc tacctcgctt tcttcttctt gctctctcac     960
aacttcgaag aggtttacca cgttatggat caccaacttg tgcctgctag agatcctctt    1020
ggagagaagt cacctcagaa ggatactctt cttagacgtc aagtgctcac tagctgtaac    1080
gttggtggtg cttggcttgc tcaacttaac ggtggactta actatcagat agagcaccac    1140
```

```
ttgttcccta gagttcacca cggttactac gctgctatta gccctatagt tagagcttac    1200
tgccgtaggc ttaatatcca gtatattcac ttcgctaccg tggctgagaa ccttgctagc    1260
actagtagat tccttagtca acaaggtgtg gctcctcaag ttaagcctag agctgcttaa    1320
```

<210> SEQ ID NO 129
<211> LENGTH: 439
<212> TYPE: PRT
<213> ORGANISM: Monosiga brevicollis

<400> SEQUENCE: 129

```
Met Ala Ser Ser Val Glu Arg Asp Asp Leu Val Trp Val Asn Asn Val
1               5                   10                  15

Pro Tyr Asn Val Lys Glu Phe Ala Ser Arg His Pro Gly Gly Lys Thr
            20                  25                  30

Phe Val Ser Leu Tyr Gly Gly Arg Asp Ala Thr Asp Ala Phe Ala Thr
        35                  40                  45

Tyr His Arg Arg Thr Phe Pro His Lys Ser Met Gln Gly Tyr Ala Val
    50                  55                  60

Pro Lys Glu Val Ala Ala Gln His Glu Pro Val Ala Ser Ser Ser Leu
65                  70                  75                  80

Ser Glu Asp Asp Pro Asp Phe Leu Asn Leu Cys Arg Glu Val Asn Glu
                85                  90                  95

Phe Leu His Lys Thr Gly Arg Gly Lys Gly Phe Ala Pro Pro Val Tyr
            100                 105                 110

Tyr Leu Lys Val Ala Leu Ile Leu Val Ala Ala Val Val Leu Glu Val
        115                 120                 125

Ser Val Val Arg Glu Pro Asn Val Phe Leu Ala Ala Leu Leu Gly Phe
    130                 135                 140

Val Phe Ala Leu Ile Gly Leu Asn Ile Gln His Asp Ala Asn His Gly
145                 150                 155                 160

Ala Val Ser Gln Arg Pro Trp Ile Asn Ile Val Leu Gly Met Thr Gln
                165                 170                 175

Asp Trp Ile Gly Gly Asn Ser Leu Leu Trp Leu His Gln His Thr Thr
            180                 185                 190

Ile His His Ile Glu Cys Asn Asp Leu Asp His Asp Arg Asp Met Met
        195                 200                 205

Asp Asn Pro Val Leu Arg Phe Ser Pro Leu Arg Ser Arg Trp Phe Phe
    210                 215                 220

Gln Ser Leu Gln Gly Phe Tyr Phe Leu Ala Leu Glu Ala Gly Tyr Ala
225                 230                 235                 240

Ala Lys Val Ile Ile Gly Asp Trp Tyr Asn Leu Leu Leu Asn Met Tyr
                245                 250                 255

Glu Gly Val Pro Ile Ser Arg Thr Val Pro Gly Trp Arg Trp Trp Ser
            260                 265                 270

Ser Val Leu Ala Arg Ile Cys Trp Leu Val Arg Leu Val Ala Ile Pro
        275                 280                 285

Val Tyr Leu His Gly Trp Gln Ala Trp Leu Pro Ser Leu Leu Val Leu
    290                 295                 300

Ala Thr Val Gly Gly Phe Tyr Leu Ala Phe Phe Leu Leu Ser His
305                 310                 315                 320

Asn Phe Glu Glu Val Tyr His Val Met Asp His Gln Leu Val Pro Ala
                325                 330                 335

Arg Asp Pro Leu Gly Glu Lys Ser Pro Gln Lys Asp Thr Leu Leu Arg
            340                 345                 350
```

```
Arg Gln Val Leu Thr Ser Cys Asn Val Gly Gly Ala Trp Leu Ala Gln
        355                 360                 365

Leu Asn Gly Gly Leu Asn Tyr Gln Ile Glu His His Leu Phe Pro Arg
    370                 375                 380

Val His His Gly Tyr Tyr Ala Ala Ile Ser Pro Ile Val Arg Ala Tyr
385                 390                 395                 400

Cys Arg Arg Leu Asn Ile Gln Tyr Ile His Phe Ala Thr Val Ala Glu
                405                 410                 415

Asn Leu Ala Ser Thr Ser Arg Phe Leu Ser Gln Gln Gly Val Ala Pro
            420                 425                 430

Gln Val Lys Pro Arg Ala Ala
        435

<210> SEQ ID NO 130
<211> LENGTH: 1515
<212> TYPE: RNA
<213> ORGANISM: Monosiga brevicollis

<400> SEQUENCE: 130
ccacgcgucc gcccacgcgu ccgaucugac cagagcguca uggcuaguuc aguugagagg      60
gacgaucuug uuuggguuaa caacgugcca uacaacguga aagaguucgc uaguagacac     120
ccuggugguu agacuuucgu uagccuuuac ggugguaggg acgcacugaa cgcuuucgcu     180
acuuaucacc guagaacuuu cccucacaaa ucuaugcagg guuacgcugu ccuaaagaa      240 guugcugcuc aacacgagcc uguugcuagc ucuagccuua gcgaggacga uccgauuuc      300 cuuaaucucu gcagagaggu uaacgaguuc cuucacaaga cugguagagg uaagggauuc     360
gcuccuccug uuuacuaccu uaaaguggcu cuuauccucg uugcugcugu guuucucgaa     420
guuaguguug uuagggaacc uaacguuuuc cuugcugcuc uccuuggauu cguguucgcu     480
cuuauaggac uuaauauuca gcacgacgcu aaucacggug cuguuaguca aagaccuugg     540
aucaauaucg ugcucggaau gacucaggau uggauaggug uaacucacu ucuuuggcuu      600 caccagcaca cuacuauuca ccacauagag uguaacgacc ucgaucacga uagggauaug     660
auggauaacc cugugcuuag guuuagcccu cuuagaucac guugguucuu caaagccuu      720 cagggauucu acuuccuugc ucuugaggcu gguuacgcug cuaaaguuau uaucggagac     780
ugguauaacc ucuugcuuaa uauguacgag ggugugccua uuagagaac uguuccuggu      840 uggagguggu ggucuagugu ucuugcuaga aucgcuggc ucguuagacu uguugcuauc      900
ccuguuuacc uucacgguug gcaagcuugg cuuccuagcc uucuuguucu ugcuacuguu     960
ggaggauucu accucgcuuu cuucuucuug cucucucaca acuucgaaga gguuuaccac    1020
guuauggauc accaacuugu gccugcuaga gaucccucuug gagagaaguc accucagaag    1080
gauacucuuc uuagacguca agugcucacu agcuguaacg uggugggugc uuggcuugcu    1140
caacuuaacg guggacuuaa cuaucagaua gagcaccacu uguccccuag auucaccac    1200 gguuacuacg cugcuauuag cccuauaguu agagcuuacu gccguaggcu uaauauccag    1260
uauauucacu ucgcuaccgu ggcugagaac uugcuagca cuaguagauu ccuuagucaa    1320
caaggugugg cuccucaagu uaagccuaga gcugcuuaag ccugaacagg caauaaucgc    1380
aagucugccc cugccucagu gaccacccga ccauaugugu gucuuugcuc uuggcucuug    1440
gaggacgcaa aauuccacgc uuucuugucc ugguguuuga uugugacagu gguugcuggu    1500
gcaauuggcg caugu                                                    1515
```

```
<210> SEQ ID NO 131
<211> LENGTH: 104
<212> TYPE: DNA
<213> ORGANISM: Artificial sequence
<220> FEATURE:
<223> OTHER INFORMATION: Primer

<400> SEQUENCE: 131
ataaaagtat caacaaaaaa ttgttaatat acctctatac tttaacgtca aggagaaaaa      60
accccggatc ggcgcgccac catggctagt tcagttgaga ggga                     104

<210> SEQ ID NO 132
<211> LENGTH: 101
<212> TYPE: DNA
<213> ORGANISM: Artificial sequence
<220> FEATURE:
<223> OTHER INFORMATION: Primer

<400> SEQUENCE: 132
aactataaaa aaataaatag ggacctagac ttcaggttgt ctaactcctt cctttcggt       60 tagagcggat ttaattaatt aagcagctct aggcttaact t                        101
```

FATTY ACID DESATURASES, ELONGASES, ELONGATION COMPONENTS AND USES THEREOF

RELATED APPLICATIONS

This application is a national stage application (under 35 U.S.C. §371) of PCT/EP2011/068237, filed Oct. 19, 2011, which claims benefit of U.S. Provisional Application No. 61/405,255, filed Oct. 21, 2010, European Application No. 10188419.5, filed Oct. 21, 2010, U.S. Provisional Application No. 61/431,456, filed Jan. 11, 2011, and European Application No. 11150545.9, filed Jan. 11, 2011.

SUBMISSION OF SEQUENCE LISTING

The Sequence Listing associated with this application is filed in electronic format via EFS-Web and hereby incorporated by reference into the specification in its entirety. The name of the text file containing the Sequence Listing is Sequence_Listing_17418_00111. The size of the text file is 215 KB and the text file was created on Apr. 17, 2013.

The invention in principle pertains to the field of recombinant manufacture of fatty acids. It provides nucleic acid molecules which encode desaturases, elongases and elongase components. The invention also provides recombinant expression vectors containing Desaturase, KCS, KCR, DH, ECR nucleic acid molecules, host cells into which the expression vectors have been introduced, and methods for large-scale production of long chain polyunsaturated fatty acids (LCPUFAs), e.g. ARA, EPA and DHA.

Fatty acids are carboxylic acids with long-chain hydrocarbon side groups that play a fundamental role in many biological processes. Fatty acids are rarely found free in nature but, rather, occur in esterified form as the major component of lipids. As such, lipids/fatty acids are sources of energy (e.g., b-oxidation). In addition, lipids/fatty acids are an integral part of cell membranes and, therefore, are indispensable for processing biological or biochemical information.

Fatty acids can be divided into two groups: saturated fatty acids formed of single carbon bonds and the unsaturated fatty acids which contain one or more carbon double bonds in cis-configuration. Unsaturated fatty acids are produced by terminal desaturases that belong to the class of nonheme-iron enzymes. Each of these enzymes are part of an electron-transport system that contains two other proteins, namely cytochrome $b_5$ and NADH-cytochrome $b_5$ reductase. Specifically, such enzymes catalyze the formation of double bonds between the carbon atoms of a fatty acid molecule, for example, by catalyzing the oxygen-dependent dehydrogenation of fatty acids (Sperling et al, 2003). Human and other mammals have a limited spectrum of desaturases that are required for the formation of particular double bonds in unsaturated fatty acids and thus, have a limited capacity for synthesizing essential fatty acids, e.g., long chain polyunsaturated fatty acids (LCPUFAs). Thus, humans have to take up some fatty acids through their diet. Such essential fatty acids include, for example, linoleic acid (C18:2) and linolenic acid (C18:3). In contrast, insects, microorganisms and plants are able to synthesize a much larger variety of unsaturated fatty acids and their derivatives. Indeed, the biosynthesis of fatty acids is a major activity of plants and microorganisms.

Long chain polyunsaturated fatty acids (LCPUFAs) such as docosahexaenoic acid (DHA, 22:6(4,7,10,13,16,19)) are essential components of cell membranes of various tissues and organelles in mammals (nerve, retina, brain and immune cells). For example, over 30% of fatty acids in brain phospholipid are 22:6 (n-3) and 20:4 (n-6) (Crawford, M. A., et al., (1997) Am. J. Clin. Nutr. 66:1032 S-1041S). In retina, DHA accounts for more than 60% of the total fatty acids in the rod outer segment, the photosensitive part of the photoreceptor cell (Giusto, N. M., et al. (2000) Prog. Lipid Res. 39:315-391). Clinical studies have shown that DHA is essential for the growth and development of the brain in infants, and for maintenance of normal brain function in adults (Martinetz, M. (1992) J. Pediatr. 120:S129-S138). DHA also has significant effects on photoreceptor function involved in the signal transduction process, rhodopsin activation, and rod and cone development (Giusto, N. M., et al, (2000) Prog. Lipid Res. 39:315-391). In addition, some positive effects of DHA were also found on diseases such as hypertension, arthritis, atherosclerosis, depression, thrombosis and cancers (Horrocks, L. A. and Yeo, Y. K. (1999) Pharmacol, Res. 40:211-215). Therefore, appropriate dietary supply of the fatty acid is important for human health. Because such fatty acids cannot be efficiently synthesized by infants, young children and senior citizens, it is particularly important for these individuals to adequately intake these fatty acids from the diet (Spector, A. A. (1999) Lipids 34:S1-S3).

Currently the major sources of DHA are oils from fish and algae. Fish oil is a major and traditional source for this fatty acid, however, it is usually oxidized by the time it is sold. In addition, the supply of fish oil is highly variable, particularly in view of the shrinking fish populations. Moreover, the algal source of oil is expensive due to low yield and the high costs of extraction.

EPA and ARA are both delta (d) 5 essential fatty acids. They form a unique class of food and feed constituents for humans and animals. EPA belongs to the n-3 series with five double bonds in the acyl chain. EPA is found in marine food and is abundant in oily fish from North Atlantic. ARA belongs to the n-6 series with four double bonds. The lack of a double bond in the ω-3 position confers on ARA different properties than those found in EPA. The eicosanoids produced from AA have strong inflammatory and platelet aggregating properties, whereas those derived from EPA have anti-inflammatory and anti-platelet aggregating properties. ARA can be obtained from some foods such as meat, fish and eggs, but the concentration is low.

Gamma-linolenic acid (GLA) is another essential fatty acid found in mammals. GLA is the metabolic intermediate for very long chain n-6 fatty acids and for various active molecules. In mammals, formation of long chain polyunsaturated fatty acids is rate-limited by Δ6 desaturation. Many physiological and pathological conditions such as aging, stress, diabetes, eczema, and some infections have been shown to depress the Δ6 desaturation step. In addition, GLA is readily catabolized from the oxidation and rapid cell division associated with certain disorders, e.g., cancer or inflammation. Therefore, dietary supplementation with GLA can reduce the risks of these disorders. Clinical studies have shown that dietary supplementation with GLA is effective in treating some pathological conditions such as atopic eczema, premenstrual syndrome, diabetes, hypercholesterolemia, and inflammatory and cardiovascular disorders.

Although biotechnology offers an attractive route for the production of specialty fatty acids, current techniques fail to provide an efficient means for the large scale production of unsaturated fatty acids. Accordingly, there exists a need for an improved and efficient method of producing unsaturated fatty acids, such as DHA, EPA and ARA.

Thus, the present invention relates to a polynucleotide comprising a nucleic acid sequence elected from the group consisting of:
a) a nucleic acid sequence having a nucleotide sequence as shown in SEQ ID NOs: 1, 4, 7, 10, 13, 16, 19, 22, 25, 28, 31, 34, 37, 40, 46, 49, 52, 55, 58, 61 or 128
b) a nucleic acid sequence encoding a polypeptide having an amino acid sequence as shown in SEQ ID NOs: 2, 5, 8, 11, 14, 17, 20, 23, 26, 29, 32, 35, 38, 41, 44, 47, 50, 53, 56, 59, 62 or 129
c) a nucleic acid sequence being at least 70% identical to the nucleic acid sequence of a) or b), wherein said nucleic acid sequence encodes a polypeptide having desaturase, keto-acyl-CoA synthase (KCS), keto-acyl-CoA reductase (KCR), dehydratase (DH) or enoyl-CoA reductase (ECR) activity;
d) a nucleic acid sequence encoding a polypeptide having desaturase, keto-acyl-CoA synthase (KCS), keto-acyl-CoA reductase (KCR), dehydratase (DH) or enoyl-CoA reductase (ECR) activity and having an amino acid sequence which is at least 70% identical to the amino acid sequence of any one of a) to c); and
e) a nucleic acid sequence which is capable of hybridizing under stringent conditions to any one of a) to d), wherein said nucleic acid sequence encodes a polypeptide having desaturase, keto-acyl-CoA synthase (KCS), keto-acyl-CoA reductase (KCR), dehydratase (DH) or enoyl-CoA reductase (ECR) activity.

The term "polynucleotide" as used in accordance with the present invention relates to a polynucleotide comprising a nucleic acid sequence which encodes a polypeptide having desaturase, keto-acyl-CoA-synthase, keto-acyl-CoA-reductase, dehydratase and enoyl-CoA-reductase activity. Preferably, the polypeptide encoded by the polynucleotide of the present invention having desaturase, KCS, KCR, DH and ECR activity upon expression in a plant shall be capable of increasing the amount of PUFA and, in particular, LCPUFA in, e.g., seed oils or the entire plant or parts thereof. Such an increase is, preferably, statistically significant when compared to a LCPUFA producing transgenic control plant which expresses the minimal set of desaturases and elongases requiered for LCPUFA synthesis but does not express the polynucleotide of the present invention. Whether an increase is significant can be determined by statistical tests well known in the art including, e.g., Student's t-test. More preferably, the increase is an increase of the amount of triglycerides containing LCPUFA of at least 5%, at least 10%, at least 15%, at least 20% or at least 30% compared to said control. Preferably, the LCPUFA referred to before is a polyunsaturated fatty acid having a C-20, C-22 or C-24 fatty acid body, more preferably, ARA, EPA or DHA. Suitable assays for measuring the activities mentioned before are described in the accompanying Examples.

The term "desaturase" encompasses all enymatic activities and enzymes catalyzing the desaturation of fatty acids with different lengths and numbers of unsaturated carbon atom double bonds. Specifically this includes delta 4 (d4)-desaturase, catalyzing the dehydrogenation of the $4^{th}$ and $5^{th}$ carbon atom. Delta 5 (d5)-desaturase catalyzing the dehydrogenation of the $5^{th}$ and $6^{th}$ carbon atom. Delta 6 (d6)-desaturase catalyzing the dehydrogenation of the $6^{th}$ and $7^{th}$ carbon atom. Delta 8 (d8)-desaturase catalyzing the dehydrogenation of the $8^{th}$ and $9^{th}$ carbon atom. Delta 9 (d9)-desaturase catalyzing the dehydrogenation of the $9^{th}$ and $10^{th}$ carbon atom. Delta 12 (d12)-desaturase catalyzing the dehydrogenation of the $12^{th}$ and $13^{th}$ carbon atom. Delta 15 (d15)-desaturase catalyzing the dehydrogenation of the $15^{th}$ and $16^{th}$ carbon atom.

The terms "elongase" and "deltaxElo (dxElo)" are synonymous to KCS and refer to keto-acyl-CoA-synthase enzymatic activity, which allows to introduce two carbon atoms in a fatty acid whereby the fatty acid is elongated. Specifically, dxElo(No) catalyzes the introduction of two carbon atoms into fatty acids having 18 carbon atoms and double bonds in the positions 5, 6, 9, 12 and/or 15, respectively.

The term "KCR" as used herein refer to keto-acyl-CoA-reductase activity, which reduces the keto-group of keto-acyl-CoA to a hydroxyl-group, in the process of fatty acid elongation.

The term "DH" as used herein refers to dehydratase activity, removing the hydroxyl-group leading to the formation of a acyl-2-en-CoA ester (delta-2-enoyl-CoA) and $H_2O$ during fatty acid elongation.

The term "ECR" as used herein refers to enoyl-CoA reductase activity, reducing the double bond of delta-2-enoyl-CoA, in course of fatty acid elongation, generating the elongated acyl-CoA ester.

Fatty acid elongation is catalyzed in four steps, represented by four enzymes: KCS (keto-acyl-CoA-synthase), KCR (keto-acyl-CoA-reductase), DH (dehydratase) and ECR (enoyl-CoA-reductase). In the first step a fatty acid-CoA ester is condensed with malonyl-CoA producing a keto-acly-CoA intermediate, which is elongated by two carbon atoms, and $CO_2$. The keto-group of the intermediate is then reduced by the KCR to a hydroxyl-group. In the next step the DH cleaves of the hydroxyl-group ($H_2O$ is produced), forming a acyl-2-en-CoA ester (delta-2-enoyl-CoA). In the final step the double bound at position 2, 3 is reduced by the ECR forming the elongated acyl-CoA ester (Buchanan, Gruissem, Jones (2000) Biochemistry & Molecular biology of plants, American Society of Plant Physiologists).

In the studies underlying this invention, enzymes with superior desaturase, KCS, KCR, DH, and ECR catalytic activities for the production of PUFA has been provided.

More preferably, polynucleotides having a nucleic acid sequence as shown in SEQ ID NOs: 1 encoding polypeptides having amino acid sequences as shown in SEQ ID NOs: 2 or variants thereof, preferably, exhibit d5-desaturase activity.

Polynucleotides having a nucleic acid sequence as shown in SEQ ID NOs: 4 encoding polypeptides having amino acid sequences as shown in SEQ ID NOs: 5 or variants thereof, preferably, exhibit d6-desaturase activity.

Polynucleotides having a nucleic acid sequence as shown in SEQ ID NOs: 7 and 128 encoding polypeptides having amino acid sequences as shown in SEQ ID NOs: 8 and 129 or variants thereof, preferably, exhibit d4-desaturase activity.

Polynucleotides having a nucleic acid sequence as shown in SEQ ID NOs: 10 encoding polypeptides having amino acid sequences as shown in SEQ ID NOs: 11 or variants thereof, preferably, exhibit d8-desaturase activity.

Polynucleotides having a nucleic acid sequence as shown in SEQ ID NOs: 13 encoding polypeptides having amino acid sequences as shown in SEQ ID NOs: 14 or variants thereof, preferably, exhibit d9-desaturase activity.

Polynucleotides having a nucleic acid sequence as shown in SEQ ID NOs: 16 encoding polypeptides having amino acid sequences as shown in SEQ ID NOs: 17 or variants thereof, preferably, exhibit d12-desaturase activity.

Polynucleotides having a nucleic acid sequence as shown in SEQ ID NOs: 19 encoding polypeptides having amino acid sequences as shown in SEQ ID NOs: 20 or variants thereof, preferably, exhibit d15-desaturase activity.

Polynucleotides having a nucleic acid sequence as shown in SEQ ID NOs: 22, 25, 28, 31, 34, 37, 40, 43 or 46 encoding polypeptides having amino acid sequences as shown in SEQ ID NOs: 23, 26, 29, 32, 35, 38, 41, 44 or 46 or variants thereof, preferably, exhibit keto-acyl-CoA synthase activity.

Polynucleotides having a nucleic acid sequence as shown in SEQ ID NOs: 49, 52 or 55 encoding polypeptides having amino acid sequences as shown in SEQ ID NOs: 50, 53 or 56 or variants thereof, preferably, exhibit keto-acyl-CoA reductase activity.

Polynucleotides having a nucleic acid sequence as shown in SEQ ID NOs: 58 encoding polypeptides having amino acid sequences as shown in SEQ ID NOs: 59 or variants thereof, preferably, exhibit dehydratase activity.

Polynucleotides having a nucleic acid sequence as shown in SEQ ID NOs: 61 encoding polypeptides having amino acid sequences as shown in SEQ ID NOs: 62 or variants thereof, preferably, exhibit enoyl-CoA-reductase activity.

A polynucleotide encoding a polypeptide having a desaturase, KCS, KCR, DH and ECR activity as specified above has been obtained in accordance with the present invention, preferably, from *Nannochloropsis oculata*. However, orthologs, paralogs or other homologs may be identified from other species. Preferably, they are obtained from plants such as algae, for example *Isochrysis, Mantoniella, Ostreococcus* or *Crypthecodinium*, algae/diatoms such as *Phaeodactylum, Thalassiosira* or *Thraustochytrium*, mosses such as *Physcomitrella* or *Ceratodon*, or higher plants such as the Primulaceae such as *Aleuritia, Calendula stellata, Osteospermum spinescens* or *Osteospermum hyoseroides*, microorganisms such as fungi, such as *Aspergillus, Phytophthora, Entomophthora, Mucor* or *Mortierella*, bacteria such as *Shewanella*, yeasts or animals. Preferred animals are nematodes such as *Caenorhabditis*, insects or vertebrates. Among the vertebrates, the nucleic acid molecules may, preferably, be derived from Euteleostomi, Actinopterygii; Neopterygii; Teleostei; Euteleostei, Protacanthopterygii, Salmoniformes; Salmonidae or *Oncorhynchus*, more preferably, from the order of the Salmoniformes, most preferably, the family of the Salmonidae, such as the genus *Salmo*, for example from the genera and species *Oncorhynchus mykiss, Trutta trutta* or *Salmo trutta fario*. Moreover, the nucleic acid molecules may be obtained from the diatoms such as the genera *Thalassiosira* or *Phaeodactylum*.

Thus, the term "polynucleotide" as used in accordance with the present invention further encompasses variants of the aforementioned specific polynucleotides representing orthologs, paralogs or other homologs of the polynucleotide of the present invention. Moreover, variants of the polynucleotide of the present invention also include artificially generated muteins. Said muteins include, e.g., enzymes which are generated by mutagenesis techniques and which exhibit improved or altered substrate specificity, or codon optimized polynucleotides. The polynucleotide variants, preferably, comprise a nucleic acid sequence characterized in that the sequence can be derived from the aforementioned specific nucleic acid sequences shown in any one of SEQ ID NOs: 1, 4, 7, 10, 13, 16, 19, 22, 25, 28, 31, 34, 37, 40, 46, 49, 52, 55, 58, 61 or 128 by a polynucleotide encoding a polypeptide having an amino acid sequence as shown in any one of SEQ ID NOs: 2, 5, 8, 11, 14, 17, 20, 23, 26, 29, 32, 35, 38, 41, 44, 47, 50, 53, 56, 59, 62 or 129 by at least one nucleotide substitution, addition and/or deletion, whereby the variant nucleic acid sequence shall still encode a polypeptide having a desaturase, KCS, KCR, DH and ECR activity as specified above. Variants also encompass polynucleotides comprising a nucleic acid sequence which is capable of hybridizing to the aforementioned specific nucleic acid sequences, preferably, under stringent hybridization conditions. These stringent conditions are known to the skilled worker and can be found in Current Protocols in Molecular Biology, John Wiley & Sons, N.Y. (1989), 6.3.1-6.3.6. A preferred example for stringent hybridization conditions are hybridization conditions in 6× sodium chloride/sodium citrate (=SSC) at approximately 45° C., followed by one or more wash steps in 0.2×SSC, 0.1% SDS at 50 to 65° C. The skilled worker knows that these hybridization conditions differ depending on the type of nucleic acid and, for example when organic solvents are present, with regard to the temperature and concentration of the buffer. For example, under "standard hybridization conditions" the temperature differs depending on the type of nucleic acid between 42° C. and 58° C. in aqueous buffer with a concentration of 0.1 to 5×SSC (pH 7.2). If organic solvent is present in the abovementioned buffer, for example 50% formamide, the temperature under standard conditions is approximately 42° C. The hybridization conditions for DNA:DNA hybrids are, preferably, 0.1×SSC and 20° C. to 45° C., preferably between 30° C. and 45° C. The hybridization conditions for DNA:RNA hybrids are, preferably, 0.1×SSC and 30° C. to 55° C., preferably between 45° C. and 55° C. The abovementioned hybridization temperatures are determined for example for a nucleic acid with approximately 100 bp (=base pairs) in length and a G+C content of 50% in the absence of formamide. The skilled worker knows how to determine the hybridization conditions required by referring to textbooks such as the textbook mentioned above, or the following textbooks: Sambrook et al., "Molecular Cloning", Cold Spring Harbor Laboratory, 1989; Hames and Higgins (Ed.) 1985, "Nucleic Acids Hybridization: A Practical Approach", IRL Press at Oxford University Press, Oxford; Brown (Ed.) 1991, "Essential Molecular Biology: A Practical Approach", IRL Press at Oxford University Press, Oxford. Alternatively, polynucleotide variants are obtainable by PCR-based techniques such as mixed oligonucleotide primer-based amplification of DNA, i.e. using degenerated primers against conserved domains of the polypeptides of the present invention. Conserved domains of the polypeptide of the present invention may be identified by a sequence comparison of the nucleic acid sequences of the polynucleotides or the amino acid sequences of the polypeptides of the present invention. Oligonucleotides suitable as PCR primers as well as suitable PCR conditions are described in the accompanying Examples. As a template, DNA or cDNA from bacteria, fungi, plants or animals may be used. Further, variants include polynucleotides comprising nucleic acid sequences which are at least 50%, at least 55%, at least 60%, at least 65%, at least 70%, at least 75%, at least 80%, at least 85%, at least 90%, at least 95%, at least 98% or at least 99% identical to the nucleic acid sequences shown in any one of SEQ ID NOs: 1, 4, 7, 10, 13, 16, 19, 22, 25, 28, 31, 34, 37, 40, 46, 49, 52, 55, 58, 61 or 128 preferably, encoding polypeptides retaining desaturase, KCS, KCR, DH and ECR activity as specified above. Moreover, also encompassed are polynucleotides which comprise nucleic acid sequences encoding a polypeptide having an amino acid sequences which are at least 50%, at least 55%, at least 60%, at least 65%, at least 70%, at least 75%, at least 80%, at least 85%, at least 90%, at least 95%, at least 98% or at least 99% identical to the amino acid sequences shown in any one of SEQ ID NOs:2, 5, 8, 11, 14, 17, 20, 23, 26, 29, 32, 35, 38, 41, 44, 47, 50, 53, 56, 59, 62 or 129 wherein the polypeptide, preferably, retains desaturase, KCS, KCR, DH and ECR activity as specified above. The percent identity values are, preferably, calculated over the entire amino acid or nucleic acid sequence region. A series of programs based on a variety of algorithms is available to the skilled worker for comparing different sequences. In a preferred embodiment, the percent identity between two amino acid sequences is determined using the Needleman and Wunsch algorithm (Needleman 1970, J. Mol. Biol. (48):444-453) which has been incorporated into the needle program in the EMBOSS software package (*EMBOSS: The European Molecular Biology Open Software Suite*, Rice, P., Longden, I., and Bleasby, A, Trends in Genetics 16(6), 276-277, 2000), using either a BLOSUM 45 or PAM250 scoring matrix for distantly related proteins, or either a BLOSUM 62 or PAM160 scoring matrix for closer related proteins, and a gap opening penalty of 16, 14, 12, 10, 8, 6, or 4 and a gap entension pentalty of 0.5, 1, 2, 3, 4, 5, or 6. Guides for local installation of the EMBOSS package as well as links to WEB-Services can be found at http://emboss.sourceforge.net. A preferred, non-limiting example of parameters to be used for aligning two amino acid sequences using the needle program are the default parameters, including the EBLOSUM62 scoring matrix, a gap opening penalty of 10 and a gap extension penalty of 0.5. In yet another preferred embodiment, the percent identity between two nucleotide sequences is determined using the needle program in the EMBOSS software package (*EMBOSS: The European Molecular Biology Open Software Suite*, Rice, P., Longden, I., and Bleasby, A, Trends in Genetics 16(6), 276-277, 2000), using the EDNAFULL scoring matrix and a gap opening penalty of 16, 14, 12, 10, 8, 6, or 4 and a gap extension penalty of 0.5, 1, 2, 3, 4, 5, or 6. A preferred, non-limiting example of parameters to be used in conjunction for aligning two nucleic acid sequences using the needle program are the default parameters, including the EDNAFULL scoring matrix, a gap opening penalty of 10 and a gap extension penalty of 0.5. The nucleic acid and protein sequences of the present invention can further be used as a "query sequence" to perform a search against public databases to, for example, identify other family members or related sequences. Such searches can be performed using the BLAST series of programs (version 2.2) of Altschul et al. (Altschul 1990, J. Mol. Biol. 215:403-10). BLAST using desaturase, KCS, KCR, DH and ECR nucleic acid sequences of the invention as query sequence can be performed with the BLASTn, BLASTx or the tBLASTx program using default parameters to obtain either nucleotide sequences (BLASTn, tBLASTx) or amino acid sequences (BLASTx) homologous to desaturase, KCS, KCR, DH and ECR sequences of the invention. BLAST using desaturase, KCS, KCR, DH and ECR protein sequences of the invention as query sequence can be performed with the BLASTp or the tBLASTn program using default parameters to obtain either amino acid sequences (BLASTp) or nucleic acid sequences (tBLASTn) homologous to desaturase, KCS, KCR, DH and ECR sequences of the invention. To obtain gapped alignments for comparison purposes, Gapped BLAST using default parameters can be utilized as described in Altschul et al. (Altschul 1997, Nucleic Acids Res. 25(17):3389-3402).

TABLE 1

Relation of sequence types: DNA or PRT (Protein) of query- and hit-sequences for various BLAST programs

| Input query sequence | Converted Query | Algorithm | Converted Hit | Actual Database |
|---|---|---|---|---|
| DNA | | BLASTn | | DNA |
| PRT | | BLASTp | | PRT |
| DNA | PRT | BLASTx | | PRT |
| PRT | | tBLASTn | PRT | DNA |
| DNA | PRT | tBLASTx | PRT | DNA |

A polynucleotide comprising a fragment of any of the aforementioned nucleic acid sequences is also encompassed as a polynucleotide of the present invention. The fragments shall encode polypeptides which still have desaturase, KCS, KCR, DH or ECR activity as specified above. Accordingly, the polypeptide may comprise or consist of the domains of the polypeptide of the present invention conferring the said biological activity. A fragment as meant herein, preferably, comprises at least 50, at least 100, at least 250 or at least 500 consecutive nucleotides of any one of the aforementioned nucleic acid sequences or encodes an amino acid sequence comprising at least 20, at least 30, at least 50, at least 80, at least 100 or at least 150 consecutive amino acids of any one of the aforementioned amino acid sequences.

The variant polynucleotides or fragments referred to above, preferably, encode polypeptides retaining desaturase, KCS, KCR, DH or ECR activity to a significant extent, preferably, at least 10%, at least 20%, at least 30%, at least 40%, at least 50%, at least 60%, at least 70%, at least 80% or at least 90% of the desaturase, KCS, KCR, DH or ECR activity exhibited by any of the polypeptide shown in any one of SEQ ID NOs: 2, 5, 8, 11, 14, 17, 20, 23, 26, 29, 32, 35, 38, 41, 44, 47, 50, 53, 56, 59, 62 and 129. The activity may be tested as described in the accompanying Examples.

The polynucleotides of the present invention either essentially consist of the aforementioned nucleic acid sequences or comprise the aforementioned nucleic acid sequences. Thus, they may contain further nucleic acid sequences as well. Preferably, the polynucleotide of the present invention may comprise in addition to an open reading frame further untranslated sequence at the 3' and at the 5' terminus of the coding gene region: at least 500, preferably 200, more preferably 100 nucleotides of the sequence upstream of the 5' terminus of the coding region and at least 100, preferably 50, more preferably 20 nucleotides of the sequence downstream of the 3' terminus of the coding gene region. Furthermore, the polynucleotides of the present invention may encode fusion proteins wherein one partner of the fusion protein is a polypeptide being encoded by a nucleic acid sequence recited above. Such fusion proteins may comprise as additional part other enzymes of the fatty acid or PUFA biosynthesis pathways, polypeptides for monitoring expression (e.g., green, yellow, blue or red fluorescent proteins, alkaline phosphatase and the like) or so called "tags" which may serve as a detectable marker or as an auxiliary measure for purification purposes. Tags for the different purposes are well known in the art and comprise FLAG-tags, 6-histidine-tags, MYC-tags and the like.

The polynucleotide of the present invention shall be provided, preferably, either as an isolated polynucleotide (i.e. purified or at least isolated from its natural context such as its natural gene locus) or in genetically modified or exogenously (i.e. artificially) manipulated form. An isolated polynucleotide can, for example, comprise less than approximately 5 kb, 4 kb, 3 kb, 2 kb, 1 kb, 0.5 kb or 0.1 kb of nucleotide sequences which naturally flank the nucleic acid molecule in the genomic DNA of the cell from which the nucleic acid is derived. The polynucleotide, preferably, is provided in the form of double or single stranded molecule. It will be understood that the present invention by referring to any of the aforementioned polynucleotides of the invention also refers to complementary or reverse complementary strands of the specific sequences or variants thereof referred to before. The polynucleotide encompasses DNA, including cDNA and genomic DNA, or RNA polynucleotides.

However, the present invention also pertains to polynucleotide variants which are derived from the polynucleotides of the present invention and are capable of interefering with the transcription or translation of the polynucleotides of the present invention. Such variant polynucleotides include anti-sense nucleic acids, ribozymes, siRNA molecules, morpholino nucleic acids (phosphorodiamidate morpholino oligos), triple-helix forming oligonucleotides, inhibitory oligonucleotides, or micro RNA molecules all of which shall specifically recognize the polynucleotide of the invention due to the presence of complementary or substantially complementary sequences. These techniques are well known to the skilled artisan. Suitable variant polynucleotides of the aforementioned kind can be readily designed based on the structure of the polynucleotides of this invention.

Moreover, comprised are also chemically modified polynucleotides including naturally occurring modified polynucleotides such as glycosylated or methylated polynucleotides or artificial modified ones such as biotinylated polynucleotides.

In the studies underlying the present invention, advantageously, polynucleotides where identified encoding desaturases, keto-acyl-CoA-synthases, keto-acyl-CoA-reductases, dehydratases and enoyl-CoA-reductases from *Nannochloropsis oculata* or *Monosiga brevicollis*. In particular, the *Nannochloropsis oculata* d4-desaturase (d4Des(No)), d5-desaturase (d5Des(No)), d6-desaturase (d6Des(No)), d8-desaturase (d8Des(No)), d9-desaturase (d9Des(No)), d12-desaturase (d12Des(No)), d15-desaturase (d15Des (No)) keto-acyl-CoA-synthase (Elo(No)), keto-acyl-CoA-reductase (KCR(No)), dehydratase (DH(No)) and enoyl-CoA-reductase (ECR(No)) have been identified. In addition, in particular, the *Monosiga brevicollis* d4-desautrase d4Des (Mb) has been identified. The polynucleotides of the present invention are particularly suitable for the recombinant manufacture of LCPUFAs and, in particular, arachidonic acid (ARA), eicosapentaenoic acid (EPA) and/or docosapentaenoic acid (DHA).

In a preferred embodiment of the polynucleotide of the present invention, said polynucleotide further comprises an expression control sequence operatively linked to the said nucleic acid sequence.

The term "expression control sequence" as used herein refers to a nucleic acid sequence which is capable of governing, i.e. initiating and controlling, transcription of a nucleic acid sequence of interest, in the present case the nucleic sequences recited above. Such a sequence usually comprises or consists of a promoter or a combination of a promoter and enhancer sequences. Expression of a polynucleotide comprises transcription of the nucleic acid molecule, preferably, into a translatable mRNA. Additional regulatory elements may include transcriptional as well as translational enhancers. The following promoters and expression control sequences may be, preferably, used in an expression vector according to the present invention. The cos, tac, trp, tet, trp-tet, lpp, lac, lpp-lac, laclq, T7, T5, T3, gal, trc, ara, SP6, λ-PR or λ-PL promoters are, preferably, used in Gram-negative bacteria. For Gram-positive bacteria, promoters amy and SPO2 may be used. From yeast or fungal promoters ADC1, AOX1r, GAL1, MFα, AC, P-60, CYC1, GAPDH, TEF, rp28, ADH are, preferably, used. For animal cell or organism expression, the promoters CMV-, SV40-, RSV-promoter (Rous sarcoma virus), CMV-enhancer, SV40-enhancer are preferably used. From plants the promoters CaMV/35S (Franck 1980, Cell 21: 285-294], PRP1 (Ward 1993, Plant. Mol. Biol. 22), SSU, OCS, lib4, usp, STLS1, B33, nos or the ubiquitin or phaseolin promoter. Also preferred in this context are inducible promoters, such as the promoters described in EP 0 388 186 A1 (i.e. a benzylsulfonamide-inducible promoter), Gatz 1992, Plant J. 2:397-404 (i.e. a tetracyclin-inducible promoter), EP 0 335 528 A1 (i.e. a abscisic-acid-inducible promoter) or WO 93/21334 (i.e. a ethanol- or cyclohexenol-inducible promoter). Further suitable plant promoters are the promoter of cytosolic FBPase or the ST-LSI promoter from potato (Stockhaus 1989, EMBO J. 8, 2445), the phosphoribosylpyrophosphate amidotransferase promoter from *Glycine max* (Genbank accession No. U87999) or the node-specific promoter described in EP 0 249 676 A1. Particularly preferred are promoters which enable the expression in tissues which are involved in the biosynthesis of fatty acids. Also particularly preferred are seed-specific promoters such as the USP promoter in accordance with the practice, but also other promoters such as the LeB4, DC3, phaseolin or napin promoters. Further especially preferred promoters are seed-specific promoters which can be used for monocotyledonous or dicotyledonous plants and which are described in U.S. Pat. No. 5,608,152 (napin promoter from oilseed rape), WO 98/45461 (oleosin promoter from *Arobidopsis*, U.S. Pat. No. 5,504,200 (phaseolin promoter from *Phaseolus vulgaris*), WO 91/13980 (Bce4 promoter from *Brassica*), by Baeumlein et al., Plant J., 2, 2, 1992:233-239 (LeB4 promoter from a legume), these promoters being suitable for dicots. The following promoters are suitable for monocots: lpt-2 or lpt-1 promoter from barley (WO 95/15389 and WO 95/23230), hordein promoter from barley and other promoters which are suitable and which are described in WO 99/16890. In principle, it is possible to use all natural promoters together with their regulatory sequences, such as those mentioned above, for the novel process. Likewise, it is possible and advantageous to use synthetic promoters, either additionally or alone, especially when they mediate a seed-specific expression, such as, for example, as described in WO 99/16890. In a particular embodiment, seed-specific promoters are utilized to enhance the production of the desired PUFA or LCPUFA.

The term "operatively linked" as used herein means that the expression control sequence and the nucleic acid of interest are linked so that the expression of the said nucleic acid of interest can be governed by the said expression control sequence, i.e. the expression control sequence shall be functionally linked to the said nucleic acid sequence to be expressed. Accordingly, the expression control sequence and, the nucleic acid sequence to be expressed may be physically linked to each other, e.g., by inserting the expression control sequence at the 5"end of the nucleic acid sequence to be expressed. Alternatively, the expression control sequence and the nucleic acid to be expressed may be merely in physical proximity so that the expression control sequence is capable of governing the expression of at least one nucleic acid sequence of interest. The expression control sequence and the nucleic acid to be expressed are, preferably, separated by not more than 500 bp, 300 bp, 100 bp, 80 bp, 60 bp, 40 bp, 20 bp, 10 bp or 5 bp.

In a further preferred embodiment of the polynucleotide of the present invention, said polynucleotide further comprises a terminator sequence operatively linked to the nucleic acid sequence.

The term "terminator" as used herein refers to a nucleic acid sequence which is capable of terminating transcription. These sequences will cause dissociation of the transcription machinery from the nucleic acid sequence to be transcribed. Preferably, the terminator shall be active in plants and, in particular, in plant seeds. Suitable terminators are known in the art and, preferably, include polyadenylation signals such as the SV40-poly-A site or the tk-poly-A site or one of the plant specific signals indicated in Loke et al. (Loke 2005, Plant Physiol 138, pp. 1457-1468), downstream of the nucleic acid sequence to be expressed.

The present invention also relates to a vector comprising the polynucleotide of the present invention.

The term "vector", preferably, encompasses phage, plasmid, viral vectors as well as artificial chromosomes, such as bacterial or yeast artificial chromosomes. Moreover, the term also relates to targeting constructs which allow for random or site-directed integration of the targeting construct into genomic DNA. Such target constructs, preferably, comprise DNA of sufficient length for either homolgous or heterologous recombination as described in detail below. The vector encompassing the polynucleotide of the present invention, preferably, further comprises selectable markers for propagation and/or selection in a host. The vector may be incorporated into a host cell by various techniques well known in the art. If introduced into a host cell, the vector may reside in the cytoplasm or may be incorporated into the genome. In the latter case, it is to be understood that the vector may further comprise nucleic acid sequences which allow for homologous recombination or heterologous insertion. Vectors can be introduced into prokaryotic or eukaryotic cells via conventional transformation or transfection techniques. The terms "transformation" and "transfection", conjugation and transduction, as used in the present context, are intended to comprise a multiplicity of prior-art processes for introducing foreign nucleic acid (for example DNA) into a host cell, including calcium phosphate, rubidium chloride or calcium chloride co-precipitation, DEAE-dextran-mediated transfection, lipofection, natural competence, carbon-based clusters, chemically mediated transfer, electroporation or particle bombardment. Suitable methods for the transformation or transfection of host cells, including plant cells, can be found in Sambrook et al. (Molecular Cloning: A Laboratory Manual, $2^{nd}$ ed., Cold Spring Harbor Laboratory, Cold Spring Harbor Laboratory Press, Cold Spring Harbor, N.Y., 1989) and other laboratory manuals, such as Methods in Molecular Biology, 1995, Vol. 44, *Agrobacterium* protocols, Ed.: Gartland and Davey, Humana Press, Totowa, N.J. Alternatively, a plasmid vector may be introduced by heat shock or electroporation techniques. Should the vector be a virus, it may be packaged in vitro using an appropriate packaging cell line prior to application to host cells.

Preferably, the vector referred to herein is suitable as a cloning vector, i.e. replicable in microbial systems. Such vectors ensure efficient cloning in bacteria and, preferably, yeasts or fungi and make possible the stable transformation of plants. Those which must be mentioned are, in particular, various binary and co-integrated vector systems which are suitable for the T-DNA-mediated transformation. Such vector systems are, as a rule, characterized in that they contain at least the vir genes, which are required for the *Agrobacterium*-mediated transformation, and the sequences which delimit the T-DNA (T-DNA border). These vector systems, preferably, also comprise further cis-regulatory regions such as promoters and terminators and/or selection markers with which suitable transformed host cells or organisms can be identified. While co-integrated vector systems have vir genes and T-DNA sequences arranged on the same vector, binary systems are based on at least two vectors, one of which bears vir genes, but no T-DNA, while a second one bears T-DNA, but no vir gene. As a consequence, the last-mentioned vectors are relatively small, easy to manipulate and can be replicated both in *E. coli* and in *Agrobacterium*. These binary vectors include vectors from the pBIB-HYG, pPZP, pBecks, pGreen series. Preferably used in accordance with the invention are Bin19, pB1101, pBinAR, pGPTV and pCAMBIA. An overview of binary vectors and their use can be found in Hellens et al, Trends in Plant Science (2000) 5, 446-451. Furthermore, by using appropriate cloning vectors, the polynucleotides can be introduced into host cells or organisms such as plants or animals and, thus, be used in the transformation of plants, such as those which are published, and cited, in: Plant Molecular Biology and Biotechnology (CRC Press, Boca Raton, Fla.), chapter 6/7, pp. 71-119 (1993); F. F. White, Vectors for Gene Transfer in Higher Plants; in: Transgenic Plants, vol. 1, Engineering and Utilization, Ed.: Kung and R. Wu, Academic Press, 1993, 15-38; B. Jenes et al., Techniques for Gene Transfer, in: Transgenic Plants, vol. 1, Engineering and Utilization, Ed.: Kung and R. Wu, Academic Press (1993), 128-143; Potrykus 1991, Annu. Rev. Plant Physiol. Plant Molec. Biol. 42, 205-225.

More preferably, the vector of the present invention is an expression vector. In such an expression vector, i.e. a vector which comprises the polynucleotide of the invention having the nucleic acid sequence operatively linked to an expression control sequence (also called "expression cassette") allowing expression in prokaryotic or eukaryotic cells or isolated fractions thereof. Suitable expression vectors are known in the art such as Okayama-Berg cDNA expression vector pcDV1 (Pharmacia), pCDM8, pRc/CMV, pcDNA1, pcDNA3 (Invitrogene) or pSPORT1 (GIBCO BRL). Further examples of typical fusion expression vectors are pGEX (Pharmacia Biotech Inc; Smith 1988, Gene 67:31-40), pMAL (New England Biolabs, Beverly, Mass.) and pRIT5 (Pharmacia, Piscataway, N.J.), where glutathione S-transferase (GST), maltose E-binding protein and protein A, respectively, are fused with the recombinant target protein. Examples of suitable inducible nonfusion *E. coli* expression vectors are, inter alia, pTrc (Amann 1988, Gene 69:301-315) and pET 11d (Studier 1990, Methods in Enzymology 185, 60-89). The target gene expression of the pTrc vector is based on the transcription from a hybrid trp-lac fusion promoter by host RNA polymerase. The target gene expression from the pET 11d vector is based on the transcription of a T7-gn10-lac fusion promoter, which is mediated by a coexpressed viral RNA polymerase (T7 gn1). This viral polymerase is provided by the host strains BL21 (DE3) or HMS174 (DE3) from a resident λ-prophage which harbors a T7 gn1 gene under the transcriptional control of the IacUV 5 promoter. The skilled worker is familiar with other vectors which are suitable in prokaryotic organisms; these vectors are, for example, in *E. coli*, pLG338, pACYC184, the pBR series such as pBR322, the pUC series such as pUC18 or pUC19, the M113mp series, pKC30, pRep4, pHS1, pHS2, pPLc236, pMBL24, pLG200, pUR290, pIN-III113-B1, λgt11 or pBdCl, in *Streptomyces* pIJ101, pIJ364, pIJ702 or pIJ361, in *Bacillus* pUB110, pC194 or pBD214, in *Corynebacterium* pSA77 or pAJ667. Examples of vectors for expression in the yeast *S. cerevisiae* comprise pYep Sec1 (Baldari 1987, Embo J. 6:229-234), pMFa (Kurjan 1982, Cell 30:933-943), pJRY88 (Schultz 1987, Gene 54:113-123) and pYES2 (Invitrogen Corporation, San Diego, Calif.). Vectors and processes for the construction of vectors which are suitable for use in other fungi, such as the filamentous fungi, comprise those which are described in detail in: van den Hondel, C. A. M. J. J., & Punt, P. J. (1991) "Gene transfer systems and vector development for filamentous fungi, in: Applied Molecular Genetics of fungi, J. F. Peberdy et al., Ed., pp. 1-28, Cambridge University Press: Cambridge, or in: More Gene Manipulations in Fungi (J. W. Bennett & L. L. Lasure, Ed., pp. 396-428: Academic Press: San Diego). Further suitable yeast vectors are, for example, pAG-1, YEp6, YEp13 or pEMBLYe23. As an alternative, the polynucleotides of the present invention can be also expressed in insect cells using baculovirus expression vectors. Baculovirus vectors which are available for the expression of proteins in cultured insect cells (for example Sf9 cells) comprise the pAc series (Smith 1983, Mol. Cell. Biol. 3:2156-2165) and the pVL series (Lucklow 1989, Virology 170:31-39).

The polynucleotide of the present invention can be expressed in single-cell plant cells (such as algae), see Falciatore 1999, Marine Biotechnology 1 (3):239-251 and the references cited therein, and plant cells from higher plants (for example Spermatophytes, such as arable crops) by using plant expression vectors. Examples of plant expression vectors comprise those which are described in detail in: Becker 1992, Plant Mol. Biol. 20:1195-1197; Bevan 1984, Nucl. Acids Res. 12:8711-8721; Vectors for Gene Transfer in Higher Plants; in: Transgenic Plants, Vol. 1, Engineering and Utilization, Ed.: Kung and R. Wu, Academic Press, 1993, p. 15-38. A plant expression cassette, preferably, comprises regulatory sequences which are capable of controlling the gene expression in plant cells and which are functionally linked so that each sequence can fulfill its function, such as transcriptional termination, for example polyadenylation signals. Preferred polyadenylation signals are those which are derived from *Agrobacterium tumefaciens* T-DNA, such as the gene 3 of the Ti plasmid pTiACH5, which is known as octopine synthase (Gielen 1984, EMBO J. 3, 835) or functional equivalents of these, but all other terminators which are functionally active in plants are also suitable. Since plant gene expression is very often not limited to transcriptional levels, a plant expression cassette preferably comprises other functionally linked sequences such as translation enhancers, for example the overdrive sequence, which comprises the 5'-untranslated tobacco mosaic virus leader sequence, which increases the protein/RNA ratio (Gallie 1987, Nucl. Acids Research 15:8693-8711). As described above, plant gene expression must be functionally linked to a suitable promoter which performs the expression of the gene in a timely, cell-specific or tissue-specific manner. Promoters which can be used are constitutive promoters (Benfey 1989, EMBO J. 8:2195-2202) such as those which are derived from plant viruses such as 35S CAMV (Franck 1980, Cell 21:285-294), 19S CaMV (see U.S. Pat. No. 5,352,605 and WO 84/02913) or plant promoters such as the promoter of the Rubisco small subunit, which is described in U.S. Pat. No. 4,962,028. Other preferred sequences for the use in functional linkage in plant gene expression cassettes are targeting sequences which are required for targeting the gene product into its relevant cell compartment (for a review, see Kermode 1996, Crit. Rev. Plant Sci, 15, 4: 285-423 and references cited therein), for example into the vacuole, the nucleus, all types of plastids, such as amyloplasts, chloroplasts, chromoplasts, the extracellular space, the mitochondria, the endoplasmic reticulum, oil bodies, peroxisomes and other compartments of plant cells. As described above, plant gene expression can also be facilitated via a chemically inducible promoter (for a review, see Getz 1997, Annu. Rev. Plant Physiol. Plant Mol. Biol., 48:89-108). Chemically inducible promoters are particularly suitable if it is desired that genes are expressed in a time-specific manner. Examples of such promoters are a salicylic-acid-inducible promoter (WO 95/19443), a tetracyclin-inducible promoter (Gatz 1992, Plant J. 2, 397-404) and an ethanol-inducible promoter. Promoters which respond to biotic or abiotic stress conditions are also suitable promoters, for example the pathogen-induced PRP1-gene promoter (Ward 1993, Plant Mol. Biol. 22:361-366), the heat-inducible hsp80 promoter from tomato (U.S. Pat. No. 5,187,267), the cold-inducible alpha-amylase promoter from potato (WO 96/12814) or the wound-inducible pinII promoter (EP 0 375 091 A). The promoters which are especially preferred are those which bring about the expression of genes in tissues and organs in which fatty acid, lipid and oil biosynthesis takes place, in seed cells such as the cells of endosperm and of the developing embryo. Suitable promoters are the napin gene promoter from oilseed rape (U.S. Pat. No. 5,608,152), the USP promoter from *Vicia faba* (Baeumlein 1991, Mol. Gen. Genet. 225 (3):459-67), the oleosin promoter from *Arabidopsis* (WO 98/45461), the phaseolin promoter from *Phaseolus vulgaris* (U.S. Pat. No. 5,504, 200), the Bce4 promoter from *Brassica* (WO 91/13980) or the legumin B4 promoter (LeB4; Baeumlein 1992, Plant Journal, 2 (2):233-9), and promoters which bring about the seed-specific expression in monocotyledonous plants such as maize, barley, wheat, rye, rice and the like. Suitable promoters to be taken into consideration are the lpt2 or lpt1 gene promoter from barley (WO 95/15389 and WO 95/23230) or those which are described in WO 99/16890 (promoters from the barley hordein gene, the rice glutelin gene, the rice oryzin gene, the rice prolamin gene, the wheat gliadin gene, wheat glutelin gene, the maize zein gene, the oat glutelin gene, the *sorghum* kasirin gene, the rye secalin gene). Likewise, especially suitable are promoters which bring about the plastid-specific expression since plastids are the compartment in which the precursors and some end products of lipid biosynthesis are synthesized. Suitable promoters such as the viral RNA-polymerase promoter, are described in WO 95/16783 and WO 97/06250, and the clpP promoter from *Arabidopsis*, described in WO 99/46394.

The abovementioned vectors are only a small overview of vectors to be used in accordance with the present invention. Further vectors are known to the skilled worker and are described, for example, in: Cloning Vectors (Ed., Pouwels, P. H., et al., Elsevier, Amsterdam-New York-Oxford, 1985, ISBN 0 444 904018). For further suitable expression systems for prokaryotic and eukaryotic cells see the chapters 16 and 17 of Sambrook, loc cit.

It follows from the above that, preferably, said vector is an expression vector. More preferably, the said polynucleotide of the present invention is under the control of a seed-specific promoter in the vector of the present invention. A preferred seed-specific promoter as meant herein is selected from the group consisting of Conlinin 1, Conlinin 2, napin, LuFad3, USP, LeB4, Arc, Fae, ACP, LuPXR, and SBP. For details, see, e.g., US 2003-0159174.

Moreover, the present invention relates to a host cell comprising the polynucleotide or the vector of the present invention.

Preferably, said host cell is a plant cell and, more preferably, a plant cell obtained from an oilseed crop. More preferably, said oilseed crop is selected from the group consisting of flax (*Linum* sp.), rapeseed (*Brassica* sp.), soybean (*Glycine* and *Soja* sp.), sunflower (*Helianthus* sp.), cotton (*Gossypium* sp.), corn (*Zea mays*), olive (*Olea* sp.), safflower (*Carthamus* sp.), cocoa (*Theobroma* cacoa), peanut (*Arachis* sp.), hemp, camelina, *crambe*, oil palm, coconuts, groundnuts, sesame seed, castor bean, *lesquerella*, tallow tree, sheanuts, tungnuts, kapok fruit, poppy seed, jojoba seeds and *perilla*.

Also preferably, said host cell is a microorganism. More preferably, said microorganism is a bacterium, a fungus or algae. More preferably, it is selected from the group consisting of *Candida, Cryptococcus, Lipomyces, Rhodosporidium, Yarrowia,* and *Schizochytrium*.

Moreover, a host cell according to the present invention may also be an animal cell. Preferably, said animal host cell is a host cell of a fish or a cell line obtained therefrom. More preferably, the fish host cell is from herring, salmon, sardine, redfish, eel, carp, trout, halibut, mackerel, zander or tuna.

Generally, the controlling steps in the production of LCPUFAs, i.e., the long chain unsaturated fatty acid biosynthetic pathway, are catalyzed by membrane-associated fatty acid elongase complexes. Plants and most other eukaryotic organisms have specialized elongase system for the extension of fatty acids beyond C18 atoms. These elongase reactions have several important features in common with the fatty acid synthase complex (FAS). However, the elongase complex is different from the FAS complex as the complex is localized in the cytosol and membrane bound, ACP is not involved and the elongase 3-keto-acyl-CoA-synthase catalyzes the condensation of malonyl-CoA with an acyl primer. The elongase complex consists of four components with different catalytic functions, the keto-acyl-CoA-synthase (KCS, condensation reaction of malonyl-CoA to acyl-CoA, creation of a 2 C atom longer keto-acyl-CoA fatty acid), the keto-acyl-CoA-reductase (KCR, reduction of the 3-keto group to a 3-hydroxy-group), the dehydratase (DH, dehydration results in a delta-2-enoyl-acyl-CoA fatty acid) and the enoly-CoA-reductase (ECR, reduction of the double bond at position 2, release from the complex). For the production of LCPUFAs including ARA, EPA and/or DHA the elongation and desaturation reactions could be essential. Higher plants do not have the necessary enzyme set to produce LCPUFAs (4 or more double bonds, 20 or more C atoms). Therefore the catalytic activities have to be conferred to the plants or plant cells. Critical steps in the process of LCPUFA biosynthesis are the elongation of fatty acids from 18 to 24 carbon atoms and desaturation of carbon atoms. Polynucleotides of the present invention surprisingly catalyze the keto-acyl-CoA-synthase, keto-acyl-CoA-reductase, dehydratase, enoyl-CoA-reductase reactions and therefore catalyze the elongation of 18 carbon atoms fatty acids. Polynucleotides of the present invention surprisingly catalyze the desaturation of the $4^{th}$, $5^{th}$, $8^{th}$, $9^{th}$, $12^{th}$ and $15^{th}$ fatty acids carbon atom bonds. By delivering these enzymes increased levels of PUFAs and LCPUFAs are produced.

However, it will be understood that dependent on the host cell, further, enzymatic activities may be conferred to the host cells, e.g., by recombinant technologies. Accordingly, the present invention, preferably, envisages a host cell which in addition to the polynucleotide of the present invention comprises polynucleotides encoding such desaturases and/or elongases as required depending on the selected host cell. Preferred desaturases and/or elongases which shall be present in the host cell are at least one enzyme selected from the group consisting of: d4-desaturase, d5-desaturase, d5-elongase, d6-desaturase, d12-desaturase, d15-desaturase, ω3-desaturase d-6-elongase or d-9-elongase. Especially preferred are the bifunctional d12d15-desaturases d12d15Des(Ac) from *Acanthamoeba castellanii* (WO2007042510), d12d15Des(Cp) from *Claviceps purpurea* (WO2008006202) and d12d15Des(Lg)1 from *Lottia gigantea* (WO2009016202), the d12-desaturases d12Des (Co) from *Calendula officinalis* (WO200185968), d12Des (Lb) from *Laccaria bicolor* (WO2009016202), d12Des(Mb) from *Monosiga brevicollis* (WO2009016202), d12Des(Mg) from *Mycosphaerella graminicola* (WO2009016202), d12Des(Nh) from *Nectria haematococca* (WO2009016202), d12Des(Ol) from *Ostreococcus lucimarinus* (WO2008040787), d12Des(Pb) from *Phycomyces blakesleeanus* (WO2009016202), d12Des(Ps) from *Phytophthora sojae* (WO2006100241) and d12Des(Tp) from *Thalassiosira pseudonana* (WO2006069710), the d15-desaturases d15Des(Hr) from *Helobdella robusta* (WO2009016202), d15Des(Mc) from *Microcoleus chthonoplastes* (WO2009016202), d15Des(Mf) from *Mycosphaerella fijiensis* (WO2009016202), d15Des(Mg) from *Mycosphaerella graminicola* (WO2009016202) and d15Des (Nh)2 from *Nectria haematococca* (WO2009016202), the d4-desaturases d4Des(Eg) from *Euglena gracilis* (WO2004090123), d4Des(Tc) from *Thraustochytrium* sp. (WO2002026946) and d4Des(Tp) from *Thalassiosira pseudonana* (WO2006069710), the d5-desaturases d5Des (Ol)2 from *Ostreococcus lucimarinus* (WO2008040787), d5Des(Pp) from *Physcomitrella patens* (WO2004057001), d5Des(Pt) from *Phaeodactylum tricornutum* (WO2002057465), d5Des(Tc) from *Thraustochytrium* sp. (WO2002026946), d5Des(Tp) from *Thalassiosira pseudonana* (WO2006069710) and the d6-desaturases d6Des(Cp) from *Ceratodon purpureus* (WO2000075341), d6Des(Ol) from *Ostreococcus lucimarinus* (WO2008040787), d6Des (Ot) from *Ostreococcus tauri* (WO2006069710), d6Des(Pf) from *Primula farinosa* (WO2003072784), d6Des(Pir)_BO from *Pythium irregulare* (WO2002026946), d6Des(Pir) from *Pythium irregulare* (WO2002026946), d6Des(Plu) from *Primula luteola* (WO2003072784), d6Des(Pp) from *Physcomitrella patens* (WO200102591), d6Des(Pt) from *Phaeodactylum tricornutum* (WO2002057465), d6Des(Pv) from *Primula vialii* (WO2003072784) and d6Des(Tp) from *Thalassiosira pseudonana* (WO2006069710), the d8-desaturases d8Des(Ac) from *Acanthamoeba castellanii* (EP1790731), d8Des(Eg) from *Euglena gracilis* (WO200034439) and d8Des(Pm) from *Perkinsus marinus* (WO2007093776), the o3-desaturases o3Des(Pi) from *Phytophthora infestans* (WO2005083053), o3Des(Pir) from *Pythium irregulare* (WO2008022963), o3Des(Pir)2 from *Pythium irregulare* (WO2008022963) and o3Des(Ps) from *Phytophthora sojae* (WO2006100241), the bifunctional d5d6-elongases d5d6Elo(Om)2 from *Oncorhynchus mykiss* (WO2005012316), d5d6Elo(Ta) from *Thraustochytrium*

*aureum* (WO2005012316) and d5d6Elo(Tc) from *Thraustochytrium* sp. (WO2005012316), the d5-elongases d5Elo (At) from *Arabidopsis thaliana* (WO2005012316), d5Elo (At)2 from *Arabidopsis thaliana* (WO2005012316), d5Elo (Ci) from *Ciona intestinalis* (WO2005012316), d5Elo(Ol) from *Ostreococcus lucimarinus* (WO2008040787), d5Elo (Ot) from *Ostreococcus tauri* (WO2005012316), d5Elo(Tp) from *Thalassiosira pseudonana* (WO2005012316) and d5Elo(Xl) from *Xenopus laevis* (WO2005012316), the d6-elongases d6Elo(Ol) from *Ostreococcus lucimarinus* (WO2008040787), d6Elo(Ot) from *Ostreococcus tauri* (WO2005012316), d6Elo(Pi) from *Phytophthora infestans* (WO2003064638), d6Elo(Pir) from *Pythium irregulare* (WO2009016208), d6Elo(Pp) from *Physcomitrella patens* (WO2001059128), d6Elo(Ps) from *Phytophthora sojae* (WO2006100241), d6Elo(Ps)2 from *Phytophthora sojae* (WO2006100241), d6Elo(Ps)3 from *Phytophthora sojae* (WO2006100241), d6Elo(Pt) from *Phaeodactylum tricornutum* (WO2005012316), d6Elo(Tc) from *Thraustochytrium* sp. (WO2005012316) and d6Elo(Tp) from *Thalassiosira pseudonana* (WO2005012316), the d9-elongases d9Elo (Ig) from *Isochrysis galbana* (WO2002077213), d9Elo(Pm) from *Perkinsus marinus* (WO2007093776) and d9Elo(Ro) from *Rhizopus oryzae* (WO2009016208). Particularly, if the manufacture of ARA is envisaged in higher plants, the enzymes recited in table 5 or 6, below (i.e. additionally a d6-desaturase, d6-elongase, d5-desaturase, and d12-desaturase) or enzymes having essentially the same activity may be combined in a host cell. If the manufacture of EPA is envisaged in higher plants, the enzymes recited in table 7, below (i.e. additionally a d6-desaturase, d6-elongase, d5-desaturase, d12-desaturase, omega 3-desaturase and d15-desaturase), or enzymes having essentially the same activity may be combined in a host cell. If the manufacture of DHA is envisaged in higher plants, the enzymes recited in table 8, below (i.e. aditinonally a d6-desaturase, d6-elongase, d5-desaturase, d12-desaturase, omega 3-desaturase, d15-desaturase, d5-elongase, and d4-desaturase), or enzymes having essentially the same activity may be combined in a host cell.

The present invention also relates to a cell, preferably a host cell as specified above or a cell of a non-human organism specified elsewhere herein, said cell comprising a polynucleotide which is obtained from the polynucleotide of the present invention by a point mutation, a truncation, an inversion, a deletion, an addition, a substitution and homologous recombination. How to carry out such modifications to a polynucleotide is well known to the skilled artisan and has been described elsewhere in this specification in detail.

The present invention furthermore pertains to a method for the manufacture of a polypeptide encoded by a polynucleotide of any the present invention comprising a) cultivating the host cell of the invention under conditions which allow for the production of the said polypeptide; and b) obtaining the polypeptide from the host cell of step a).

Suitable conditions which allow for expression of the polynucleotide of the invention comprised by the host cell depend on the host cell as well as the expression control sequence used for governing expression of the said polynucleotide. These conditions and how to select them are very well known to those skilled in the art. The expressed polypeptide may be obtained, for example, by all conventional purification techniques including affinity chromatography, size exclusion chromatography, high pressure liquid chromatography (HPLC) and precipitation techniques including antibody precipitation. It is to be understood that the method may—although preferred—not necessarily yield an essentially pure preparation of the polypeptide. It is to be understood that depending on the host cell which is used for the aforementioned method, the polypeptides produced thereby may become posttranslationally modified or processed otherwise.

The present invention encompasses a polypeptide encoded by the polynucleotide of the present invention or which is obtainable by the aforementioned method.

The term "polypeptide" as used herein encompasses essentially purified polypeptides or polypeptide preparations comprising other proteins in addition. Further, the term also relates to the fusion proteins or polypeptide fragments being at least partially encoded by the polynucleotide of the present invention referred to above. Moreover, it includes chemically modified polypeptides. Such modifications may be artificial modifications or naturally occurring modifications such as phosphorylation, glycosylation, myristylation and the like (Review in Mann 2003, Nat. Biotechnol, 21, 255-261, review with focus on plants in Huber 2004, Curr. Opin. Plant Biol. 7, 318-322). Currently, more than 300 posttranslational modifications are known (see full ABFRC Delta mass list at http://www.abrf.org/index.cfm/dm.home). The polypeptide of the present invention shall exhibit the desaturase, keto-acyl-CoA-synthase, keto-acyl-CoA-reductase, dehydratase and enoyl-CoA-reductase activity referred to above.

Encompassed by the present invention is, furthermore, an antibody which specifically recognizes the polypeptide of the invention.

Antibodies against the polypeptides of the invention can be prepared by well known methods using a purified polypeptide according to the invention or a suitable fragment derived therefrom as an antigen. A fragment which is suitable as an antigen may be identified by antigenicity determining algorithms well known in the art. Such fragments may be obtained either from the polypeptide of the invention by proteolytic digestion or may be a synthetic peptide. Preferably, the antibody of the present invention is a monoclonal antibody, a polyclonal antibody, a single chain antibody, a chimerized antibody or a fragment of any of these antibodies, such as Fab, Fv or scFv fragments etc. Also comprised as antibodies by the present invention are bispecific antibodies, synthetic antibodies or chemically modified derivatives of any of the aforementioned antibodies. The antibody of the present invention shall specifically bind (i.e. does significantly not cross react with other polypeptides or peptides) to the polypeptide of the invention. Specific binding can be tested by various well known techniques. Antibodies or fragments thereof can be obtained by using methods which are described, e.g., in Harlow and Lane "Antibodies, A Laboratory Manual", CSH Press, Cold Spring Harbor, 1988. Monoclonal antibodies can be prepared by the techniques originally described in Köhler 1975, Nature 256, 495, and Galfré 1981, Meth. Enzymol. 73, 3, which comprise the fusion of mouse myeloma cells to spleen cells derived from immunized mammals. The antibodies can be used, for example, for the immunoprecipitation, immunolocalization or purification (e.g., by affinity chromatography) of the polypeptides of the invention as well as for the monitoring of the presence of said variant polypeptides, for example, in recombinant organisms, and for the identification of proteins or compounds interacting with the proteins according to the invention.

Moreover, the antibody according to the present invention can be applied for identifying the presence or absence of the polypeptides of the present invention. Preferably, the antibody is used for identifying non-human transgenic organisms as specified elsewhere herein and, preferably, transgenic plants, which comprise the polypeptides of the present invention. To this end, the antibody may be provided in form of a kit which allows for identifying non-human transgenic organisms and, preferably, transgenic plants comprising the polypeptides of the present invention. The kit, in addition to the antibody of the present invention, may further comprise a detection agent for detecting a complex of the antibody of the invention and the polypeptide of the invention.

Moreover, the present invention contemplates a non-human transgenic organism comprising the polynucleotide or the vector of the present invention.

Preferably, the non-human transgenic organism is a plant, plant part, or plant seed. Preferred plants to be used for introducing the polynucleotide or the vector of the invention are plants which are capable of synthesizing fatty acids, such as all dicotyledonous or monocotyledonous plants, algae or mosses. It is to be understood that host cells derived from a plant may also be used for producing a plant according to the present invention. Preferred plants are selected from the group of the plant families Adelotheciaceae, Anacardiaceae, Asteraceae, Apiaceae, Betulaceae, Boraginaceae, Brassicaceae, Bromeliaceae, Caricaceae, Cannabaceae, Convolvulaceae, Chenopodiaceae, Crypthecodiniaceae, Cucurbitaceae, Ditrichaceae, Elaeagnaceae, Ericaceae, Euphorbiaceae, Fabaceae, Geraniaceae, Gramineae, Juglandaceae, Lauraceae, Leguminosae, Linaceae, Prasinophyceae or vegetable plants or ornamentals such as *Tagetes*. Examples which may be mentioned are the following plants selected from the group consisting of: Adelotheciaceae such as the genera *Physcomitrella*, such as the genus and species *Physcomitrella patens*, Anacardiaceae such as the genera *Pistacia, Mangifera, Anacardium*, for example the genus and species *Pistacia vera* [pistachio], *Mangifer indica* [mango] or *Anacardium occidentals* [cashew], Asteraceae, such as the genera *Calendula, Carthamus, Centaurea, Cichorium, Cynara, Helianthus, Lactuca, Locusta, Tagetes, Valeriana*, for example the genus and species *Calendula officinalis* [common marigold], *Carthamus tinctorius* [safflower], *Centaurea cyanus* [cornflower], *Cichorium intybus* [chicory], *Cynara scolymus* [artichoke], *Helianthus annus* [sunflower], *Lactuca sativa, Lactuca crispa, Lactuca esculenta, Lactuca scariola* L. ssp. *sativa, Lactuca scariola* L. var. *integrate, Lactuca scariola* L. var. *integrifolia, Lactuca sativa* subsp. *romana, Locusta communis, Valeriana locusta* [salad vegetables], *Tagetes lucida, Tagetes erecta* or *Tagetes tenuifolia* [african or french marigold], Apiaceae, such as the genus *Daucus*, for example the genus and species *Daucus carota* [carrot], Betulaceae, such as the genus *Corylus*, for example the genera and species *Corylus avellana* or *Corylus colurna* [hazelnut], Boraginaceae, such as the genus *Borago*, for example the genus and species *Borago officinalis* [borage], Brassicaceae, such as the genera *Brassica, Melanosinapis, Sinapis, Arabadopsis*, for example the genera and species *Brassica napus, Brassica rapa* ssp. [oilseed rape], *Sinapis arvensis Brassica juncea, Brassica juncea* var. *juncea, Brassica juncea* var. *crispifolia, Brassica juncea* var. *foliosa, Brassica nigra, Brassica sinapioides, Melanosinapis communis* [mustard], *Brassica oleracea* [fodder beet] or *Arabidopsis thaliana*, Bromeliaceae, such as the genera *Anana, Bromelia* (pineapple), for example the genera and species *Anana comosus, Ananas ananas* or *Bromelia comosa* [pineapple], Caricaceae, such as the genus *Carica*, such as the genus and species *Carica papaya* [pawpaw], Cannabaceae, such as the genus *Cannabis*, such as the genus and species *Cannabis sativa* [hemp], Convolvulaceae, such as the genera *Ipomea, Convolvulus*, for example the genera and species *Ipomoea batatus, Ipomoea pandurata, Convolvulus batatas, Convolvulus tiliaceus, Ipomoea fastigiate, Ipomoea tiliacea, Ipomoea triloba* or *Convolvulus panduratus* [sweet potato, batate], Chenopodiaceae, such as the genus *Beta*, such as the genera and species *Beta vulgaris, Beta vulgaris* var. *altissima, Beta vulgaris* var. *Vulgaris, Beta maritima, Beta vulgaris* var. *perennis, Beta vulgaris* var. *conditiva* or *Beta vulgaris* var. *esculenta* [sugarbeet], Crypthecodiniaceae, such as the genus *Crypthecodinium*, for example the genus and species *Cryptecodinium cohnii*, Cucurbitaceae, such as the genus *Cucurbita*, for example the genera and species *Cucurbita maxima, Cucurbita mixta, Cucurbita pepo* or *Cucurbita moschata* [pumpkin/squash], Cymbellaceae such as the genera *Amphora, Cymbella, Okedenia, Phaeodactylum, Reimeria*, for example the genus and species *Phaeodactylum tricornutum*, Ditrichaceae such as the genera *Ditrichaceae, Astomiopsis, Ceratodon, Chrysoblastella, Ditrichum, Distichium, Eccremidium, Lophidion, Philibertiella, Pleuridium, Saelania, Trichodon, Skottsbergia*, for example the genera and species *Ceratodon antarcticus, Ceratodon columbiae, Ceratodon heterophyllus, Ceratodon purpureus, Ceratodon purpureus, Ceratodon purpureus* ssp. *convolutus, Ceratodon, purpureus* spp. *stenocarpus, Ceratodon purpureus* var. *rotundifolius, Ceratodon ratodon, Ceratodon stenocarpus, Chrysoblastella chilensis, Ditrichum ambiguum, Ditrichum brevisetum, Ditrichum crispatissimum, Ditrichum difficile, Ditrichum falcifolium, Ditrichum flexicaule, Ditrichum giganteum, Ditrichum heteromallum, Ditrichum lineare, Ditrichum lineare, Ditrichum montanum, Ditrichum montanum, Ditrichum pallidum, Ditrichum punctulatum, Ditrichum pusillum, Ditrichum pusillum* var. *tortile, Ditrichum rhynchostegium, Ditrichum schimperi, Ditrichum tortile, Distichium capillaceum, Distichium hagenii, Distichium inclinatum, Distichium macounii, Eccremidium floridanum, Eccremidium whiteleggei, Lophidion strictus, Pleuridium acuminatum, Pleuridium alternifolium, Pleuridium holdridgei, Pleuridium mexicanum, Pleuridium ravenelii, Pleuridium subulatum, Saelania glaucescens, Trichodon borealis, Trichodon cylindricus* or *Trichodon cylindricus* var. *oblongus*, Elaeagnaceae such as the genus *Elaeagnus*, for example the genus and species *Olea europaea* [olive], Ericaceae such as the genus *Kalmia*, for example the genera and species *Kalmia latifolia, Kalmia angustifolia, Kalmia microphylla, Kalmia polifolia, Kalmia occidentalis, Cistus chamaerhodendros* or *Kalmia lucida* [mountain laurel], Euphorbiaceae such as the genera *Manihot, Janipha, Jatropha, Ricinus*, for example the genera and species *Manihot utilissima, Janipha manihot, Jatropha manihot, Manihot aipil, Manihot dulcis, Manihot manihot, Manihot melanobasis, Manihot esculents* [manihot] or *Ricinus communis* [castor-oil plant], Fabaceae such as the genera *Pisum, Albizia, Cathormion, Feuillea, Inga, Pithecolobium, Acacia, Mimosa, Medicajo, Glycine, Dolichos, Phaseolus, Soja*, for example the genera and species *Pisum sativum, Pisum arvense, Pisum humile* [pea], *Albizia berteriana, Albizia julibrissin, Albizia lebbeck, Acacia berteriana, Acacia littoralis, Albizia berteriana, Albizzia berteriana, Cathormion berteriana, Feuillea berteriana, Inga fragrans, Pithecellobium berterianum, Pithecellobium fragrans, Pithecolobium berterianum, Pseudalbizzia berteriana, Acacia julibrissin, Acacia nemu, Albizia nemu, Feuilleea julibrissin, Mimosa julibrissin, Mimosa speciosa, Sericanrda julibrissin, Acacia lebbeck, Acacia macrophylla, Albizia lebbek, Feuilleea lebbeck, Mimosa lebbeck, Mimosa speciosa* [silk tree], *Medicago sativa, Medicago falcata, Medicago varia* [alfalfa], *Glycine max Dolichos soja, Glycine gracilis, Glycine his-*

*pida, Phaseolus max, Soja hispida* or *Soja max* [soybean], Funariaceae such as the genera *Aphanorrhegma, Entosthodon, Funaria, Physcomitrella, Physcomitrium*, for example the genera and species *Aphanorrhegma serratum, Entosthodon attenuatus, Entosthodon bolanderi, Entosthodon bonplandii, Entosthodon californicus, Entosthodon drummondii, Entosthodon jamesonii, Entosthodon leibergii, Entosthodon neoscoticus, Entosthodon rubrisetus, Entosthodon spathulifolius, Entosthodon tucsoni, Funaria americana, Funaria bolanderi, Funaria calcarea, Funaria californica, Funaria calvescens, Funaria convoluta, Funaria flavicans, Funaria groutiana, Funaria hygrometrica, Funaria hygrometrica* var. *arctica, Funaria hygrometrica* var. *calvescens, Funaria hygrometrica* var. *convoluta, Funaria hygrometrica* var. *muralis, Funaria hygrometrica* var. *utahensis, Funaria microstoma, Funaria microstoma* var. *obtusifolia, Funaria muhlenbergii, Funaria orcuttii, Funaria plano-convexa, Funaria polaris, Funaria ravenelii, Funaria rubriseta, Funaria serrata, Funaria sonorae, Funaria sublimbatus, Funaria tucsoni, Physcomitrella californica, Physcomitrella patens, Physcomitrella readeri, Physcomitrium australe, Physcomitrium californicum, Physcomitrium collenchymatum, Physcomitrium coloradense, Physcomitrium cupuliferum, Physcomitrium drummondii, Physcomitrium eurystomum, Physcomitrium flexifolium, Physcomitrium hookeri, Physcomitrium hookeri* var. *serratum, Physcomitrium immersum, Physcomitrium kellermanii, Physcomitrium megalocarpum, Physcomitrium pyriforme, Physcomitrium pyriforme* var. *serratum, Physcomitrium rufipes, Physcomitrium sandbergii, Physcomitrium subsphaericum, Physcomitrium washingtoniense*, Geraniaceae, such as the genera *Pelargonium, Cocos, Oleum*, for example the genera and species *Cocos nucifera, Pelargonium grossularioides* or *Oleum cocois* [coconut], Gramineae, such as the genus *Saccharum*, for example the genus and species *Saccharum officinarum*, Juglandaceae, such as the genera *Juglans, Wallia*, for example the genera and species *Juglans regia, Juglans ailanthifolia, Juglans sieboldiana, Juglans cinerea, Wallia cinerea, Juglans bixbyi, Juglans californica, Juglans hindsii, Juglans intermedia, Juglans jamaicensis, Juglans major, Juglans microcarpa, Juglans nigra* or *Wallia nigra* [walnut], Lauraceae, such as the genera *Persea, Laurus*, for example the genera and species *Laurus nobilis* [bay], *Persea americana, Persea gratissima* or *Persea persea* [avocado], Leguminosae, such as the genus *Arachis*, for example the genus and species *Arachis hypogaea* [peanut], Linaceae, such as the genera *Linum, Adenolinum*, for example the genera and species *Linum usitatissimum, Linum humile, Linum austriacum, Linum bienne, Linum angustifolium, Linum catharticum, Linum flavum, Linum grandiflorum, Adenolinum grandiflorum, Linum lewisii, Linum narbonense, Linum perenne, Linum perenne* var. *lewisii, Linum pratense* or *Linum trigynum* [linseed], Lythrarieae, such as the genus *Punica*, for example the genus and species *Punica granatum* [pomegranate], Malvaceae, such as the genus *Gossypium*, for example the genera and species *Gossypium hirsutum, Gossypium arboreum, Gossypium barbadense, Gossypium herbaceum* or *Gossypium thurberi* [cotton], Marchantiaceae, such as the genus *Marchantia*, for example the genera and species *Marchantia berteroana, Marchantia foliacea, Marchantia macropora*, Musaceae, such as the genus *Musa*, for example the genera and species *Musa nana, Musa acuminata, Musa paradisiaca, Musa* spp. [banana], Onagraceae, such as the genera *Camissonia, Oenothera*, for example the genera and species *Oenothera biennis* or *Camissonia brevipes* [evening primrose], Palmae, such as the genus *Elacis*, for example the genus and species *Elaeis guineensis* [oil palm], Papaveraceae, such as the genus *Papaver*, for example the genera and species *Papaver orientale, Papaver rhoeas, Papaver dubium* [poppy], Pedaliaceae, such as the genus *Sesamum*, for example the genus and species *Sesamum indicum* [sesame], Piperaceae, such as the genera *Piper, Artanthe, Peperomia, Steffensia*, for example the genera and species *Piper aduncum, Piper amalago, Piper angustifolium, Piper auritum, Piper betel, Piper cubeba, Piper longum, Piper nigrum, Piper retrofractum, Artanthe adunca, Artanthe elongata, Peperomia elongata, Piper elongatum, Steffensia elongata* [cayenne pepper], Poaceae, such as the genera *Hordeum, Secale, Avena, Sorghum, Andropogon, Holcus, Panicum, Oryza, Zea* (maize), *Triticum*, for example the genera and species *Hordeum vulgare, Hordeum jubatum, Hordeum murinum, Hordeum secalinum, Hordeum distichon, Hordeum aegiceras, Hordeum hexastichon, Hordeum hexastichum, Hordeum irregulare, Hordeum sativum, Hordeum secalinum* [barley], *Secale cereale* [rye], *Avena sativa, Avena fatua, Avena byzantina, Avena fatua* var. *sativa, Avena hybrida* [oats], *Sorghum bicolor, Sorghum halepense, Sorghum saccharatum, Sorghum vulgare, Andropogon drummondii, Holcus bicolor, Holcus sorghum, Sorghum aethiopicum, Sorghum arundinaceum, Sorghum caffrorum, Sorghum cernuum, Sorghum dochna, Sorghum drummondii, Sorghum durra, Sorghum guineense, Sorghum lanceolatum, Sorghum nervosum, Sorghum saccharatum, Sorghum subglabrescens, Sorghum verticilliflorum, Sorghum vulgare, Holcus halepensis, Sorghum miliaceum, Panicum militaceum* [millet], *Oryza sativa, Oryza latifolia* [rice], *Zea mays* [maize], *Triticum aestivum, Triticum durum, Triticum turgidum, Triticum hybernum, Triticum macha, Triticum sativum* or *Triticum vulgare* [wheat], Porphyridiaceae, such as the genera *Chroothece, Flintiella, Petrovanella, Porphyridium, Rhodella, Rhodosorus, Vanhoeffenia*, for example the genus and species *Porphyridium cruentum*, Proteaceae, such as the genus *Macadamia*, for example the genus and species *Macadamia intergrifolia [macadamia]*, Prasinophyceae such as the genera *Nephroselmis, Prasinococcus, Scherffelia, Tetraselmis, Mantoniella, Ostreococcus*, for example the genera and species *Nephroselmis olivacea, Prasinococcus capsulatus, Scherffelia dubia, Tetraselmis chui, Tetraselmis suecica, Mantoniella squamata, Ostreococcus tauri*, Rubiaceae such as the genus *Cofea*, for example the genera and species *Cofea* spp., *Coffea arabica, Coffea canephora* or *Coffea liberica* [coffee], Scrophulariaceae such as the genus *Verbascum*, for example the genera and species *Verbascum blattaria, Verbascum chaixii, Verbascum densiflorum, Verbascum lagurus, Verbascum longifolium, Verbascum lychnitis, Verbascum nigrum, Verbascum olympicum, Verbascum phlomoides, Verbascum phoenicum, Verbascum pulverulentum* or *Verbascum thapsus* [mullein], Solanaceae such as the genera *Capsicum, Nicotiana, Solanum, Lycopersicon*, for example the genera and species *Capsicum annuum, Capsicum annuum* var. *glabriusculum, Capsicum frutescens* [pepper], *Capsicum annuum* [paprika], *Nicotiana tabacum, Nicotiana alata, Nicotiana attenuate, Nicotiana glauca, Nicotiana langsdorffii, Nicotiana obtusifolia, Nicotiana quadrivalvis, Nicotiana repanda, Nicotiana rustica, Nicotiana sylvestris* [tobacco], *Solanum tuberosum* [potato], *Solanum melongena* [eggplant], *Lycopersicon esculentum, Lycopersicon lycopersicum, Lycopersicon pyriforme, Solanum integrifolium* or *Solanum lycopersicum* [tomato], Sterculiaceae, such as the genus *Theobroma*, for example the genus and species *Theobroma cacao* [cacao] or Theaceae, such as the genus *Camellia*, for example the genus and species *Camellia sinensis* [tea]. In particular preferred plants to be used as transgenic plants in accordance with the present invention are oil fruit crops which comprise large amounts of lipid compounds, such as peanut, oilseed rape, canola, sunflower, safflower, poppy, mustard, hemp, castor-oil plant, olive, sesame, *Calendula, Punica*, evening primrose, mullein, thistle, wild roses, hazelnut, almond, *macadamia*, avocado, bay, pumpkin/squash, linseed, soybean, pistachios, borage, trees (oil palm, coconut, walnut) or crops such as maize, wheat, rye, oats, triticale, rice, barley, cotton, cassava, pepper, *Tagetes*, Solanaceae plants such as potato, tobacco, eggplant and tomato, *Vicia* species, pea, alfalfa or bushy plants (coffee, cacao, tea), *Salix* species, and perennial grasses and fodder crops. Preferred plants according to the invention are oil crop plants such as peanut, oilseed rape, canola, sunflower, safflower, poppy, mustard, hemp, castor-oil plant, olive, *Calendula, Punica*, evening primrose, pumpkin/squash, linseed, soybean, borage, trees (oil palm, coconut). Especially preferred are sunflower, safflower, tobacco, mullein, sesame, cotton, pumpkin/squash, poppy, evening primrose, walnut, linseed, hemp, thistle or safflower. Very especially preferred plants are plants such as safflower, sunflower, poppy, evening primrose, walnut, linseed, or hemp.

Preferred mosses are *Physcomitrella* or *Ceratodon*. Preferred algae are *Isochrysis, Mantoniella, Ostreococcus* or *Crypthecodinium*, and algae/diatoms such as *Phaeodactylum* or *Thraustochytrium*. More preferably, said algae or mosses are selected from the group consisting of: *Shewanella, Physcomitrella, Thraustochytrium, Fusarium, Phytophthora, Ceratodon, Isochrysis, Aleurita, Muscarioides, Mortierella, Phaeodactylum, Cryphthecodinium*, specifically from the genera and species *Thalassiosira pseudonona, Euglena gracilis, Physcomitrella patens, Phytophthora infestans, Fusarium graminaeum, Cryptocodinium cohnii, Ceratodon purpureus, Isochrysis galbana, Aleurita farinosa, Thraustochytrium* sp., *Muscarioides viallii, Mortierella alpina, Phaeodactylum tricornutum* or *Caenorhabditis elegans* or especially advantageously *Phytophthora infestans, Thalassiosira pseudonona* and *Cryptocodinium cohnii*.

Transgenic plants may be obtained by transformation techniques as elsewhere in this specification. Preferably, transgenic plants can be obtained by T-DNA-mediated transformation. Such vector systems are, as a rule, characterized in that they contain at least the vir genes, which are required for the *Agrobacterium*-mediated transformation, and the sequences which delimit the T-DNA (T-DNA border). Suitable vectors are described elsewhere in the specification in detail.

Also encompassed are transgenic non-human animals comprising the vector or polynucleotide of the present invention. Preferred non-human transgenic animals envisaged by the present invention are fish, such as herring, salmon, sardine, redfish, eel, carp, trout, halibut, mackerel, zander or tuna.

However, it will be understood that dependent on the non-human transgenic organism specified above, further, enzymatic activities may be conferred to the said organism, e.g., by recombinant technologies. Accordingly, the present invention, preferably, envisages a non-human transgenic organism specified above which in addition to the polynucleotide of the present invention comprises polynucleotides encoding such desaturases and/or elongases as required depending on the selected host cell. Preferred desaturases and/or elongases which shall be present in the organism are at least one enzyme selected from the group of desaturases and/or elongases or the combinations specifically recited elsewhere in this specification (see above and tables 5, 6 and 7).

Furthermore, the present invention encompasses a method for the manufacture of polyunsaturated fatty acids comprising:
a) cultivating the host cell of the invention under conditions which allow for the production of polyunsaturated fatty acids in said host cell; and
b) obtaining said polyunsaturated fatty acids from the said host cell.

The term "polyunsaturated fatty acids (PUFA)" as used herein refers to fatty acids comprising at least two, preferably, three, four, five or six, double bonds. Moreover, it is to be understood that such fatty acids comprise, preferably from 18 to 24 carbon atoms in the fatty acid chain. More preferably, the term relates to long chain PUFA (LCPUFA) having from 20 to 24 carbon atoms in the fatty acid chain. Preferred unsaturated fatty acids in the sense of the present invention are selected from the group consisting of DGLA 20:3 (8,11,14), ARA 20:4 (5,8,11,14), iARA 20:4(8,11,14,17), EPA 20:5 (5,8,11,14,17), DPA 22:5 (4,7,10,13,16), DHA 22:6 (4,7,10,13,16,19), 20:4 (8,11,14,17), more preferably, arachidonic acid (ARA) 20:4 (5,8,11,14), eicosapentaenoic acid (EPA) 20:5 (5,8,11,14,17), and docosahexaenoic acid (DHA) 22:6 (4,7,10,13,16,19). Thus, it will be understood that most preferably, the methods provided by the present invention pertaining to the manufacture of ARA, EPA or DHA. Moreover, also encompassed are the intermediates of LCPUFA which occur during synthesis. Such intermediates are, preferably, formed from substrates by the desaturase, keto-acyl-CoA-synthase, keto-acyl-CoA-reductase, dehydratase and enoyl-CoA-reductase activity of the polypeptide of the present invention. Preferably, substrates encompass LA 18:2 (9,12), GLA 18:3 (6,9,12), DGLA 20:3 (8,11,14), ARA 20:4 (5,8,11,14), eicosadienoic acid 20:2 (11,14), eicosatetraenoic acid 20:4 (8,11,14,17), eicosapentaenoic acid 20:5 (5,8,11,14,17).

The term "cultivating" as used herein refers maintaining and growing the host cells under culture conditions which allow the cells to produce the said polyunsaturated fatty acid, i.e. the PUFA and/or LCPUFA referred to above. This implies that the polynucleotide of the present invention is expressed in the host cell so that the desaturase, keto-acyl-CoA-synthase, keto-acyl-CoA-reductase, dehydratase and enoyl-CoA-reductase activity is present. Suitable culture conditions for cultivating the host cell are described in more detail below.

The term "obtaining" as used herein encompasses the provision of the cell culture including the host cells and the culture medium as well as the provision of purified or partially purified preparations thereof comprising the polyunsaturated fatty acids, preferably, ARA, EPA, DHA, in free or in -CoA bound form, as membrane phospholipids or as triacylglyceride estres. More preferably, the PUFA and LCPUFA are to be obtained as triglyceride esters, e.g., in form of an oil. More details on purification techniques can be found elsewhere herein below.

The host cells to be used in the method of the invention are grown or cultured in the manner with which the skilled worker is familiar, depending on the host organism. Usually, host cells are grown in a liquid medium comprising a carbon source, usually in the form of sugars, a nitrogen source, usually in the form of organic nitrogen sources such as yeast extract or salts such as ammonium sulfate, trace elements such as salts of iron, manganese and magnesium and, if appropriate, vitamins, at temperatures of between 0° C. and 100° C., preferably between 10° C. and 60° C. under oxygen or anaerobic atmosphere depedent on the type of organism. The pH of the liquid medium can either be kept constant, that is to say regulated during the culturing period, or not. The cultures can be grown batchwise, semibatchwise or continuously. Nutrients can be provided at the beginning of the fermentation or administerd semicontinuously or continuously: The produced PUFA or LCPUFA can be isolated from the host cells as described above by processes known to the skilled worker, e.g., by extraction, distillation, crystallization, if appropriate precipitation with salt, and/or chromatography. It might be required to disrupt the host cells prior to purification. To this end, the host cells can be disrupted beforehand. The culture medium to be used must suitably meet the requirements of the host cells in question. Descriptions of culture media for various microorganisms which can be used as host cells according to the present invention can be found in the textbook "Manual of Methods for General Bacteriology" of the American Society for Bacteriology (Washington D.C., USA, 1981). Culture media can also be obtained from various commercial suppliers. All media components are sterilized, either by heat or by filter sterilization. All media components may be present at the start of the cultivation or added continuously or batchwise, as desired. If the polynucleotide or vector of the invention which has been introduced in the host cell further comprises an expressible selection marker, such as an antibiotic resistance gene, it might be necessary to add a selection agent to the culture, such as a antibiotic in order to maintain the stability of the introduced polynucleotide. The culture is continued until formation of the desired product is at a maximum. This is normally achieved within 10 to 160 hours. The fermentation broths can be used directly or can be processed further. The biomass may, according to requirement, be removed completely or partially from the fermentation broth by separation methods such as, for example, centrifugation, filtration, decanting or a combination of these methods or be left completely in said broth. The fatty acid preparations obtained by the method of the invention, e.g., oils, comprising the desired PUFA or LCPUFA as triglyceride esters are also suitable as starting material for the chemical synthesis of further products of interest. For example, they can be used in combination with one another or alone for the preparation of pharmaceutical or cosmetic compositions, foodstuffs, or animal feeds. Chemically pure triglycerides comprising the desired PUFA or LCPUFA can also be manufactured by the methods described above. To this end, the fatty acid preparations are further purified by extraction, distillation, crystallization, chromatography or combinations of these methods. In order to release the fatty acid moieties from the triglycerides, hydrolysis may be also required. The said chemically pure triglycerides or free fatty acids are, in particular, suitable for applications in the food industry or for cosmetic and pharmacological compositions.

Moreover, the present invention relates to a method for the manufacture of poly-unsaturated fatty acids comprising:
 a) cultivating the non-human transgenic organism of the invention under conditions which allow for the production of poly-unsaturated fatty acids in said host cell; and
 b) obtaining said poly-unsaturated fatty acids from the said non-human transgenic organism.

Further, it follows from the above that a method for the manufacture of an oil, lipid or fatty acid composition is also envisaged by the present invention comprising the steps of any one of the aforementioned methods and the further step of formulating PUFA or LCPUFA as oil, lipid or fatty acid composition. Preferably, said oil, lipid or fatty acid composition is to be used for feed, foodstuffs, cosmetics or medicaments. Accordingly, the formulation of the PUFA or LCPUFA shall be carried out according to the GMP standards for the individual envisaged products. For example, an oil may be obtained from plant seeds by an oil mill. However, for product safety reasons, sterilization may be required under the applicable GMP standard. Similar standards will apply for lipid or fatty acid compositions to be applied in cosmetic or pharmaceutical compositions. All these measures for formulating oil, lipid or fatty acid compositions as products are comprised by the aforementioned manufacture.

For the production of ARA it is, preferably, envisaged to cultivate a host cell of the invention or a non-human transgenic organism which comprises a combination of polynucleotides of the present invention. Preferably, a combination of the polynucleotides of the invention is envisaged which encode a d12 desaturase, a d6 desaturase, a d6 elongase, a d5 desaturase KCR, DH and ECR (see also Table 6 in the accompanying Examples).

For the production of ARA it is, alternatively but also preferably, envisaged to cultivate a host cell of the invention or a non-human transgenic organism which comprises a combination of polynucleotides of the present invention. Preferably, a combination of the polynucleotides of the invention is envisaged which encode a d12 desaturase, a d9 elongase, a d8 desaturase, a d6 elongase, a d5 desaturase KCR, DH and ECR (see also Table 7 in the accompanying Examples).

For the production of EPA it is, preferably, envisaged to cultivate a host cell of the invention or a non-human transgenic organism which comprises a combination of polynucleotides of the present invention. Preferably, a combination of the polynucleotides which are preferably applied for the ARA production specified above is used together with a polynucleotide of the present invention encoding a d15 desaturase and a polynucleotide of the present invention encoding a omega-3 desaturase (i.e. a combination of the activities referred to either in Table 6 with those of Table 8 or Table 7 with those of Table 8; see also Table 8 in the accompanying Examples).

For the production of DHA it is, preferably, envisaged to cultivate a host cell of the invention or a non-human transgenic organism which comprises a combination of polynucleotides of the present invention. Preferably, a combination of the polynucleotides which are preferably applied for the EPA production specified above is used together with a polynucleotide of the present invention encoding a d5 elongase and a polynucleotide of the present invention encoding a d4 desaturase (i.e. a combination of the activities referred to either in Table 6 and Table 8 with those of Table 9 or Table 7 and Table 8 with those of Table 9; see also Table 9 in the accompanying Examples).

The present invention also relates to an oil comprising a polyunsaturated fatty acid obtainable by the aforementioned methods.

The term "oil" refers to a fatty acid mixture comprising unsaturated and/or saturated fatty acids which are esterified to triglycerides. Preferably, the triglycerides in the oil of the invention comprise PUFA or LCPUFA as referred to above. The amount of esterified PUFA and/or LCPUFA is, preferably, approximately 30%, a content of 50% is more preferred, a content of 60%, 70%, 80% or more is even more preferred. The oil may further comprise free fatty acids, preferably, the PUFA and LCPUFA referred to above. For the analysis, the fatty acid content can be, e.g., determined by GC analysis after converting the fatty acids into the methyl esters by transesterification. The content of the various fatty acids in the oil or fat can vary, in particular depending on the source. The oil, however, shall have a non-naturally occurring composition with respect to the PUFA and/or LCPUFA composition and content. It is known that most of the fatty acids in plant oil are esterified in triacylglycerides. Accordingly, in the oil of the invention, the PUFAs and LCPUFAs are, preferably, also occur in esterified form in the triacylglcerides. It will be understood that such a unique oil composition and the unique esterification pattern of PUFA and LCPUFA in the triglycerides of the oil shall only be obtainable by applying the methods of the present invention specified above. Moreover, the oil of the invention may comprise other molecular species as well. Specifically, it may comprise minor impurities of the polynucleotide or vector of the invention. Such impurities, however, can be detected only by highly sensitive techniques such as PCR.

All references cited in this specification are herewith incorporated by reference with respect to their entire disclosure content and the disclosure content specifically mentioned in this specification.

FIGURES

The FIGURE shows the production of d4/d5/d6/d15 desaturated fatty acids in yeast transformed with pYes-pd4Des(Mb), pYes-pd5Des_c738(No) or pYes-pd6Des_c2410(No) construct. The fatty acid spectrum of transgenic yeast fed with different fatty acid are depicted. A: control pYes fed with 22:4n-6, B: pYes fed with 22:5n-3, C: pYes-pd4Des(Mb) fed with 22:4n-6, D: pYes-pd4Des(Mb) fed with 22:5n-3, E: pYes control fed with 20:3n-6, F: pYes control fed with 20:4n-3, G: pYes-pd5Des_c738(No) fed with 20:3n-6, H: pd5Des_c738(No) fed with 20:4n-3, I: control pYes fed with 18:2n-6, J: pYes control fed with 18:3n-3, K: pYes-pd6Des_c2410(No) fed with 18:2n-6 and L: pYes-pd6Des_c2410(No) fed with 18:3n-3.

The invention will now be illustrated by the following Examples which, however, shall not be construed as limiting the scope of the invention.

EXAMPLES

Example 1

General Cloning Methods

Cloning methods as e.g. use of restriction endonucleases to cut double stranded DNA at specific sites, agarose gel electrophoreses, purification of DNA fragments, transfer of nucleic acids onto nitrocellulose and nylon membranes, ligation of DNA fragments, transformation of E. coli cells and culture of bacteria were performed as described in Sambrook et al. (1989) (Cold Spring Harbor Laboratory Press: ISBN 0-87965-309-6).

Example 2

Sequence Analysis of Recombinant DNA

Sequencing of recombinant DNA molecules was performed using a laser-fluorescence DNA sequencer (Applied Biosystems Inc, USA) employing the sanger method (Sanger et al. (1977) Proc. Natl. Acad. Sci. USA 74, 5463-5467). Expression constructs harboring fragments obtained by polymerase chain reaction were subjected to sequencing to confirm the correctness of the expression cassettes consisting of promoter, nucleic acid molecule to be expressed and terminator to avoid mutations that might result from handling of the DNA during cloning, e.g. due to incorrect primers, mutations from exposure to UV-light or errors of polymerases.

Example 3

Cloning of Yeast Expression Construct Via Homologous Recombination

The open reading frame listed in SEQ ID NOs: 1, 4, 7, 10, 13, 16, 19, 22, 25, 28, 31, 34, 37, 40, 43, 46, 49, 52, 55, 58, 61 and 128 encoding polypeptides with the amino acid sequence SEQ ID NOs: 2, 5, 8, 11, 14, 17, 20, 23, 26, 29, 32, 35, 38, 41, 44, 47, 50, 53, 56, 59, 62 and 129 that have desaturase, elongase, KCR, DH and ECR activity can be amplified using the primers listed in table 2 in a polymerase chain reaction. By doing so, the open reading frame is 5' fused to about 60 nucleotides of the 3' end of the GAL1 promoter sequence with simultanious introduction of an Asc I and/or Nco I restriction site between the fusion site and 3' fused to about 60 nucleotides of the 5' end of the CYC1 terminator sequence with simultanious introduction of an Pac I restriction site. To integrate these fragments into pYES2.1 TOPO downstream of the galactose inducible GAL1 Promoter via homologous recombination, the vector pYES2.1 (Invitrogen) can be digested using the restriction endonucleases Pvu II and Xba I, and Saccharomyces cerevisiae can be transformed with 5 to 20 ng of linearized pYES2.1 TOPO vector and 20 to 100 ng PCR product per 50 µl competent cells using the transformation method described by Schiestl et al. (Schiestl et al. (1989) Curr. Genet. 16(5-6), pp. 339-346), to obtain pYes-pd5Des_c738 (No), pYes-pd6Des_c2410(No), pYes-pd4Des_c5834(No), pYes-pd8Des_c20493(No), pYes-pd9Des_c3000(No), pYes-pd12Des_c6209(No), pYes-pd15Des_c3421(No), pYes-pdxElo_c1013(No), pYes-pdxElo_c10303(No), pYes-pdxElo_c2186(No), pYes-pdxElo_c2529(No), pYes-pdxElo_c37(No), pYes-pdxElo_c38(No), pYes-pdxElo_c4958 (No), pYes-pdxElo_c21679(No), pYes-pdxElo_Irc26016 (No), pYes-pKCR_c20574(No), pYes-pKCR_c20772(No), pYes-pKCR_c2845(No), pYes-pDH_c7190(No), pYes-pECR_c41(No) and pYes-pd4Des(Mb) in various wildtype yeasts. Positive transformants can be selected based on the complementation of the URA auxotrophy of the chosen S. cerevisiae strain. To validate the correctness of the expression construct harbored by a particular yeast clone, plasmids can be isolated as described in Current Protocols in Molecular Biology (Hoffmann, Curr. Protoc. Mol. Biol. 2001 May; Chapter 13:Unit 13.11), transformed into E. coli for amplification and subjected to sequencing of the expression cassette as described in Example 2.

TABLE 2

Primer sequences for cloning polynucleotides of desaturase, keto-acyl-CoA-synthase, keto-acyl-CoA-reductase, dehydratase and enoyl-CoA-reductase of the invention for expression in yeast

| Gene-Name | Primer | SEQ ID ID |
|---|---|---|
| pd5Des_c738(No) | Forward: ataaaagtatcaacaaaaaattgttaatatacctctatactttaacgtcaaggagaaaaaaccccgatcggcgcgccaccatgccgccccagaacgacgccgc | 64 |
| | Reverse: aactataaaaaaataaatagggacctagacttcaggttgtctaactccttccttttcggttagagcggatttaattaactagcccatgtgcacctccgccg | 65 |
| pd6Des_c2410(No) | Forward: ataaaagtatcaacaaaaaattgttaatatacctctatactttaacgtcaaggagaaaaaaccccgatcggcgcgccaccatgggacgcggtgcgagcggat | 66 |
| | Reverse: aactataaaaaaataaatagggacctagacttcaggttgtctaactccttccttttcggttagagcggatttaattaattacatggcggggaagtcggcca | 67 |
| pd4Des_c5834(No) | Forward: ataaaagtatcaacaaaaaattgttaatatacctctatactttaacgtcaaggagaaaaaaccccgatcggcgcgccaccatggccgatgtcgagtccatcaa | 68 |
| | Reverse: aactataaaaaaataaatagggacctagacttcaggttgtctaactccttccttttcggttagagcggatttaattaattacgaagaggaggttatgttgg | 69 |
| pd8Des_c20493(No) | Forward: ataaaagtatcaacaaaaaattgttaatatacctctatactttaacgtcaaggagaaaaaaccccgatcggcgcgccaccatggcgccgcgcgatgtggagac | 70 |
| | Reverse: aactataaaaaaataaatagggacctagacttcaggttgtctaactccttccttttcggttagagcggatttaattaattaccccgccgccgccgtt-gttg | 71 |
| pd9Des_c3000(No) | Forward: ataaaagtatcaacaaaaaattgttaatatacctctatactttaacgtcaaggagaaaaaaccccgatcggcgcgccaccatggtcttccagctcgcccgaga | 72 |
| | Reverse: aactataaaaaaataaatagggacctagacttcaggttgtctaactccttccttttcggttagagcggatttaattaattaattgtacttggggtgat-tac | 73 |
| pd12Des_c6209(No) | Forward: ataaaagtatcaacaaaaaattgttaatatacctctatactttaacgtcaaggagaaaaaaccccgatcggcgcgccaccatgggacgcggcggtgagaagac | 74 |
| | Reverse: aactataaaaaaataaatagggacctagacttcaggttgtctaactccttccttttcggttagagcggatttaattaactatgctcgctgcttgta-gaaca | 75 |
| pd15Des_c3421(No) | Forward: ataaaagtatcaacaaaaaattgttaatatacctctatactttaacgtcaaggagaaaaaaccccgatcggcgcgccaccatggttgagcaaacattgccgac | 76 |
| | Reverse: aactataaaaaaataaatagggacctagacttcaggttgtctaactccttccttttcggttagagcggatttaattaattacggaggggaggaagaacggg | 77 |

TABLE 2-continued

Primer sequences for cloning polynucleotides of desaturase, keto-acyl-CoA-synthase, keto-acyl-CoA-reductase, dehydratase and enoyl-CoA-reductase of the invention for expression in yeast

| Gene-Name | Primer | SEQ ID ID |
|---|---|---|
| pdxElo_c1013(No) | Forward: ataaaagtatcaacaaaaaattgttaatatacctctatactttaacgtcaaggagaaaaaaccccggatcggcgcgccaccatgaagtgggtcctgcaagaagg | 78 |
| | Reverse: aactataaaaaaataaatagggacctagacttcaggttgtctaactccttccttttcggttagagcggatttaattaactactgtgcttttgtcttac-cct | 79 |
| pdxElo_c10303(No) | Forward: ataaaagtatcaacaaaaaattgttaatatacctctatactttaacgtcaaggagaaaaaaccccggatcggcgcgccaccatgtcttggttttggaccccgc | 80 |
| | Reverse: aactataaaaaaataaatagggacctagacttcaggttgtctaactccttccttttcggttagagcggatttaattaattacgccatcttctttccat-tcc | 81 |
| pdxElo_c2186(No) | Forward: ataaaagtatcaacaaaaaattgttaatatacctctatactttaacgtcaaggagaaaaaaccccggatcggcgcgccaccatgctgagcaaaagcttcaatac | 82 |
| | Reverse: aactataaaaaaataaatagggacctagacttcaggttgtctaactccttccttttcggttagagcggatttaattaactactgtgctttct-tcaagtcca | 83 |
| pdxElo_c2529(No) | Forward: ataaaagtatcaacaaaaaattgttaatatacctctatactttaacgtcaaggagaaaaaaccccggatcggcgcgccaccatggaggccccctcccgcacct | 84 |
| | Reverse: aactataaaaaaataaatagggacctagacttcaggttgtctaactccttccttttcggttagagcggatttaattaatcacctttctggggaggcacccg | 85 |
| pdxElo_c37(No) | Forward: ataaaagtatcaacaaaaaattgttaatatacctctatactttaacgtcaaggagaaaaaaccccggatcggcgcgccaccatggccgccgccctctttcaga | 86 |
| | Reverse: aactataaaaaaataaatagggacctagacttcaggttgtctaactccttccttttcggttagagcggatttaattaattaaatcttcttgagagccg-gct | 87 |
| pdxElo_c38(No) | Forward: ataaaagtatcaacaaaaaattgttaatatacctctatactttaacgtcaaggagaaaaaaccccggatcggcgcgccaccatgtcgttcctcattcgcactcc | 88 |
| | Reverse: aactataaaaaaataaatagggacctagacttcaggttgtctaactccttccttttcggttagagcggatttaattaattaaatcgtcttcgtct-tgggct | 89 |
| pdxElo_c4958(No) | Forward: ataaaagtatcaacaaaaaattgttaatatacctctatactttaacgtcaaggagaaaaaaccccggatcggcgcgccaccatggcagtggcctttgctcgaggt | 90 |
| | Reverse: aactataaaaaaataaatagggacctagacttcaggttgtctaactccttccttttcggttagagcggatttaattaatcaaccctgctgctcccgc-cta | 91 |

TABLE 2-continued

Primer sequences for cloning polynucleotides of desaturase, keto-acyl-CoA-synthase, keto-acyl-CoA-reductase, dehydratase and enoyl-CoA-reductase of the invention for expression in yeast

| Gene-Name | Primer | SEQ ID ID |
|---|---|---|
| pdxElo_c21679(No) | Forward: ataaaagtatcaacaaaaaattgttaatatacctctatactttaacgtcaaggagaaaaaaccccggatcggcgcgccaccatgctttcagtttatttccccgc | 92 |
| | Reverse: aactataaaaaaataaatagggacctagacttcaggttgtctaactccttcctttcggttagagcggatttaattaacacgtgcaagcttacccatacgg | 93 |
| pdxElo_lrc26016(No) | Forward: ataaaagtatcaacaaaaaattgttaatatacctctatactttaacgtcaaggagaaaaaaccccggatcggcgcgccaccatgcccaagcttccagagatctc | 94 |
| | Reverse: aactataaaaaaataaatagggacctagacttcaggttgtctaactccttcctttcggttagagcggatttaattaattacatcgccttgattttcttgg | 95 |
| pKCR_c20574(No) | Forward: ataaaagtatcaacaaaaaattgttaatatacctctatactttaacgtcaaggagaaaaaaccccggatcggcgcgccaccatgggtctcgacgtgaaggagaa | 96 |
| | Reverse: aactataaaaaaataaatagggacctagacttcaggttgtctaactccttcctttcggttagagcggatttaattaactacgcagcggccttgatctcct | 97 |
| pKCR_c20772(No) | Forward: ataaaagtatcaacaaaaaattgttaatatacctctatactttaacgtcaaggagaaaaaaccccggatcggcgcgccaccatggcatctaaaggtggcaatttt | 98 |
| | Reverse: aactataaaaaaataaatagggacctagacttcaggttgtctaactccttcctttcggttagagcggatttaattaatcaagcgctcttctcattcttct | 99 |
| pKCR_c2845(No) | Forward: ataaaagtatcaacaaaaaattgttaatatacctctatactttaacgtcaaggagaaaaaaccccggatcggcgcgccaccatggcgttggacgtgaaggagaa | 100 |
| | Reverse: aactataaaaaaataaatagggacctagacttcaggttgtctaactccttcctttcggttagagcggatttaattaactactttactcccccttttccctt | 101 |
| pDH_c7190(No) | Forward: ataaaagtatcaacaaaaaattgttaatatacctctatactttaacgtcaaggagaaaaaaccccggatcggcgcgccaccatgggaggtggcagtaaaagcgg | 102 |
| | Reverse: aactataaaaaaataaatagggacctagacttcaggttgtctaactccttcctttcggttagagcggatttaattaactattcggccttccggctctcc | 103 |
| pECR_c41(No) | Forward: ataaaagtatcaacaaaaaattgttaatatacctctatactttaacgtcaaggagaaaaaaccccggatcggcgcgccaccatgggcaagcctcagcgagccaa | 104 |
| | Reverse: aactataaaaaaataaatagggacctagacttcaggttgtctaactccttcctttcggttagagcggatttaattaactaaaacccagcgtatcccttga | 105 |

TABLE 2-continued

Primer sequences for cloning polynucleotides of desaturase, keto-acyl-CoA-synthase, keto-acyl-CoA-reductase, dehydratase and enoyl-CoA-reductase of the invention for expression in yeast

| Gene-Name | Primer | SEQ ID ID |
|---|---|---|
| pd4Des(Mb) | Forward: ataaaagtatcaacaaaaaattgttaatatacctctatactttaacgtcaaggagaaaaaacccccggatcggcgcgccaccatggctagttcagttgagaggga | 131 |
| | Reverse: aactataaaaaaataaatagggacctagacttcaggttgtctaactccttcctttccggttagagcggatttaattaattaagcagctctaggct-taactt | 132 |

A list of identified full-length coding sequences is shown in Table 3.

TABLE 3

Coding polynucleotide sequences, amino acid sequences encoded thereby and expressed sequences (mRNA) of desaturases, elongases or elongase component from Nannochloropsis oculata of the invention.

| Gene name | Activity | ORF in bp | SEQ-ID No. | Amino acids | SEQ-ID No. | mRNA in bp | SEQ-ID No. |
|---|---|---|---|---|---|---|---|
| pd5Des_c738(No) | d5-desaturase | 1581 | 1 | 526 | 2 | 1972 | 3 |
| pd6Des_c2410(No) | d6-desaturase | 1425 | 4 | 474 | 5 | 1565 | 6 |
| pd4Des_c5834(No) | d4-desaturase | 1527 | 7 | 508 | 8 | 1963 | 9 |
| pd8Des_c20493(No) | d8-desaturase | 1449 | 10 | 482 | 11 | 1954 | 12 |
| pd9Des_c3000(No) | d9-desaturase | 1080 | 13 | 359 | 14 | 1534 | 15 |
| pd12Des_c6209(No) | d12-desaturase | 1317 | 16 | 438 | 17 | 2049 | 18 |
| pd15Des_c3421(No) | d15-desaturase | 1242 | 19 | 413 | 20 | 2079 | 21 |
| pdxElo_c1013(No) | KCS | 906 | 22 | 301 | 23 | 1086 | 24 |
| pdxElo_c10303(No) | KCS | 1023 | 25 | 340 | 26 | 1894 | 27 |
| pdxElo_c2186(No) | KCS | 1095 | 28 | 364 | 29 | 1685 | 30 |
| pdxElo_c2529(No) | KCS | 951 | 31 | 316 | 32 | 1060 | 33 |
| pdxElo_c37(No) | KCS | 831 | 34 | 276 | 35 | 1302 | 36 |
| pdxElo_c38(No) | KCS | 897 | 37 | 298 | 38 | 2441 | 39 |
| pdxElo_c4958(No) | KCS | 903 | 40 | 300 | 41 | 1053 | 42 |
| pdxElo_c21679(No) | KCS | 1485 | 43 | 495 | 44 | 1755 | 45 |
| pdxElo_lrc26016(No) | KCS | 966 | 46 | 321 | 47 | 1689 | 48 |
| pKCR_c20574(No) | KCR | 1071 | 49 | 356 | 50 | 1304 | 51 |
| pKCR_c20772(No) | KCR | 978 | 52 | 325 | 53 | 1115 | 54 |
| pKCR_c2845(No) | KCR | 1044 | 55 | 347 | 56 | 1751 | 57 |
| pDH_c7190(No) | DH | 768 | 58 | 202 | 59 | 1293 | 60 |
| pECR_c41(No) | ECR | 1620 | 61 | 539 | 62 | 2229 | 63 |
| pd4Des(Mb) | d4-desaturase | 1320 | 128 | 439 | 129 | 1515 | 130 |

Example 4

Activity Assay in Yeast

As an example the activity of identified polypeptides was confirmed by heterologous expression in yeast. Table 4 shows the activity assay of the control yeasts transformed with the empty pYes vector, pYes-pd4Des(Mb), pYes-pd5Des_c738(No) and pYes-pd6Des_c2410(No) construct. In the gas chromatograms of yeast extracts, transformed with pYes-pd4Des(Mb) and fed with 22:4n-6 or 22:5n-3, the d4-desaturated fatty acids 22:5n-6 and 22:6n-3 were detected (FIG. 1, Table 4). This result shows that pYes-pd4Des(Mb) has d4-desaturase activtiy. In the gas chromatograms of yeast extracts, transformed with pYes-pd5 Des_c738(No) and fed with 20:3n-6 or 20:4n-3, the d5-desaturated fatty acids 20:4n-6 and 20:5n-3 were detected (FIG. 1, Table 4). The fatty acids 20:4n-6 and 20:5n-3 were not present in yeast transformed with the control vector and fed with 20:3n-6 and 20:4n-3. This analysis shows that pYes-pd5 Des_c738(No) has d5-desaturase activity.

Only in the gas chromatograms of yeast extracts, transformed with pYes-pd6Des_c2410(No) and fed with 18:2n-6 or 18:3n-3, the d6-desaturated fatty acids 18:3n-6 and 18:4n-3 were detected (FIG. 1, Table 4). This result unambiguously demonstrates that pd6Des_c2410 (No) has d6-desaturase activity. Additionally, the detected 18:4n-3 product suggests that pYes-pd6Des_c2410 (No) has also d15-desaturase activity.

TABLE 4

Yeast feeding experiment. The substrate and product fatty acid are given as percentage of the total fatty acid pool. The chromatograms of the measurement are shown in FIG. 1.

| Vector | Substrate | | Product | | Conversion (%) | Activity | FIG. |
|---|---|---|---|---|---|---|---|
| pYes | 22:4n-6 | 73.28 | 22:5n-6 | 0.00 | 0.00 | — | 1A |
| pYes | 22:5n-3 | 72.01 | 22:6n-3 | 0.00 | 0.00 | — | 1B |
| pYes-pd4Des(Mb) | 22:4n-6 | 66.77 | 22:5n-6 | 7.35 | 9.91 | d4Des | 1C |
| pYes-pd4Des(Mb) | 22:5n-3 | 64.10 | 22:6n-3 | 7.74 | 10.78 | d4Des | 1D |
| pYes | 20:3n-6 | 89.93 | 20:4n-6 | 0.00 | 0.00 | — | 1E |
| pYes | 20:4n-3 | 60.64 | 20:5n-3 | 0.00 | 0.00 | — | 1F |
| pd5Des_c738(No) | 20:3n-6 | 85.00 | 20:4n-6 | 4.12 | 4.62 | d5Des | 1G |
| pd5Des_c738(No) | 20:4n-3 | 58.89 | 20:5n-3 | 6.75 | 10.29 | d5Des | 1H |
| pYes | 18:2n-6 | 20.9 | 18:3n-6 | 0.0 | 0.00 | — | 1I |
| pYes | 18:3n-3 | 13.2 | 18:4n-3 | 0.0 | 0.00 | — | 1J |
| pYes-pd6Des_c2410(No) | 18:2n-6 | 20.2 | 18:3n-6 | 10.6 | 34.46 | d6Des | 1K |
| pYes-pd6Des_c2410(No) | 18:2n-6 | 20.2 | 18:4n-3 | 2.0 | 9.00 | d15Des | 1K |
| pYes-pd6Des_c2410(No) | 18:3n-3 | 5.3 | 18:4n-3 | 6.9 | 56.44 | d6Des | 1L |

Additionally the activity of the identified Elo component polypeptides were analyzed. The fatty acids 18:3n-6 and 18:4n-3 were fed to yeasts expressing pdxElo_c37(No) and pdxElo_c1013(No). As a control, yeasts transformed with the empty pYes vector were included in the experiment. In contrast to control-yeasts, yeasts transformed with pYes-pdx Elo_c37(No) or pYes-pdxElo_c1013(No) produced 20:3n-6 or 20:4-3, this demonstrates that pdxElo_c37(No) and pdxElo_c1013(No) have d6-Elongase activity.

TABLE 5

Yeast feeding experiment. The substrate and product fatty acid are given as percentage of the total fatty acid pool.

| Vector | Substrate | | Product | | Conversion (%) | Activity |
|---|---|---|---|---|---|---|
| pYes | 18:3n-6 | 63.87 | 20:3n-6 | 0.00 | 0.00 | — |
| pYes | 18:4n-3 | 71.28 | 20:4n-3 | 0.00 | 0.00 | — |
| pYes-pdxElo_c37(No) | 18:3n-6 | 72.97 | 20:3n-6 | 3.35 | 4.39 | d6Elo |
| pYes-pdxElo_c37(No) | 18:4n-3 | 69.09 | 20:4n-3 | 0.77 | 1.11 | d6Elo |
| pYes-pdxElo_c1013(No) | 18:3n-6 | 70.39 | 20:3n-6 | 1.49 | 2.07 | d6Elo |
| pYes | 18:2n-6 | 42.74 | 20:2n-6 | 0.00 | 0.00 | — |
| pd9Elo_c21679(No | 18:2n-6 | 47.81 | 20:2n-6 | 0.54 | 1.12 | d9Elo |

Example 5

Expression of Desaturase, KCS, KCR, DH and ECR in Plants

The novel desaturases, KCS, KCR, DH and ECR from *Nannochloropsis oculata* can be cloned into a plant transformation vector as described in WO2003/093482, WO2005/083093 or WO20071093776.

Exemplary suitable combinations of genes for the production of ARA, EPA and DHA are described in table 6, 7, 8 and 9.

TABLE 6

Gene combinations for the production of arachidonic acid. At least one enzyme with a d12-desaturase, d6-desaturase, d6-elongase and d5-desaturase activity are required for arachidonic acid. Various biosynthetic steps can be catalyzed by enzymes of *Nannochloropsis oculata* of the present invention.

| Activity | Gene | Source organism | SEQ ID NO: |
|---|---|---|---|
| d12-desaturase | d12Des(Ps) | *Phytophthora soja* | 106 |
| | pd12Des_c6209(No) | *Nannochloropsis oculata* | 16 |
| d6-desaturase | d6Des(Ot) | *Ostreococcus tauri* | 108 |
| | pd6Des(No) | *Nannochloropsis oculata* | 4 |
| d6-elongase | d6Elo(Tp) | *Thalassiosira pseudonana* | 110 |
| | d6Elo(Pp) | *Physcomitrella patens* | 112 |
| | pdxElo_c1013(No) | *Nannochloropsis oculata* | 22 |
| | pdxElo_c10303(No) | *Nannochloropsis oculata* | 25 |
| | pdxElo_c2186(No) | *Nannochloropsis oculata* | 28 |
| | pdxElo_c2529(No) | *Nannochloropsis oculata* | 31 |
| | pdxElo_c37(No) | *Nannochloropsis oculata* | 34 |
| | pdxElo_c38(No) | *Nannochloropsis oculata* | 37 |
| | pdxElo_c4958(No) | *Nannochloropsis oculata* | 40 |
| | pdxElo_c21679(No) | *Nannochloropsis oculata* | 43 |
| | pdxElo_lrc26016(No) | *Nannochloropsis oculata* | 46 |
| d5-desaturase | d5Des(Tc) | *Thraustochytrium sp.* | 114 |
| | pd5Des_c738(No) | *Nannochloropsis oculata* | 1 |
| KCR | pKCR_c20574(No) | *Nannochloropsis oculata* | 49 |
| | pKCR_c20772(No) | *Nannochloropsis oculata* | 52 |
| | pKCR_c2845(No) | *Nannochloropsis oculata* | 55 |
| DH | pDH_c7190(No) | *Nannochloropsis oculata* | 58 |
| ECR | pECR_c41(No) | *Nannochloropsis oculata* | 61 |

Arachidonic acid may be produced by an alternative pathway involving d9-elongase and d8-desaturase activity. Table 7 shows a combination of genes for this pathway.

TABLE 7

Gene combinations of the alternative pathway for the production of arachidonic acid. Several biosynthetic steps can be catalyzed by enzymes of *Nannochloropsis oculata* of the present invention.

| Activity | Gene | Source organism | SEQ ID NO: |
|---|---|---|---|
| d12-desaturase | d12Des(Ps) | *Phytophthora soja* | 106 |
| | pd12Des_c6209(No) | *Nannochloropsis oculata* | 16 |
| d9-elongase | d9Elo(Ig) | *Isochrysis galbana* | 116 |
| | pdxElo_c21679(No) | *Nannochloropsis oculata* | 43 |
| d8-desaturase | d8Des(Pm) | *Perkinsus marinus* | 113 |
| | pd8Des_c20493(No) | *Nannochloropsis oculata* | 10 |

TABLE 7-continued

Gene combinations of the alternative pathway for the production of arachidonic acid. Several biosynthetic steps can be catalyzed by enzymes of *Nannochloropsis oculata* of the present invention.

| Activity | Gene | Source organism | SEQ ID NO: |
|---|---|---|---|
| d6-elongase | pdxElo_c1013(No) | *Nannochloropsis oculata* | 22 |
| | pdxElo_c10303(No) | *Nannochloropsis oculata* | 25 |
| | pdxElo_c2186(No) | *Nannochloropsis oculata* | 28 |
| | pdxElo_c2529(No) | *Nannochloropsis oculata* | 31 |
| | pdxElo_c37(No) | *Nannochloropsis oculata* | 34 |
| | pdxElo_c38(No) | *Nannochloropsis oculata* | 37 |
| | pdxElo_c4958(No) | *Nannochloropsis oculata* | 40 |
| | pdxElo_c21679(No) | *Nannochloropsis oculata* | 43 |
| | pdxElo_lrc26016(No) | *Nannochloropsis oculata* | 46 |
| d5-desaturase | d5Des(Tc) | *Thraustochytrium* sp. | 114 |
| | pd5Des_c738(No) | *Nannochloropsis oculata* | 1 |
| KCR | pKCR_c20574(No) | *Nannochloropsis oculata* | 49 |
| | pKCR_c20772(No) | *Nannochloropsis oculata* | 52 |
| | pKCR_c2845(No) | *Nannochloropsis oculata* | 55 |
| DH | pDH_c7190(No) | *Nannochloropsis oculata* | 58 |
| ECR | pECR_c41(No) | *Nannochloropsis oculata* | 61 |

For the production of EPA, the genes listed in table 8 are combined with the genes listed in table 6 or 7.

TABLE 8

For the production of EPA, in addition to combinations of genes listed in table 6 or 7, the expression of genes of this table are required.

| Activity | Gene | Source organism | SEQ ID NO: |
|---|---|---|---|
| d15-desaturase | d15Des(Hr) | *Helobdella robusta* | 120 |
| | pd15Des_c3421(No) | *Nannochloropsis oculata* | 19 |
| omega-3 desaturase | o3Des(Pi) | *Phytophthora infestans* | 122 |

In addition to the genes of table 5, 6, 7, the genes listed in table 8 are required for the biosynthesis of DHA. These genes allow to elongate EPA by 2 carbon atom and dehydrogenation at the 4$^{th}$ and 5$^{th}$ carbon atom, resulting in the generation of DHA.

TABLE 9

For the production of DHA, in addition to the genes of table 6 or 7 and 8, the genes of this table are required.

| Activity | Gene | Source organism | SEQ ID NO: |
|---|---|---|---|
| d5-elongase | d5Elo(Ot) | *Ostreococcus tauri* | 124 |
| d4-desaturase | d4Des(Tc) | *Thraustochytrium* sp. | 126 |
| | pd4Des_c5834(No) | *Nannochloropsis oculata* | 7 |
| | pd4Des(Mb) | *Monosiga brevicollis* | 128 |

Transgenic rapeseed lines are generated as described in Deblaere et al. (1984), (Nucl. Acids. Res. 13, 4777-4788) and seeds of transgenic rapeseed plants are analyzed as described in Qiu et al. (2001) (J. Biol. Chem. 276, 31561-31566).

REFERENCE LIST

Arondel, V., Lemieux, B., Hwang, I., Gibson, S., Goodman, H. M., and Somerville, C. R. (1992). Map-based cloning of a gene controlling omega-3 fatty acid desaturation in *Arabidopsis*. Science 258, 1353-1355.

Broadwater, J. A., Whittle, E., and Shanklin, J. (2002). Desaturation and hydroxylation. Residues 148 and 324 of *Arabidopsis* FAD2, in addition to substrate chain length, exert a major influence in partitioning of catalytic specificity. J. Biol. Chem. 277, 15613-15620.

Broun, P., Shanklin, J., Whittle, E., and Somerville, C. (1998b). Catalytic plasticity of fatty acid modification enzymes underlying chemical diversity of plant lipids. Science 282, 1315-1317.

Calvo, A. M., Gardner, H. W., and Keller, N. P. (2001). Genetic connection between fatty acid metabolism and sporulation in *Aspergillus nidulans*. J. Biol. Chem. 276, 25766-25774.

Knutzon, D. S., Thurmond, J. M., Huang, Y. S., Chaudhary, S., Bobik, E. G., Jr., Chan, G. M., Kirchner, S. J., and Mukerji, P. (1998). Identification of Delta5-dehydratase from *Mortierella* alpina by heterologous expression in Bakers' yeast and canola. J. Biol. Chem. 273, 29360-29366.

Mantle, P. G. and Nisbet, L. J. (1976). Differentiation of *Claviceps purpurea* in axenic culture. J. Gen. Microbiol. 93, 321-334.

Mey, G., Oeser, B., Lebrun, M. H., and Tudzynski, P. (2002). The biotrophic, non-appressorium-forming grass pathogen *Claviceps purpurea* needs a Fus3/Pmk1 homologous mitogen-activated protein kinase for colonization of rye ovarian tissue. Mol. Plant Microbe Interact. 15, 303-312.

Okuley, J., Lightner, J., Feldmann, K., Yadav, N., Lark, E., and Browse, J. (1994). *Arabidopsis* FAD2 gene encodes the enzyme that is essential for polyunsaturated lipid synthesis. Plant Cell 6, 147-158.

Qi, B., Fraser, T., Mugford, S., Dobson, G., Sayanova, O., Butler, J., Napier, J. A., Stobart, A. K., and Lazarus, C. M. (2004). Production of very long chain polyunsaturated omega-3 and omega-6 fatty acids in plants. Nat. Biotechnol. 22, 739-745.

Shanklin, J. and Cahoon, E. B. (1998). DESATURATION AND RELATED MODIFICATIONS OF FATTY ACIDS1. Annu. Rev. Plant Physiol Plant Mol. Biol. 49, 611-641

Tudzynski, P., Correia, T., and Keller, U. (2001). Biotechnology and genetics of ergot alkaloids. Appl. Microbiol. Biotechnol. 57, 593-605.

The invention claimed is:

1. A polynucleotide comprising an expression control sequence operatively linked to a heterologous nucleic acid sequence selected from the group consisting of:
   a) the nucleic acid sequence of SEQ ID NO: 128;
   b) a nucleic acid sequence encoding a polypeptide having the amino acid sequence of SEQ ID NO: 129;
   c) a nucleic acid sequence having at least 85% sequence identity to the entire length of the nucleic acid sequence of a), wherein said nucleic acid sequence encodes a polypeptide having delta-4 desaturase activity; and
   d) a nucleic acid sequence encoding a polypeptide having delta-4 desaturase activity and comprising an amino acid sequence having at least 85% sequence identity to the entire length of the amino acid sequence of SEQ ID NO: 129.

2. The polynucleotide of claim 1, wherein said polynucleotide further comprises a terminator sequence operatively linked to said nucleic acid sequence.

3. A vector comprising the polynucleotide of claim 1.

4. A host cell comprising the polynucleotide of claim 1 or a vector comprising said polynucleotide.

5. A method for the manufacture of a polypeptide, comprising:
   a) cultivating a host cell comprising the polynucleotide of claim 1 or a vector comprising said polynucleotide under conditions allowing for production of a polypeptide encoded by said polynucleotide; and
   b) obtaining said polypeptide from the host cell of step a).

6. An isolated polypeptide encoded by the polynucleotide of claim 1.

7. A non-human transgenic organism comprising the polynucleotide of claim 1 or a vector comprising said polynucleotide, wherein said non-human transgenic organism is a plant, plant part, plant seed, or microorganism.

8. The non-human transgenic organism of claim 7, wherein the microorganism is a fungus, algae, moss, or yeast.

9. A method for the manufacture of at least one polyunsaturated fatty acid, comprising:
   a) cultivating the host cell of claim 4 under conditions allowing for production of at least one polyunsaturated fatty acid in said host cell; and
   b) obtaining said at least one polyunsaturated fatty acid from said host cell.

10. A method for the manufacture of at least one polyunsaturated fatty acid, comprising:
    a) cultivating the non-human transgenic organism of claim 7 under conditions allowing for production of at least one polyunsaturated fatty acid in said non-human transgenic organism; and
    b) obtaining said at least one polyunsaturated fatty acid from said non-human transgenic organism.

11. The method of claim 9, wherein said at least one polyunsaturated fatty acid is arachidonic acid (ARA), eicosapentaenoic acid (EPA), and/or docosahexaenoic acid (DHA).

12. A method for the manufacture of an oil, lipid or fatty acid composition, comprising:
    a) manufacturing at least one polyunsaturated fatty acid by the method of claim 9; and
    b) formulating the at least one polyunsaturated fatty acid in an oil, lipid or fatty acid composition.

13. The method of claim 12, wherein said oil, lipid or fatty acid composition is to be used for feed, foodstuffs, cosmetics or medicaments.

14. The polynucleotide of claim 1, wherein the nucleic acid sequence encodes a polypeptide having delta-4 desaturase activity and comprising an amino acid sequence having at least 90% sequence identity to the entire length of the amino acid sequence of SEQ ID NO: 129.

15. The polynucleotide of claim 1, wherein the nucleic acid sequence encodes a polypeptide having delta-4 desaturase activity and comprising an amino acid sequence having at least 95% sequence identity to the entire length of the amino acid sequence of SEQ ID NO: 129.

16. A method for the manufacture of polyunsaturated fatty acids, comprising:
    a) cultivating a plant comprising the polynucleotide of claim 1 or a vector comprising said polynucleotide under conditions which allow for the production of polyunsaturated fatty acids in said plant or seeds thereof; and b) obtaining said polyunsaturated fatty acids from said plant or seeds thereof.

17. A method for the manufacture of an oil-, lipid- or fatty acid-composition, comprising:
   a) cultivating a plant comprising the polynucleotide of claim 1 or a vector comprising said polynucleotide under conditions which allow for the production of polyunsaturated fatty acids in said plant or seeds thereof; and
   b) obtaining an oil-, lipid- or fatty acid-composition from said plant or seeds thereof.

18. A method for the manufacture of polyunsaturated fatty acids, comprising:
   a) obtaining an oil-, lipid- or fatty acid-composition produced by the method of claim 17; and
   b) obtaining polyunsaturated fatty acids from said oil-, lipid- or fatty acid-composition.

19. The method of claim 16, wherein the polyunsaturated fatty acids are obtained from the seeds of said plant.

20. The method of claim 17, wherein the oil-, lipid- or fatty acid-composition is obtained from the seeds of said plant.

\* \* \* \* \*